United States Patent
Nasveschuk et al.

(10) Patent No.: US 11,623,929 B2
(45) Date of Patent: Apr. 11, 2023

(54) SPIROCYCLIC COMPOUNDS

(71) Applicant: C4 Therapeutics, Inc., Watertown, MA (US)

(72) Inventors: Christopher G. Nasveschuk, Stoneham, MA (US); Fabian Dey, Basel (CH); Annick Goergler, Colmar (FR); Roger Norcross, Basel (CH); Philipp Schmid, Basel (CH)

(73) Assignee: C4 Therapeutics, Inc., Watertown, MA (US)

( * ) Notice: Subject to any disclaimer, the term of this patent is extended or adjusted under 35 U.S.C. 154(b) by 0 days.

(21) Appl. No.: 17/103,621

(22) Filed: Nov. 24, 2020

(65) Prior Publication Data

US 2021/0070763 A1    Mar. 11, 2021

Related U.S. Application Data

(63) Continuation of application No. PCT/US2019/035223, filed on Jun. 3, 2019.

(30) Foreign Application Priority Data

Jun. 4, 2018 (EP) .................. 18175701.4

(51) Int. Cl.
*C07D 487/10* (2006.01)
*C07D 519/00* (2006.01)
*A61P 35/00* (2006.01)

(52) U.S. Cl.
CPC ............ *C07D 487/10* (2013.01); *A61P 35/00* (2018.01); *C07D 519/00* (2013.01)

(58) Field of Classification Search
None
See application file for complete search history.

(56) References Cited

U.S. PATENT DOCUMENTS

| | | | |
|---|---|---|---|
| 5,635,517 | A | 6/1997 | Muller et al. |
| 6,306,663 | B1 | 10/2001 | Kenten et al. |
| 7,041,298 | B2 | 5/2006 | Deshaies et al. |
| 7,208,157 | B2 | 4/2007 | Deshaies et al. |
| 2014/0302523 | A1 | 10/2014 | Crews et al. |
| 2014/0356322 | A1 | 12/2014 | Crews et al. |
| 2015/0119435 | A1 | 4/2015 | Crews et al. |
| 2015/0274738 | A1 | 10/2015 | Gray et al. |
| 2015/0291562 | A1 | 10/2015 | Crew et al. |
| 2016/0022642 | A1 | 1/2016 | Crews et al. |
| 2016/0045607 | A1 | 2/2016 | Crew et al. |
| 2016/0046661 | A1 | 2/2016 | Gray et al. |
| 2016/0058572 | A1 | 3/2016 | Crew et al. |
| 2016/0176916 | A1 | 6/2016 | Bradner et al. |
| 2016/0214972 | A1 | 7/2016 | Jin et al. |
| 2016/0272639 | A1 | 9/2016 | Crew et al. |
| 2017/0008904 | A1 | 1/2017 | Crew et al. |
| 2017/0037004 | A1 | 2/2017 | Crew et al. |
| 2018/0085465 | A1 | 3/2018 | Bradner et al. |

FOREIGN PATENT DOCUMENTS

| | | |
|---|---|---|
| WO | WO 2002/059106 A1 | 8/2002 |
| WO | WO 2008/027542 A2 | 3/2008 |
| WO | WO 2008/033567 A1 | 3/2008 |
| WO | WO 2008/039489 A2 | 4/2008 |
| WO | WO 2008/115516 A2 | 9/2008 |
| WO | WO 2009/042177 A1 | 4/2009 |
| WO | WO 2009/139880 A1 | 11/2009 |
| WO | WO 2009/145899 A1 | 12/2009 |
| WO | WO 2010/053732 A1 | 5/2010 |
| WO | WO 2010/107485 A1 | 9/2010 |
| WO | WO 2013/106646 A2 | 7/2013 |
| WO | WO 2013/124026 A1 | 8/2013 |
| WO | WO 2013/170147 A1 | 11/2013 |
| WO | WO 2016/065139 A1 | 4/2016 |
| WO | WO 2016/105518 A1 | 6/2016 |
| WO | WO 2016/146985 A1 | 9/2016 |
| WO | WO 2016/169989 A1 | 10/2016 |
| WO | WO 2016/191178 A1 | 12/2016 |
| WO | WO 2016/197032 A1 | 12/2016 |
| WO | WO 2016/197114 A1 | 12/2016 |
| WO | WO 2017/007612 A1 | 1/2017 |
| WO | WO 2017/024317 A2 | 2/2017 |
| WO | WO 2017/024318 A1 | 2/2017 |
| WO | WO 2017/024319 A1 | 2/2017 |
| WO | WO 2017/079267 A1 | 5/2017 |
| WO | WO 2017/161119 A1 | 9/2017 |
| WO | WO 2017/176708 A1 | 10/2017 |
| WO | WO 2017/176957 A1 | 10/2017 |

(Continued)

OTHER PUBLICATIONS

STN Next Registry Search (Year: 2014).*
U.S. Pat. No. 10,646,575, B2, U.S. Appl. No. 16/186,339, Phillips et al., May 12, 2020.
U.S. Pat. No. 10,660,968, B2, U.S. Appl. No. 16/186,334, Phillips et al., May 26, 2020.
U.S. Pat. No. 10,849,982, B2, U.S. Appl. No. 16/186,341, Phillips et al., Dec. 1, 2020.
U.S. Pat. No. 10,905,768, B2, U.S. Appl. No. 16/872,225, Phillips et al., Feb. 2, 2021.
U.S. Pat. No. 11,185,592, B2, U.S. Appl. No. 16/882,236, Phillips et al., Nov. 30, 2021.
2020/0140456, A1, U.S. Appl. No. 16/721,650, Phillips et al., May 7, 2020.
2020/0207764, A1, U.S. Appl. No. 16/809,325, Norcross et al., Jul. 2, 2020.
2020/0207783, A1, U.S. Appl. No. 16/809,336, Norcross et al., Jul. 2, 2020.
2020/0207733, A1, U.S. Appl. No. 16/809,345, Norcross et al., Jul. 2, 2020.
2020/0308171, A1, U.S. Appl. No. 16/903,237, Jaeschke et al., Oct. 1, 2020.

(Continued)

*Primary Examiner* — Jeffrey S Lundgren
*Assistant Examiner* — Michael J Schmitt
(74) *Attorney, Agent, or Firm* — Knowles Intellectual Properly Strategies, LLC

(57) ABSTRACT

The present invention provides compounds and intermediates. The present invention also provides compounds which bind to the ubiquitously expressed E3 ligase protein cereblon (CRBN) and their use for the treatment of abnormal cellular proliferation. The present invention also provides compounds that may be used as synthetic intermediates in the synthesis of bifunctional compounds used for targeted protein degradation.

20 Claims, No Drawings

(56) References Cited

FOREIGN PATENT DOCUMENTS

| WO | WO 2017/176958 A1 | 10/2017 |
|---|---|---|
| WO | WO 2017/180417 A1 | 10/2017 |
| WO | WO 2017/201069 A1 | 11/2017 |
| WO | WO 2017/201449 A1 | 11/2017 |
| WO | WO 2018/051107 A1 | 3/2018 |
| WO | WO 2018/052945 A1 | 3/2018 |
| WO | WO 2018/052949 A1 | 3/2018 |
| WO | WO 2018/053354 A1 | 3/2018 |
| WO | WO 2018/071606 A1 | 4/2018 |
| WO | WO 2018/085247 A1 | 5/2018 |
| WO | WO 2018/102067 A2 | 6/2018 |
| WO | WO 2018/102725 A1 | 6/2018 |
| WO | WO 2018/118598 A1 | 6/2018 |
| WO | WO 2018/118947 A1 | 6/2018 |
| WO | WO 2018/119357 A1 | 6/2018 |
| WO | WO 2018/119441 A1 | 6/2018 |
| WO | WO 2018/119448 A1 | 6/2018 |
| WO | WO 2018/140809 A1 | 8/2018 |
| WO | WO 2018/144649 A1 | 8/2018 |
| WO | WO 2018/169777 A1 | 9/2018 |
| WO | WO 2018/189554 A1 | 10/2018 |
| WO | WO 2019/032632 A1 | 2/2019 |

OTHER PUBLICATIONS

2021/0009559, A1, U.S. Appl. No. 17/031,550, Henderson et al, Jan. 14, 2021.
2021/0032245, A1, U.S. Appl. No. 17/072,896, Nasveschuk et al, Feb. 4, 2021.
2021/0198256, A1, U.S. Appl. No. 17/192,634, Nasveschuk et al., Jul. 1, 2021.
2022/0098194, A1, U.S. Appl. No. 17/541,035, Nasveschuk et al., Mar. 31, 2022.
U.S. Appl. No. 16/874,475, Phillips et al., filed May 15, 2020.
U.S. Appl. No. 17/107,781, Phillips et al., filed Nov. 30, 2020.
U.S. Appl. No. 17/121,389, Phillips et al., filed Dec. 14, 2020.
U.S. Appl. No. 17/351,935, Phillips et al., filed Jun. 18, 2021.
U.S. Appl. No. 17/465,583, Nasveschuk et al., filed Sep. 2, 2021.
U.S. Appl. No. 17/498,617, Henderson et al., filed Oct. 11, 2021.
U.S. Appl. No. 17/524,558, Phillips et al., filed Nov. 11, 2021.
U.S. Appl. No. 17/576,582, Norcross et al., filed Jan. 14, 2022.
U.S. Appl. No. 17/723,199, Henderson et al., filed Apr. 18, 2022.
Bartlett, et al. "The evolution of thalidomide and its IMiD derivatives as anticancer agents." Nat Rev Cancer 2004, 4(4):312-322.
Bemdsen et al. "New insights into ubiquitin E3 ligase mechanism" Nat. Struct. Mol. Biol. 2014, 21:301-307.
Bondeson et al. "Catalytic in vivo protein knockdown by small-molecule PROTACs" Nature Chemical Biology 2015, 11:611-617.
Buckley et al. "HaloPROTACS: Use of Small Molecule PROTACS to Induce Degradation of HaloTag Fusion Proteins" ACS Chemical Biology 2015, 10:1831-1837.
Buckley et al. "Small-Molecule Control of Intracellular Protein Levels through Modulation of the Ubiquitin Proteasome System" Angewandte Reviews, 2014, 53:2312-2330.
Burkhard et al. "Synthesis and Stability of Oxetane Analogs of Thalidomide and Lenalidomide" Organic Letters 2013, 15(17):4312-4315.
C4 Therapeutics Presentation Patel—"Diverse Utility of Targeted Protein Degradation at C4 Therapeutics," ChemBio, 1 page, Sep. 17, 2017.
C4 Therapeutics Presentation Patel—"Advances in the Medicinal Chemistry of Targeted Protein Degradation," 24 pages, Sep. 27, 2018.
C4 Therapeutics Presentation Phillips—"Targeted Protein Degradation," A new class of small-molecule drugs; applied pharmaceutical chemistry, Cambridge, MA, Apr. 5, 2018; 38 pages.
C4 Therapeutics Presentation Phillips—"Small Molecule Driven Targeted Protein Degradation", ChemBio in the Hub 47, Cambridge, MA, 47 pages (Oct. 22, 2018).
C4 Therapeutics Presentation Chrissy Henderson, "Development of AchillesTAG degradation systems and their application to control CAR-T activity," ChemBio in the Hub, Watertown, MA 1 page (Oct. 22, 2018).
C4 Therapeutics Presentation Austin Elam, et al.—"Application of Biophysical Techniques to the Targeted Protein Degradation Therapeutic Strategy" Gibbs BioChem, Cambridge, MA), 1 page, Sep. 24, 2017.
C4 Therapeutics Presentation Fisher—"Targeted Protein Degradation", Targeted Protein Degradation Summit, Boston, MA, 39 pages, Oct. 24-25, 2018.
Chamberlain et al. "Structure of the human cereblon-DDB1-lenalidomide complex reveals basis for responsiveness to thalidomide analogs" Nature Structural and Molecule Biology, 2014, 21(9):803-809.
Chang, X. and Stewart, K. A. "What is the functional role of the thalidomide binding protein cereblon?" Int J Biochem Mol Bio. 2011, 2(3):287-294.
Contino-Pepin, et al., "Preliminary biological evaluations of new thalidomide analogues for multiple sclerosis application", Bioorganic & Medicinal Chemistry Letters, 2009, 19(3), 878-881.
Corson et al. "Design and applications of bifunctional small molecules: Why two heads are better than one" ACS Chemical Biology 2008, 3(11): 677-692.
Crews, C. M. "Targeting the undruggable proteome: the small molecules of my dreams" Chemistry and Biology 2010, 17(6):551-555.
Deshaies et al. "Ring domain E3 ubiquitin ligases." Ann. Rev. Biochem. 2009, 78:399-434.
Faden et al. "Generic tools for conditionally altering protein abundance and phenotypes on domain" Biol. Chem. 2014, 395(7-8):737-762.
Fischer et al. "Structure of the DDB1-CRBN E3 ubiquitin ligase in complex with thalidomide" Nature 2014, 512:49-53.
Fischer et al. "The Molecular Basis of CRL4DDB2/CSA Ubiquitin Ligase Architecture, Targeting, and Activation," Cell 2011, 147:1024-1039.
Gosink et al. "Redirecting the Specificity of Ubiquitination by Modifying Ubiquitin-Conjugating Enzymes" Proc. Natl. Acad. Sci. USA 1995, 92:9117-9121.
International Application No. PCT/US19/35223, filed Jun. 3, 2019; International Search Report and Written Opinion dated Oct. 31, 2019, 10 pages.
Ito et al., "Identification of a Primary Target of thalidomide teratogenicity", Science, 2010, 327(5971), 1345-1350, XP0055062167.
Itoh et al. "Protein knockdown using methyl bestatin-ligand hybrid molecules: design and synthesis of inducers of ubiquitination-mediated degradation of cellular retinoic acid-binding proteins" Journal of the American Chemical Society 2010, 132(16), 5820-5826.
Jacques et al. "Differentiation of anti-inflammatory and antitumorigenic properties of stabilized enantiomers of thalidomide analogs" PNAS 2015, 112:E1471-E1479.
Kronke et al. "Lenalidomide Causes Selective Degradation of IKZF1 and IKZF3 in Multiple Myeloma Cells" Science 2014, 343(6168):301-305.
Kronke et al. "Lenalidomide induces ubiquitination and degradation of CDK1 [alpha] in del(5q) MDS" Nature 2015, 523(7559): 183-188.
Lai et al. "Modular PROTAC Design for the Degradation of Oncogenic BCR-ABL" Angewandte Chemie International Edition 2016, 55:807-810.
Lee et al. "Targeted Degradation of the Aryl Hydrocarbon Receptor by the PROTAC Approach: A Useful Chemical Genetic Tool" ChemBioChem 2007, 8:2058-2062.
Liu et al. "Design and biological characterization of hybrid compounds of curcumin and thalidomide for multiple myeloma" Organic and Biomolecular Chemistry 2013, 11:4757.
Lu et al. "Hijacking the E3 Ubiquitin Ligase Cereblon to Efficiently Target BRD4" Chemistry and Biology 2015, 22(6):755-763.
Lu et al. "The myeloma drug lenalidomide promotes the cereblon-dependent destruction of Ikaros proteins" Science 2014, 343:305-309.

(56) References Cited

OTHER PUBLICATIONS

Nawaz et al. "Proteasome-Dependent Degradation of the Human Estrogen Receptor" Proc. Natl. Acad. Sci. USA 1999, 96:1858-1862.
Neklesa et al. "Small-molecule hydrophobic tagging-induced degradation of HaloTag fusion proteins." Nat Chem Biol 2011, 7(8):538-543.
Prevet et al. "Microwave-assisted synthesis of functionalized spirohydantoins as 3-D privileged fragments for scouting the chemical space," Tetrahedron Letters, May 18, 2016, vol. 57, pp. 2888-2894.
Pubmed Compound Summary for CID 51072057, Tert-butyl 4-[9-(4-cyanophenyl)-3-(3,5-dichlorophenyl)-1-methyl-2,4-dioxo-1,3,7-triazaspiro[4,4]nonan-7-yl]benzoate, U.S. National Library of Medicine, May 3, 2011; pp. 1-17; p. 2 (https://pubchem.ncbi.nlm.nih.gov/compound/51072057).
Pubmed Compound Summary for CID 45792656, '7-Cyclopropyl-1,3,7-triazaspiro[4,4]nonane-2m4-dione, U.S. National Library of Medicine, Jun. 21, 2010, pp. 1-13; (https://pubchem.ncbi.nlm.nih.gov/compound/45792656).
Pubmed Compound Summary for CID 70731020, '7-(1,2,4)Triazolo[4,3-a]pyridine-3-yl)-2,7-diazaspiro[4,4]nonane-1,3-dione, U.S. National Library of Medicine, Mar. 4, 2013, pp. 1-11; (https://pubchem.ncbi.nlm.nih.gov/compound/70731020).
Raina et al. "Chemical Inducers of Targeted Protein Degradation" Journal of Biological Chemistry 2010, 285:11057-11060.
Rodriguez-Gonzalez et al. "Targeting steroid hormone receptors for ubiquitination and degradation in breast and prostate cancer" Oncogene 2008, 27:7201-7211.
Ruchelman et al. "Isosteric analogs of lenalidomide and pomalidomide: Synthesis and biological activity" Bioorganic and Medicinal Chemistry Letters 2012, 23:360-365.
Sakamoto et al. "Development of Protacs to Target Cancer-Promoting Proteins for Ubiquitination and Degradation" Molecular and Cellular Proteomics 2003, 2(12):1350-1357.
Sakamoto et al. "Protacs: chimeric molecules that target proteins to the Skpl-Cullin-F box complex for ubiquitination and degradation" PNAS 2001, 98(15):8554-8559.
Schneekloth et al. "Chemical approaches to controlling intracellular protein degradation" Chembiochem 2005, 6(1):40-46.
Schneekloth et al. "Chemical Genetic Control of Protein Levels: Selective in Vivo Targeted Degradation" Journal of the American Chemical Society 2004, 126(12):3748-3754.
Schneekloth et al. "Targeted Intracellular Protein Degradation Induced by a Small Molecule: En Route to Chemical Proteomics" Bioorganic and Medicinal Chemistry Letters 2008, 18:5904-5908.
Shoji, et al., "Modified DNA Aptamer That Binds the (R)-Isomer of a Thalidomide Derivative with High Enantioselectivity", J. Am. Chem. Soc., 2007, 129, 1456-1464.
Spratt et al. "RBRE3 ubiquitin ligases: new structures, new insights, new questions." Biochem. 2014, 458:421-437.
Toure et al. "Small-Molecule PROTACs: New Approaches to Protein Degradation" Angewandte Chemie International Edition 2016, 55:1966-1973.
Wang et al. "Roles of F-box proteins in cancer." Nat. Rev. Cancer 2014, 14:233-347.
Winter et al. "Phthalimide conjugation as a strategy for in vivo target protein degradation" Science 2015, 348(6241):1376-1381.
Zengerle et al. "Selective Small Molecule Induced Degradation of the BET Bromodomain Protein BRD4" ACS Chem. Biol. 2015, 10:1770-1777.
Zhou et al. "Harnessing the Ubiquitination Machinery to Target the Degradation of Specific Cellular Proteins" Molecular Cell 2000, 6:751-756.

* cited by examiner

SPIROCYCLIC COMPOUNDS

CROSS-REFERENCE TO RELATED APPLICATIONS

This application is a continuation of International Application No. PCT/US2019/035233, filed in the International Patent Cooperation Treaty, U.S. Receiving Office on Jun. 3, 2019, which claims the benefit of European Patent Application No. 18175701.4, filed Jun. 4, 2018. The entirety of these applications is hereby incorporated by reference herein for all purposes.

FIELD OF THE INVENTION

The present invention provides compounds which bind to the ubiquitously expressed E3 ligase protein cereblon (CRBN), which can alter the substrate specificity of the CRBN E3 ubiquitin ligase complex, resulting in breakdown of intrinsic downstream proteins. The present invention also provides compounds that can be used as synthetic intermediates in the preparation of bifunctional compounds for use in targeted protein degradation. The present compounds are thus useful for the treatment or prophylaxis of abnormal cellular proliferation, including tumors and cancer.

BACKGROUND OF THE INVENTION

Protein degradation is a highly regulated and essential process that maintains cellular homeostasis. The selective identification and removal of damaged, misfolded, or excess proteins is achieved via the ubiquitin-proteasome pathway (UPP). The UPP is central to the regulation of almost all cellular processes, including antigen processing, apoptosis, biogenesis of organelles, cell cycling, DNA transcription and repair, differentiation and development, immune response and inflammation, neural and muscular degeneration, morphogenesis of neural networks, modulation of cell surface receptors, ion channels and the secretory pathway, the response to stress and extracellular modulators, ribosome biogenesis and viral infection.

Covalent attachment of multiple ubiquitin molecules by an E3 ubiquitin ligase to a terminal lysine residue marks the protein for proteasome degradation, where the protein is digested into small peptides and eventually into its constituent amino acids that serve as building blocks for new proteins. Defective proteasomal degradation has been linked to a variety of clinical disorders including Alzheimer's disease, Parkinson's disease, Huntington's disease, muscular dystrophies, cardiovascular disease, and cancer among others.

There are over 600 E3 ubiquitin ligases which facilitate the ubiquitination of different proteins in vivo, which can be divided into four families: HECT-domain E3s, U-box E3s, monomeric RING E3s and multi-subunit E3s. See generally Li et al. (*PLOS One*, 2008, 3, 1487) titled "Genome-wide and functional annotation of human E3 ubiquitin ligases identifies MULAN, a mitochondrial E3 that regulates the organelle's dynamics and signaling."; Berndsen et al. (*Nat. Struct. Mol. Biol.,* 2014, 21, 301-307) titled "New insights into ubiquitin E3 ligase mechanism"; Deshaies et al. (*Ann. Rev. Biochem.,* 2009, 78, 399-434) titled "RING domain E3 ubiquitin ligases."; Spratt et al. (*Biochem.* 2014, 458, 421-437) titled "RBR E3 ubiquitin ligases: new structures, new insights, new questions."; and Wang et al. (*Nat. Rev. Cancer,* 2014, 14, 233-347) titled "Roles of F-box proteins in cancer."

Cereblon is a protein that in humans is encoded by the CRBN gene. CRBN orthologs are highly conserved from plants to humans, which underscores its physiological importance. Cereblon forms part of an E3 ubiquitin ligase protein complex which interacts with damaged DNA binding protein 1 (DDB1), forming an E3 ubiquitin ligase complex with Cullin 4 (CUL4A) and the E2-binding protein ROC1 (also known as RBX1) where it functions as a substrate receptor to select proteins for ubiquitination. Through a mechanism that has not been completely elucidated, cereblon ubiquitination of target proteins results in increased levels of fibroblast growth factor 8 (FGF8) and fibroblast growth factor 10 (FGF10). FGF8 in turn regulates a number of developmental processes, such as limb and auditory vesicle formation. The net result is that this E3 ubiquitin ligase complex is important for limb outgrowth in embryos. In the absence of cereblon, DDB1 forms a complex with DDB2 that functions as a DNA damage-binding protein.

In unrelated parallel research, Ito et al. (*Science* 2010, 327, 1345-1350) titled "Identification of a Primary Target of Thalidomide Teratogenicity", described that cereblon is a thalidomide binding protein. The study revealed that thalidomide-cereblon binding in vivo may be responsible for thalidomide teratogenicity. After the discovery that thalidomide causes teratogenicity in the mid-1960's, the compound and related structures were notwithstanding found to be useful as anti-inflammatory, anti-angiogenic and anti-cancer agents (see Bartlett et al. (*Nat. Rev. Cancer* 2004, 4, 314-322) titled "The Evolution of Thalidomide and Its Imid Derivatives as Anticancer Agents"). Thalidomide has been approved for the treatment of certain neoplastic diseases, including multiple myeloma, and is currently under investigation for use in treating a variety of other types of cancer along with the structural derivatives lenalidomide and pomalidomide (see Martiniani, R. et al. "Biological activity of lenalidomide and its underlying therapeutic effects in multiple myeloma" Adv Hematol, 2012, 2012:842945; and Terpos, E. et al. "Pomalidomide: a novel drug to treat relapsed and refractory multiple myeloma" Oncotargets and Therapy, 2013, 6:531).

The disclosure that thalidomide binds to the cereblon E3 ubiquitin ligase led to research to investigate incorporating thalidomide and certain derivatives into compounds for the targeted destruction of proteins. Celgene has disclosed imids for similar uses, including those in U.S. Pat. Nos. 6,045,501; 6,315,720; 6,395,754; 6,561,976; 6,561,977; 6,755,784; 6,869,399; 6,908,432; 7,141,018; 7,230,012; 7,820,697; 7,874,984; 7,959,566; 8,204,763; 8,315,886; 8,589,188; 8,626,531; 8,673,939; 8,735,428; 8,741,929; 8,828,427; 9,056,120; 9,101,621; and 9,101,622.

Patent applications filed by C4 Therapeutics, Inc., that describe compounds capable of binding to an E3 ubiquitin ligase and a target protein for degradation include: WO 2017/197051 titled "Amine-Linked C3-Glutarimide Degronimers for Target Protein Degradation"; WO 2017/197055 titled "Heterocyclic Degronimers for Target Protein Degradation"; WO 2017/197036 titled "Spirocyclic Degronimers for Target Protein Degradation"; WO 2017/197046 20 titled "C3-Carbon Linked Glutarimide Degronimers for Target Protein Degradation"; WO 2017/197056 titled "Bromodomain Targeting Degronimers for Target Protein Degradation."; and WO 2018/237026 titled "N/O-Linked Degrons and Degronimers for Protein Degradation."

Other patent applications that describe protein degrading compounds include: WO 2015/160845; WO 2016/105518;

WO 2016/118666; WO 2016/149668; WO 2016/197032; WO 2016/197114; WO 2017/007612; WO 2017/011371; WO 2017/011590; WO 2017/030814; WO 2017/046036; WO 2017/176708; WO 2017/176957; WO 2017/176598; WO 2017/180417; WO 2018/052945; WO 2018/052949; WO 2018/053354; WO 2018/071606; WO 2018/102067; WO 2018/102725; WO 2018/118598; WO 2018/119357; WO 2018/119441; WO 2018/119448; WO 2018/140809; WO 2018/144649; and WO 2018/226542. Other relevant patent applications include: WO 2013/020557; WO 2013/063560; WO 2013/106643; WO 2016/011906; WO 2017/024318; and WO 2017/117473.

There is a need for new compounds and methods of treatment that bind to the E3 ligase protein cereblon for use in the treatment of various medical conditions, notably abnormal cellular proliferation. There is also a need for new compounds that may be used in the preparation of bifunctional molecules that are used in the degradation of proteins that are involved in disease processes.

SUMMARY OF THE INVENTION

In a first aspect, compounds and their uses and manufacture are provided that bind to cereblon and enhance the ubiquitination of proteins by a cereblon-containing E3 ubiquitin ligase complex, which results in protein degradation and thus is useful for the treatment of abnormal cellular proliferation and other disorders as described herein. In a second aspect, compounds are provided that contain a chemical moiety capable of binding to cereblon, which can be used as synthetic intermediates in the preparation of bifunctional compounds that cause degradation of a selected protein via the ubiquitin proteasome pathway (UPP).

The compounds described herein can be administered to a host, for example, a human, in need thereof, in an effective amount, optionally as a pharmaceutically acceptable salt, and optionally in a pharmaceutically acceptable composition. The compounds can be administered for any therapeutic indication which can be treated by modulating the function or activity of the cereblon-containing E3 Ubiquitin Ligase Protein Complex, including but not limited to the treatment of abnormal cell proliferation, such as cancer or a tumor. In certain embodiments, the compounds as described herein can modulate the natural activity of cereblon.

The invention includes new compounds of Formula I, Formula II, Formula III, Formula IV, Formula V, Formula VI, Formula VII, Formula VIII-a, Formula VIII-b, Formula VIII-c, Formula IX, Formula X, Formula XI, Formula XII-a, Formula XII-b, Formula XII-c, Formula XIII, and Formula XIV. In addition, the invention includes the use of compounds generally in Formula XV for the treatment of a therapeutic condition that can be treated by modulating the function or activity of the cereblon-containing E3 Ubiquitin Ligase Protein Complex. The invention also includes the use of compounds generally in Formula XVI in the preparation of bifunctional compounds that degrade a target protein by the ubiquitin proteasome pathway (UPP). The invention also includes compounds of Formula XVII-a, Formula XVII-b, Formula XVII-c, Formula XVII-d, Formula XVII-e, Formula XVII-f, and Formula XVII-g.

In one aspect, a compound is provided of Formula I:

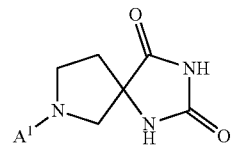

(I)

or a pharmaceutically acceptable salt thereof; wherein:
$A^1$ is selected from the group consisting of aryl and aryl substituted with $R^1$; and
$R^1$ is selected from the group consisting of: —C(=O)—O—$C_{1-6}$-alkyl; —COOH; —NH—(C=O)—$C_{1-6}$-alkyl; —NH$_2$; and —NO$_2$.

In another aspect, a compound is provided of Formula II:

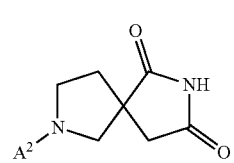

(II)

or a pharmaceutically acceptable salt thereof; wherein
$A^2$ is aryl substituted with $R^1$;
and all other variables are as defined herein.

In another aspect, a compound is provided of Formula III:

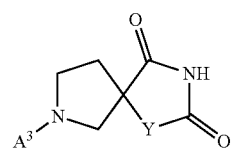

(III)

or a pharmaceutically acceptable salt thereof, wherein:
Y is NH or CH$_2$;
$A^3$ is selected from the group consisting of heteroaryl and heteroaryl substituted with $R^2$ and
$R^2$ is selected from the group consisting of: —COH; —C(=O)—O—$C_{1-6}$-alkyl; —NH$_2$; and —NO$_2$.

In another aspect, a compound is provided of Formula IV:

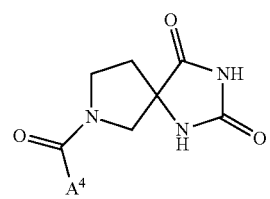

(IV)

or a pharmaceutically acceptable salt thereof; wherein:
$A^4$ is aryl substituted with Ria; and
$R^{1a}$ is selected from the group consisting of: —C(=O)—O—$C_{1-6}$-alkyl; —COOH; and —NO$_2$.

In another aspect, a compound is provided of Formula V:

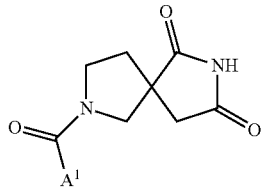

(V)

or a pharmaceutically acceptable salt thereof, wherein all variables are as defined herein.

In another aspect, a compound is provided of Formula VI:

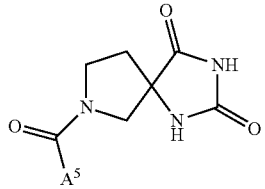

(VI)

or a pharmaceutically acceptable salt thereof; wherein:
$A^5$ is heteroaryl substituted with $R^{2a}$; and
$R^{2a}$ is selected from the group consisting of —COOH and —C(=O)—O—$C_{1-6}$-alkyl.

In another aspect, a compound is provided of Formula VII:

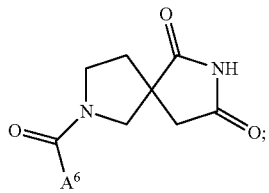

(VII)

or a pharmaceutically acceptable salt thereof; wherein:
$A^6$ is heteroaryl substituted with $R^2$; and
all other variables are as defined herein.

In another aspect, a compound is provided of Formula VIII-a, VIII-b, or VIII-c:

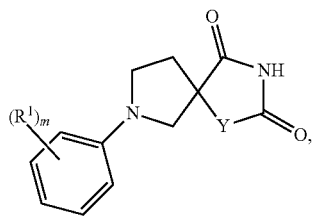

(VIII-a)

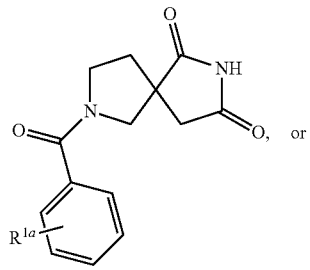

(VIII-b)

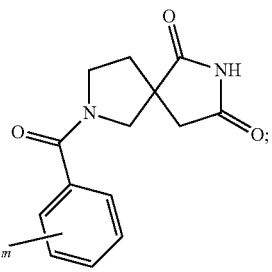

(VIII-c)

or a pharmaceutically acceptable salt thereof; wherein:
m is 0 or 1; and
all other variables are as defined herein.

In another aspect, a compound is provided of Formula IX:

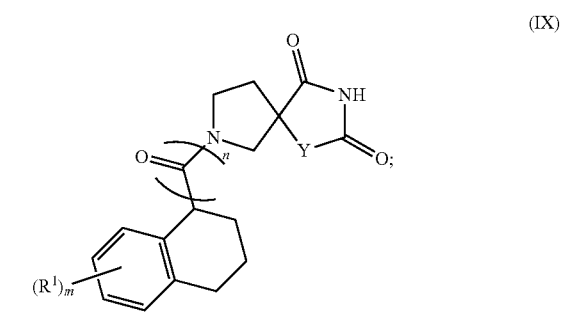

(IX)

or a pharmaceutically acceptable salt thereof; wherein:
n is 0 or 1; and
all other variables are as defined herein.

In another aspect, a compound is provided of Formula X:

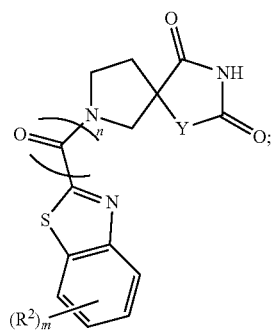

(X)

or a pharmaceutically acceptable salt thereof;
wherein all variables are as defined herein.

In another aspect, a compound is provided of Formula XI:

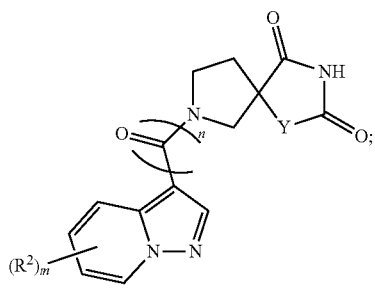
(XI)

or a pharmaceutically acceptable salt thereof;
wherein all variables are as defined herein.

In another aspect, a compound is provided of Formula XII-a, XII-b, or XII-c:

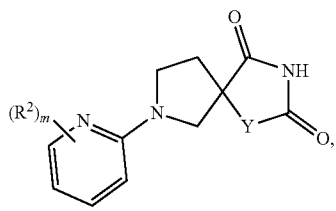
(XII-a)

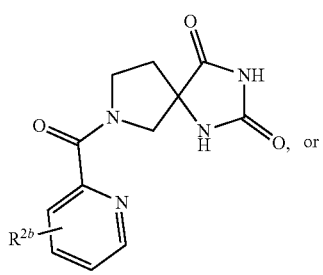
(XII-b)

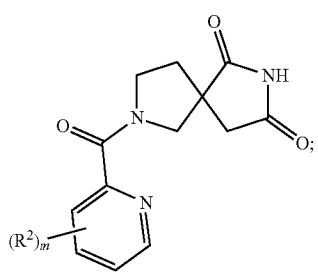
(XII-c)

or a pharmaceutically acceptable salt thereof; wherein:
$R^{2b}$ is selected from the group consisting of: —COOH; —C(=O)—O—$C_{1-6}$-alkyl; and —$NO_2$; and
all other variables are as defined herein.

In another aspect, a compound is provided of Formula XIII:

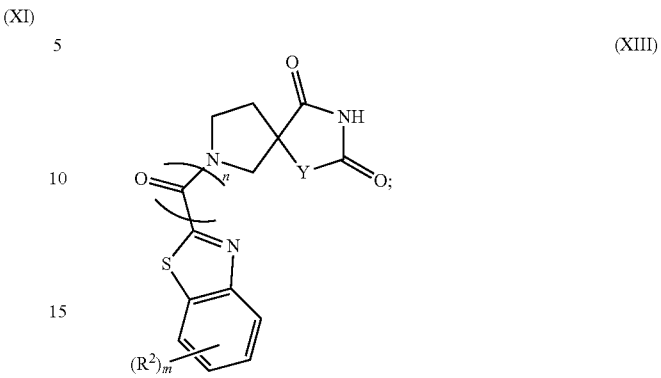
(XIII)

or a pharmaceutically acceptable salt thereof; wherein all variables are as defined herein.

In another aspect, a compound is provided of Formula XIV:

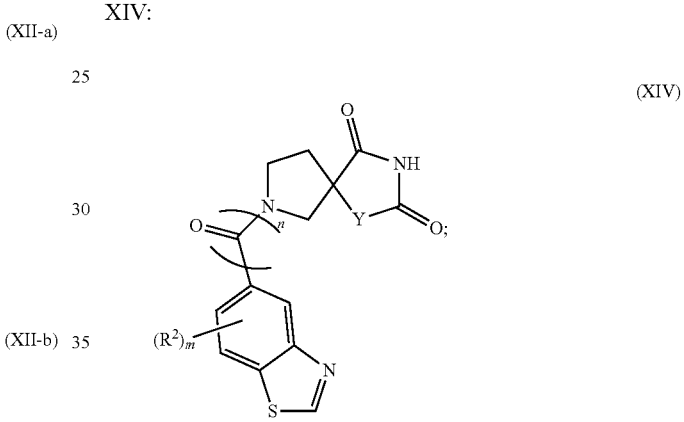
(XIV)

or a pharmaceutically acceptable salt thereof; wherein all variables are as defined herein.

The present invention provides compounds of Formula XV, or a pharmaceutically acceptable salt thereof,

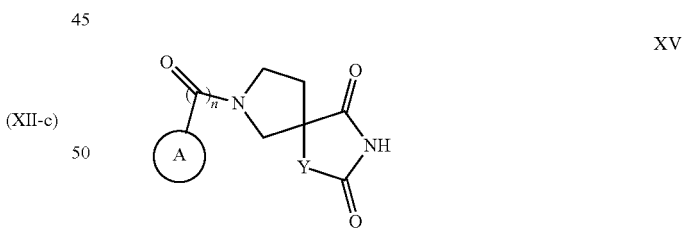
XV wherein the substituents and variables are as described below and in the claims, or a pharmaceutically acceptable salt thereof.

The present compounds are useful for the therapeutic and/or prophylactic treatment of cancer.

The compounds of the present invention can further be used as part of bifunctional compounds that comprise the compounds of present invention as E3 Ubiquitin Ligase moiety that is linked to a moiety that binds to a target protein where the target protein is proximate to the ubiquitin ligase to effect degradation of said protein.

In another aspect, the use of a compound for the treatment of a therapeutic condition which can be treated by modulation the function or activity of the cereblon containing E3 Ubiquitin Ligase Protein Complex is provided of Formula XV:

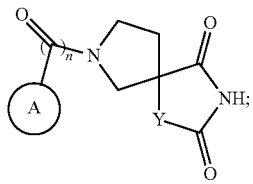

(XV)

or a pharmaceutically acceptable salt thereof; wherein:

A is selected from the group consisting of: aryl; aryl substituted by $R^1$; heteroaryl; and heteroaryl substituted by $R^2$; and all over variables are as defined herein.

For clarity, as used herein,

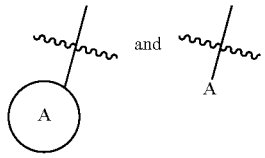

both refer the same group which is selected from aryl; aryl substituted by $R^1$; heteroaryl; and heteroaryl substituted by $R^2$.

The compounds of Formula I, Formula II, Formula III, Formula IV, Formula V, Formula VI, Formula VII, Formula VIII-a to Formula VIII-c, Formula IX, Formula X, Formula XI, Formula XII-a to XII-c, Formula XIII, Formula XIV, and Formula XV are useful as therapeutic agents when administered in an effective amount to a host, typically a human, for the treatment of a medical disorder including, but not limited to, abnormal cellular proliferation, including a tumor or cancer, or a myelo- or lymphoproliferative disorder such as B- or T-cell lymphomas, multiple myeloma, Waldenstrom's macroglobulinemia, Wiskott-Aldrich syndrome, or a post-transplant lymphoproliferative disorder; an immune disorder, including autoimmune disorder such as Addison disease, Celiac disease, Dermatomyositis, Graves disease, thyroiditis, multiple sclerosis, pernicious anemia, reactive arthritis, lupus, or type I diabetes; a disease of cardiologic malfunction including hypercholesterolemia; an infectious disease including viral or bacterial infections; inflammatory conditions including asthma, chronic peptic ulcers, tuberculosis, rheumatoid arthritis, periodontitis, ulcerative colitis, Crohn's disease, or hepatitis.

In certain embodiments, the present invention provides the administration of an effective amount of a compound of Formula I, Formula II, Formula III, Formula IV, Formula V, Formula VI, Formula VII, Formula VIII-a to Formula VIII-c, Formula IX, Formula X, Formula XI, Formula XII-a to XII-c, Formula XIII, Formula XIV, and Formula XV to treat a patient, for example a human, having an infectious disease, wherein the therapy acts via binding to cereblon or its E3 Ubiquitin Ligase or acts through an independent mechanism, optionally in combination with another bioactive agent. The disease state or condition may be caused by a microbial agent or other exogenous agent such as a virus (as non-limiting examples, HIV, HBV, HCV, HSV, HPV, RSV, CMV, Ebola, Flavivirus, Pestivirus, Rotavirus, Influenza, Coronavirus, EBV, viral pneumonia, drug-resistant viruses, Bird Flu, RNA virus, DNA virus, adenovirus, poxvirus, Picornavirus, Togavirus, Orthomyxovirus, Retrovirus, or Hepadovirus), bacterial (including but not limited to Gram-negative, Gram-positive, Atypical, *Staphylococcus, Streptococcus, E. Coli, Salmonella, Helicobacter pylori*, meningitis, gonorrhea, Chlamydiaceae, Mycoplasmataceae, etc.), fungus, protozoa, helminth, worm, prion, parasite, or other microbe.

In another aspect, the compounds disclosed can be used as synthetic intermediates in the preparation of bifunctional compounds that cause degradation of a selected protein via the ubiquitin proteosome pathway (UPP) is provided. These compounds contain a functional group that can react with a second compound, wherein the second compound is capable of binding to a selected protein of interest, to create a bifunctional compound as described above that can cause the degradation of the selected protein via the UPP.

Thus, a compound of Formula XVI, or a pharmaceutically acceptable salt thereof, is provided:

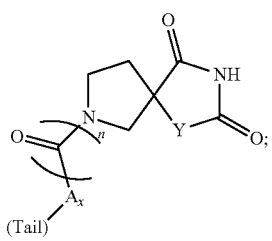

(XVI)

wherein:

$A_X$ is selected from aryl or heteroaryl;

"Tail" is a chemical moiety that contains a reactive functional group that can covalently bind to a protein binding moiety to produce a targeted protein degrader, or "Tail is a chemical moiety that can be used to modify the properties of the compound such as hydrophobicity, hydrophilicity, solubility, drug delivery, pharmacokinetics, or other properties such as charge, polarity, or fit within the active pocket;

in one embodiment, "Tail" is T, wherein T is

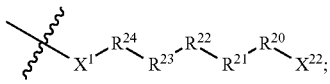

$X^1$ is selected from bond, $NR^{34}$, $CH_2$, $CHR^{34}$, $C(R^{34})_2$, O, and S;

$X^{22}$ is a functional group that can be used as a linking group to a protein binding moiety; or $X^{22}$ is a group that caps the valence and is not typically a linking group; representative examples of $X^{22}$ include, but are not limited to, halo, —$NH_2$, —$NHR^{34}$, —$N(R^{34})_2$, hydroxyl, thiol, —$B(OH)_2$, —$Sn(R^{36})_3$, —$Si(R^{36})_3$, —$OS(O)_2$alkyl, —$OS(O)_2$haloalkyl, alkenyl, alkynyl, ethynyl, ethenyl, —C(O)H, —$NR^{34}$C(O)alkene, —$NR^{34}$C(O)alkyne, cyano, —SC(O)alkyl, OC(O)alkyl, heterocycle, —C(O)OH, hydrogen, alkyl, aryl, heteroaryl, aliphatic, heteroaliphatic, and carbocyclic;

$R^{34}$ and $R^{34'}$ are independently selected at each occurrence from hydrogen, $C_1$-$C_6$alkyl (for example methyl, ethyl, cyclopropyl, or $C_1$-$C_3$alkyl), $C_1$-$C_6$haloalkyl, $C_2$-$C_6$alkenyl, $C_2$-$C_6$alkynyl, $C_3$-$C_6$cycloalkyl, $C_3$-$C_6$heterocycle, aryl, heteroaryl, —(CO)$R^{36}$, —(CS)$R^{36}$, —(C=NH)$R^{36}$, —(SO)$R^{36}$, and —(SO$_2$)$R^{36}$;

$R^{36}$ is independently selected at each occurrence from hydrogen, $C_1$-$C_6$alkyl, $C_1$-$C_6$haloalkyl, $C_2$-$C_6$alkenyl, $C_2$-$C_6$alkynyl, $C_3$-$C_6$cycloalkyl, $C_3$-$C_6$heterocycle, aryl, heteroaryl, hydroxyl, $C_1$-$C_6$alkoxy, thio, $C_1$-$C_6$thioalkyl, —NH$_2$, —NH($C_1$-$C_6$alkyl, $C_3$-$C_7$cycloalkyl, $C_3$-$C_7$heterocycle, aryl, or heteroaryl), and —N(independently $C_1$-$C_6$alkyl, $C_3$-$C_7$cycloalkyl, $C_3$-$C_7$heterocycle, aryl, or heteroaryl)$_2$;

$R^{20}$, $R^{21}$, $R^{22}$, $R^{23}$, and $R^{24}$ are independently a divalent or multivalent linking group, including but not limited to a covalent bond, alkyl, —C(O)—, —C(O)O—, —OC(O)—, —C(O)alkyl, —C(O)Oalkyl, —C(S)—, —SO$_2$—, —S(O)—, —C(S)—, —C(O)NH—, —NHC(O)—, —N(alkyl)C(O)—, —C(O)N(alkyl)-, —O—, —S—, —NH—, —N(alkyl)-, —CH(—O—$R^{26}$)—, —CH(—N$R^{34}R^{34'}$)—, —C(—O—$R^{26}$)alkyl-, —C(—N$R^{34}R^{34'}$)alkyl-, —C($R^{40}R^{40}$)—, -alkyl($R^{27}$)-alkyl($R^{28}$)—, —C($R^{27}R^{28}$)—, —P(O)(O$R^{26}$)O—, —P(O)(O$R^{26}$)—, —N$R^{34}$C(O)N$R^{34'}$—, alkene, haloalkyl, alkoxy, alkyneheteroarylalkyl, aryl, arylalkyl, heterocycle, aliphatic, heteroaliphatic, heteroaryl, lactic acid, glycolic acid, carbocycle, -(ethylene glycol)$_{1-6}$-, -(lactic-co-glycolic acid)$_{1-6}$-, -(propylene glycol)$_{1-6}$-, —O—(CH$_2$)$_{1-12}$—O—, —NH—(CH$_2$)$_{1-12}$—NH—, —NH—(CH$_2$)$_{1-12}$—O—, —O—(CH$_2$)$_{1-12}$—NH—, —S—(CH$_2$)$_{1-12}$—O—, —O—(CH$_2$)$_{1-12}$—S—, —S—(CH$_2$)$_{1-12}$—S—, —S—(CH$_2$)$_{1-12}$—NH—, and —NH—(CH$_2$)$_{1-12}$—S—, wherein the 1-6 can be independently 1, 2, 3, 4, 5, or 6, wherein the 1-12 can be independently 1, 2, 3, 4, 5, 6, 7, 8, 9, 10, 11 or 12, and wherein one or more of the CH$_2$ or NH groups can be modified by substitution of a H for a methyl, ethyl, cyclopropyl, F (if on carbon), etc, as described herein, and optionally, a heteroatom, heteroalkyl, aryl, heteroaryl or cycloaliphatic group is interspersed in the chain. Certain non-limiting examples include —O—CH(CH$_3$)—CH(CH$_3$)CH—O—, —O—CH$_2$—CH(CH$_3$)CH—O—, —O—CH(CH$_3$)—CH$_2$CH—O—, etc.

each of which $R^{20}$, $R^{21}$, $R^{22}$, $R^{23}$, and $R^{24}$ is optionally substituted with one or more substituents selected from $R^{101}$ or alternatively as described in the Definitions section; wherein at least one of $R^{20}$, $R^{21}$, $R^{22}$, $R^{23}$, and $R^{24}$ is not a bond;

$R^{101}$ is independently selected at each occurrence from hydrogen, alkyl, alkene, alkyne, haloalkyl, alkoxy, hydroxyl, aryl, heteroaryl, heterocycle, arylalkyl, heteroarylalkyl, heterocycloalkyl, aryloxy, heteroaryloxy, CN, —COOalkyl, COOH, NO$_2$, F, Cl, Br, I, CF$_3$, NH$_2$, NHalkyl, N(alkyl)$_2$, aliphatic, and heteroaliphatic;

$R^{26}$ is selected from hydrogen, alkyl, silane, arylalkyl, heteroarylalkyl, alkene, alkyne, aryl, heteroaryl, heterocyclic, aliphatic and heteroaliphatic;

$R^{27}$ and $R^{28}$ are independently selected from hydrogen, alkyl, amine, or together with the carbon atom to which they are attached, form C(O), C(S), C=CH$_2$, a $C_3$-$C_6$ spirocarbocycle, or a 4-, 5-, or 6-membered spiroheterocycle comprising 1 or 2 heteroatoms selected from N and O, or form a 1 or 2 carbon bridged ring;

$R^{40}$ is selected at each instance from: hydrogen, alkyl, alkene, alkyne, halogen, hydroxyl, alkoxy, azide, amino, cyano, —NH(aliphatic, including alkyl), —N(aliphatic, including alkyl)$_2$, —NHSO$_2$(aliphatic, including alkyl), —N(aliphatic, including alkyl)SO$_2$alkyl, —NHSO$_2$(aryl, heteroaryl or heterocyclic), —N(alkyl)SO$_2$(aryl, heteroaryl or heterocyclic) —NHSO$_2$alkenyl, —N(alkyl)SO$_2$alkenyl, —NHSO$_2$alkynyl, —N(alkyl)SO$_2$alkynyl, haloalkyl, aliphatic, heteroaliphatic, aryl, heteroaryl, heteroalkyl, heterocyclic, and carbocyclic; and all other variables are as defined herein.

In one embodiment the compound of Formula XVI can be used in the preparation of compounds that cause degradation of a selected protein via the UPP are provided:

In one aspect a compound is provided of one of the following formulas:

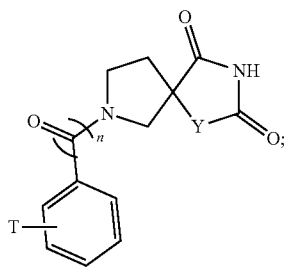

(XVII-a)

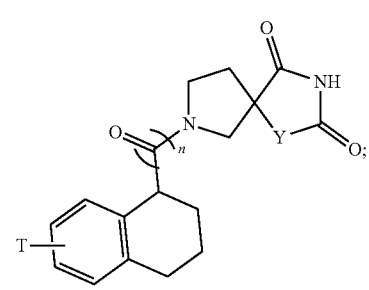

(XVII-b)

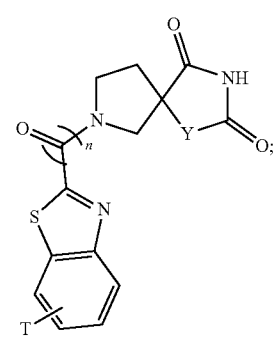

(XVII-c)

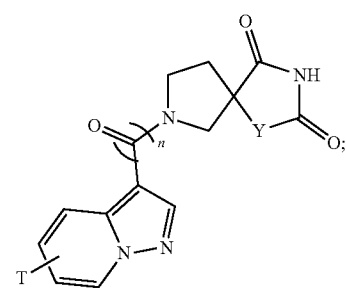

(XVII-d)

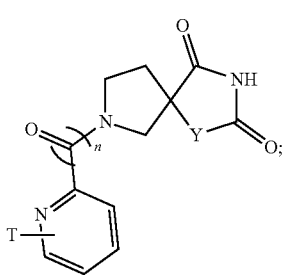
(XVII-e)

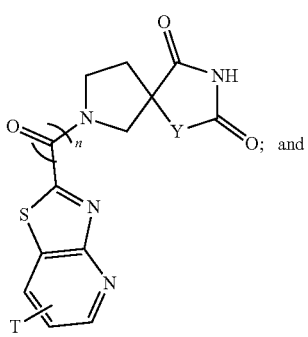
(XVII-f)

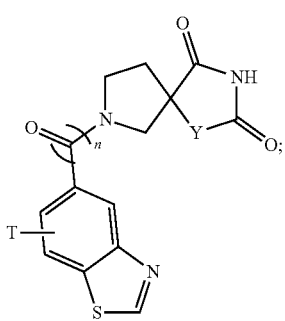
(XVII-g)

or a pharmaceutically acceptable salt thereof, wherein all variables are as defined herein.

In a first aspect, the present invention provides compounds of Formula I, Formula II, Formula III, Formula IV, Formula V, Formula VI, Formula VII, Formula VIII-a to Formula VIII-c, Formula IX, Formula X, Formula XI, Formula XII-a to XII-c, Formula XIII, Formula XIV, Formula XV, Formula XVI, and Formula XVII-a to XVII-g as defined herein for use as a therapeutically active substance.

In a further aspect, the present invention provides pharmaceutical compositions comprising a compound of Formula I, Formula II, Formula III, Formula IV, Formula V, Formula VI, Formula VII, Formula VIII-a to Formula VIII-c, Formula IX, Formula X, Formula XI, Formula XII-a to XII-c, Formula XIII, Formula XIV, Formula XV, Formula XVI, and Formula XVII-a to XVII-g as defined herein and a therapeutically inert carrier.

In certain embodiments, the compound of Formula I, Formula II, Formula III, Formula IV, Formula V, Formula VI, Formula VII, Formula VIII-a to Formula VIII-c, Formula IX, Formula X, Formula XI, Formula XII-a to XII-c, Formula XIII, Formula XIV, Formula XV, Formula XVI, and Formula XVII-a to XVII-g has at least one desired isotopic substitution of an atom, at an amount above the natural abundance of the isotope, i.e., enriched. In one embodiment, the compound of Formula I, Formula II, Formula III, Formula IV, Formula V, Formula VI, Formula VII, Formula VIII-a to Formula VIII-c, Formula IX, Formula X, Formula XI, Formula XII-a to XII-c, Formula XIII, Formula XIV, Formula XV, Formula XVI, and Formula XVII-a to XVII-g includes a deuterium or multiple deuterium atoms.

The present compounds are useful for the therapeutic and/or prophylactic treatment of cancer.

The compounds of the present invention can further be used as part of bifunctional compounds that comprise the compounds of present invention as E3 Ubiquitin Ligase moiety that is linked to a moiety that binds to a target protein where the target protein is proximate to the ubiquitin ligase to effect degradation of said protein.

Other features and advantages of the present application will be apparent from the following detailed description and claims.

The present invention therefore includes at least the following features:

a) a compound of Formula I, Formula II, Formula III, Formula IV, Formula V, Formula VI, Formula VII, Formula VIII-a to Formula VIII-c, Formula IX, Formula X, Formula XI, Formula XII-a to XII-c, Formula XIII, Formula XIV, XVI, and Formula XVII-a to XVII-g or a pharmaceutically acceptable salt thereof;

b) use of a compound of Formula I, Formula II, Formula III, Formula IV, Formula V, Formula VI, Formula VII, Formula VIII-a to Formula VIII-c, Formula IX, Formula X, Formula XI, Formula XII-a to XII-c, Formula XIII, Formula XIV, Formula XV, Formula XVI, and Formula XVII-a to XVII-g or a pharmaceutically acceptable salt thereof, in an effective amount in the treatment of a patient, typically a human, with a disorder that responds to such treatment, including by modulating the cereblon-based ubiquitination of a protein, such as for example, abnormal cellular proliferation such as a tumor or cancer, an immune or autoimmune or inflammatory disorder, a cardiologic disorder, an infectious disease, or other disorder that responds to such treatment;

c) use of a compound of Formula I, Formula II, Formula III, Formula IV, Formula V, Formula VI, Formula VII, Formula VIII-a to Formula VIII-c, Formula IX, Formula X, Formula XI, Formula XII-a to XII-c, Formula XIII, Formula XIV, Formula XV, Formula XVI, and Formula XVII-a to XVII-g or a pharmaceutically acceptable salt thereof, in the manufacture of a medicament for the treatment of a medical disorder, as further described herein;

d) a method for manufacturing a medicament intended for the therapeutic treatment of a disorder in a host, characterized in that a compound of Formula I, Formula II, Formula III, Formula IV, Formula V, Formula VI, Formula VII, Formula VIII-a to Formula VIII-c, Formula IX, Formula X, Formula XI, Formula XII-a to XII-c, Formula XIII, Formula XIV, Formula XV, Formula XVI, and Formula XVII-a to XVII-g is used in the manufacture;

e) a compound of Formula I, Formula II, Formula III, Formula IV, Formula V, Formula VI, Formula VII, Formula VIII-a to Formula VIII-c, Formula IX, Formula X, Formula XI, Formula XII-a to XII-c, Formula XIII, Formula XIV, Formula XV, Formula XVI, and Formula XVII-a to XVII-g or a pharmaceutically acceptable salt thereof, that are useful in the treatment of an abnormal cellular proliferation such as cancer in a host, including any of the cancers described herein;

f) use of a compound of Formula I, Formula II, Formula III, Formula IV, Formula V, Formula VI, Formula VII, Formula VIII-a to Formula VIII-c, Formula IX, Formula X, Formula XI, Formula XII-a to XII-c, Formula XIII, Formula XIV, Formula XV, Formula XVI, and Formula XVII-a to XVII-g or a pharmaceutically acceptable salt thereof, in the manufacture of a medicament for the treatment of an abnormal cellular proliferation such as cancer, including any of the cancers described herein;

g) a method for manufacturing a medicament intended for the therapeutic use of treating an abnormal cellular proliferation such as cancer in a host, including any of the cancers described herein, characterized in that a compound of Formula I, Formula II, Formula III, Formula IV, Formula V, Formula VI, Formula VII, Formula VIII-a to Formula VIII-c, Formula IX, Formula X, Formula XI, Formula XII-a to XII-c, Formula XIII, Formula XIV, Formula XV, Formula XVI, and Formula XVII-a to XVII-g is used in the manufacture;

h) a compound of Formula I, Formula II, Formula III, Formula IV, Formula V, Formula VI, Formula VII, Formula VIII-a to Formula VIII-c, Formula IX, Formula X, Formula XI, Formula XII-a to XII-c, Formula XIII, Formula XIV, Formula XV, Formula XVI, and Formula XVII-a to XVII-g or a pharmaceutically acceptable salt thereof, that is useful in the treatment of a tumor in a host, including any of the tumors described herein;

i) use of a compound of Formula I, Formula II, Formula III, Formula IV, Formula V, Formula VI, Formula VII, Formula VIII-a to Formula VIII-c, Formula IX, Formula X, Formula XI, Formula XII-a to XII-c, Formula XIII, Formula XIV, Formula XV, Formula XVI, and Formula XVII-a to XVII-g or a pharmaceutically acceptable salt thereof, in the manufacture of a medicament for the treatment of a tumor in a host, including any of the tumors described herein;

j) a method for manufacturing a medicament intended for the therapeutic use of treating a tumor in a host, including any of the tumors described herein, characterized in that a compound of Formula I, Formula II, Formula III, Formula IV, Formula V, Formula VI, Formula VII, Formula VIII-a to Formula VIII-c, Formula IX, Formula X, Formula XI, Formula XII-a to XII-c, Formula XIII, Formula XIV, Formula XV, Formula XVI, and Formula XVII-a to XVII-g is used in the manufacture;

k) a compound of Formula I, Formula II, Formula III, Formula IV, Formula V, Formula VI, Formula VII, Formula VIII-a to Formula VIII-c, Formula IX, Formula X, Formula XI, Formula XII-a to XII-c, Formula XIII, Formula XIV, Formula XV, Formula XVI, and Formula XVII-a to XVII-g or a pharmaceutically acceptable salt thereof, that is useful in the treatment of an immune, autoimmune, or inflammatory disorder in a host;

l) use of a compound of Formula I, Formula II, Formula III, Formula IV, Formula V, Formula VI, Formula VII, Formula VIII-a to Formula VIII-c, Formula IX, Formula X, Formula XI, Formula XII-a to XII-c, Formula XIII, Formula XIV, Formula XV, Formula XVI, and Formula XVII-a to XVII-g or a pharmaceutically acceptable salt thereof, in the manufacture of a medicament for the treatment of an immune, autoimmune, or inflammatory disorder in a host;

m) a method for manufacturing a medicament intended for the therapeutic use of treating an immune, autoimmune, or inflammatory disorder in a host, characterized in that a compound of Formula I, Formula II, Formula III, Formula IV, Formula V, Formula VI, Formula VII, Formula VIII-a to Formula VIII-c, Formula IX, Formula X, Formula XI, Formula XII-a to XII-c, Formula XIII, Formula XIV, Formula XV, Formula XVI, and Formula XVII-a to XVII-g is used in the manufacture;

n) a pharmaceutical formulation comprising an effective host-treating amount of a compound of a compound of Formula I, Formula II, Formula III, Formula IV, Formula V, Formula VI, Formula VII, Formula VIII-a to Formula VIII-c, Formula IX, Formula X, Formula XI, Formula XII-a to XII-c, Formula XIII, Formula XIV, Formula XV, Formula XVI, and Formula XVII-a to XVII-g or a pharmaceutically acceptable salt thereof, with a pharmaceutically acceptable carrier or diluent;

o) a compound of Formula I, Formula II, Formula III, Formula IV, Formula V, Formula VI, Formula VII, Formula VIII-a to Formula VIII-c, Formula IX, Formula X, Formula XI, Formula XII-a to XII-c, Formula XIII, Formula XIV, Formula XV, Formula XVI, and Formula XVII-a to XVII-g as described herein in enantiomerically or diastereomerically (as relevant) enriched form, including an isolated enantiomer or diastereomer (i.e., greater than 85, 90, 95, 97, or 99% pure);

p) a process for the preparation of therapeutic products that contain an effective amount of a compound of Formula I, Formula II, Formula III, Formula IV, Formula V, Formula VI, Formula VII, Formula VIII-a to Formula VIII-c, Formula IX, Formula X, Formula XI, Formula XII-a to XII-c, Formula XIII, Formula XIV, Formula XV, Formula XVI, and Formula XVII-a to XVII-g or a pharmaceutically acceptable salt thereof; and q) a process for the preparation of a bifunctional compound that causes degradation of a selected protein via the ubiquitin proteasome pathway, characterized in that a compound of XVI or XVII-a to XVII-g is used in the preparation of the bifunctional compound.

DETAILED DESCRIPTION OF THE INVENTION

I. Definitions

Unless otherwise stated, the following terms used in this application, including the specification and claims, have the definitions given below. It must be noted that, as used in the specification and the appended claims, the singular forms "a", "an," and "the" include plural referents unless the context clearly dictates otherwise.

The term "$C_{1-6}$-alkyl", alone or in combination with other groups, stands for a hydrocarbon radical which may be linear or branched, with single or multiple branching, wherein the alkyl group in general comprises 1 to 6 carbon atoms, for example, methyl (Me), ethyl (Et), propyl, isopropyl (i-propyl), n-butyl, i-butyl (isobutyl), 2-butyl (sec-butyl), t-butyl (tert-butyl), isopentyl, 2-ethyl-propyl (2-methyl-propyl), 1,2-dimethyl-propyl and the like. A specific group is methyl.

The term "heteroaryl" denotes a monovalent heterocyclic mono- or bicyclic ring system of 5 to 12 ring atoms, comprising 1, 2, 3 or 4 heteroatoms selected from N, O and S, the remaining ring atoms being carbon and in which all rings are aromatic. Examples of heteroaryl moieties include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolinyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, dihydroquinolyl, dihydropyrrolopyridinyl, dihydronaphthyridinyl, chromanyl, tetrahydroquinolinyl, dihydrocyclopentapyridinyl quinazolinyl, or quinoxalinyl. Particular examples are pyridinyl, benzo[d]thiazolyl, pyrazolo[1,5-a]pyridinyl and thiazolo[4,5-b]pyridin-2-yl.

In one embodiment "heteroaryl" is a 5 membered aromatic group containing 1, 2, 3, or 4 nitrogen atoms.

Non-limiting examples of 5 membered "heteroaryl" groups include pyrrole, furan, thiophene, pyrazole, imidazole, triazole, tetrazole, isoxazole, oxazole, oxadiazole, oxatriazole, isothiazole, thiazole, thiadiazole, and thiatriazole.

Additional non-limiting examples of 5 membered "heteroaryl" groups include:

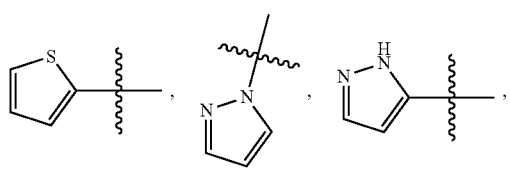

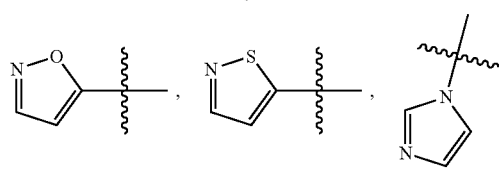

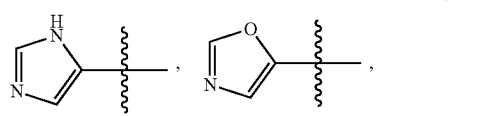

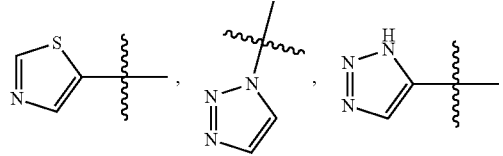

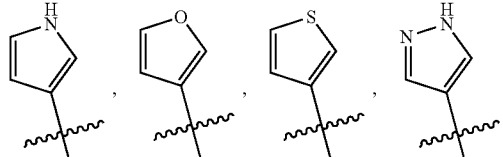

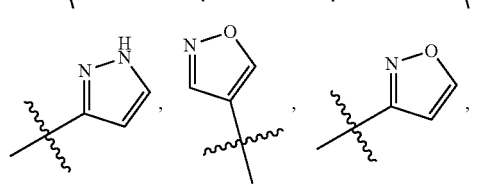

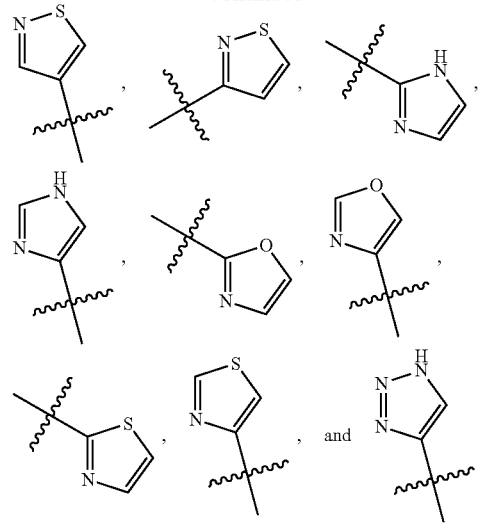

In one embodiment "heteroaryl" is a 6 membered aromatic group containing 1, 2, or 3 nitrogen atoms (i.e. pyridinyl, pyridazinyl, triazinyl, pyrimidinyl, and pyrazinyl).

Non-limiting examples of 6 membered "heteroaryl" groups with 1 or 2 nitrogen atoms include:

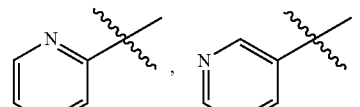

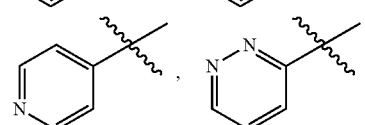

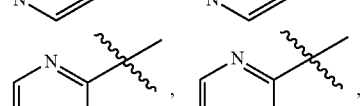

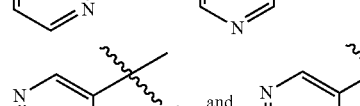

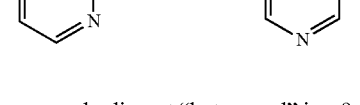

In one embodiment "heteroaryl" is a 9 membered bicyclic aromatic group containing 1 or 2 atoms selected from nitrogen, oxygen, and sulfur.

Non-limiting examples of "heteroaryl" groups that are bicyclic include indole, benzofuran, isoindole, indazole, benzimidazole, azaindole, azaindazole, purine, isobenzofuran, benzothiophene, benzoisoxazole, benzoisothiazole, benzooxazole, and benzothiazole.

Additional non-limiting examples of "heteroaryl" groups that are bicyclic include:

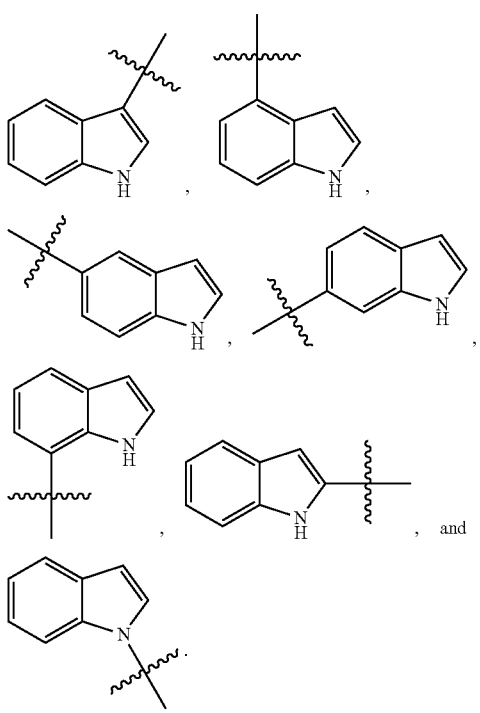

Additional non-limiting examples of "heteroaryl" groups that are bicyclic include:

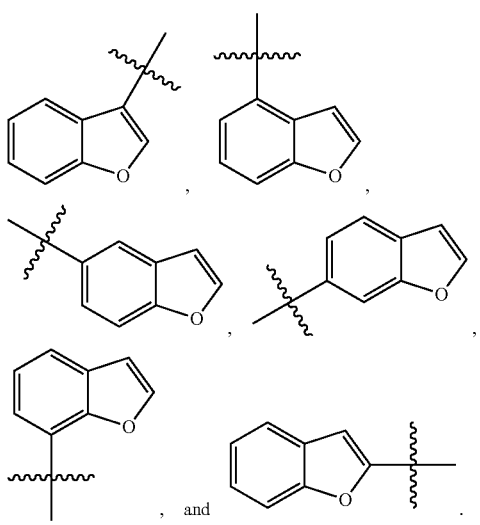

Additional non-limiting examples of "heteroaryl" groups that are bicyclic include:

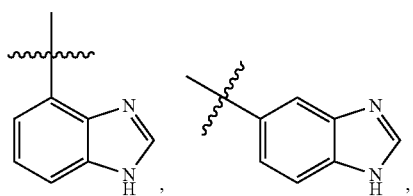

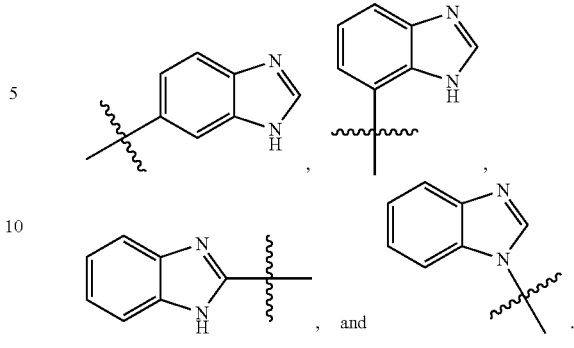

In one embodiment "heteroaryl" is a 10 membered bicyclic aromatic group containing 1 or 2 atoms selected from nitrogen, oxygen, and sulfur.

Non-limiting examples of "heteroaryl" groups that are bicyclic include quinoline, isoquinoline, quinoxaline, phthalazine, quinazoline, cinnoline, and naphthyridine.

Additional non-limiting examples of "heteroaryl" groups that are bicyclic include:

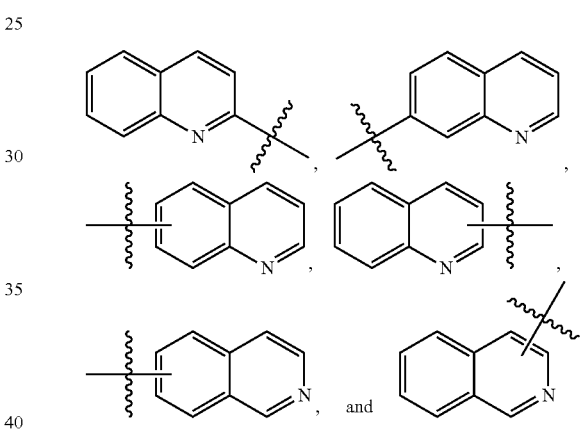

In an alternative embodiment "heteroaryl" is "optionally substituted" with 1, 2, 3, or 4 substituents.

The term "aryl" denotes a monovalent aromatic carbocyclic mono- or bicyclic ring system comprising 6 to 10 carbon ring atoms and in which at least one ring is aromatic. Examples of aryl moieties include phenyl (Ph), indanyl, 1,2,3,4-tetrahydronaphthalenyl and naphthyl. Particular examples are phenyl and 1,2,3,4-tetrahydronaphthalenyl.

In one embodiment "aryl" is a 6 carbon aromatic group (phenyl)

In one embodiment "aryl" is a 10 carbon aromatic group (napthyl)

In an alternative embodiment "aryl" is "optionally substituted" with 1, 2, 3, or 4 substituents.

"Alkenyl" is a linear or branched aliphatic hydrocarbon groups having one or more carbon-carbon double bonds that may occur at a stable point along the chain. The specified ranges as used herein indicate an alkenyl group having each member of the range described as an independent species, as described above for the alkyl moiety. In one non-limiting embodiment, the alkenyl contains from 2 to about 12 carbon atoms, more generally from 2 to about 6 carbon atoms or from 2 to about 4 carbon atoms. In certain embodiments the alkenyl is $C_2$, $C_2$-$C_3$, $C_2$-$C_4$, $C_2$-$C_5$, or $C_2$-$C_6$. Examples of alkenyl radicals include, but are not limited to ethenyl, propenyl, allyl, propenyl, butenyl and 4-methylbutenyl. The term "alkenyl" also embodies "cis" and "trans" alkenyl geometry, or alternatively, "E" and "Z" alkenyl geometry. The term "Alkenyl" also encompasses cycloalkyl or carbocyclic groups possessing at least one point of unsaturation.

"Alkynyl" is a branched or straight chain aliphatic hydrocarbon group having one or more carbon-carbon triple bonds that may occur at any stable point along the chain. The specified ranges as used herein indicate an alkynyl group having each member of the range described as an independent species, as described above for the alkyl moiety. In one non-limiting embodiment, the alkynyl contains from 2 to about 12 carbon atoms, more generally from 2 to about 6 carbon atoms or from 2 to about 4 carbon atoms. In certain embodiments the alkynyl is $C_2$, $C_2$-$C_3$, $C_2$-$C_4$, $C_2$-$C_5$, or $C_2$-$C_6$. Examples of alkynyl include, but are not limited to, ethynyl, propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl.

"Halo" and "Halogen" is independently fluorine, chlorine, bromine or iodine.

"Haloalkyl" is a branched or straight-chain alkyl groups substituted with 1 or more halo atoms described above, up to the maximum allowable number of halogen atoms. Examples of haloalkyl groups include, but are not limited to, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perhaloalkyl" means an alkyl group having all hydrogen atoms replaced with halogen atoms. Examples include but are not limited to, trifluoromethyl and pentafluoroethyl.

In one embodiment "haloalkyl" is a $C_1$-$C_{10}$haloalkyl, $C_1$-$C_9$haloalkyl, $C_1$-$C_8$haloalkyl, $C_1$-$C_7$haloalkyl, $C_1$-$C_6$haloalkyl, $C_1$-$C_5$haloalkyl, $C_1$-$C_4$haloalkyl, $C_1$-$C_3$haloalkyl, and $C_1$-$C_2$haloalkyl.

In one embodiment "haloalkyl" has one carbon.
In one embodiment "haloalkyl" has one carbon and one halogen.
In one embodiment "haloalkyl" has one carbon and two halogens.
In one embodiment "haloalkyl" has one carbon and three halogens.
In one embodiment "haloalkyl" has two carbons.
In one embodiment "haloalkyl" has three carbons.
In one embodiment "haloalkyl" has four carbons.
In one embodiment "haloalkyl" has five carbons.
In one embodiment "haloalkyl" has six carbons.

Non-limiting examples of "haloalkyl" include:

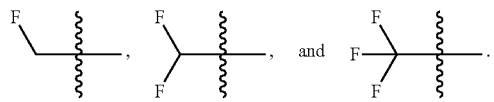

Additional non-limiting examples of "haloalkyl" include:

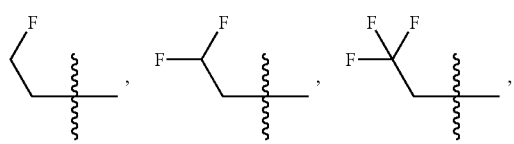

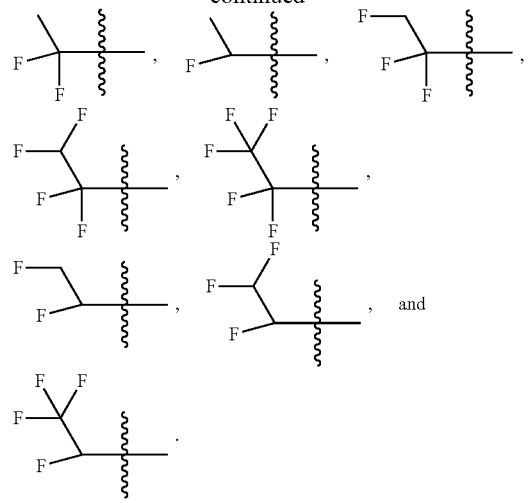

Additional non-limiting examples of "haloalkyl" include:

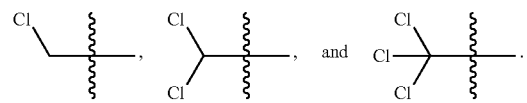

Additional non-limiting examples of "haloalkyl" include:

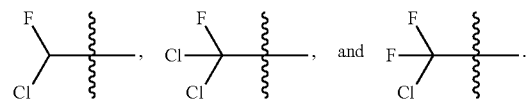

The term "heterocycle" denotes saturated and partially saturated heteroatom-containing ring radicals, wherein there are 1, 2, 3, or 4 heteroatoms independently selected from nitrogen, sulfur, boron, silicone, and oxygen. Heterocyclic rings may comprise monocyclic 3-10 membered rings, as well as 5-16 membered bicyclic ring systems (which can include bridged, fused, and spiro-fused bicyclic ring systems). It does not include rings containing —O—O—, —O—S— or —S—S-portions. Examples of saturated heterocycle groups include saturated 3- to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocycle radicals include but are not limited to, dihydrothienyl, dihydropyranyl, dihydrofuryl, and dihydrothiazolyl. Examples of partially saturated and saturated heterocycle groups include but are not limited to, pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]

oxazinyl, benzo[1,4]dioxanyl, 2,3-dihydro-1H-1λ'-benzo[d]isothiazol-6-yl, dihydropyranyl, dihydrofuryl and dihydrothiazolyl.

Heterocycle" also includes groups wherein the heterocyclic radical is fused/condensed with an aryl or carbocycle radical, wherein the point of attachment is the heterocycle ring. "Heterocycle" also includes groups wherein the heterocyclic radical is substituted with an oxo group

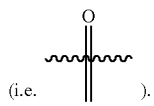

(i.e. ).

For example a partially unsaturated condensed heterocyclic group containing 1 to 5 nitrogen atoms, for example, indoline or isoindoline; a partially unsaturated condensed heterocyclic group containing 1 to 2 oxygen atoms and 1 to 3 nitrogen atoms; a partially unsaturated condensed heterocyclic group containing 1 to 2 sulfur atoms and 1 to 3 nitrogen atoms; and a saturated condensed heterocyclic group containing 1 to 2 oxygen or sulfur atoms.

In one embodiment "heterocycle" refers to a cyclic ring with one nitrogen and 3, 4, 5, 6, 7, or 8 carbon atoms.

In one embodiment "heterocycle" refers to a cyclic ring with one nitrogen and one oxygen and 3, 4, 5, 6, 7, or 8 carbon atoms.

In one embodiment "heterocycle" refers to a cyclic ring with two nitrogens and 3, 4, 5, 6, 7, or 8 carbon atoms.

In one embodiment "heterocycle" refers to a cyclic ring with one oxygen and 3, 4, 5, 6, 7, or 8 carbon atoms.

In one embodiment "heterocycle" refers to a cyclic ring with one sulfur and 3, 4, 5, 6, 7, or 8 carbon atoms.

Non-limiting examples of "heterocycle" include aziridine, oxirane, thiirane, azetidine, 1,3-diazetidine, oxetane, and thietane.

Additional non-limiting examples of "heterocycle" include pyrrolidine, 3-pyrroline, 2-pyrroline, pyrazolidine, and imidazolidine.

Additional non-limiting examples of "heterocycle" include tetrahydrofuran, 1,3-dioxolane, tetrahydrothiophene, 1,2-oxathiolane, and 1,3-oxathiolane.

Additional non-limiting examples of "heterocycle" include piperidine, piperazine, tetrahydropyran, 1,4-dioxane, thiane, 1,3-dithiane, 1,4-dithiane, morpholine, and thiomorpholine.

Additional non-limiting examples of "heterocycle" include indoline, tetrahydroquinoline, tetrahydroisoquinoline, and dihydrobenzofuran wherein the point of attachment for each group is on the heterocyclic ring.

For example,

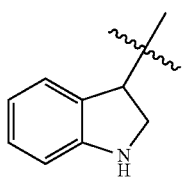 [SMILES: *C1CNc2ccccc21]

is a "heterocycle" group.

However,

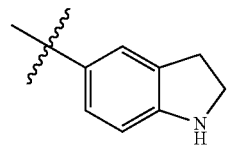 [SMILES: *c1ccc2c(c1)CCN2]

is an "aryl" group.

Non-limiting examples of "heterocycle" also include:

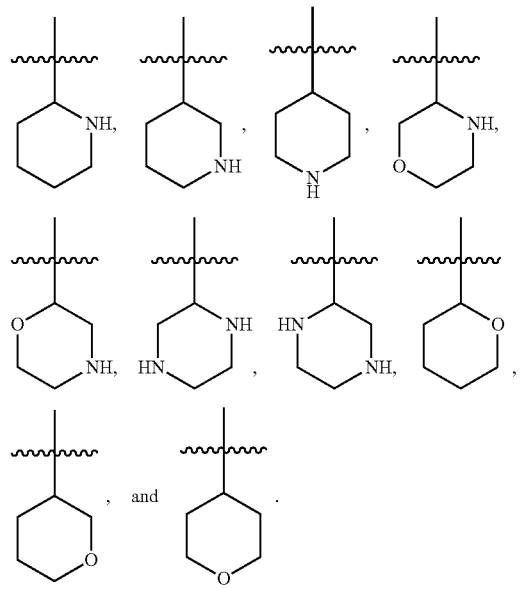

, and .

Additional non-limiting examples of "heterocycle" include:

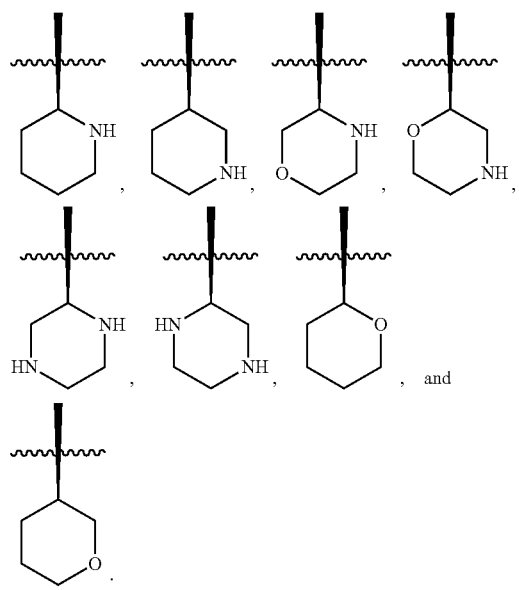

, and

.

Additional non-limiting examples of "heterocycle" include:

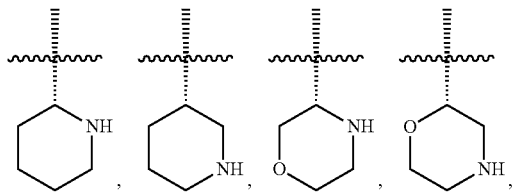

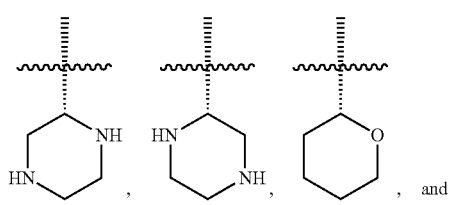

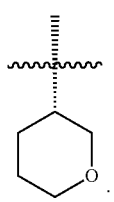

Non-limiting examples of "heterocycle" also include:

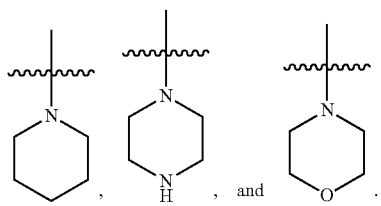

Non-limiting examples of "heterocycle" also include:

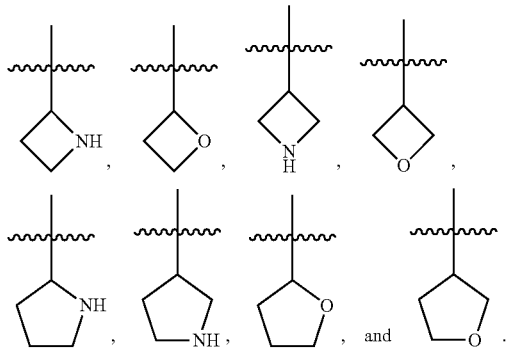

Additional non-limiting examples of "heterocycle" include:

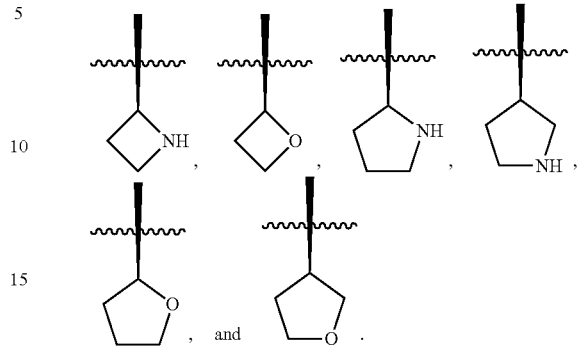

Additional non-limiting examples of "heterocycle" include:

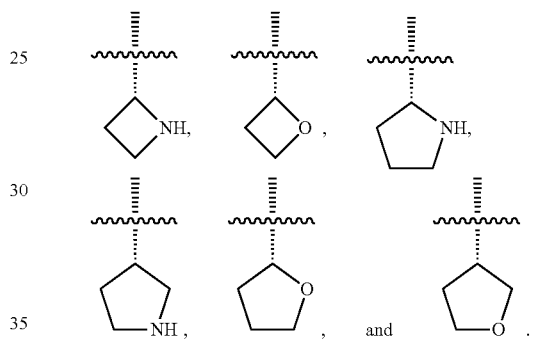

The term "optionally substituted" denotes the substitution of a group herein by a moiety including, but not limited to, $C_1$-$C_{10}$ alkyl, $C_2$-$C_{10}$ alkenyl, $C_2$-$C_{10}$ alkynyl, $C_3$-$C_{12}$ cycloalkyl, $C_3$-$C_{12}$ cycloalkenyl, $C_1$-$C_{12}$ heterocycloalkyl, $C_3$-$C_{12}$ heterocycloalkenyl, $C_1$-$C_{10}$ alkoxy, aryl, aryloxy, heteroaryl, heteroaryloxy, amino, $C_1$-$C_{10}$ alkylamino, $C_1$-$C_{10}$ dialkylamino, arylamino, diarylamino, $C_1$-$C_{10}$ alkylsulfonamino, arylsulfonamino, $C_1$-$C_{10}$ alkylimino, arylimino, $C_1$-$C_{10}$ alkylsulfonimino, arylsulfonimino, hydroxyl, halo, thio, $C_1$-$C_{10}$ alkylthio, arylthio, $C_1$-$C_{10}$ alkylsulfonyl, arylsulfonyl, acylamino, aminoacyl, aminothioacyl, amidino, guanidine, ureido, cyano, nitro, azido, acyl, thioacyl, acyloxy, carboxyl, and carboxylic ester.

As used herein, "carbocyclic", "carbocycle" or "cycloalkyl" includes a saturated or partially unsaturated (i.e., not aromatic) group containing all carbon ring atoms and from 3 to 14 ring carbon atoms ("$C_{3-14}$ cycloalkyl") and zero heteroatoms in the non-aromatic ring system. In some embodiments, a cycloalkyl group has 3 to 10 ring carbon atoms ("$C_{3-10}$ cycloalkyl"). In some embodiments, a cycloalkyl group has 3 to 9 ring carbon atoms ("$C_{3-9}$ cycloalkyl"). In some embodiments, a cycloalkyl group has 3 to 8 ring carbon atoms ("$C_{3-8}$ cycloalkyl"). In some embodiments, a cycloalkyl group has 3 to 7 ring carbon atoms ("$C_{3-7}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Exemplary $C_{3-6}$ cycloalkyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ cycloalkyl groups include, without limitation, the aforementioned $C_{3-6}$ cycloalkyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), and the like. Exemplary $C_{3-10}$ cycloalkyl groups include, without limitation, the aforementioned $C_{3-8}$ cycloalkyl groups as well as cyclononyl ($C_9$), cyclononenyl ($C_9$), cyclodecyl ($C_{10}$), cyclodecenyl ($C_{10}$), and the like. As the foregoing examples illustrate, in certain embodiments, the cycloalkyl group can be saturated or can contain one or more carbon-carbon double bonds.

In one embodiment "cycloalkyl" is a $C_3$-$C_8$cycloalkyl, $C_3$-$C_7$cycloalkyl, $C_3$-$C_6$cycloalkyl, $C_3$-$C_5$cycloalkyl, $C_3$-$C_4$cycloalkyl, $C_4$-$C_8$cycloalkyl, $C_5$-$C_8$cycloalkyl, or $C_6$-$C_8$cycloalkyl.

In one embodiment "cycloalkyl" has three carbons.
In one embodiment "cycloalkyl" has four carbons.
In one embodiment "cycloalkyl" has five carbons.
In one embodiment "cycloalkyl" has six carbons.
In one embodiment "cycloalkyl" has seven carbons.
In one embodiment "cycloalkyl" has eight carbons.
In one embodiment "cycloalkyl" has nine carbons.
In one embodiment "cycloalkyl" has ten carbons.

Non-limiting examples of "cycloalkyl" include: cyclopropyl, cyclobutyl, cyclopentyl, cyclohexyl, cycloheptyl, cyclooctyl, and cyclodecyl.

In another embodiment any suitable group may be present on a "substituted" or "optionally substituted" position if indicated that forms a stable molecule and meets the desired purpose of the invention and includes, but is not limited to, e.g., halogen (which can independently be F, Cl, Br or I); cyano; hydroxyl; nitro; azido; alkanoyl (such as a $C_2$-$C_6$ alkanoyl group); carboxamide; alkyl, cycloalkyl, alkenyl, alkynyl, alkoxy, aryloxy such as phenoxy; thioalkyl including those having one or more thioether linkages; alkylsulfinyl; alkylsulfonyl groups including those having one or more sulfonyl linkages; aminoalkyl groups including groups having more than one N atoms; aryl (e.g., phenyl, biphenyl, naphthyl, or the like, each ring either substituted or unsubstituted); arylalkyl having for example, 1 to 3 separate or fused rings and from 6 to about 14 or 18 ring carbon atoms, with benzyl being an exemplary arylalkyl group; arylalkoxy, for example, having 1 to 3 separate or fused rings with benzyloxy being an exemplary arylalkoxy group; or a saturated or partially unsaturated heterocycle having 1 to 3 separate or fused rings with one or more N, O or S atoms, or a heteroaryl having 1 to 3 separate or fused rings with one or more N, O or S atoms, e.g. coumarinyl, quinolinyl, isoquinolinyl, quinazolinyl, pyridyl, pyrazinyl, pyrimidinyl, furanyl, pyrrolyl, thienyl, thiazolyl, triazinyl, oxazolyl, isoxazolyl, imidazolyl, indolyl, benzofuranyl, benzothiazolyl, tetrahydrofuranyl, tetrahydropyranyl, piperidinyl, morpholinyl, piperazinyl, and pyrrolidinyl. Such groups may be further substituted, e.g. with hydroxy, alkyl, alkoxy, halogen and amino. In certain embodiments "optionally substituted" includes one or more substituents independently selected from halogen, hydroxyl, amino, cyano, —CHO, —COOH, —CONH$_2$, alkyl including $C_1$-$C_6$alkyl, alkenyl including $C_2$-$C_6$alkenyl, alkynyl including $C_2$-$C_6$alkynyl, —$C_1$-$C_6$alkoxy, alkanoyl including $C_2$-$C_6$alkanoyl, $C_1$-$C_6$alkylester, (mono- and di-$C_1$-$C_6$alkylamino)$C_0$-$C_2$alkyl, haloalkyl including $C_1$-$C_6$haloalkyl, hydoxy$C_1$-$C_6$alkyl, ester, carbamate, urea, sulfonamide, —$C_1$-$C_6$alkyl (heterocyclo), $C_1$-$C_6$alkyl(heteroaryl), —$C_1$-$C_6$alkyl($C_3$-$C_7$cycloalkyl), O—$C_1$-$C_6$alkyl($C_3$-$C_7$cycloalkyl), B(OH)$_2$, phosphate, phosphonate and haloalkoxy including $C_1$-$C_6$haloalkoxy. In some embodiments, the suitable group present on a "substituted" or "optionally substituted" is divalent including, but not limited to, oxo (=O), =S, =CH$_2$, etc. The suitable group on a "substituted" or "optional substituted" position may be monovalent, divalent, or trivalent such that it forms a stable molecule and meets the desired purpose of the invention.

In one embodiment a group described herein that can be substituted with 1, 2, 3, or 4 substituents is substituted with one substituent.

In one embodiment a group described herein that can be substituted with 1, 2, 3, or 4 substituents is substituted with two substituents.

In one embodiment a group described herein that can be substituted with 1, 2, 3, or 4 substituents is substituted with three substituents.

In one embodiment a group described herein that can be substituted with 1, 2, 3, or 4 substituents is substituted with four substituents.

The term "pharmaceutically acceptable" denotes an attribute of a material which is useful in preparing a pharmaceutical composition that is generally safe, non-toxic, and neither biologically nor otherwise undesirable and is acceptable for veterinary as well as human pharmaceutical use.

The term "a pharmaceutically acceptable salt" refers to a salt that is suitable for use in contact with the tissues of humans and animals. Examples of suitable salts with inorganic and organic acids are, but are not limited to, acetic acid, citric acid, formic acid, fumaric acid, hydrochloric acid, lactic acid, maleic acid, malic acid, methane-sulfonic acid, nitric acid, phosphoric acid, p-toluenesulphonic acid, succinic acid, sulfuric acid (sulphuric acid), tartaric acid, trifluoroacetic acid and the like. Particular acids are formic acid, trifluoroacetic acid and hydrochloric acid. Specific acids are hydrochloric acid, trifluoroacetic acid and fumaric acid.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—(CH$_2$)$_n$—COOH where n is 0-4, and the like, or using a different acid that produces the same counterion. Lists of additional suitable salts may be found, e.g., in *Remington's Pharmaceutical Sciences,* 17th ed., Mack Publishing Company, Easton, Pa., p. 1418 (1985).

The terms "pharmaceutically acceptable auxiliary substance" refer to carriers and auxiliary substances such as diluents or excipients that are compatible with the other ingredients of the formulation.

The term "pharmaceutical composition" encompasses a product comprising specified ingredients in pre-determined amounts or proportions, as well as any product that results, directly or indirectly, from combining specified ingredients in specified amounts. Particularly it encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The term "as defined herein" and "as described herein" when referring to a variable incorporates by reference the broad definition of the variable as well as particularly, more particularly and most particularly definitions, if any.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

The term "aromatic" denotes the conventional idea of aromaticity as defined in the literature, in particular in IUPAC—Compendium of Chemical Terminology, 2nd, A. D. McNaught & A. Wilkinson (Eds). Blackwell Scientific Publications, Oxford (1997).

The term "pharmaceutically acceptable excipient" denotes any ingredient having no therapeutic activity and being non-toxic such as disintegrators, binders, fillers, solvents, buffers, tonicity agents, stabilizers, antioxidants, surfactants or lubricants used in formulating pharmaceutical products.

Whenever a chiral carbon is present in a chemical structure, it is intended that all stereoisomers associated with that chiral carbon are encompassed by the structure as pure stereoisomers as well as mixtures thereof.

Furthermore, the invention includes all optical isomers, i.e. diastereoisomers, diastereomeric mixtures, racemic mixtures, all their corresponding enantiomers and/or tautomers as well as solvates of the compounds of formula XV.

The compounds described herein may contain one or more asymmetric centers and can therefore occur as racemates, racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within this invention. The present invention is meant to encompass all such isomeric forms of these compounds. The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography.

In the embodiments, where optically pure enantiomers are provided, optically pure enantiomer means that the compound contains >90% of the desired isomer by weight, particularly >95% of the desired isomer by weight, or more particularly >99% of the desired isomer by weight, said weight percent based upon the total weight of the isomer(s) of the compound. Chirally pure or chirally enriched compounds may be prepared by chirally selective synthesis or by separation of enantiomers. The separation of enantiomers may be carried out on the final product or alternatively on a suitable intermediate.

Isotopic Substitution

The present invention includes compounds of Formula I, Formula II, Formula III, Formula IV, Formula V, Formula VI, Formula VII, Formula VIII-a to Formula VIII-c, Formula IX, Formula X, Formula XI, Formula XII-a to XII-c, Formula XIII, Formula XIV, Formula XV, Formula XVI, and Formula XVII-a to XVII-g with at least one desired isotopic substitution of an atom, at an amount above the natural abundance of the isotope, i.e., enriched. Isotopes are atoms having the same atomic number but different mass numbers, i.e., the same number of protons but a different number of neutrons.

Examples of isotopes that can be incorporated into compound of the invention include isotopes of hydrogen, carbon, nitrogen, and oxygen such as $^2H$, $^3H$, $^{11}C$, $^{13}C$, $^{14}C$, $^{15}N$, and $^{17}O$, $^{18}O$ respectively. In one non-limiting embodiment, isotopically labelled compounds can be used in metabolic studies (with, for example $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Isotopic substitutions, for example deuterium substitutions, can be partial or complete. Partial deuterium substitution means that at least one hydrogen is substituted with deuterium. In certain embodiments, the isotope is 90, 95, or 99% or more enriched in an isotope at any location of interest. In one non-limiting embodiment, deuterium is 90, 95, or 99% enriched at a desired location.

In one non-limiting embodiment, the substitution of a hydrogen atom for a deuterium atom can be provided in any compound of Formula I, Formula II, Formula III, Formula IV, Formula V, Formula VI, Formula VII, Formula VIII-a to Formula VIII-c, Formula IX, Formula X, Formula XI, Formula XII-a to XII-c, Formula XIII, Formula XIV, Formula XV, Formula XVI, and Formula XVII-a to XVII-g. In one non-limiting embodiment, the substitution of a hydrogen atom for a deuterium atom occurs within one or more groups selected from the variables described herein. For example, when any of the groups are, or contain for example through substitution, methyl, ethyl, or methoxy, the alkyl residue may be deuterated (in non-limiting embodiments, $CDH_2$, $CD_2H$, $CD_3$, $CH_2CD_3$, $CD_2CD_3$, $CHDCH_2D$, $CHDCHD_2$, $OCDH_2$, $OCD_2H$, or $OCD_3$, etc.). In certain other embodiments, when two substitutions are combined to form a cycle, the unsubstituted carbons may be deuterated.

II. Compounds of the Present Invention

The present invention provides compounds of Formula I, Formula II, Formula III, Formula IV, Formula V, Formula VI, Formula VII, Formula VIII-a to VIII-c, Formula IX, Formula X, Formula XI, Formula XII-a to XII-c, Formula XIII, Formula XIV, Formula XVI, and Formula XVII-a to XVII-g, and pharmaceutically acceptable salt thereof. The invention also provides the use of compounds of Formula XV as further described herein.

Compounds of Formula I to Formula XIV

In one aspect, a compound is provided of Formula I:

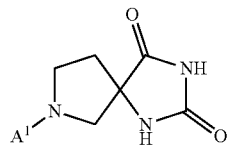

(I)

or a pharmaceutically acceptable salt thereof;
wherein all variables are as defined herein.

In some embodiments of Formula I, a compound is provided selected from:

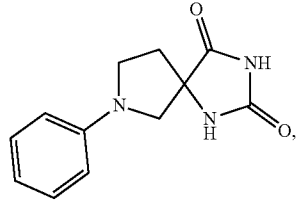

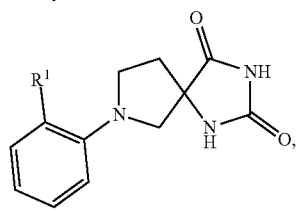

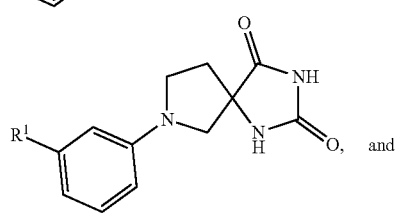

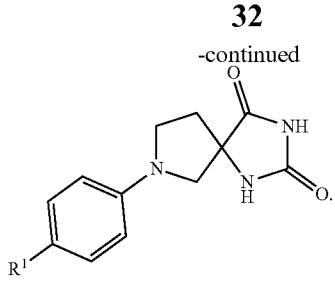

In another aspect, a compound is provided of Formula II:

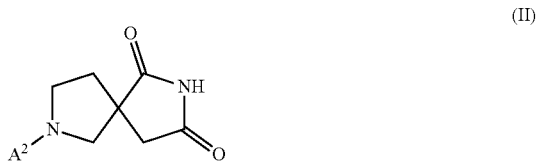

(II)

or a pharmaceutically acceptable salt thereof;
wherein all variables are as defined herein.

In some embodiments of Formula II, a compound is provided selected from:

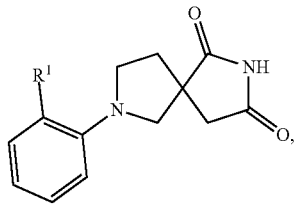

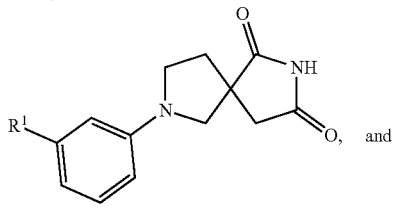

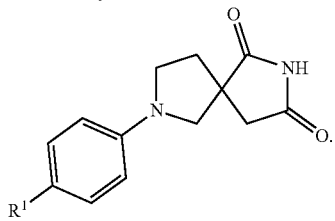

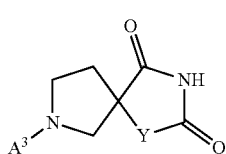

In another aspect, a compound is provided of Formula III:

(III)

or a pharmaceutically acceptable salt thereof;
wherein all variables are as defined herein.

In some embodiments of Formula III, a compound is provided selected from:
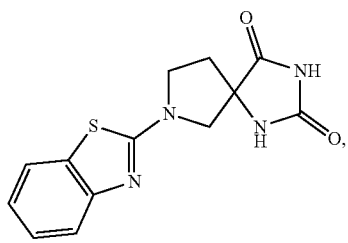
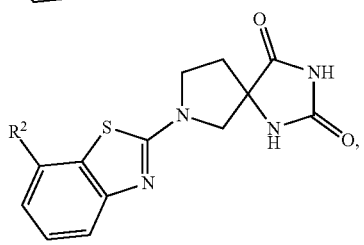
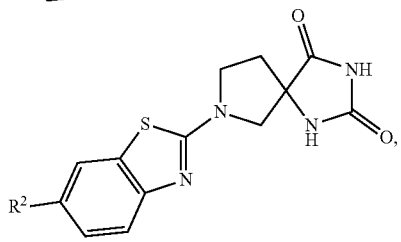
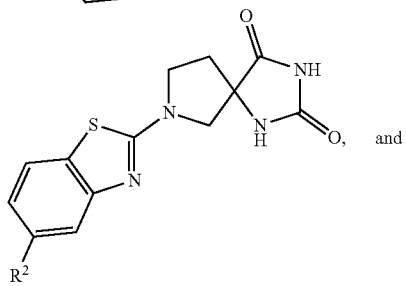
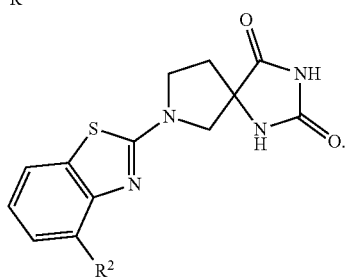
In some embodiments of Formula III, a compound is provided selected from:
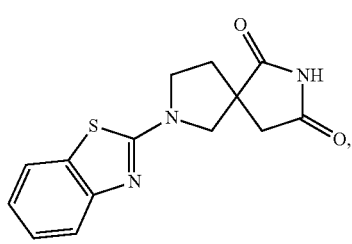
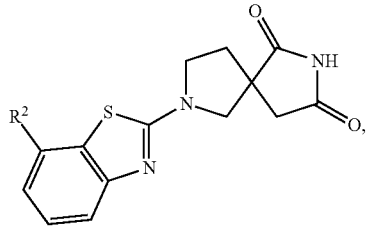
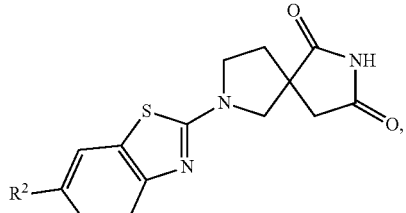
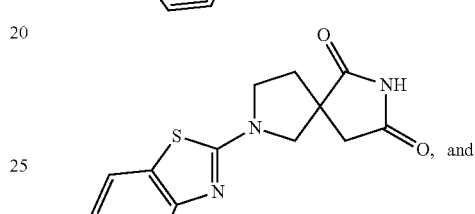
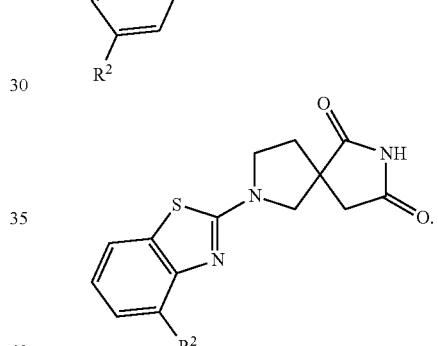
In some embodiments of Formula III, a compound is provided selected from:
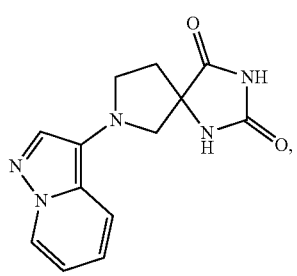
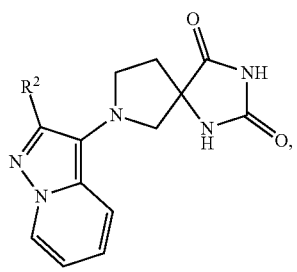

-continued
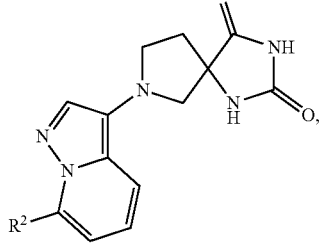
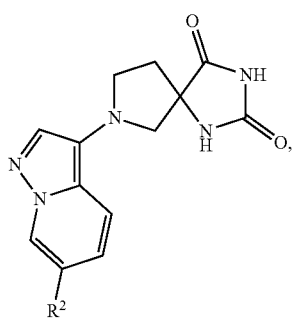
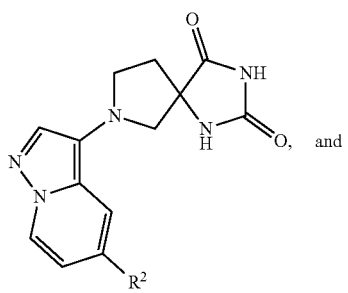, and
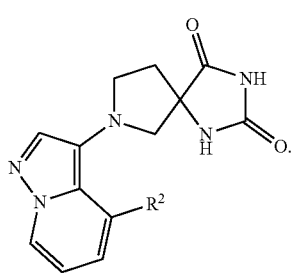.
In some embodiments of Formula III, a compound is provided selected from:
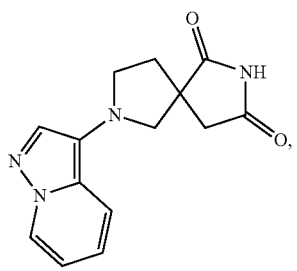
-continued
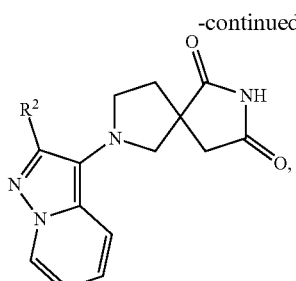
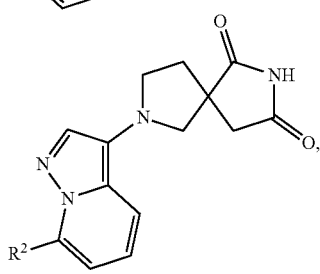
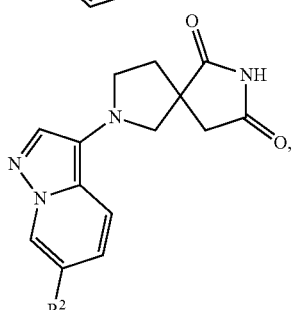
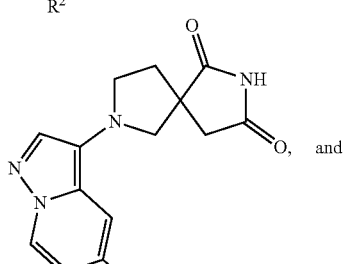, and
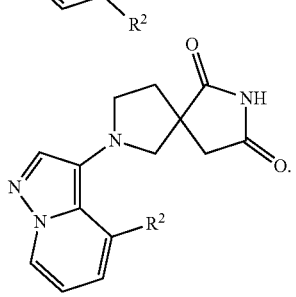.
In some embodiments of Formula III, a compound is provided selected from:
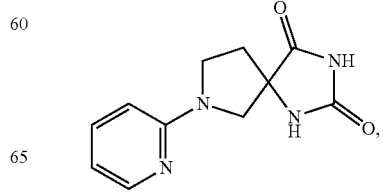

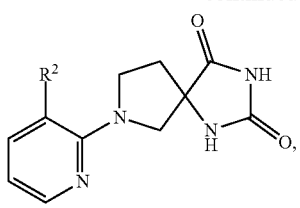
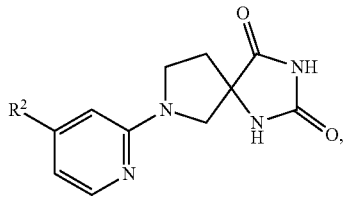, and
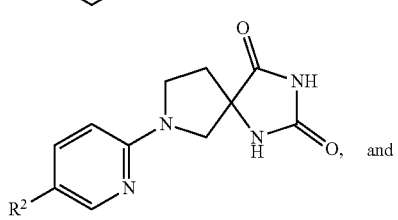
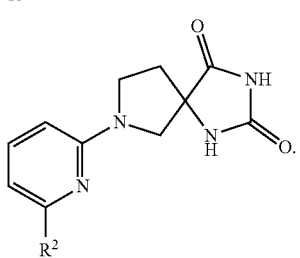
In some embodiments of Formula III, a compound is provided selected from:
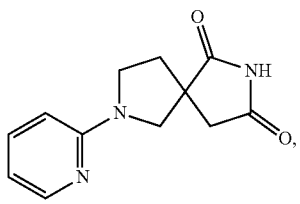
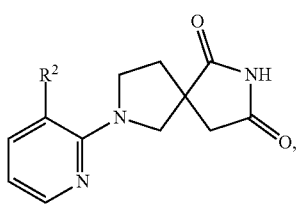
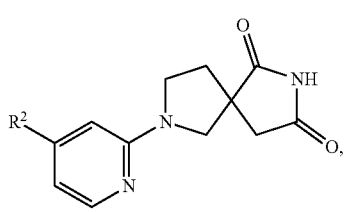
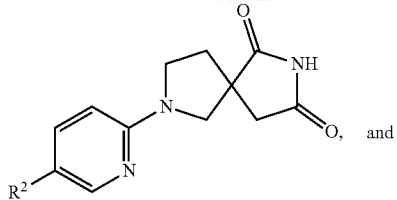, and
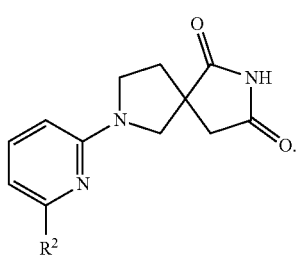
In some embodiments of Formula III, a compound is provided selected from:
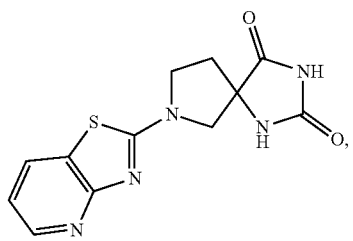
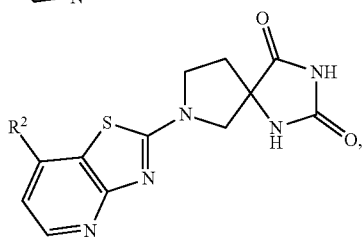
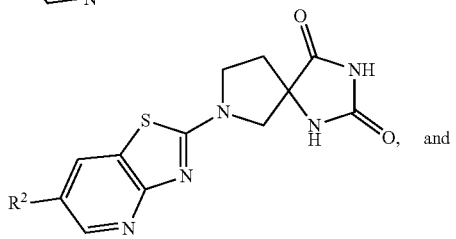, and
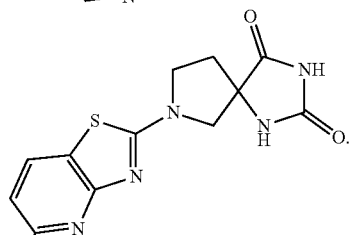

In some embodiments of Formula III, a compound is provided selected from:
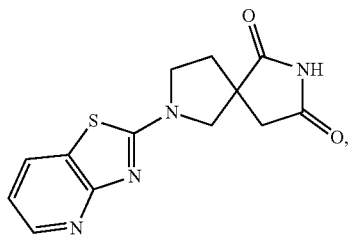
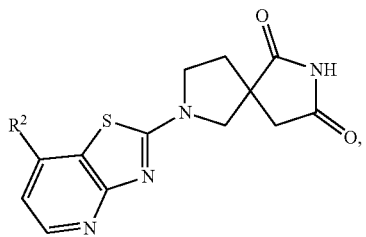
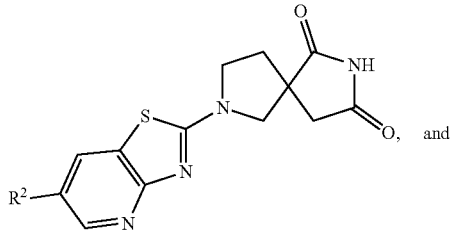 and
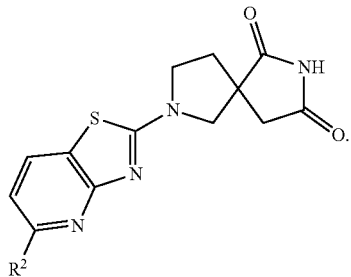
In some embodiments of Formula III, a compound is provided selected from:
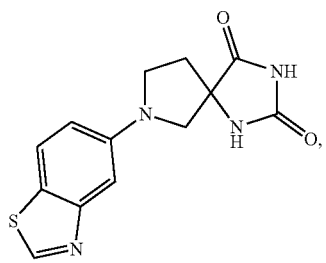
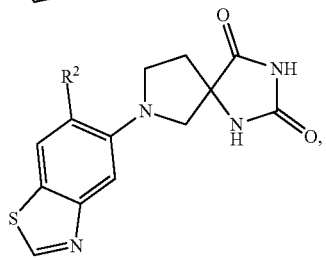
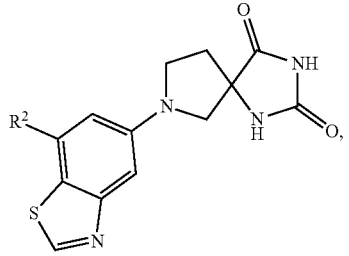
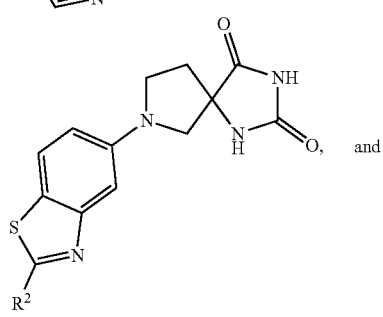 and
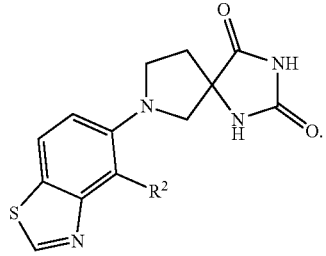
In some embodiments of Formula III, a compound is provided selected from:
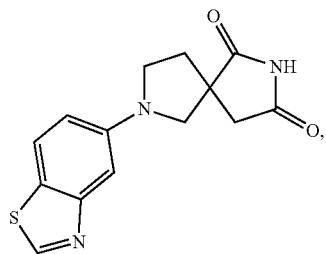
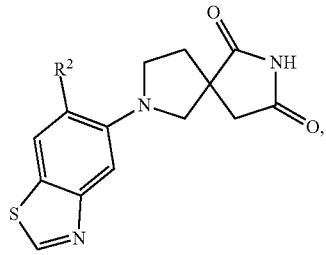
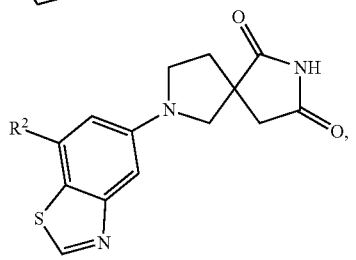

-continued

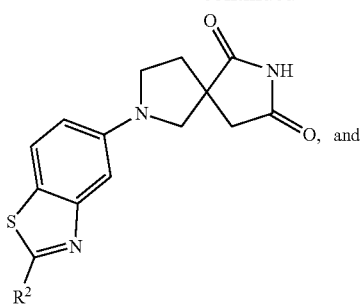

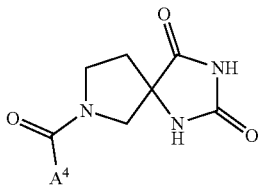

In another aspect, a compound is provided of Formula IV:

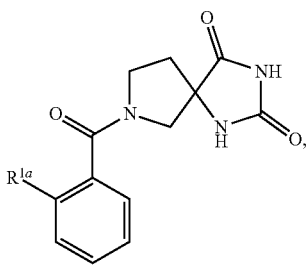
(IV)

or pharmaceutically acceptable salt thereof;
wherein all variables are as defined herein.

In some embodiments of Formula IV, a compound is provided selected from:

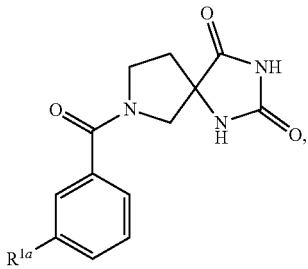

-continued

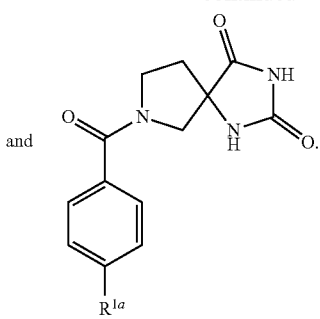

$R^{1a}$ is selected from the group consisting of: —C(=O)—O—$C_{1-6}$-alkyl; —COOH; and —NO$_2$.

In another aspect, a compound is provided of Formula V:

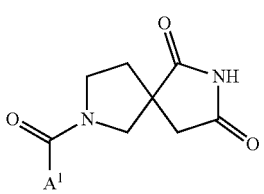
(V)

or a pharmaceutically acceptable salt thereof;
wherein all variables are as defined herein.

In some embodiments of Formula V, a compound is provided selected from:

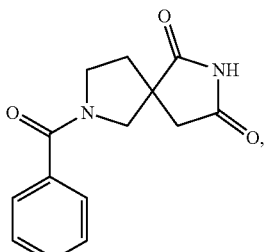

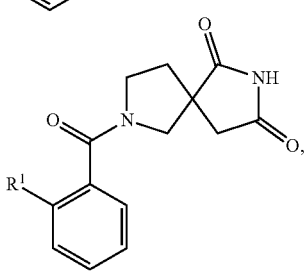

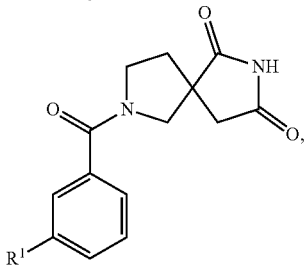

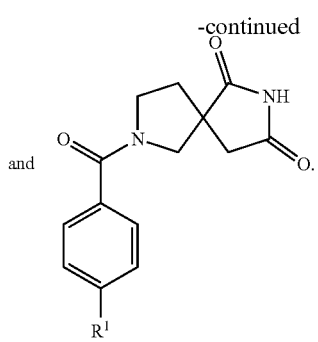
In another aspect, a compound is provided of Formula VI:
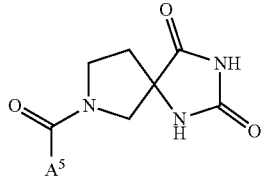
(VI)
or a pharmaceutically acceptable salt thereof;
wherein all variables are as defined herein.
In some embodiments of Formula VI, a compound is provided selected from:
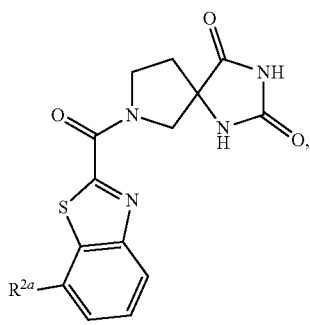
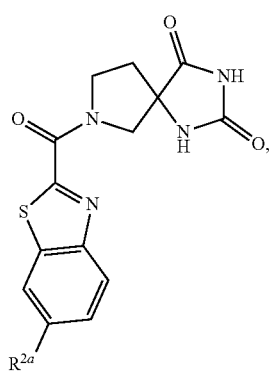
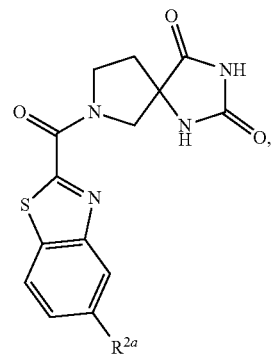
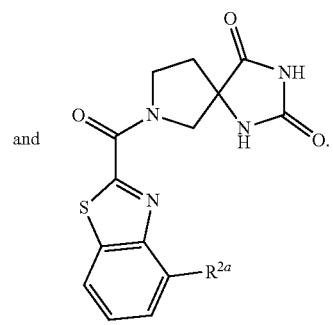
In some embodiments of Formula VI, a compound is provided selected from:
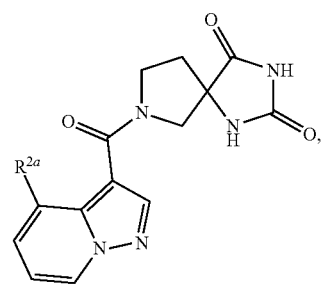
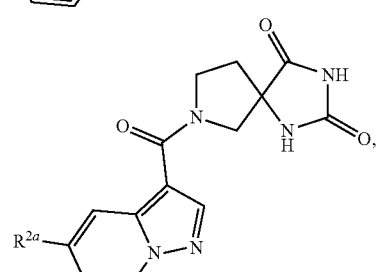
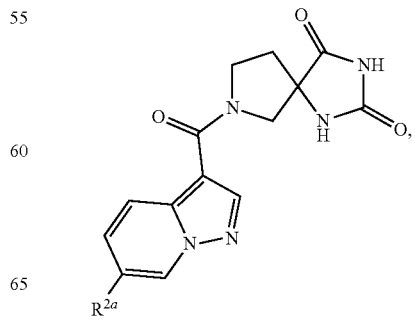

-continued
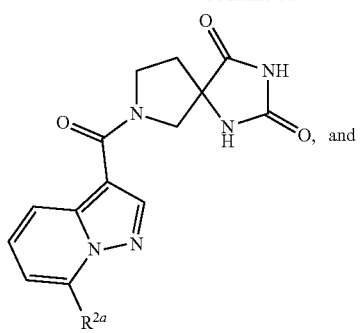, and
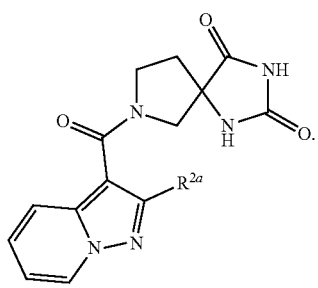
In some embodiments of Formula VI, a compound is provided selected from:
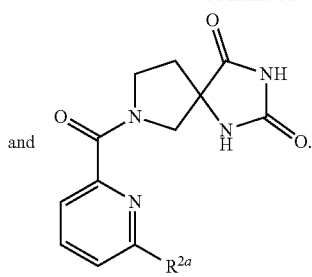
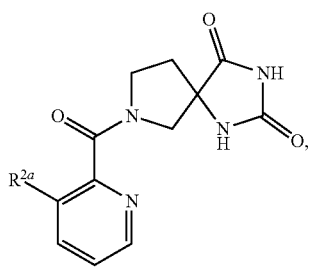
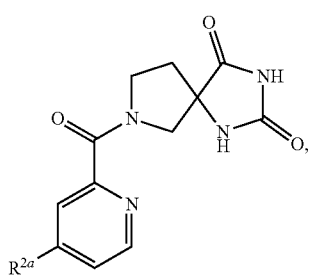
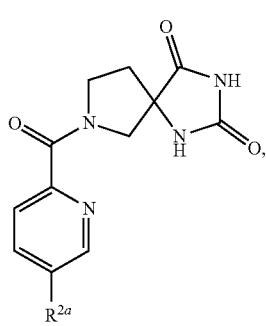
-continued
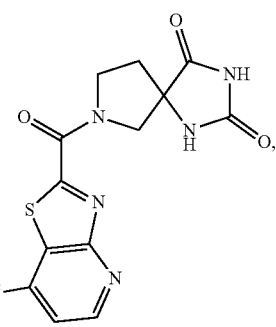 and
In some embodiments of Formula VI, a compound is provided selected from:
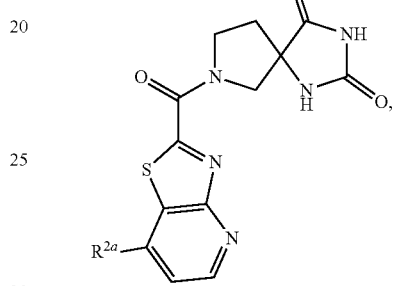
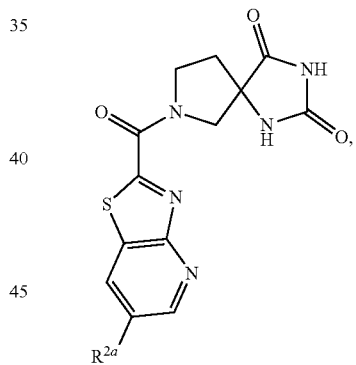
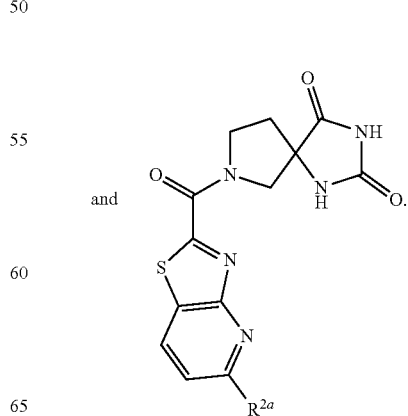 and In some embodiments of Formula VI, a compound is provided selected from:
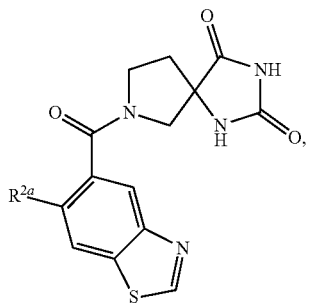
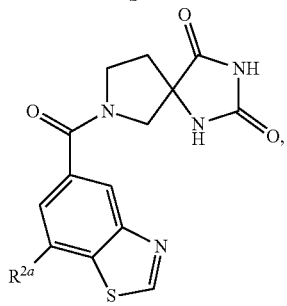
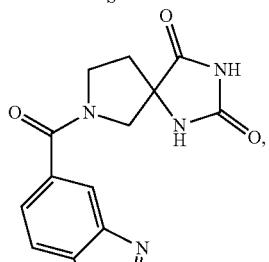
and 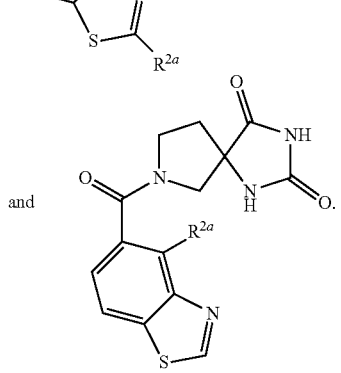
In another aspect, a compound is provided of Formula VII:
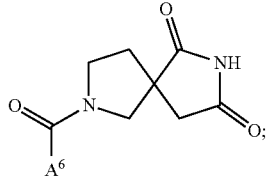
(VII)
or a pharmaceutically acceptable salt thereof;
wherein all variables are as defined herein.
In some embodiments of Formula VII, a compound is provided selected from:
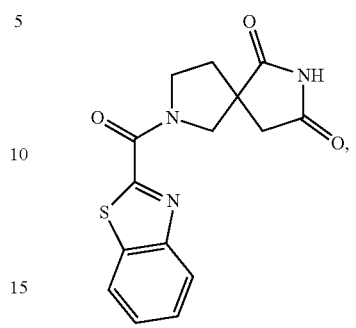
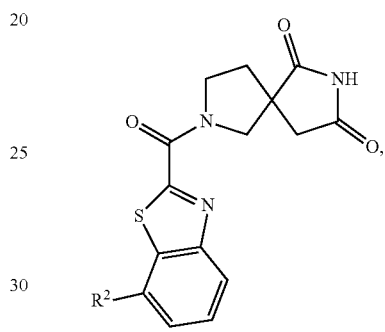
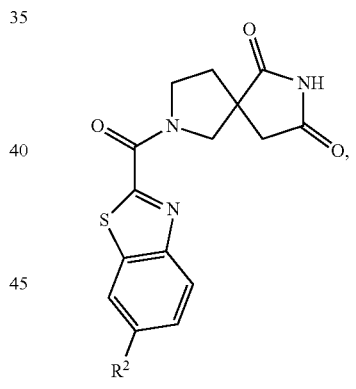
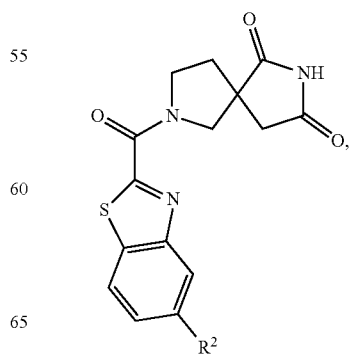

-continued
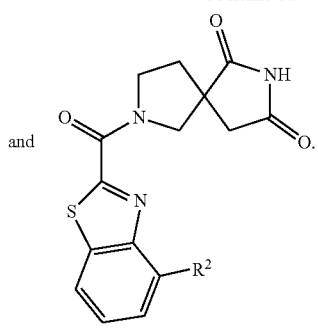
and
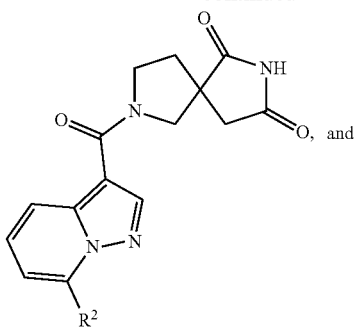
and
In some embodiments of Formula VII, a compound is provided selected from:
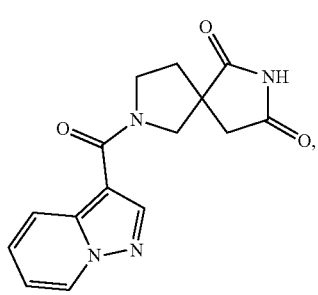
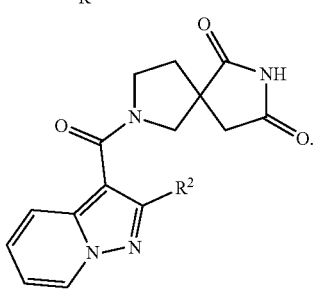
In some embodiments of Formula VII, a compound is provided selected from:
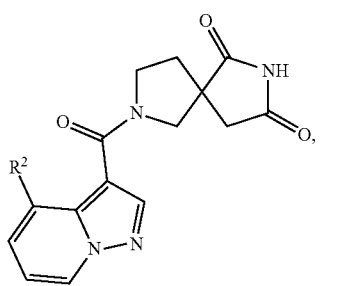
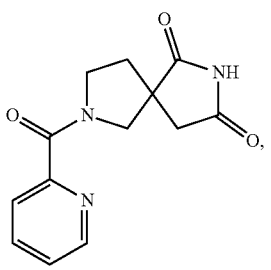
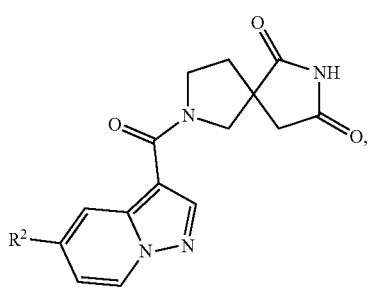
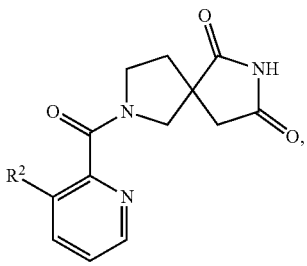
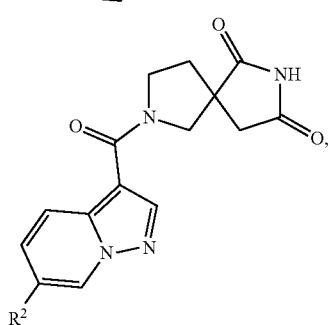
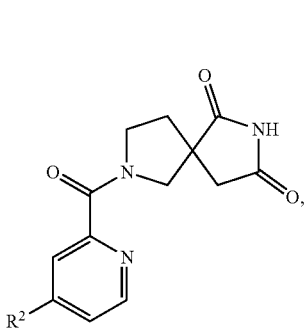

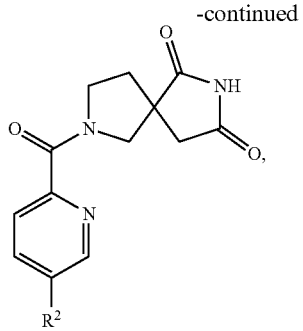
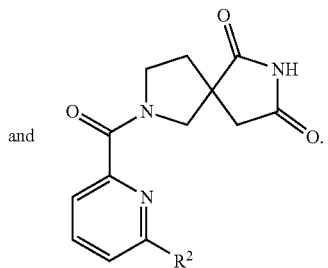
In some embodiments of Formula VII, a compound is provided selected from:
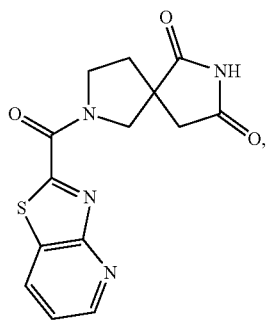
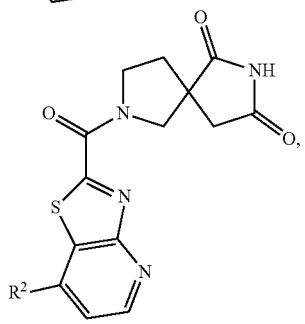
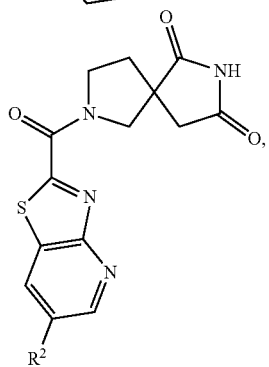
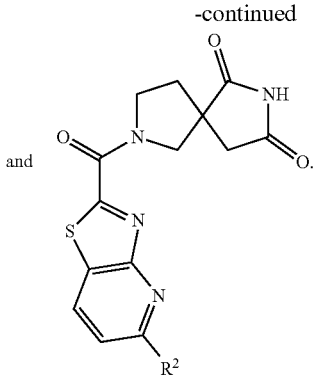
In some embodiments of Formula VII, a compound is provided selected from:
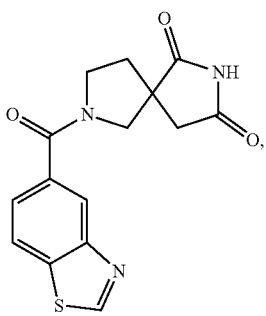
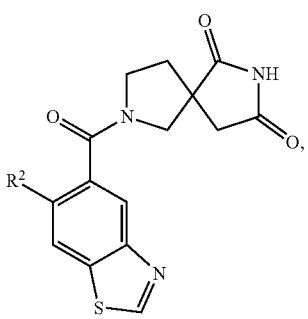
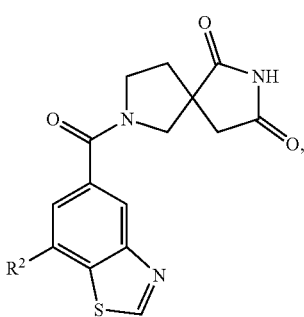

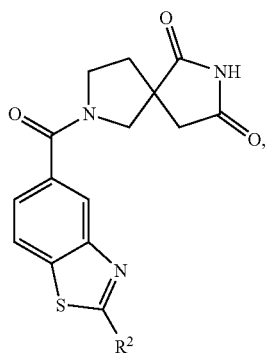
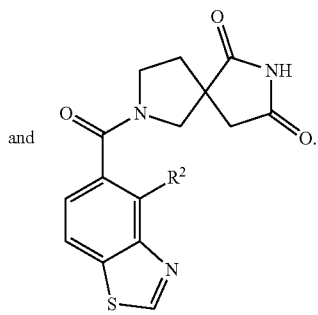
and
In another aspect, a compound is provided of Formula VIII-a, VIII-b, or VIII-c:
(VIII-a)
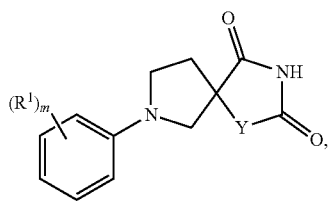
(VIII-b)
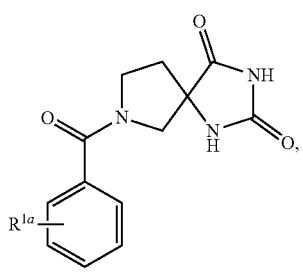
(VIII-c)
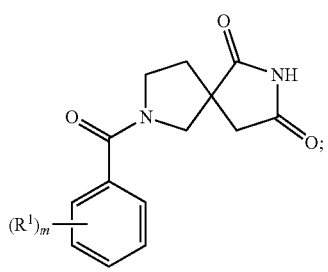
or a pharmaceutically acceptable salt thereof;
wherein all variables are as defined herein.
In some embodiments of Formula VIII-a, a compound is provided selected from:
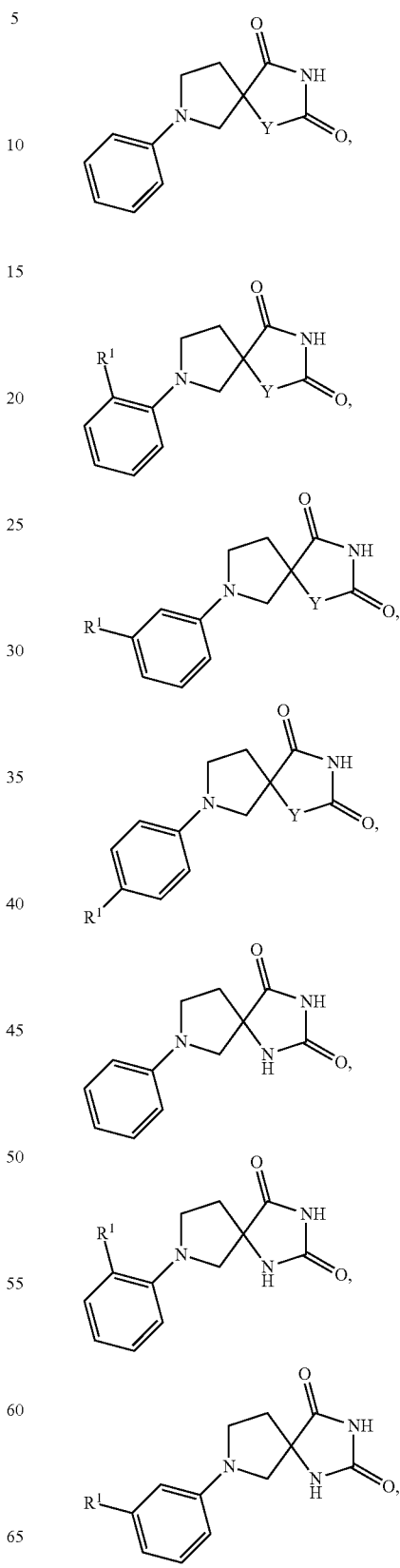

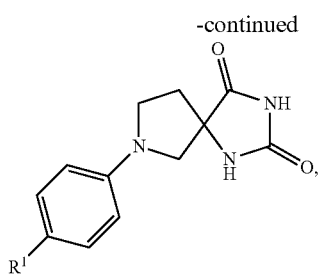
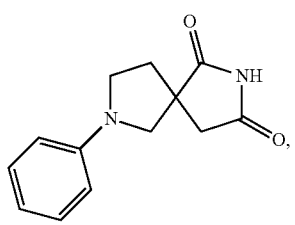
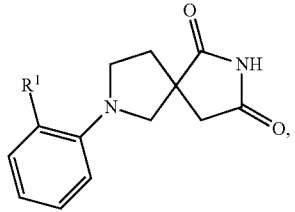
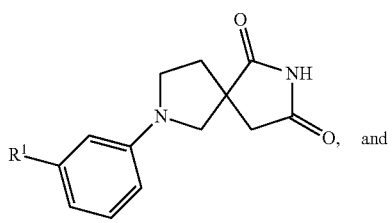
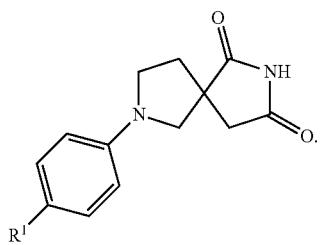
In some embodiments of Formula VIII-b, a compound is provided selected from:
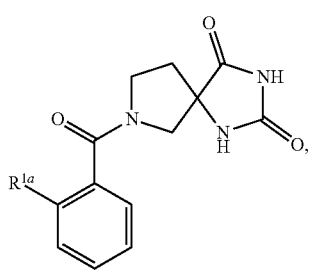
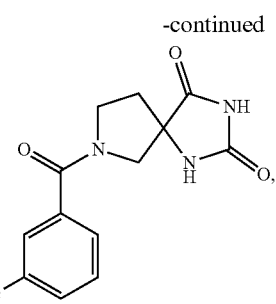
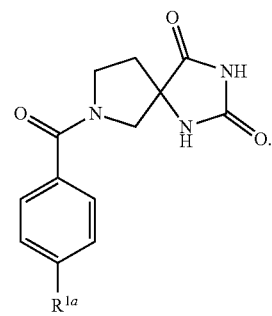
In some embodiments of Formula VIII-c, a compound is provided selected from:
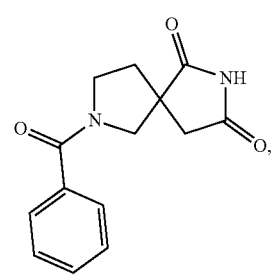
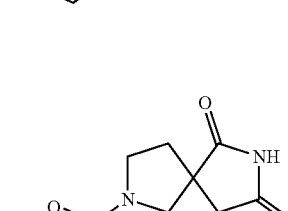
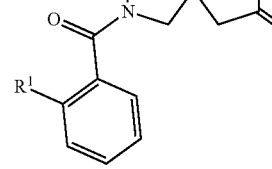
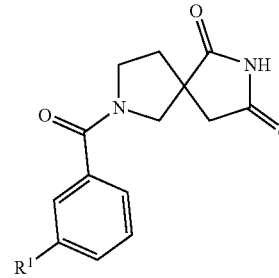

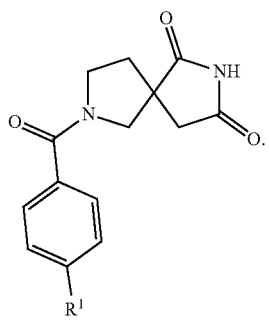
In another aspect, a compound is provided of Formula IX:
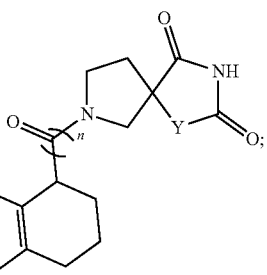
(IX)
or a pharmaceutically acceptable salt thereof;
wherein all variables are as defined herein.
In some embodiments of Formula IX, a compound is provided selected from:
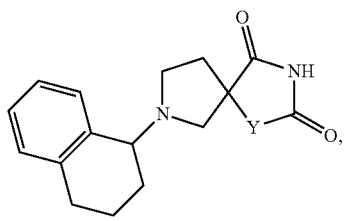
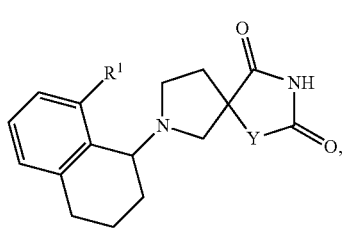
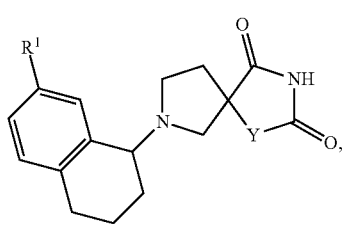
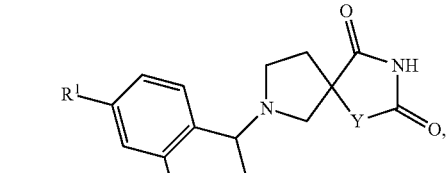
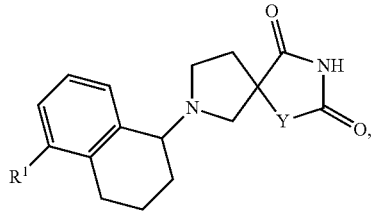
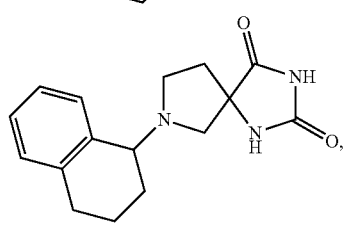
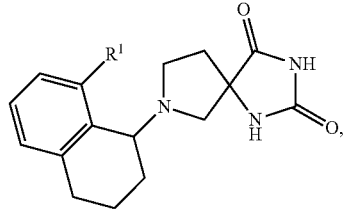
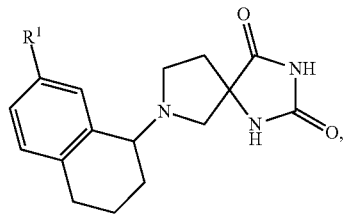
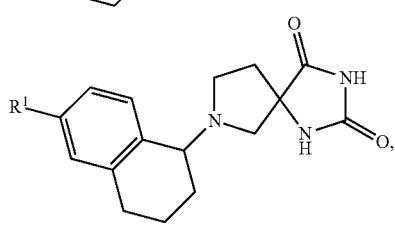
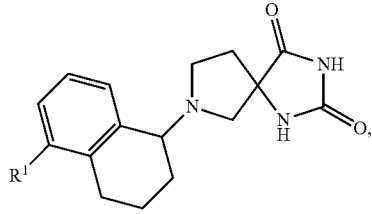
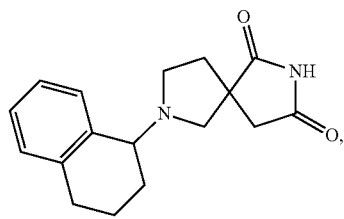

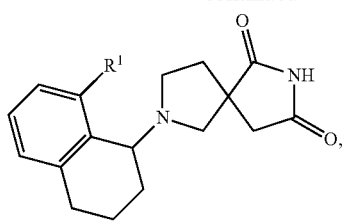
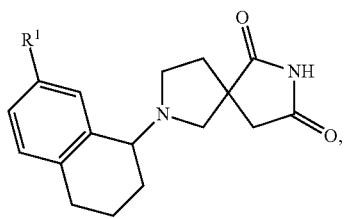
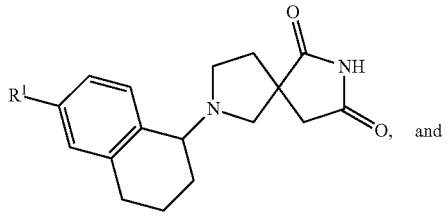
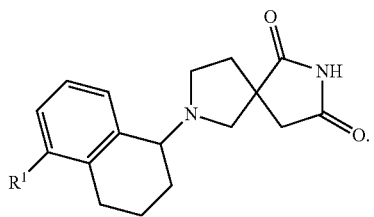
In some embodiments of Formula IX, a compound is provided selected from:
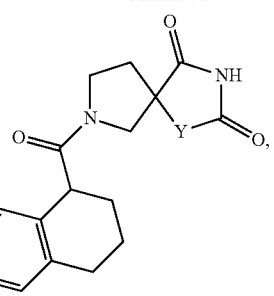
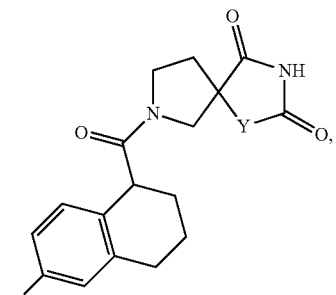
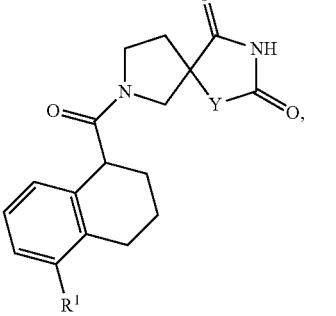
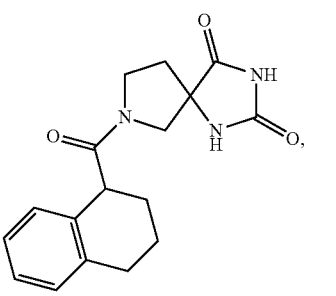
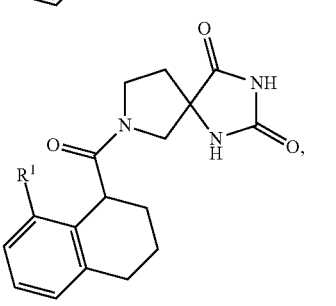

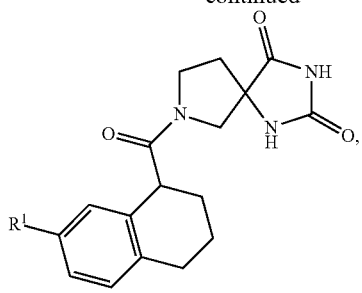
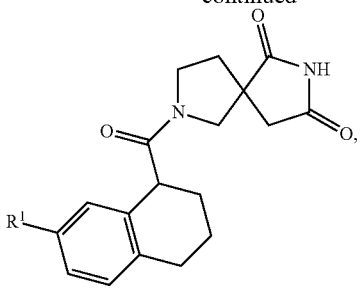
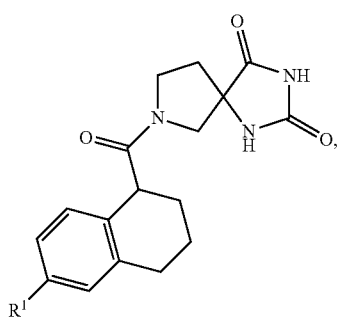
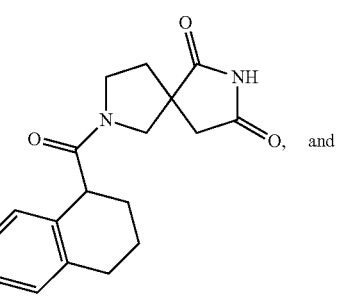
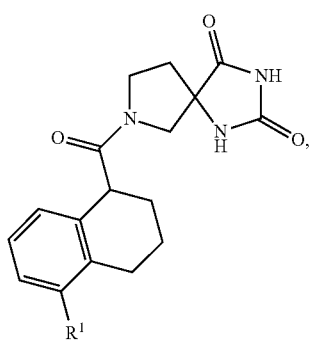
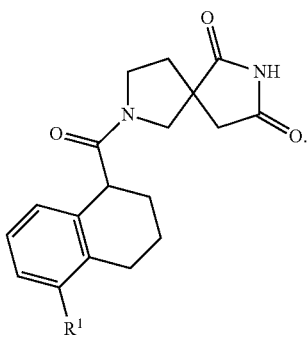
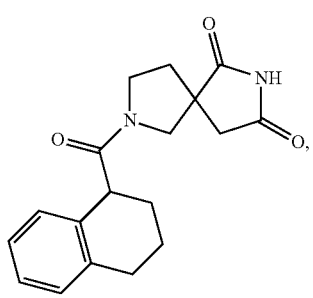
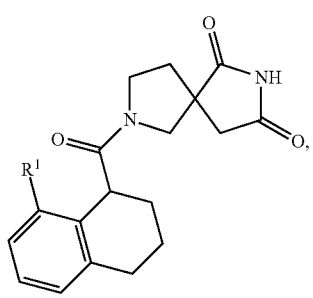
In another aspect, a compound is provided of Formula X:
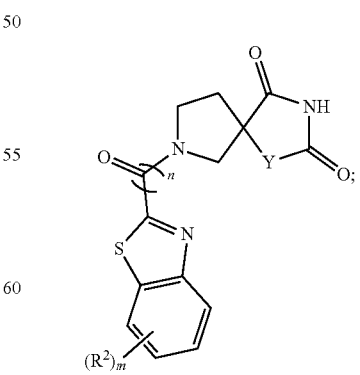
(X)
or a pharmaceutically acceptable salt thereof;
wherein all variables are as defined herein.

In some embodiments of Formula X, a compound is provided selected from:
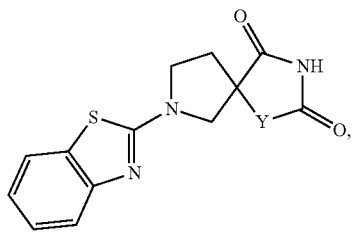
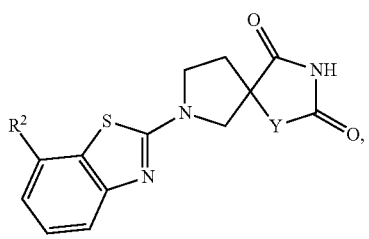
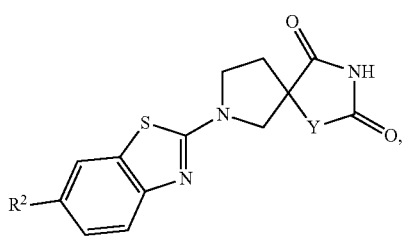
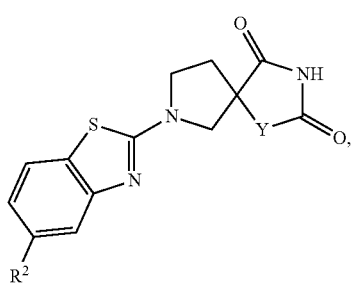
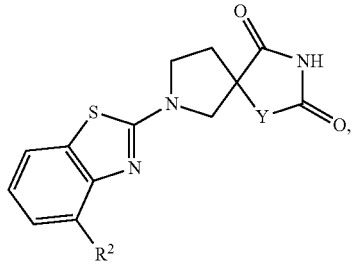
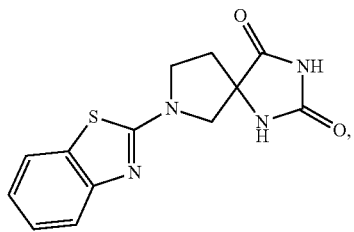
-continued
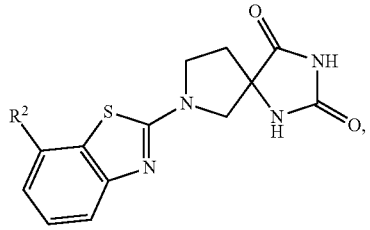
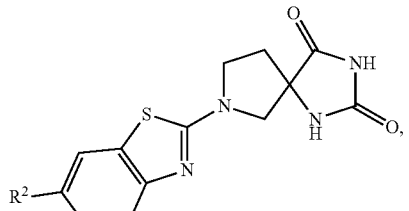
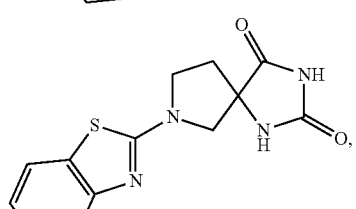
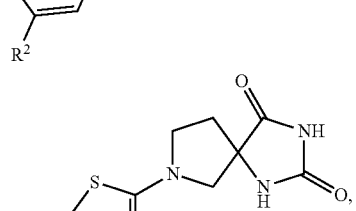

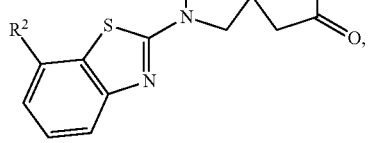
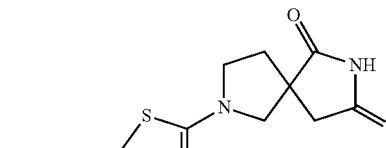
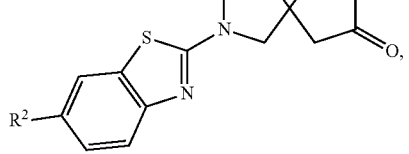

-continued
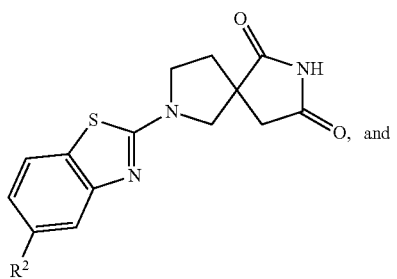
O, and
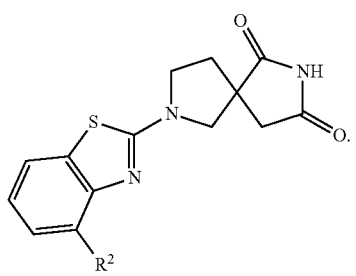
O.
In some embodiments of Formula X, a compound is provided selected from:
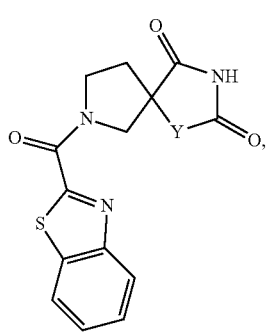
O,
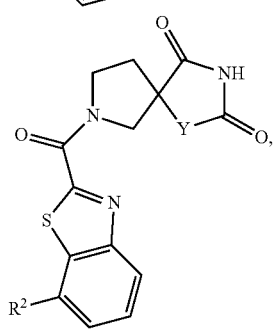
O,
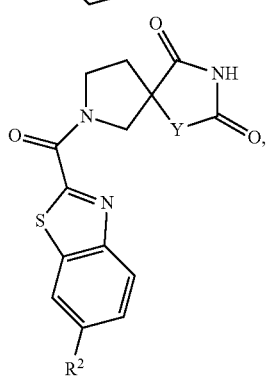
O,
-continued
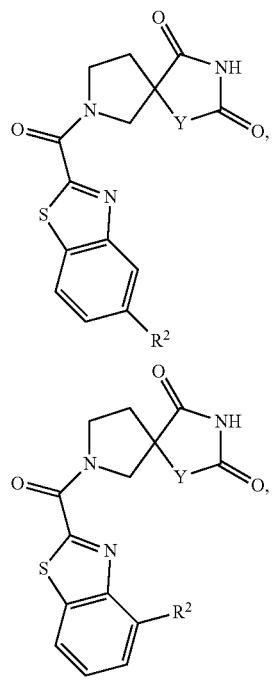
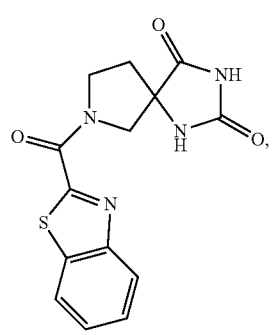
O,
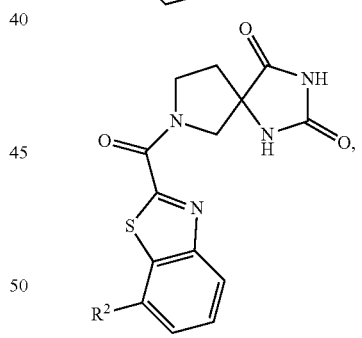
O,
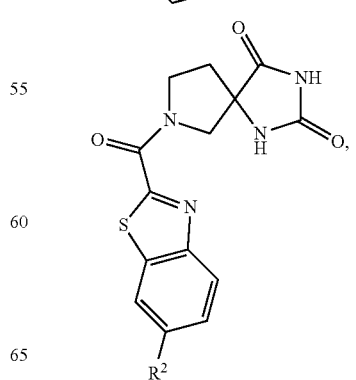
O,

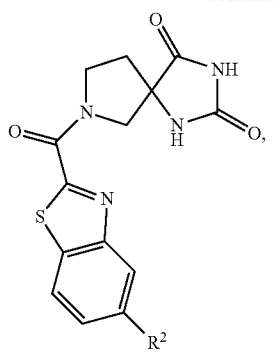
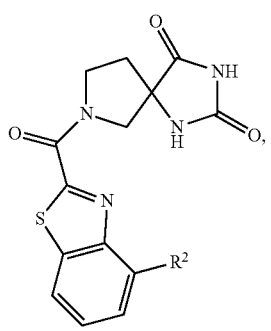
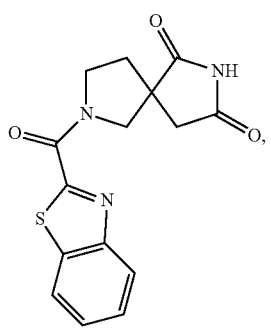
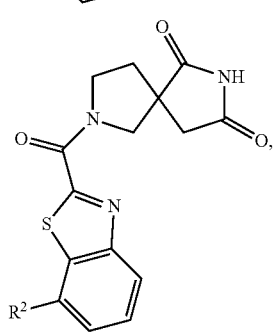
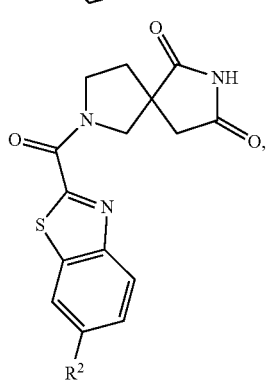
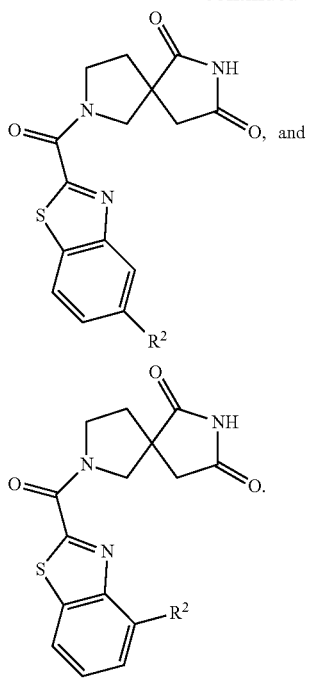
In another aspect, a compound is provided of Formula XI:
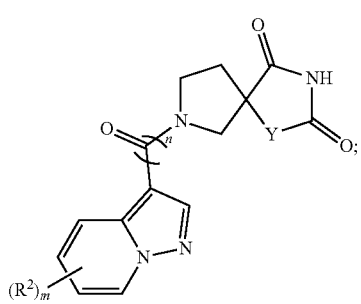
(XI)
or a pharmaceutically acceptable salt thereof;
wherein all variables are as defined herein.
In some embodiments of Formula XI, a compound is provided selected from:
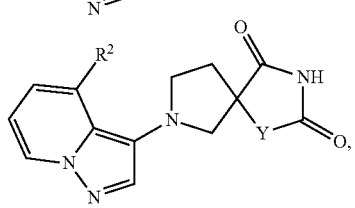

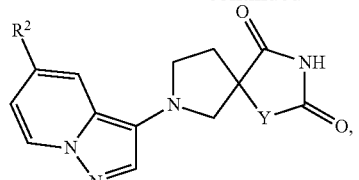
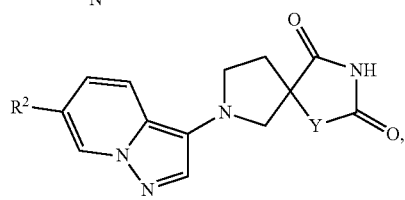
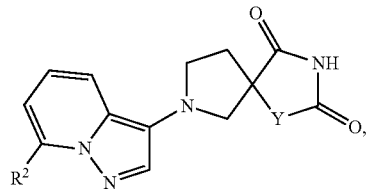
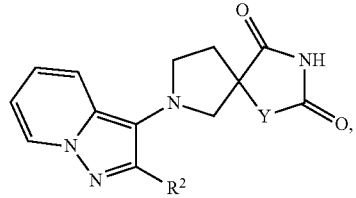
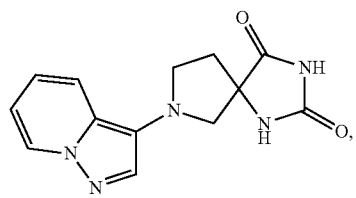
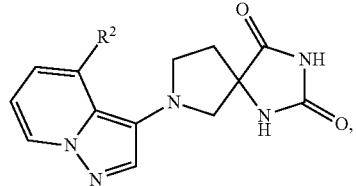
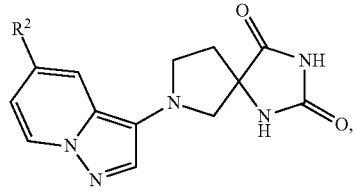
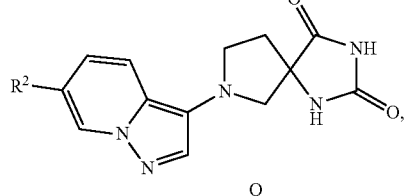
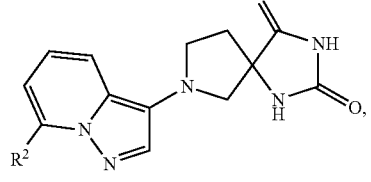
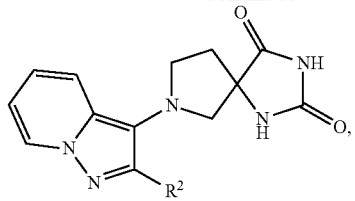
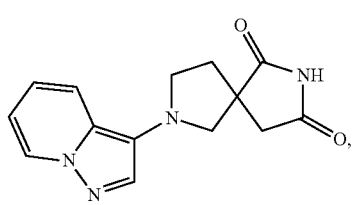
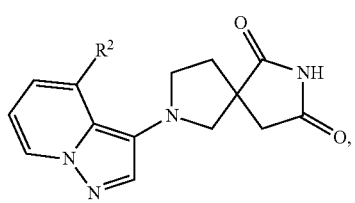
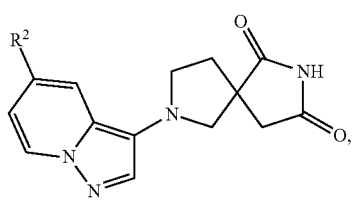
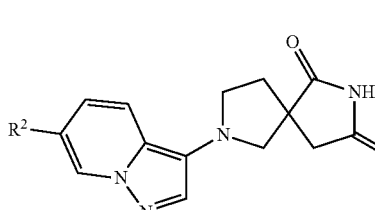
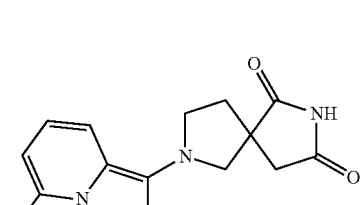
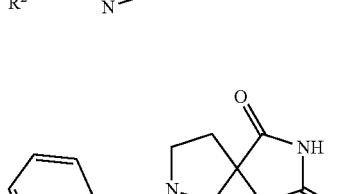
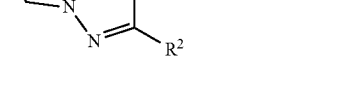

In some embodiments of Formula XI, a compound is provided selected from:
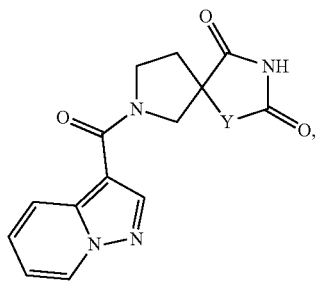
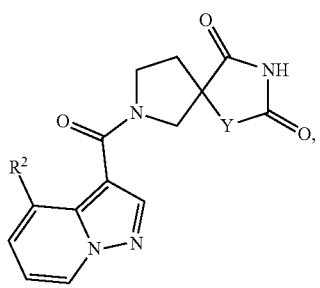
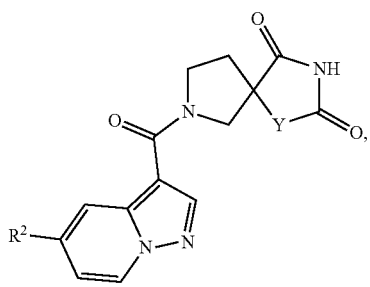
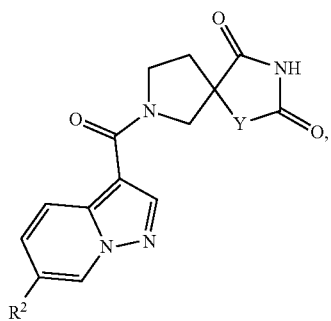
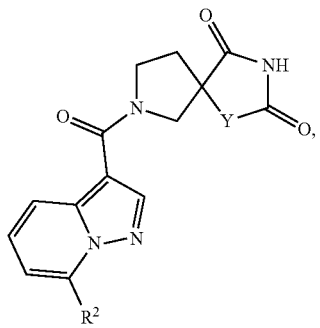
-continued
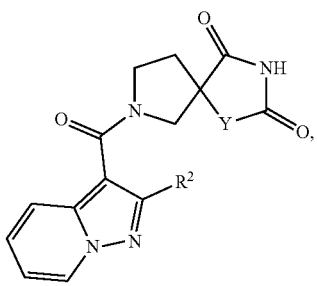
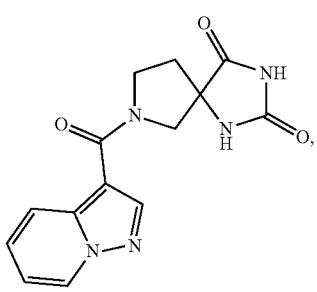
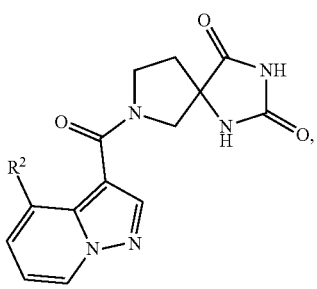
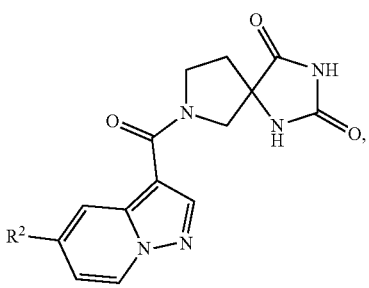
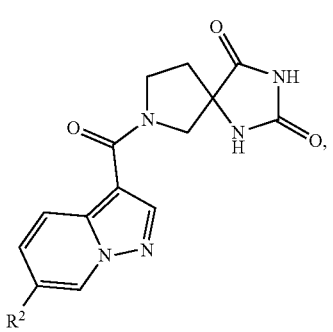

-continued
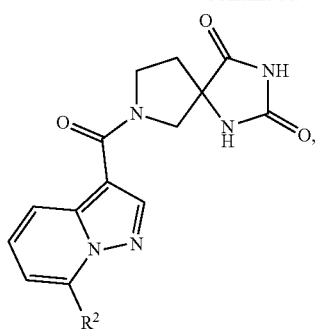
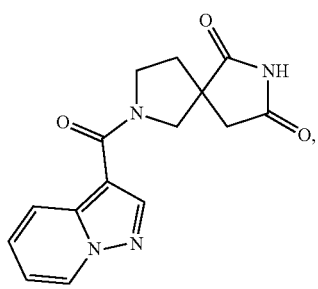
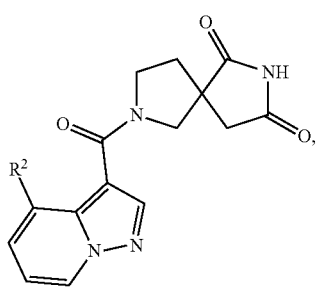
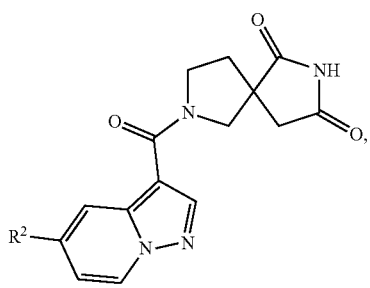
-continued
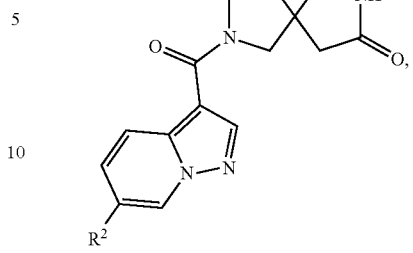
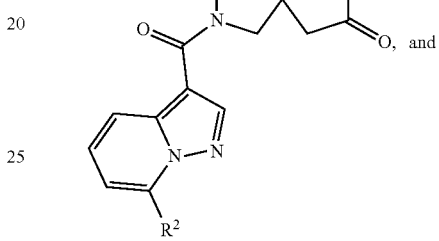
, and
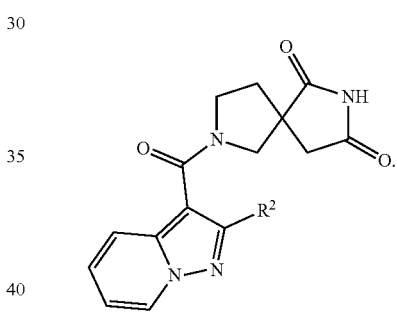
.
In another aspect, a compound is provided of Formula XII-a, XII-b, or XII-c:
(XII-a)
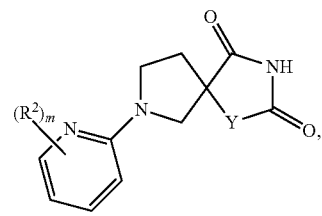
(XII-b)
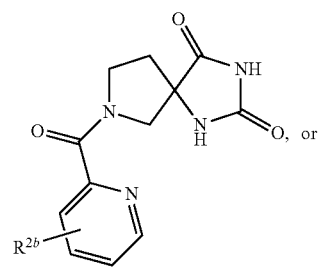
, or (XII-c)
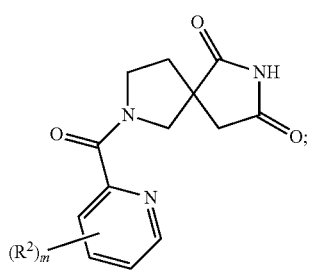
or a pharmaceutically acceptable salt thereof;
wherein all variables are as defined herein.
In some embodiments of Formula XII-a, a compound is provided selected from:
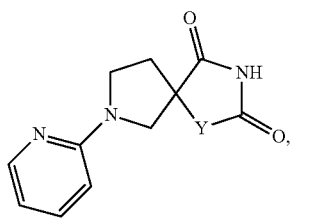
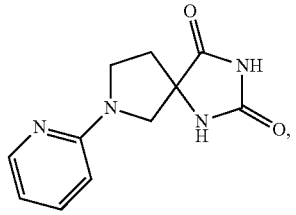
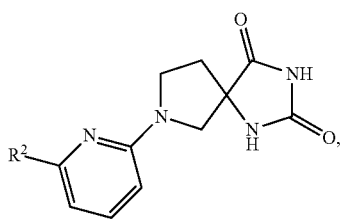
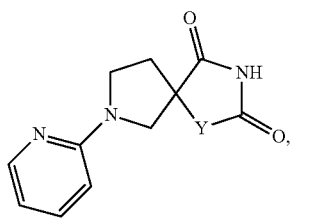
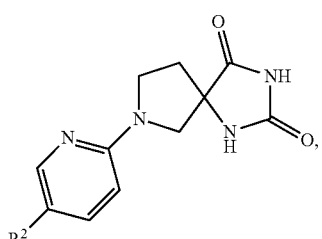
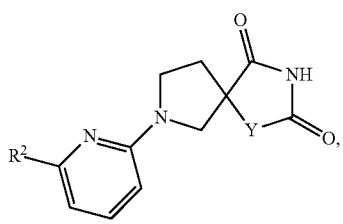
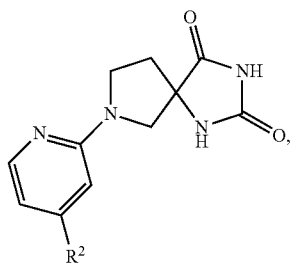
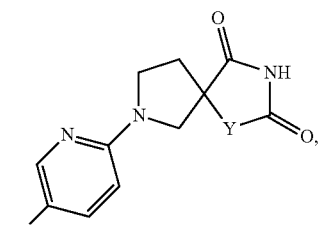
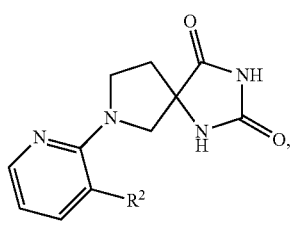
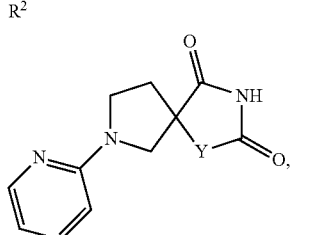
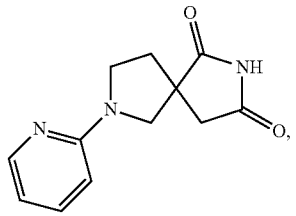
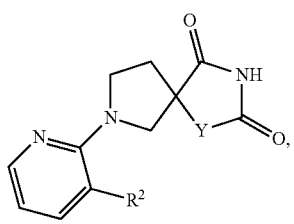
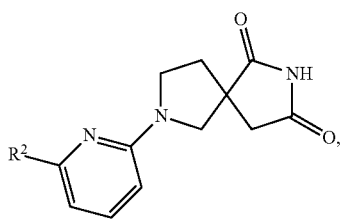

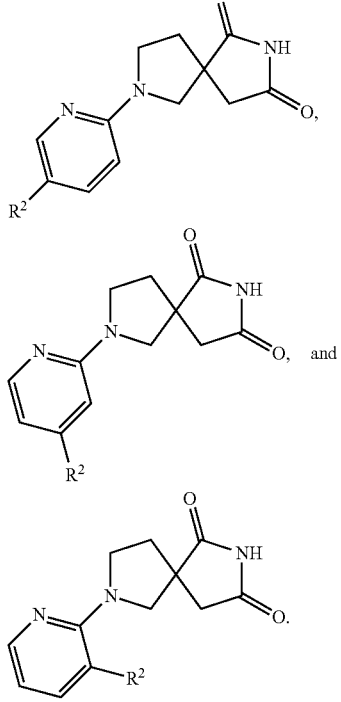
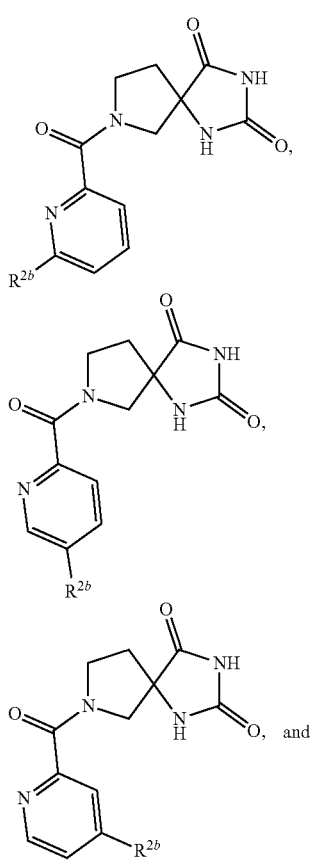
In some embodiments of Formula XII-b, a compound is provided selected from:
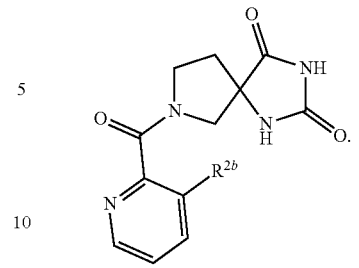
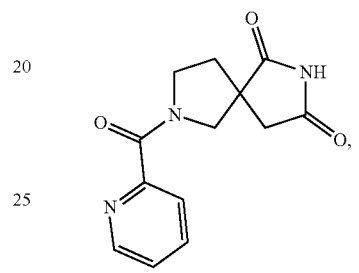
In some embodiments of Formula XII-c, a compound is provided selected from:
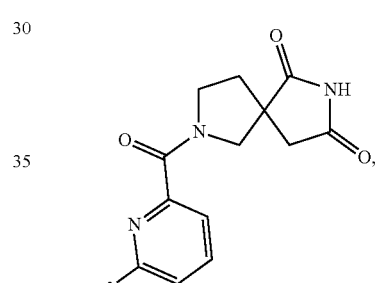
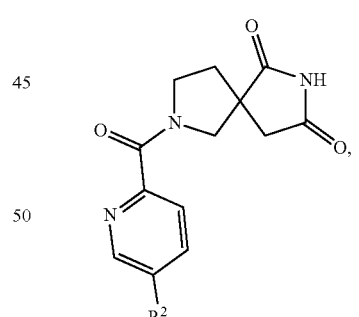
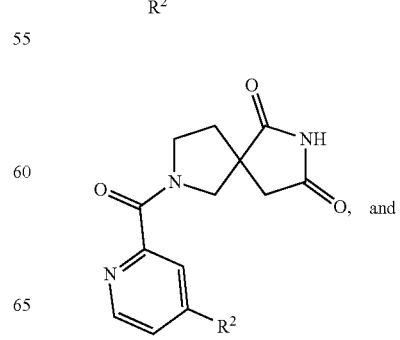

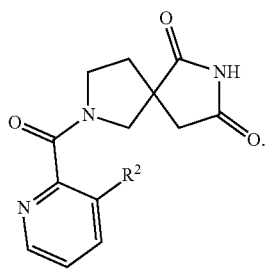
In another aspect, a compound is provided of Formula XIII:
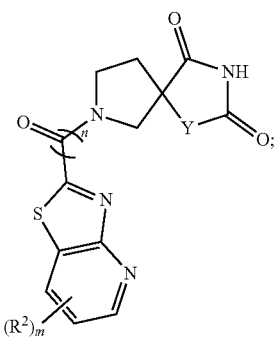
(XIII)
or a pharmaceutically acceptable salt thereof;
wherein all variables are as defined herein.
In some embodiments of Formula XIII, a compound is provided selected from:
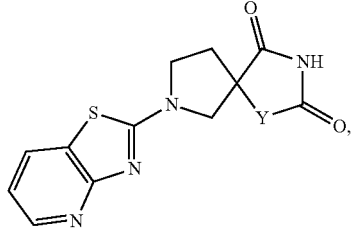
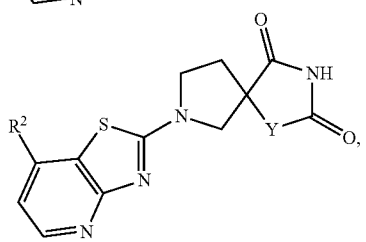
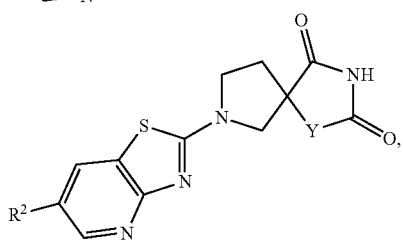
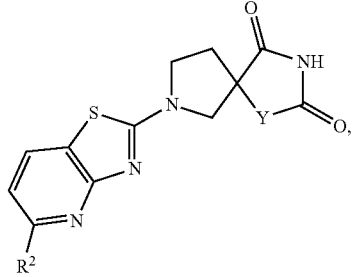
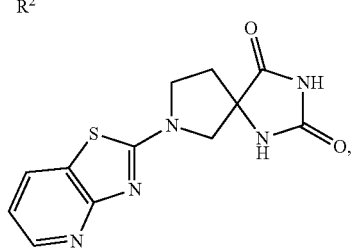
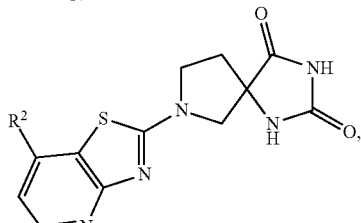
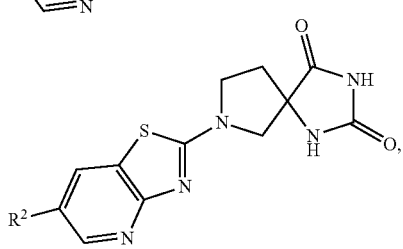
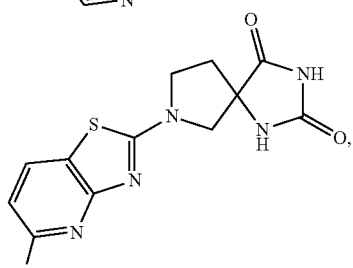
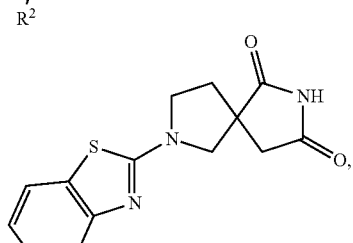
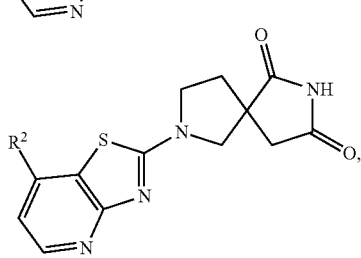

-continued
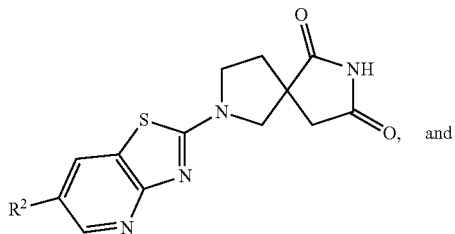
and
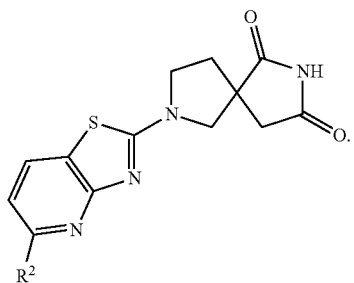
In some embodiments of Formula XIII, a compound is provided selected from:
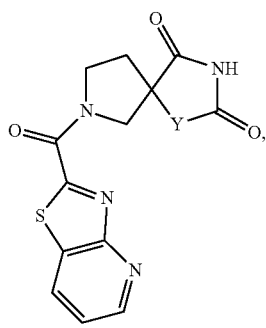
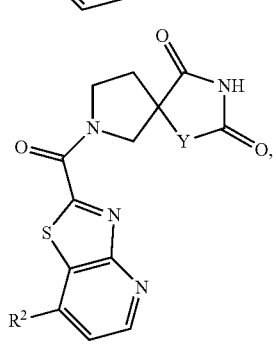
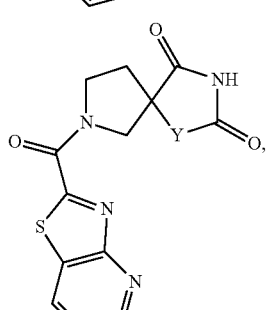
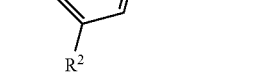
-continued
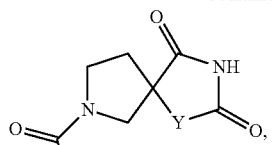
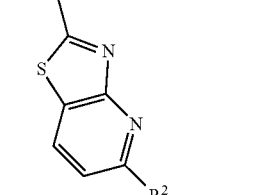
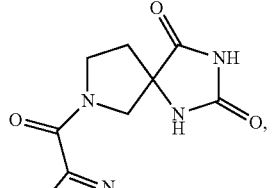
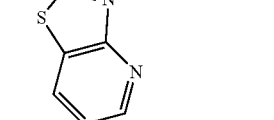
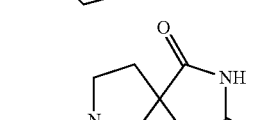
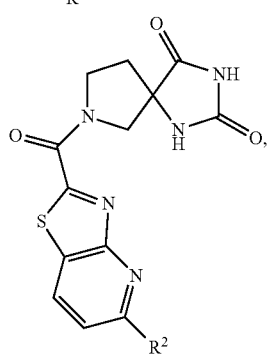

-continued
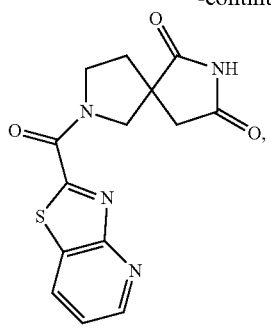
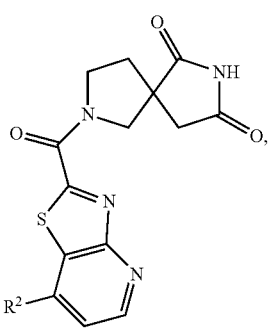
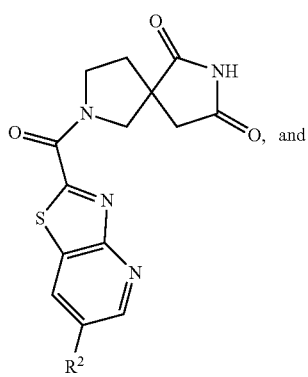
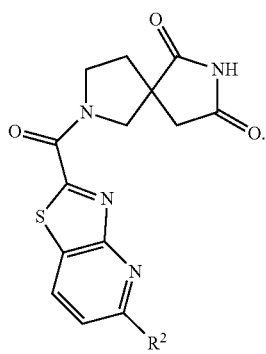
In another aspect, a compound is provided of Formula XIV:
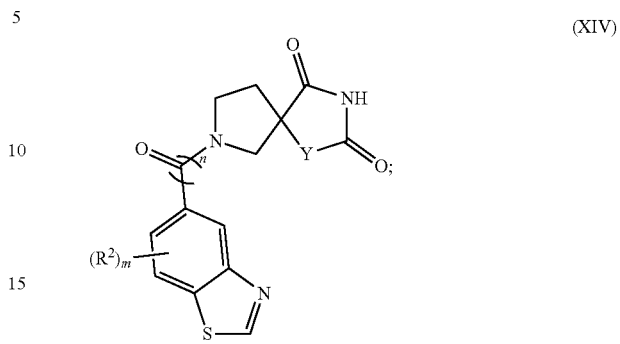
(XIV)
or a pharmaceutically acceptable salt thereof;
wherein all variables are as defined herein.
In some embodiments, a compound is provided selected from:
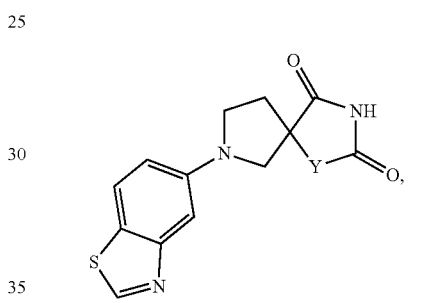
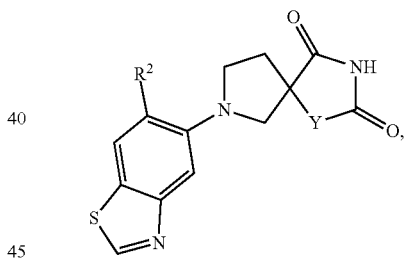
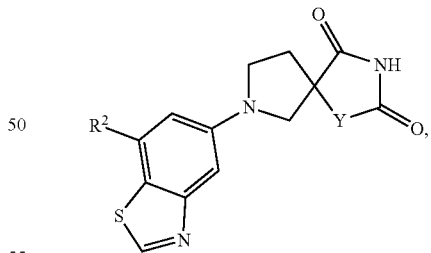
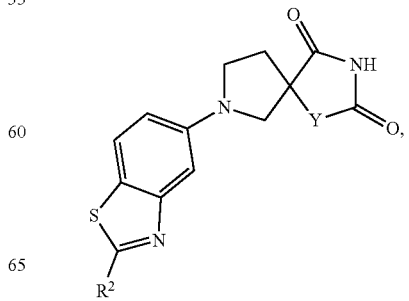

-continued
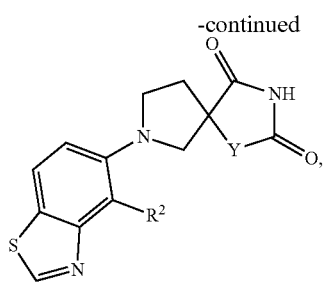
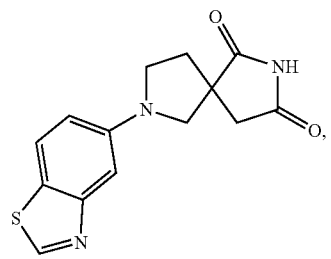
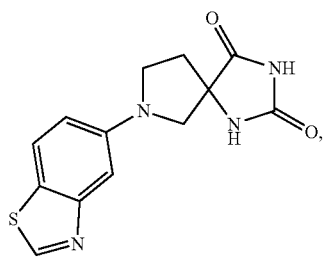
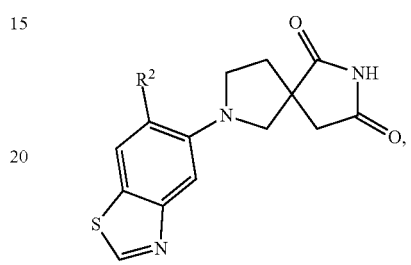
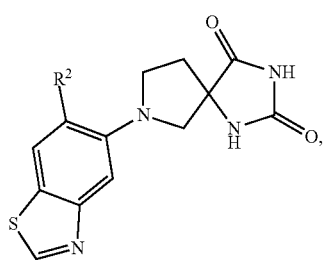
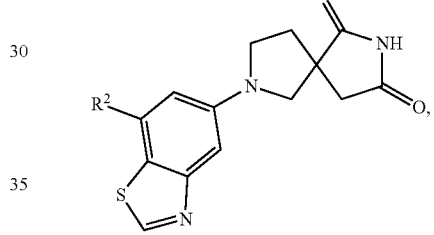
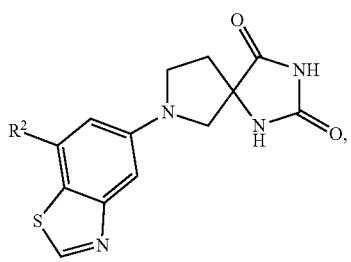
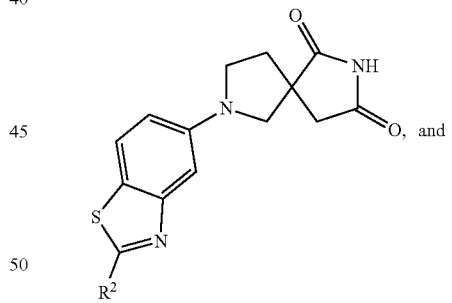
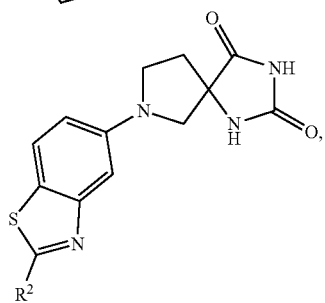
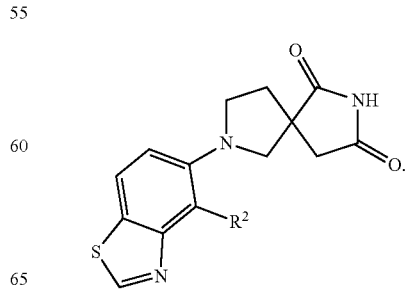

In some embodiments of Formula XIV, a compound is provided selected from:
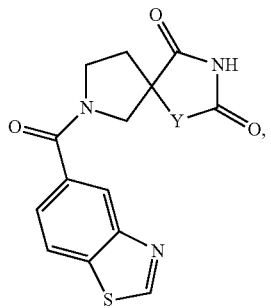
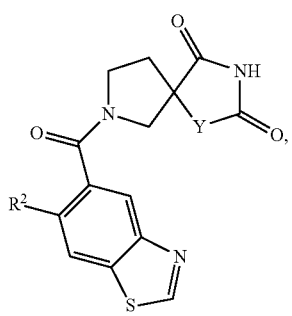
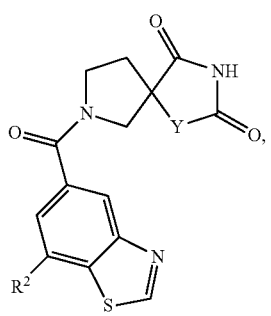
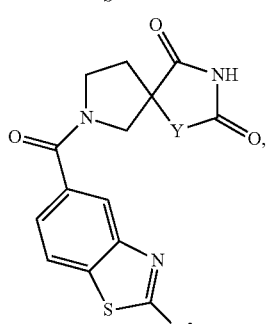
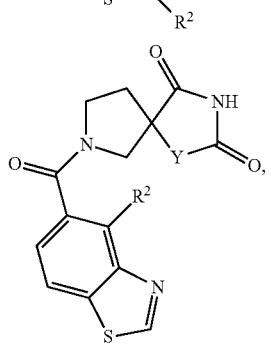
-continued
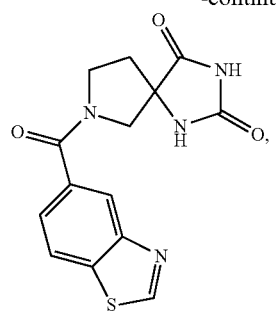
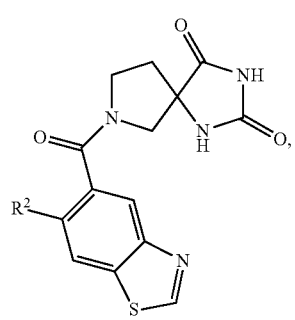
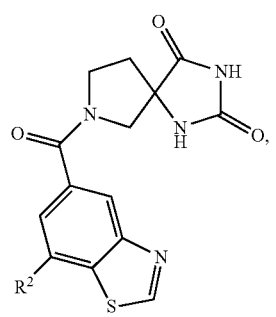
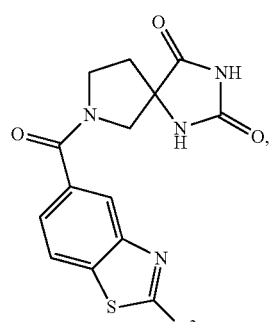
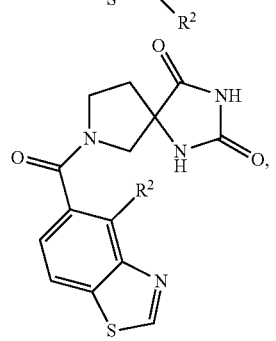

-continued

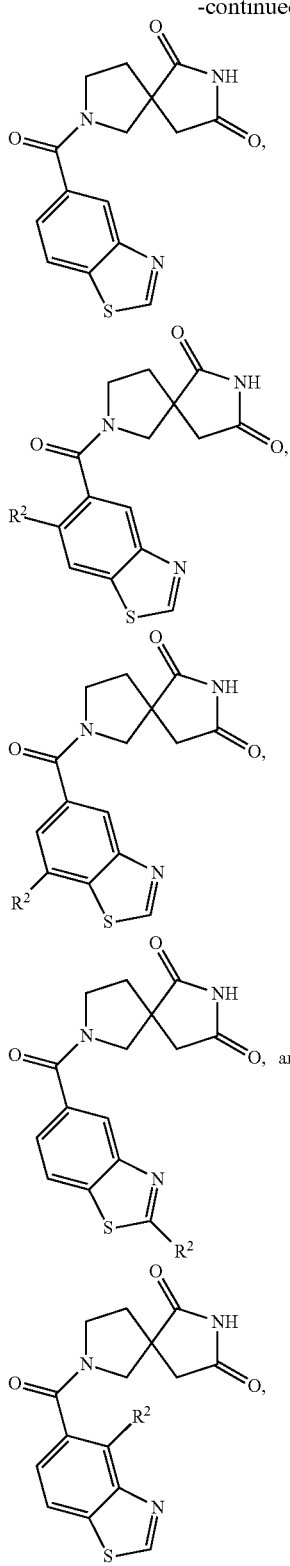

Compounds of Formula XV

In another aspect, the use of a compound of Formula XV, or a pharmaceutically acceptable salt thereof, for the treatment of a therapeutic condition which can be treated by modulating the function or activity of the cereblon containing E3 Ubiquitin Ligase Complex is provided:

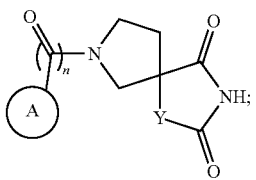

(XV)

wherein all variables are as defined herein.

In some embodiments, the compound of Formula XV for use in the methods described herein is selected from:

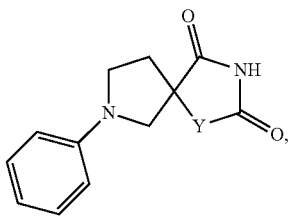

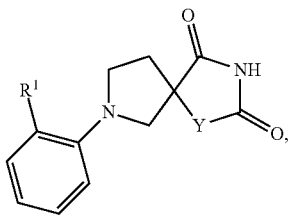

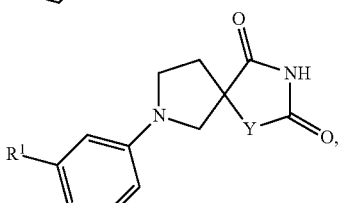

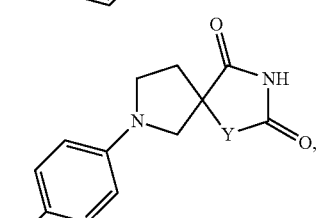

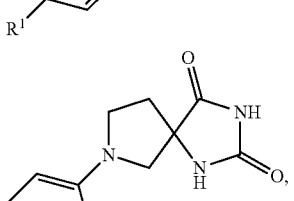

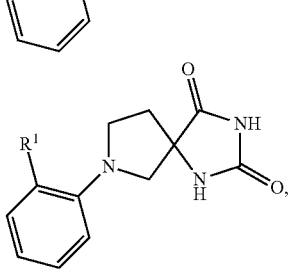

-continued
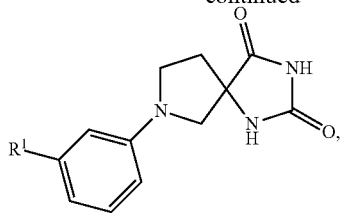
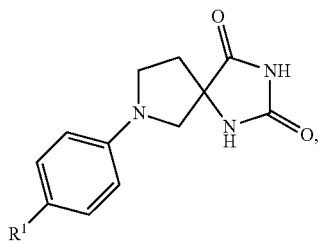
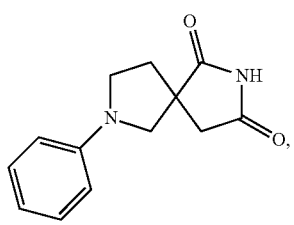
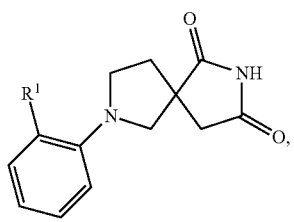
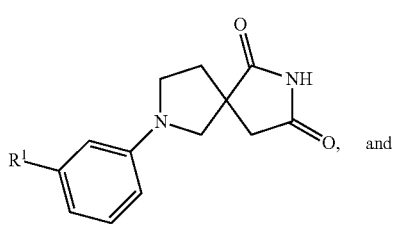 and
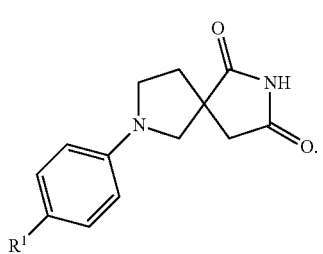
In some embodiments, the compound of Formula XV for use in the methods described herein is selected from:
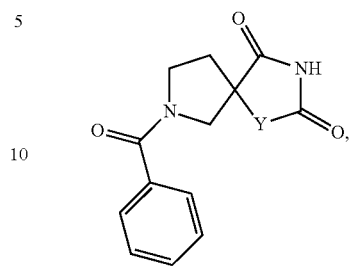
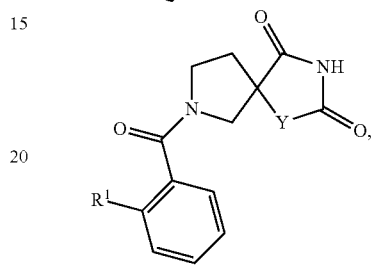
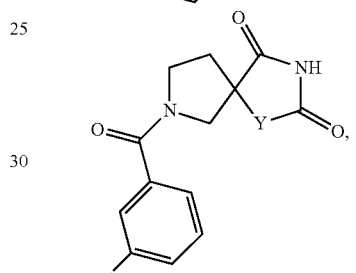
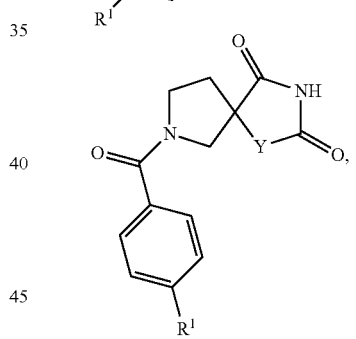
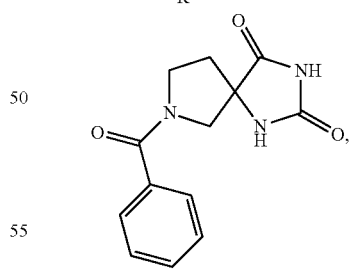
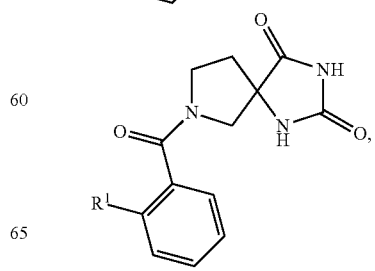

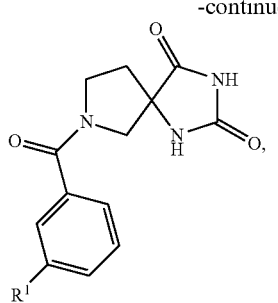
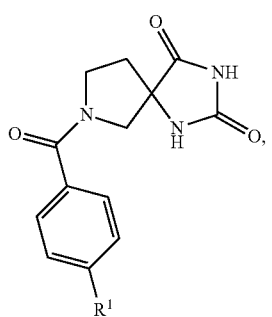
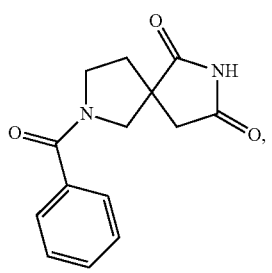
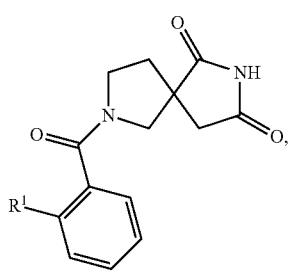
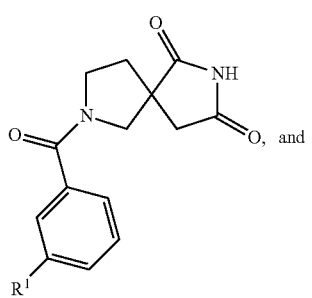
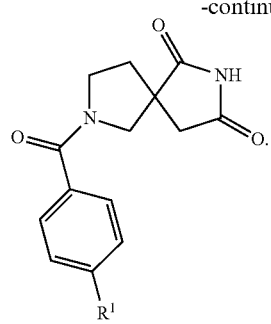
In some embodiments, the compound of Formula XV for use in the methods described herein is selected from:
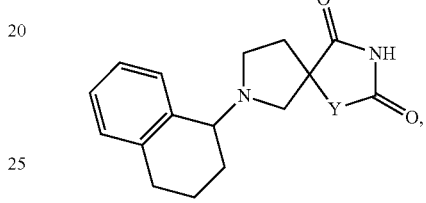
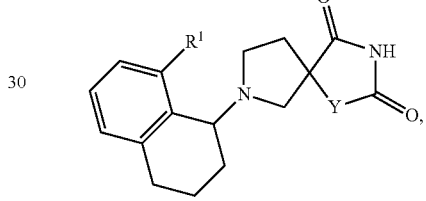
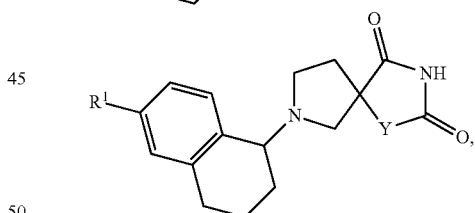
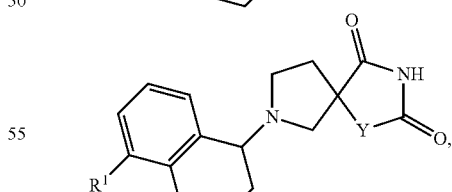
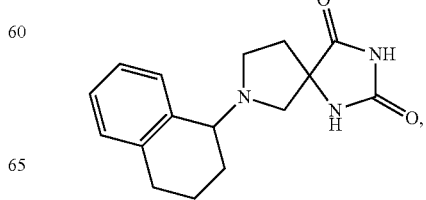

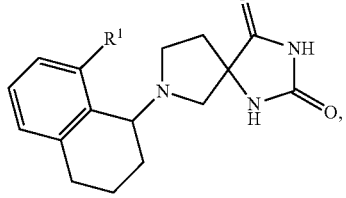
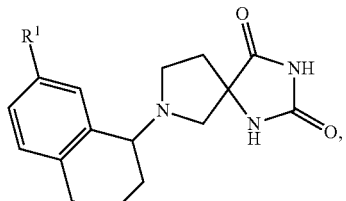
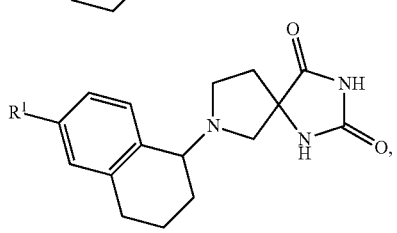
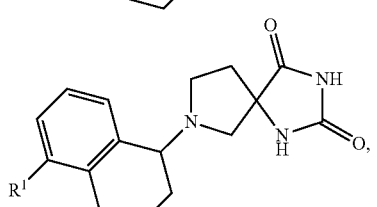
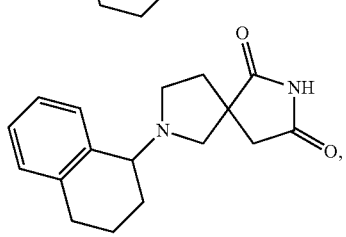
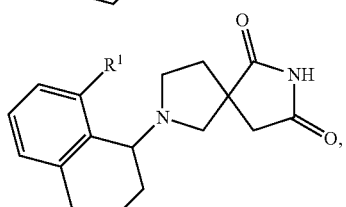
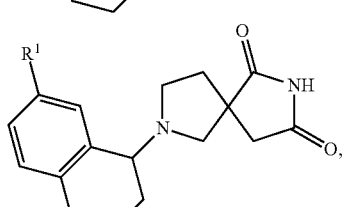
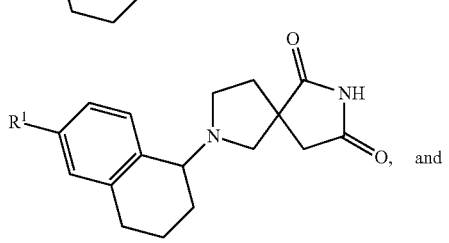
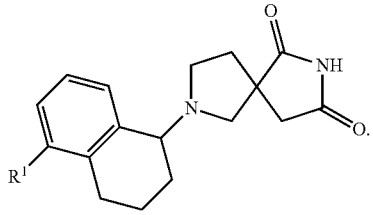
In some embodiments, the compound of Formula XV for use in the methods described herein is selected from:
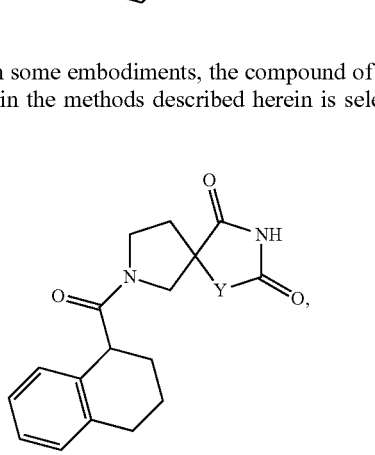
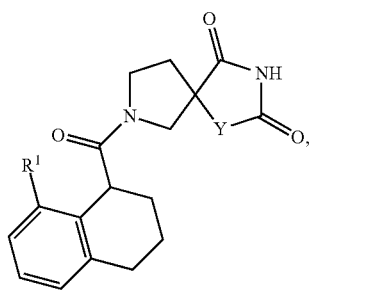
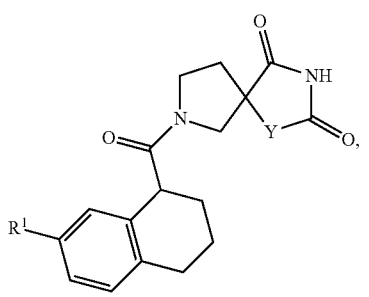
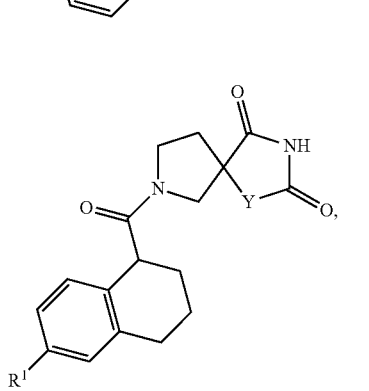

97
-continued
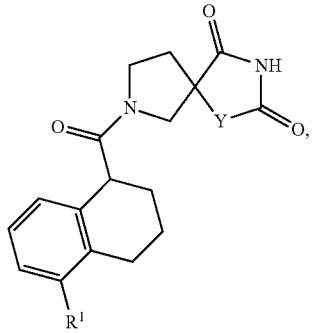
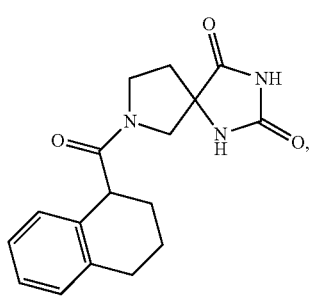
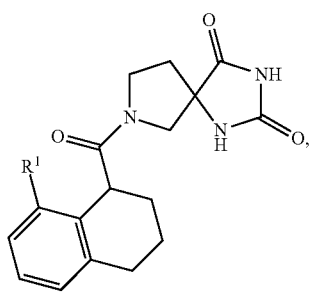
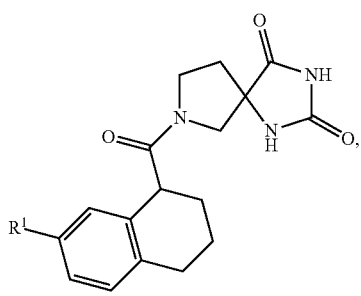
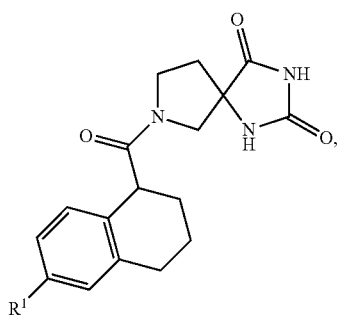
98
-continued
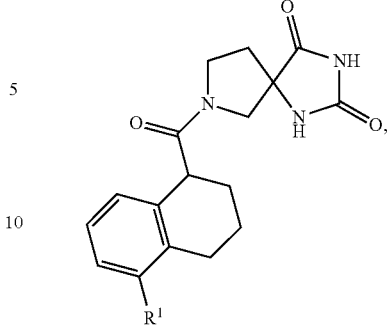
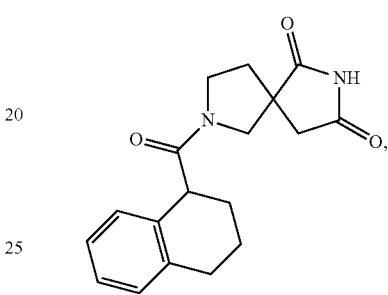
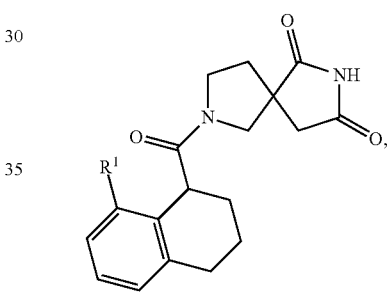
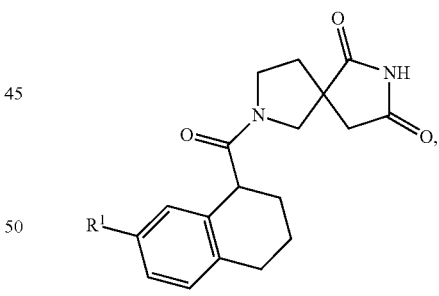
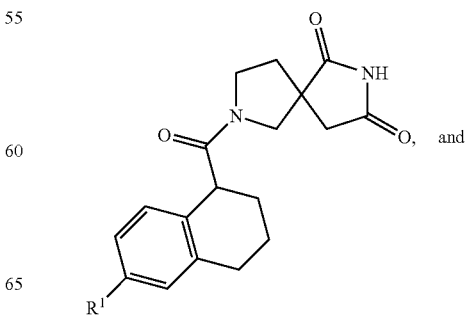, and

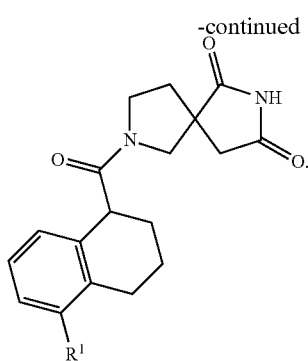
In some embodiments, the compound of Formula XV for use in the methods described herein is selected from:
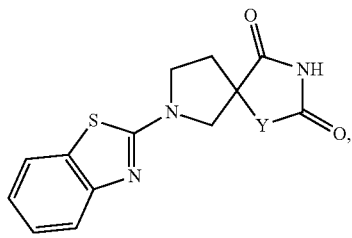
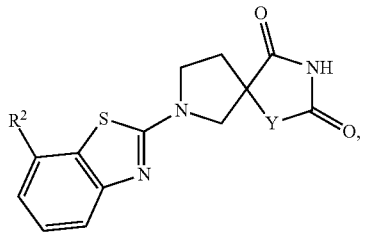
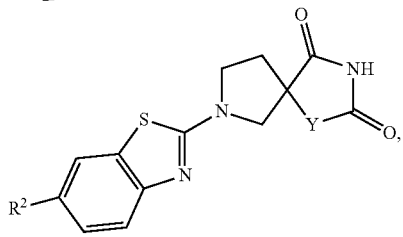
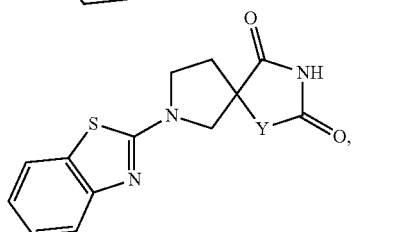
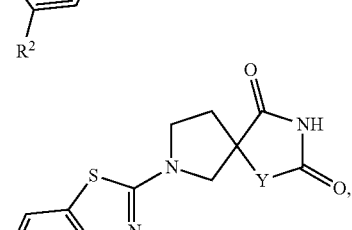
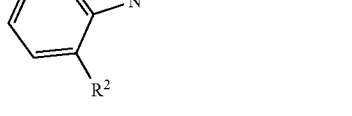
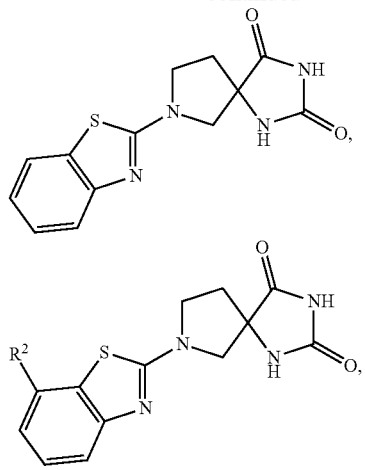
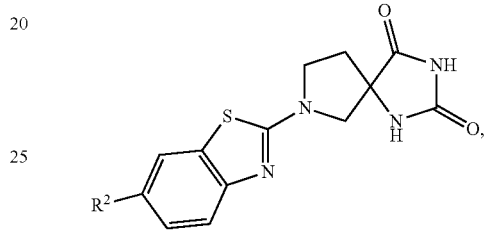
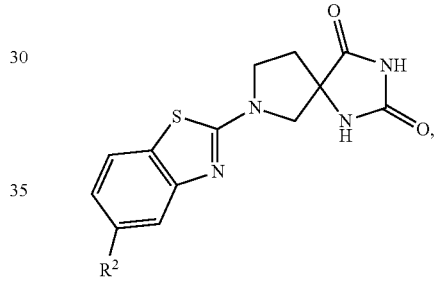
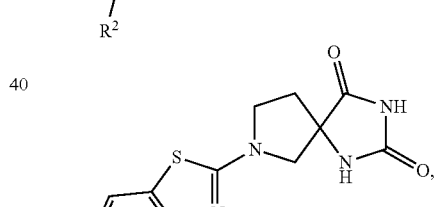
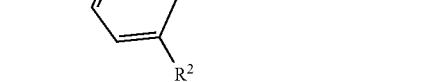
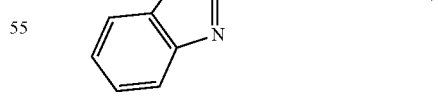
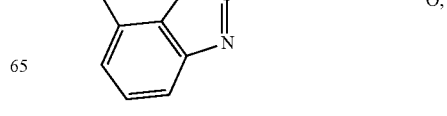

-continued
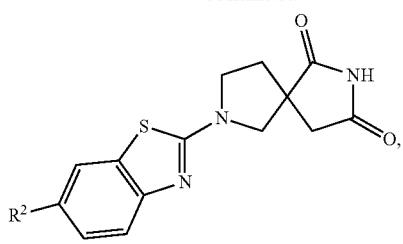
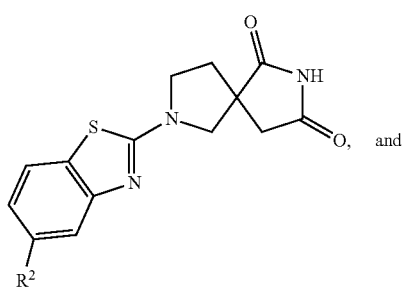
and
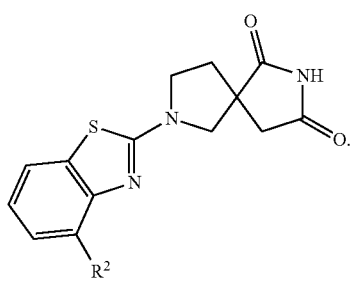
In some embodiments, the compound of Formula XV for use in the methods described herein is selected from:
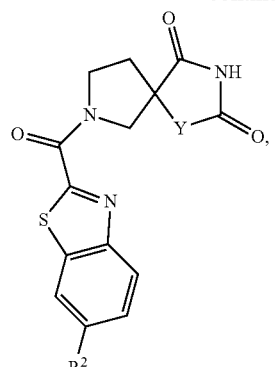
-continued
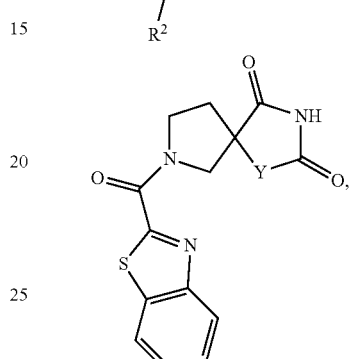
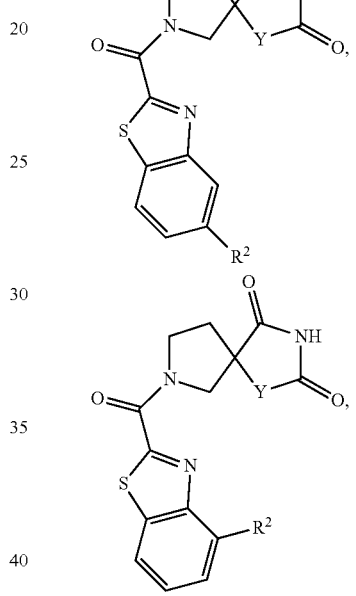

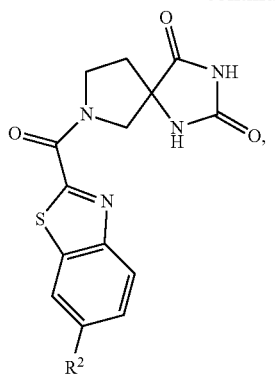
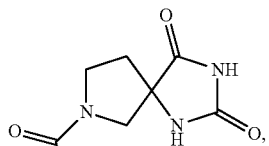
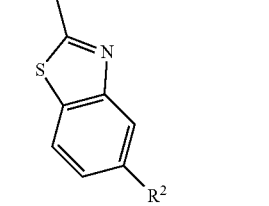
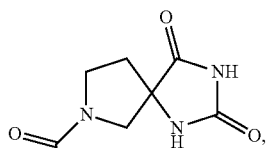
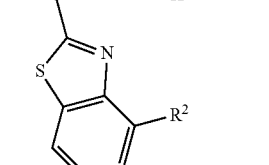
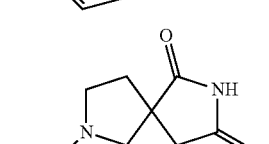
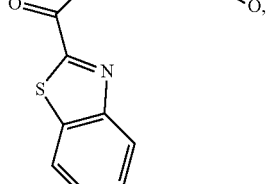
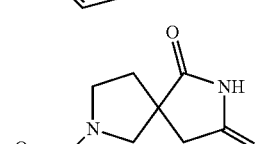
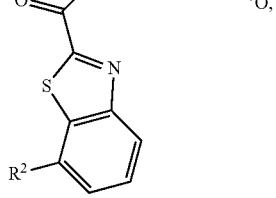
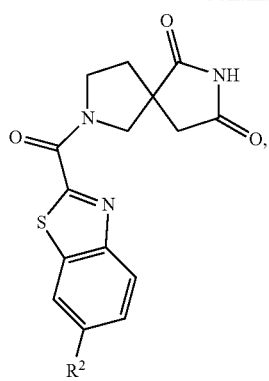
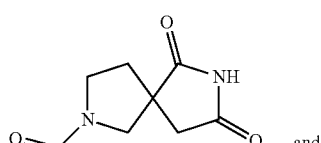
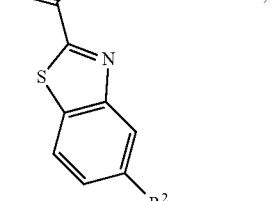
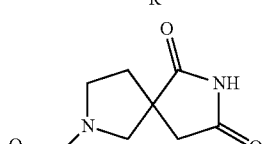
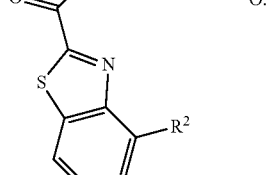
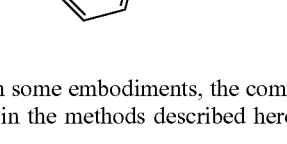
In some embodiments, the compound of Formula XV for use in the methods described herein is selected from:
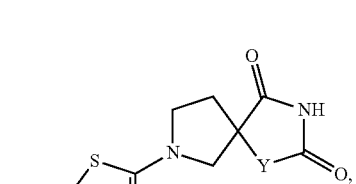
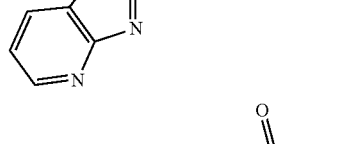
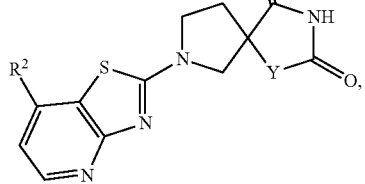

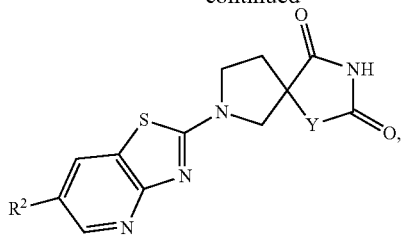
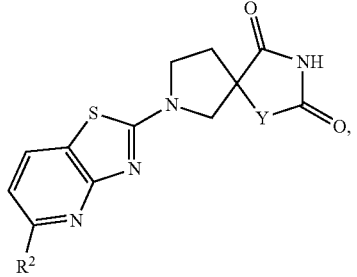
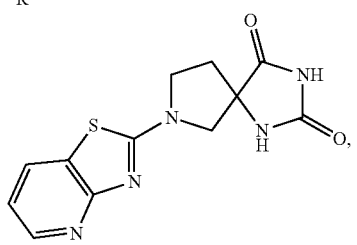
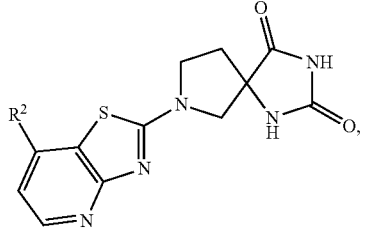
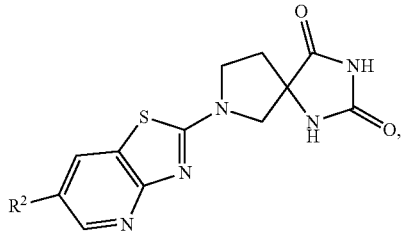
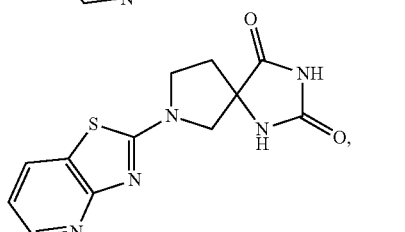
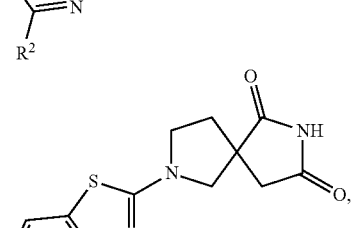
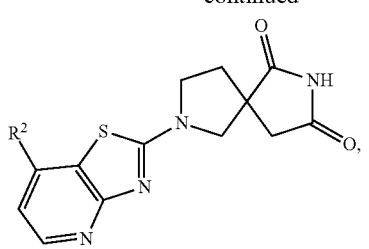
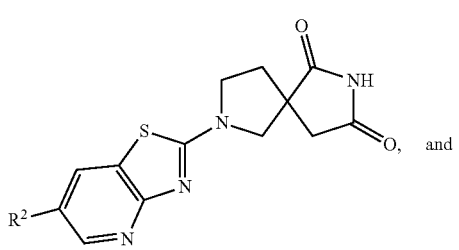
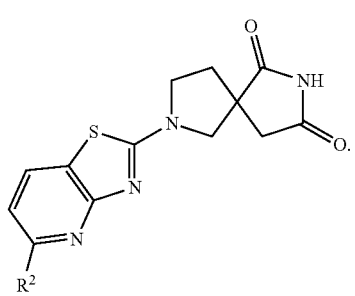
In some embodiments, the compound of Formula XV for use in the methods described herein is selected from:
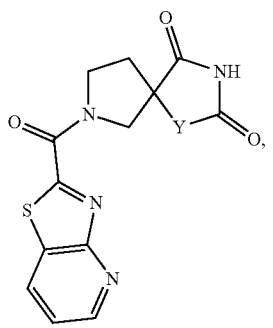
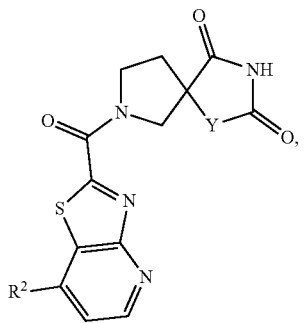

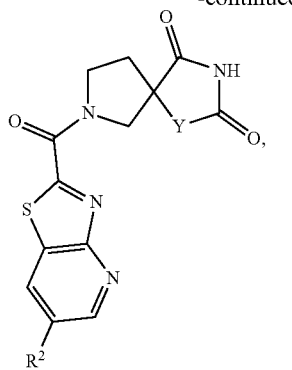
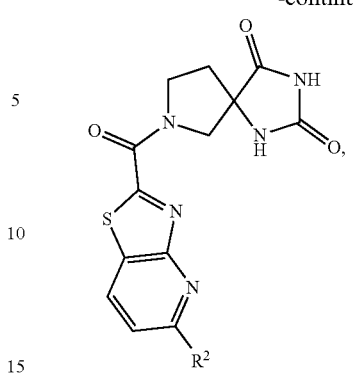
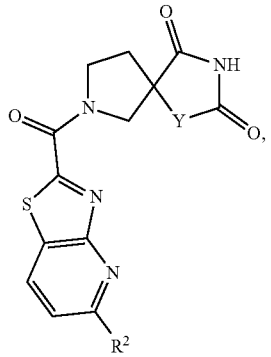
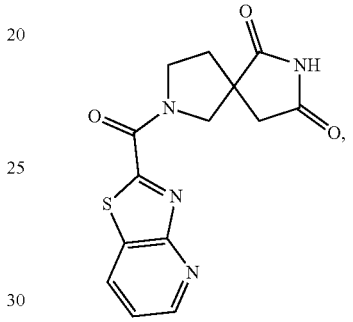
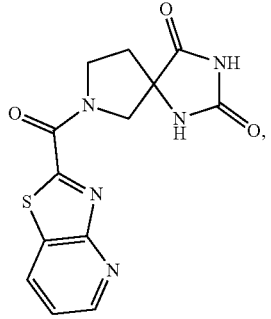
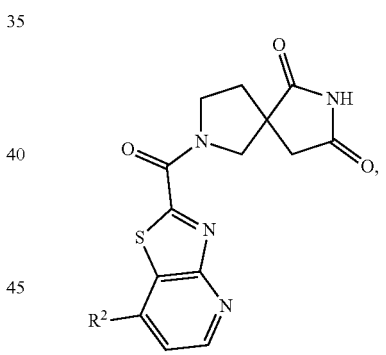
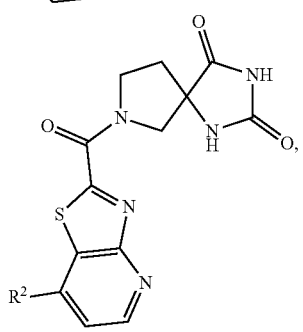
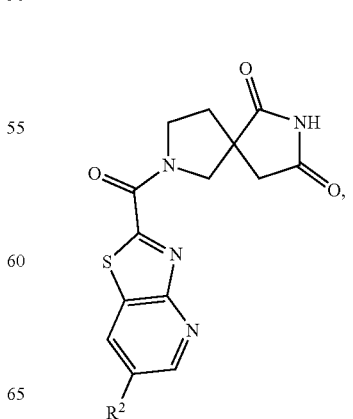
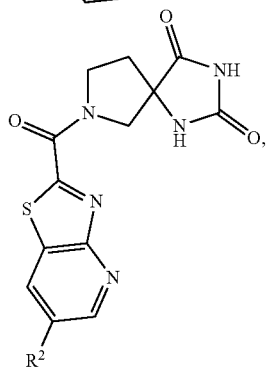

109
-continued
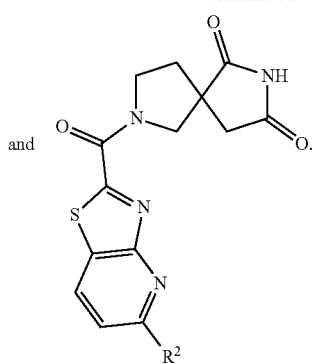
and
In some embodiments, the compound of Formula XV for use in the methods described herein is selected from:
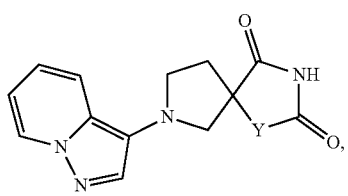
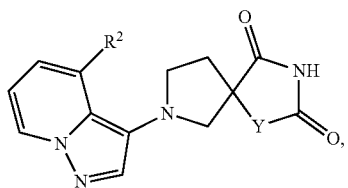
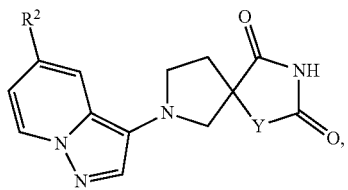
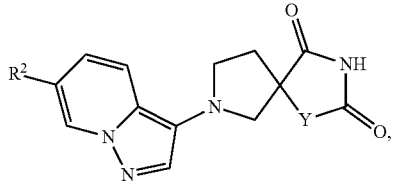
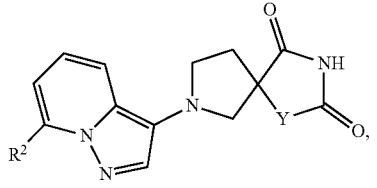
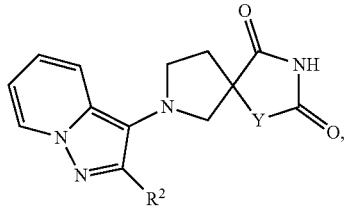
110
-continued
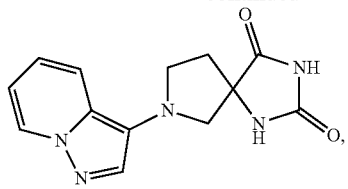
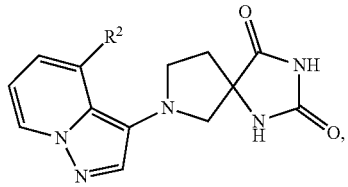
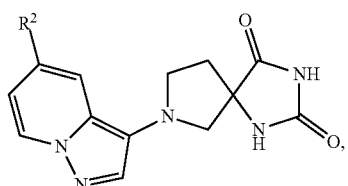
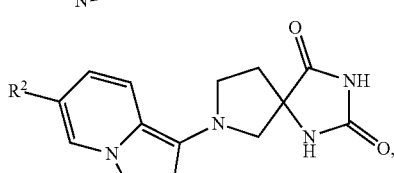
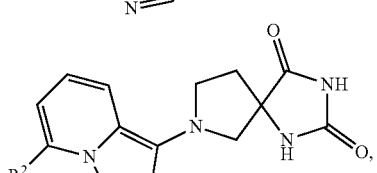
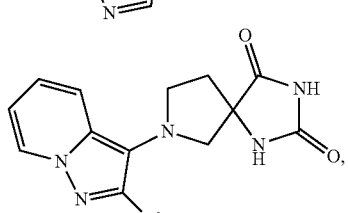
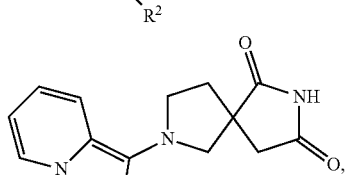
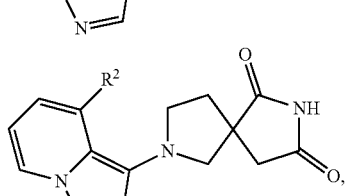
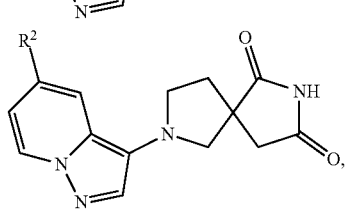

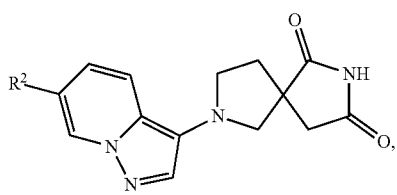
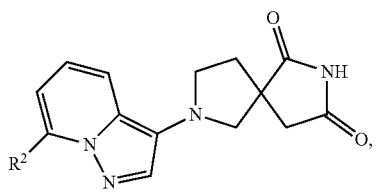
and 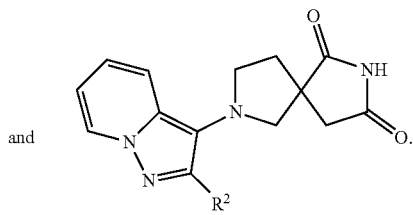
In some embodiments, the compound of Formula XV for use in the methods described herein is selected from:
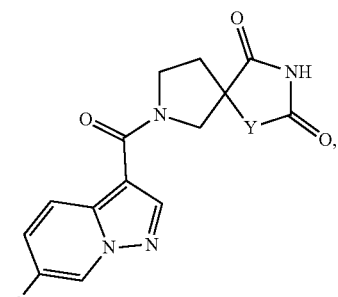
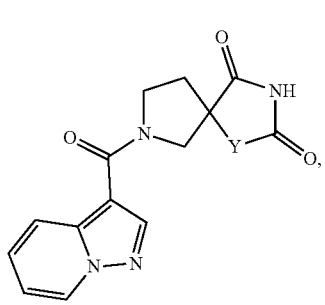
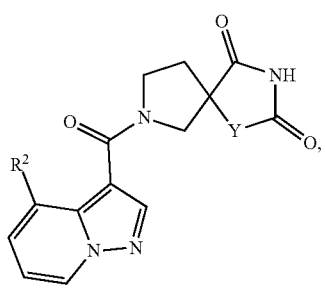
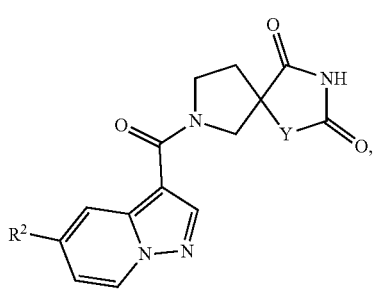
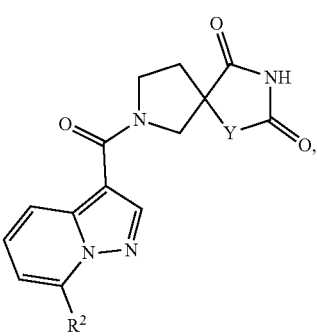
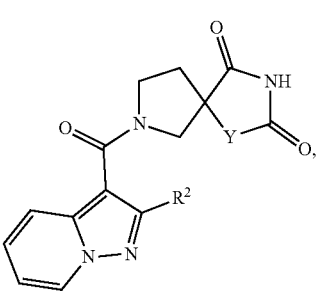
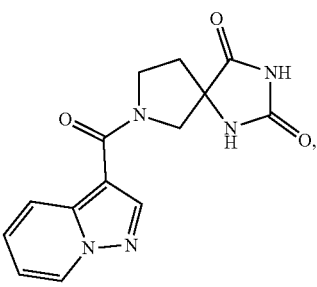
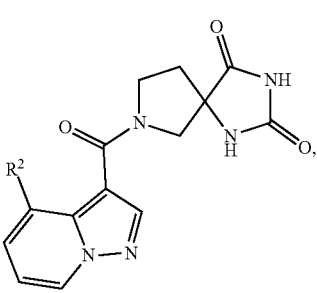

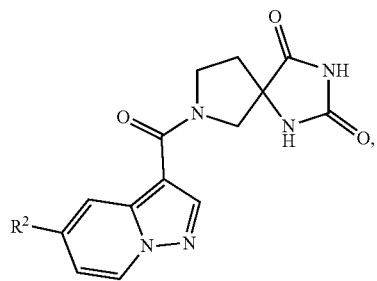
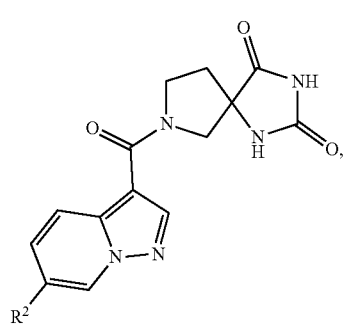
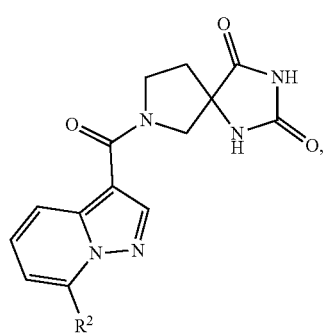
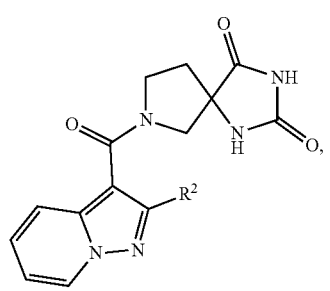
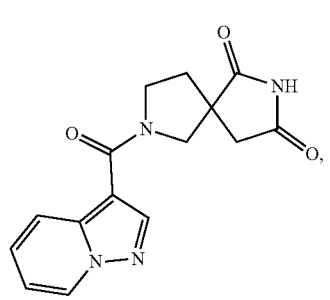
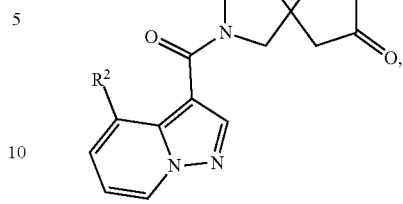
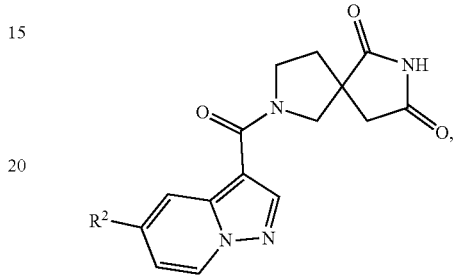
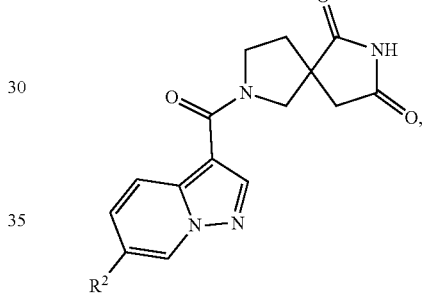
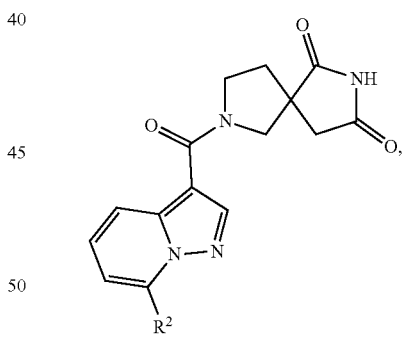
and
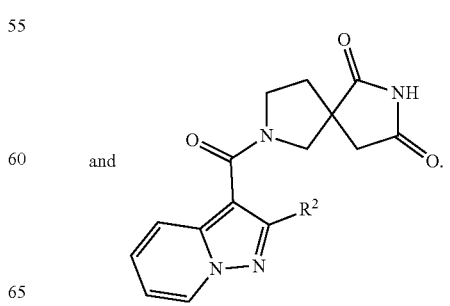

In some embodiments, the compound of Formula XV for use in the methods described herein is selected from:
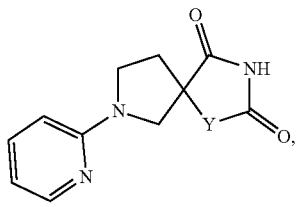
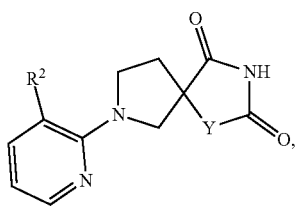
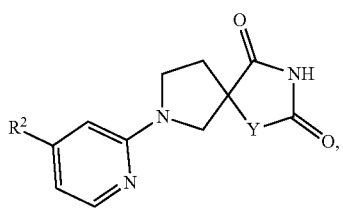
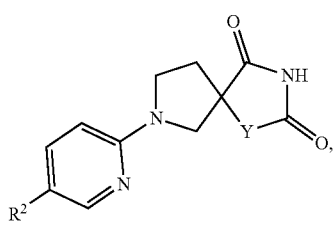
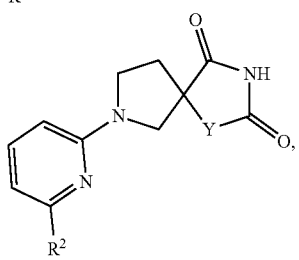
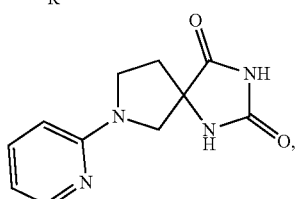
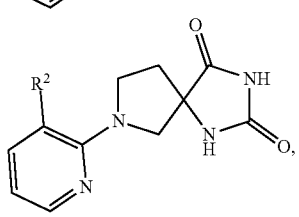
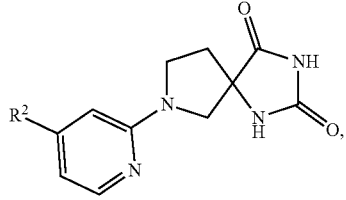
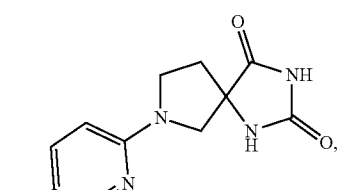
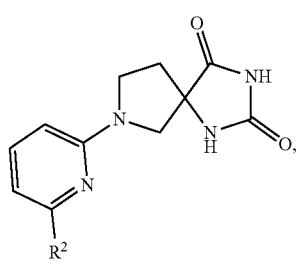
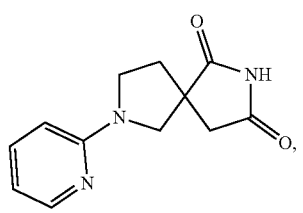
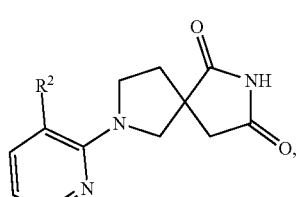
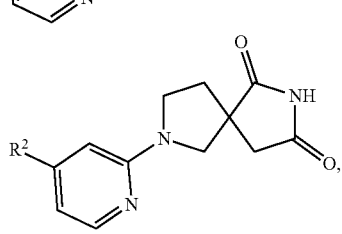
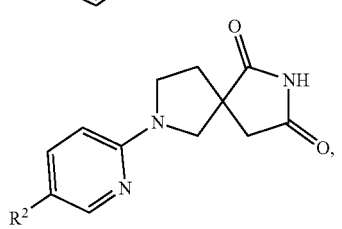

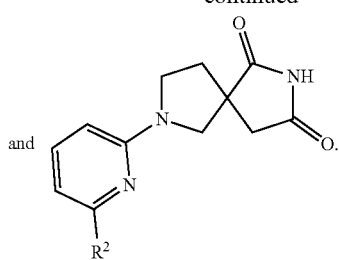
and
In some embodiments, the compound of Formula XV for use in the methods described herein is selected from:
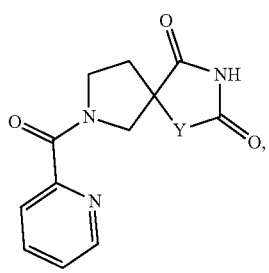
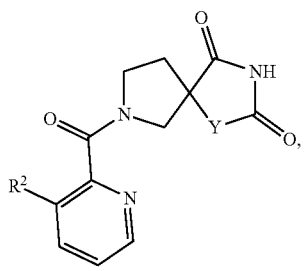
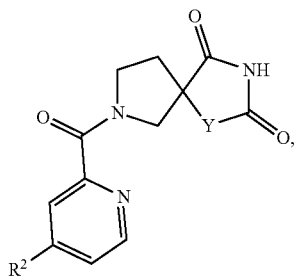
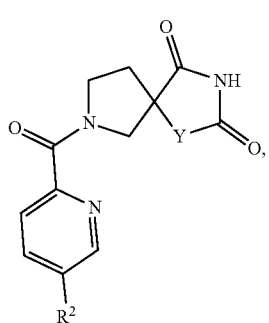
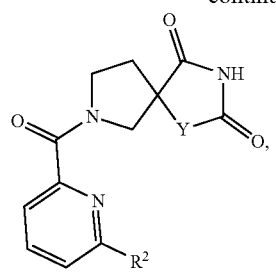
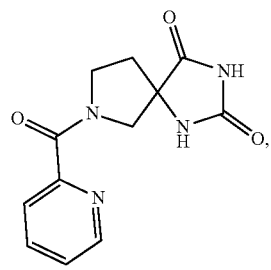
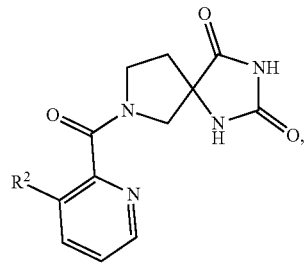
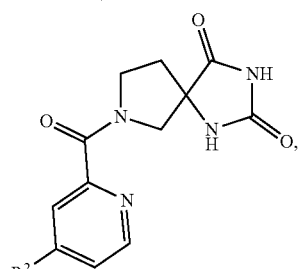
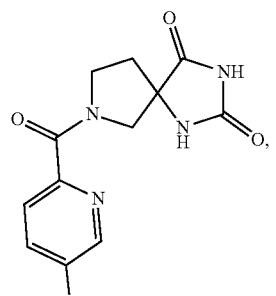
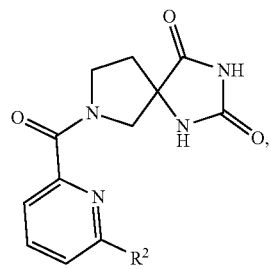

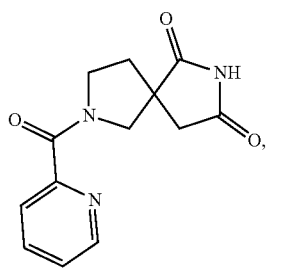
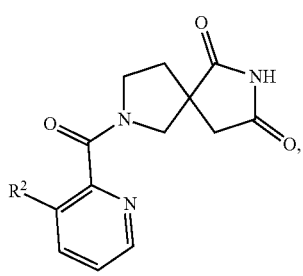
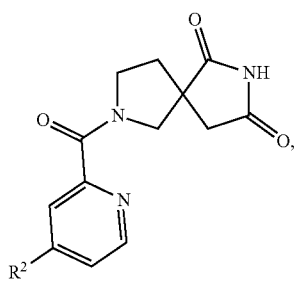
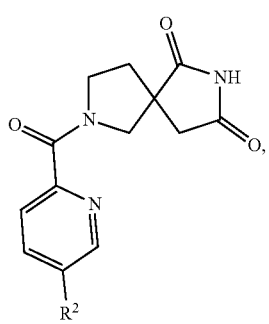
and
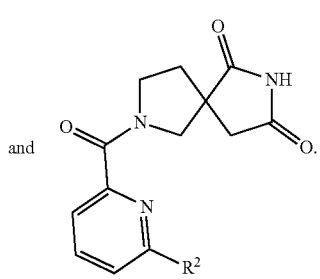
In some embodiments, the compound of Formula XV for use in the methods described herein is selected from:
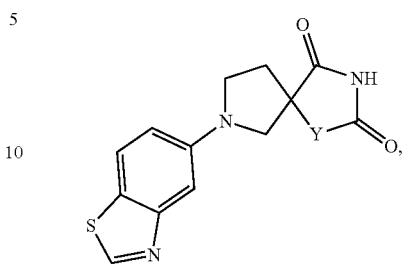
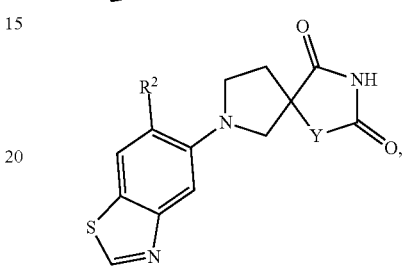
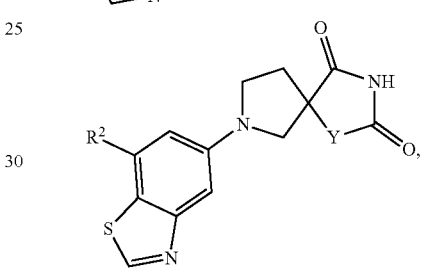
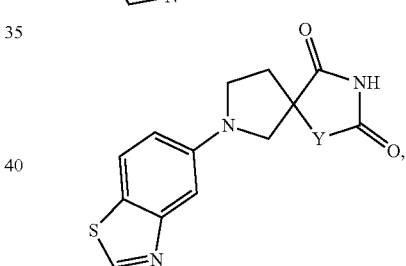
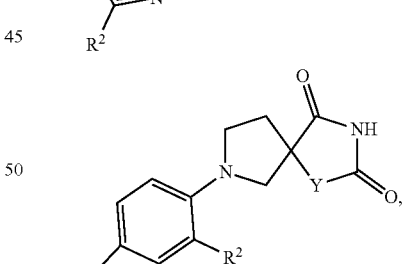
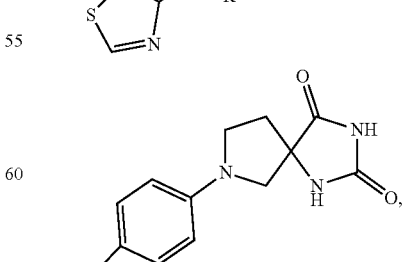

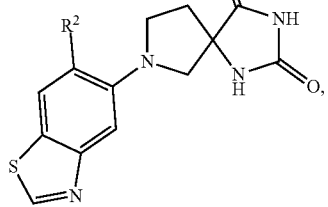
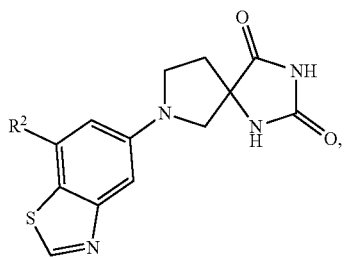
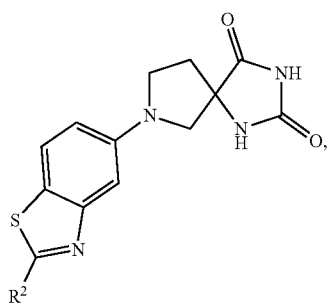
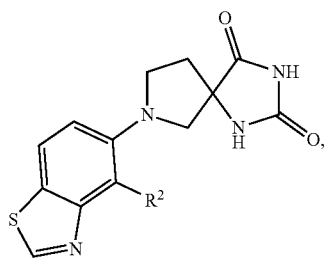
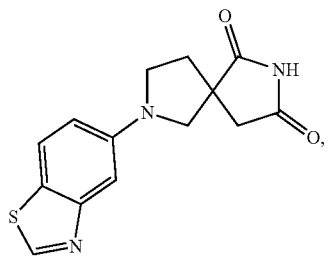
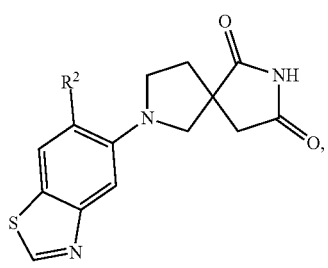
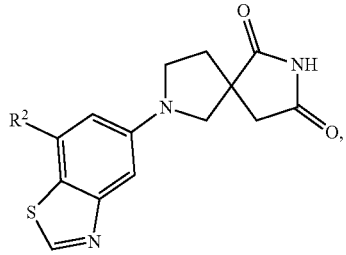
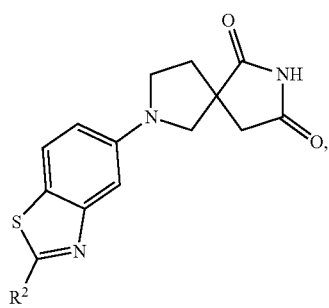
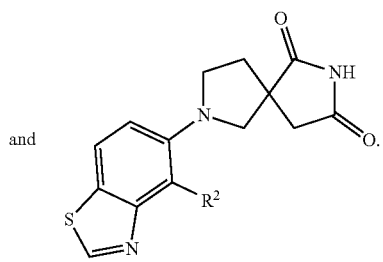
and 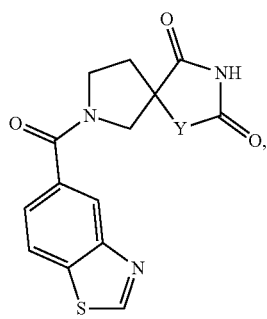
In some embodiments, the compound of Formula XV for use in the methods described herein is selected from:
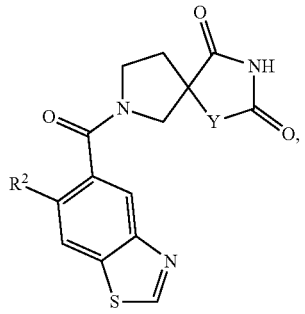

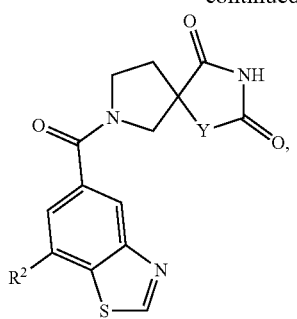
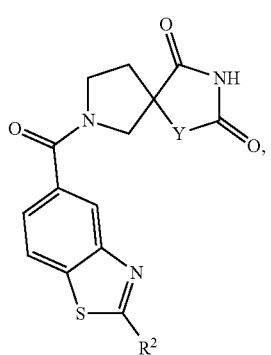
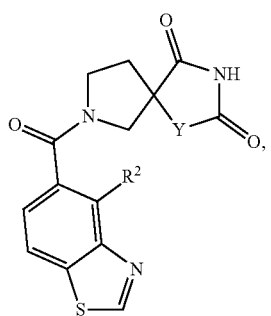
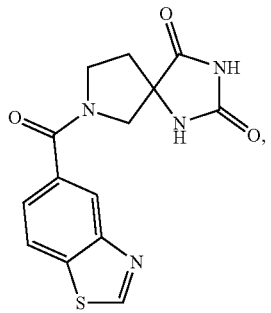
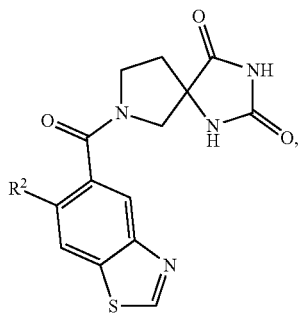
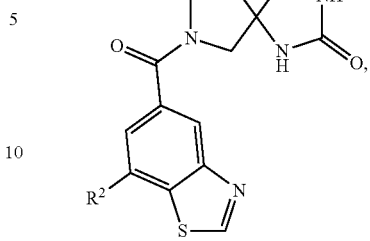
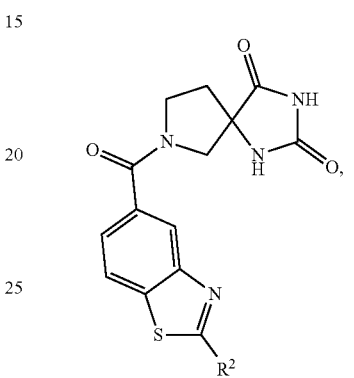
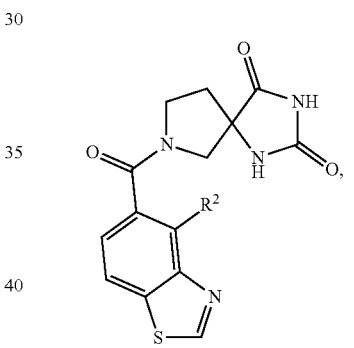
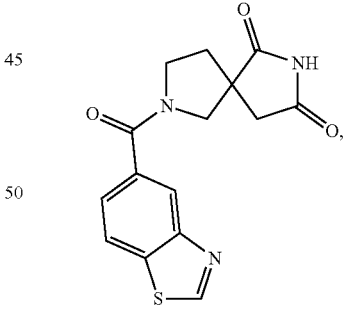
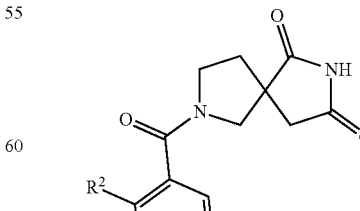

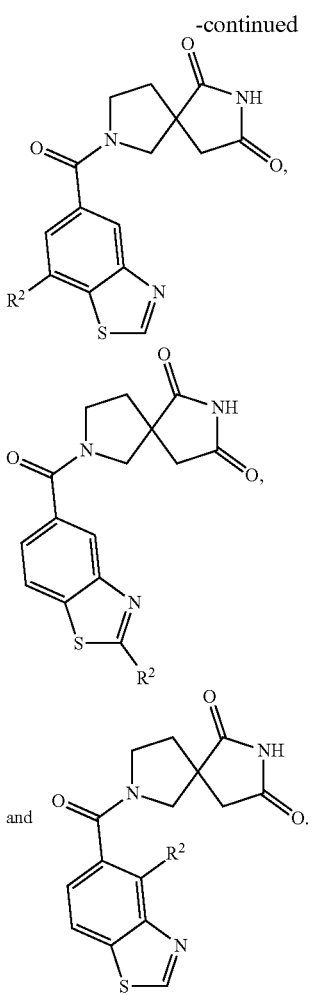

A compound of Formula XV for use in the methods described herein is also provided in the following enumerated embodiments, all of which may be separately combined.

E1: One embodiment of the invention provides a compound of Formula XV, or a pharmaceutically acceptable salt thereof,

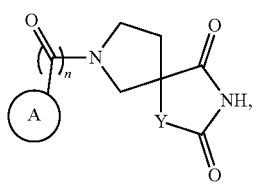

(XV)

wherein
Y is NH or CH$_2$,
n is 0 or 1,
A is selected from the group consisting of
i.) aryl,
ii.) aryl substituted by R$^1$,
iii.) heteroaryl, and
iv.) heteroaryl substituted by R$^2$;

R$^1$ is selected from the group consisting of
i.) —C(=O)—O—C$_{1-6}$-alkyl,
ii.) —COOH,
iii.) —NH—C(=O)—C$_{1-6}$-alkyl,
iv.) —NH$_2$, and
v.) —NO$_2$;

R$^2$ is selected from the group consisting of
i.) —COOH,
ii.) —C(=O)—O—C$_{1-6}$-alkyl,
iii.) —NH$_2$, and
—NO$_2$.

E2: The compound of Formula XV, or pharmaceutically acceptable salts thereof, as described herein, wherein
Y is NH or CH$_2$,
n is 0 or 1,
A is selected from the group consisting of
i.) aryl,
ii.) aryl substituted by R$^1$,
iii.) heteroaryl, and
iv.) heteroaryl substituted by R$^2$;
R$^1$ is —NH—C(=O)—C$_{1-6}$-alkyl; and
R$^2$ is —C(=O)—O—C$_{1-6}$-alkyl.

E3: The compound of Formula XV, or pharmaceutically acceptable salts thereof, as described herein, wherein
A is selected from the group consisting of
i.) aryl, in particular phenyl or 1,2,3,4-tetrahydronaphthalenyl,
ii.) aryl, in particular phenyl, substituted by R$^1$, in particular —NH—C(=O)—C$_{1-6}$-alkyl,
iii.) heteroaryl, in particular benzo[d]thiazolyl, pyrazolo[1,5-a]pyridinyl, thiazolo[4,5-b]pyridin-2-yl and
iv.) heteroaryl, in particular pyridinyl substituted by R$^2$, in particular —C(=O)—O—C$_{1-6}$-alkyl.

E4: The compound of Formula XV, or pharmaceutically acceptable salts thereof, as described herein, wherein A is aryl, in particular phenyl or 1,2,3,4-tetrahydronaphthalenyl.

E5: The compound of Formula XV, or pharmaceutically acceptable salts thereof, as described herein, wherein A is phenyl.

E6: The compound of Formula XV, or pharmaceutically acceptable salts thereof, as described herein, wherein A is 1,2,3,4-tetrahydronaphthalenyl.

E7: The compound of Formula XV, or pharmaceutically acceptable salts thereof, as described herein, wherein A is aryl, in particular phenyl, substituted by R$^1$, in particular —NH—C(=O)—C$_{1-6}$-alkyl.

E8: The compound of Formula XV, or pharmaceutically acceptable salts thereof, as described herein, wherein A is phenyl, substituted by —NH—C(=O)—C$_{1-6}$-alkyl.

E9: The compound of formula XV, or pharmaceutically acceptable salts thereof, as described herein, wherein A is phenyl, substituted by —NH—C(=O)—CH$_3$.

E10: The compound of formula XV, or pharmaceutically acceptable salts thereof, as described herein, wherein A is heteroaryl, in particular benzo[d]thiazolyl, pyrazolo[1,5-a]pyridinyl, thiazolo[4,5-b]pyridin-2-yl.

E11: The compound of formula XV, or pharmaceutically acceptable salts thereof, as described herein, wherein A is benzo[d]thiazolyl.

E12: The compound of formula XV, or pharmaceutically acceptable salts thereof, as described herein, wherein A is pyrazolo[1,5-a]pyridinyl.

E13: The compound of formula XV, or pharmaceutically acceptable salts thereof, as described herein, wherein A is thiazolo[4,5-b]pyridin-2-yl.

E14: The compound of formula XV, or pharmaceutically acceptable salts thereof, as described herein, wherein A is heteroaryl, in particular pyridinyl substituted by $R^2$, in particular —C(=O)—O—$C_{1-6}$-alkyl.

E15: The compound of formula XV, or pharmaceutically acceptable salts thereof, as described herein, wherein A is pyridinyl substituted by —C(=O)—O—$C_{1-6}$-alkyl.

E16: The compound of formula XV, or pharmaceutically acceptable salts thereof, as described herein, wherein A is pyridinyl substituted by —C(=O)—O—$CH_3$.

E17: The compound of formula XV, or pharmaceutically acceptable salts thereof, as described herein, wherein Y is NH.

E18: The compound of formula XV, or pharmaceutically acceptable salts thereof, as described herein, wherein Y is $CH_2$.

E19: The compound of formula XV, or pharmaceutically acceptable salts thereof, as described herein, wherein n is 0.

E20: The compound of formula XV, or pharmaceutically acceptable salts thereof, as described herein, wherein n is 1.

E21: The compound of formula XV, or pharmaceutically acceptable salts thereof, as described herein, selected from the group consisting of
  7-((S)-1,2,3,4-tetrahydronaphthalene-1-carbonyl)-1,3,7-triazaspiro[4.4]nonane-2,4-dione,
  7-benzoyl-1,3,7-triazaspiro[4.4]nonane-2,4-dione,
  7-(benzo[d]thiazol-2-yl)-1,3,7-triazaspiro[4.4]nonane-2,4-dione,
  7-(pyrazolo[1,5-a]pyridine-3-carbonyl)-1,3,7-triazaspiro[4.4]nonane-2,4-dione,
  methyl 6-(2,4-dioxo-1,3,7-triazaspiro[4.4]nonan-7-yl)nicotinate,
  N-(3-(2,4-dioxo-1,3,7-triazaspiro[4.4]nonane-7-carbonyl)phenyl)acetamide,
  N-(4-(2,4-dioxo-1,3,7-triazaspiro[4.4]nonane-7-carbonyl)phenyl)acetamide,
  7-(thiazolo[4,5-b]pyridin-2-yl)-1,3,7-triazaspiro[4.4]nonane-2,4-dione,
  7-(benzo[d]thiazole-5-carbonyl)-1,3,7-triazaspiro[4.4]nonane-2,4-dione,
  (R)-7-(benzo[d]thiazole-5-carbonyl)-1,3,7-triazaspiro[4.4]nonane-2,4-dione,
  (S)-7-(benzo[d]thiazole-5-carbonyl)-1,3,7-triazaspiro[4.4]nonane-2,4-dione,
  7-(benzo[d]thiazol-2-yl)-2,7-diazaspiro[4.4]nonane-1,3-dione,
  7-benzoyl-2,7-diazaspiro[4.4]nonane-1,3-dione,
  methyl 6-(6,8-dioxo-2,7-diazaspiro[4.4]nonan-2-yl)nicotinate, and
  7-(pyrazolo[1,5-a]pyridine-3-carbonyl)-2,7-diazaspiro[4.4]nonane-1,3-dione.

E22: A compound, or pharmaceutically acceptable salts thereof, having a chemical structure comprising:

P-L-C wherein
L is a linker group;
C is a compound of formula I as described herein, wherein L is chemically linked to C; and
P is a protein targeting moiety that binds to a target protein or a target polypeptide,
  wherein L is chemically linked to P.

E23: The compound of formula P-L-C as described herein, wherein L is selected from the group consisting of:

i) —NHCH$_2$—(CH$_2$)$_{1-30}$—C(=O)NH—, in particular —NHCH$_2$—(CH$_2$)$_6$—C(=O)NH—, and
ii) —NH—(CH$_2$CH$_2$O)$_{1-25}$—C(=O)NH—.

E24: The compound of formula P-L-C as described herein, which is selected from the group consisting of
i) P—NHCH$_2$—(CH$_2$)$_{1-30}$—C(=O)NH—C, in particular P—NHCH$_2$—(CH$_2$)$_6$—C(=O)NH—C, and
ii) P—NH—(CH$_2$CH$_2$O)$_{1-25}$—C(=O)NH—C.

E25: The compound of formula P-L-C as described herein, wherein P is a BRD4 inhibitor, in particular wherein P is

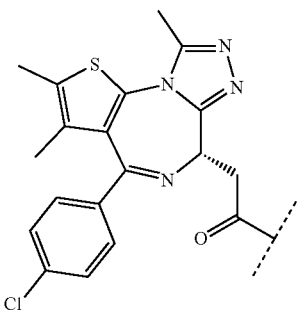

E26: A certain embodiment of the invention relates to the compound of Formula XV as described herein, or a pharmaceutically acceptable salt thereof, for use as therapeutically active substance.

E27: A certain embodiment of the invention relates to the compound of Formula XV as described herein, or a pharmaceutically acceptable salt thereof, for the use in the therapeutic and/or prophylactic treatment of cancer.

E28: A certain embodiment of the invention relates to the compound of Formula XV as described herein, or a pharmaceutically acceptable salt thereof, for the manufacture of a medicament for the therapeutic and/or prophylactic treatment of cancer.

E29: A certain embodiment of the invention relates to a pharmaceutical composition comprising the compound of Formula XV as described herein, or a pharmaceutically acceptable salt thereof, and a pharmaceutically acceptable auxiliary substance.

E30: A certain embodiment of the invention relates to a method for the therapeutic and/or prophylactic treatment of cancer, by administering the compound of Formula XV as E31: A certain embodiment of the invention relates to the compound of P-L-C as described herein, or a pharmaceutically acceptable salt thereof, for use as therapeutically active substance.

E32: A certain embodiment of the invention relates to the compound of P-L-C as described herein, or a pharmaceutically acceptable salt thereof, for the use in the therapeutic and/or prophylactic treatment of cancer.

E33: A certain embodiment of the invention relates to the compound of P-L-C as described herein, or a pharmaceutically acceptable salt thereof, for the manufacture of a medicament for the therapeutic and/or prophylactic treatment of cancer.

E34: A certain embodiment of the invention relates to a pharmaceutical composition comprising the compound of P-L-C as described herein, or a pharmaceutically acceptable salt thereof, and a pharmaceutically acceptable auxiliary substance, in particular an inert carrier.

E35: A certain embodiment of the invention relates to a method for the therapeutic and/or prophylactic treatment of cancer, by administering the compound of P-L-C as described herein, or a pharmaceutically acceptable salt thereof, to a patient.

Furthermore, the invention includes all optical isomers, i.e. diastereoisomers, diastereomeric mixtures, racemic mixtures, all their corresponding enantiomers and/or tautomers as well as solvates of the compounds of formula I.

Salts of Compounds of Formula XV

In cases where the compounds of Formula XV are basic they may be converted to a corresponding acid addition salt. The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or may be brought out of solution with a less polar solvent.

Insofar as their preparation is not described in the examples, the compounds of formula XV or formula P-L-C as well as all intermediate products can be prepared according to analogous methods or according to the methods set forth herein. Starting materials are commercially available, known in the art or can be prepared by methods known in the art or in analogy thereto.

It will be appreciated that the compounds of general formula XV or formula P-L-C in this invention may be derivatised at functional groups to provide derivatives which are capable of conversion back to the parent compound in vivo.

Compounds of Formula XVI

In another aspect, a compound of Formula XVI, or a pharmaceutically acceptable salt thereof, is provided:

(XIV)

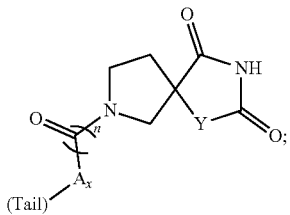

wherein all variables are as defined herein.

In some embodiments, a compound of Formula XVI is provided selected from:

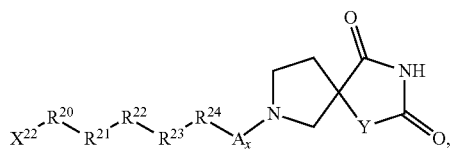

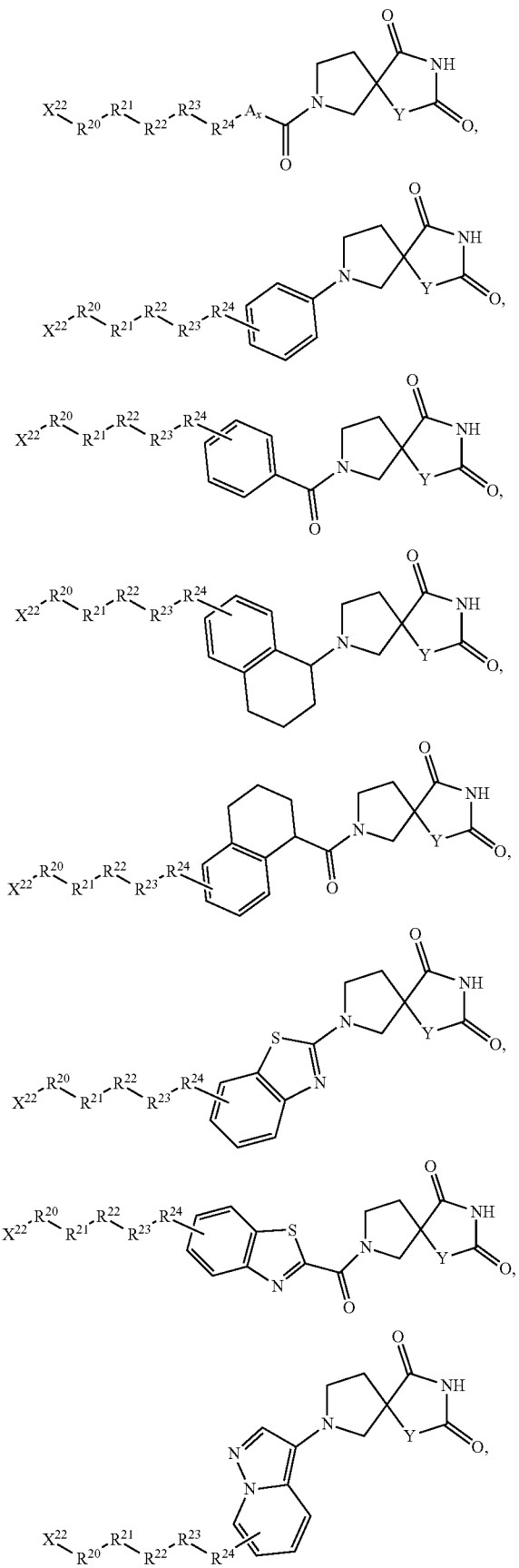

-continued
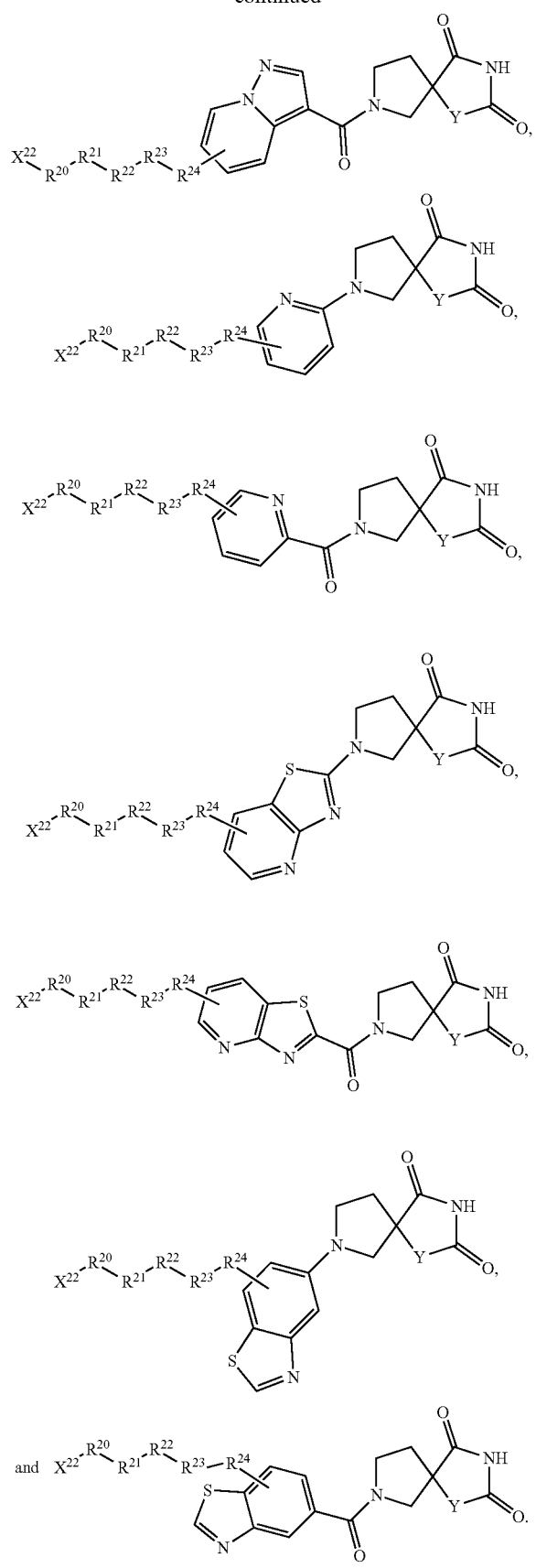
In some embodiments of Formula XVI, a compound is provided selected from:
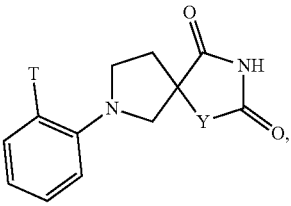
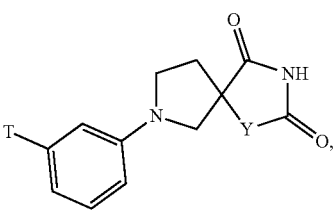
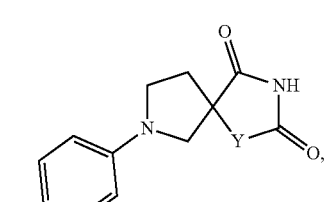
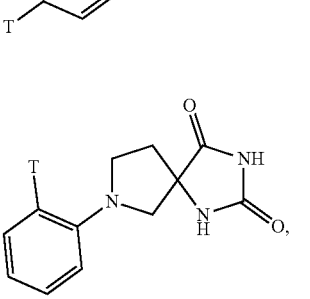
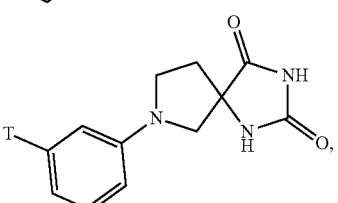
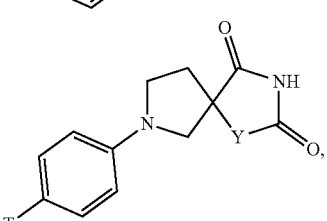
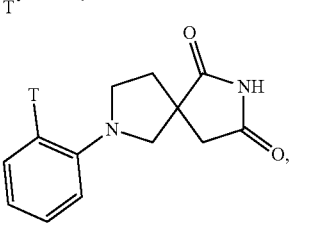

-continued
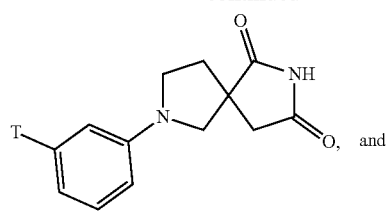
O, and
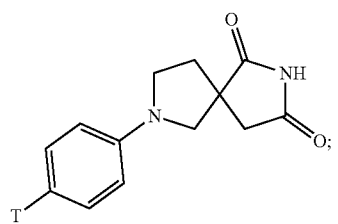
wherein T is
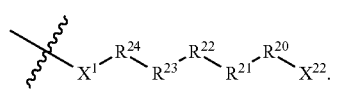
In some embodiments of Formula XVI, a compound is provided selected from:
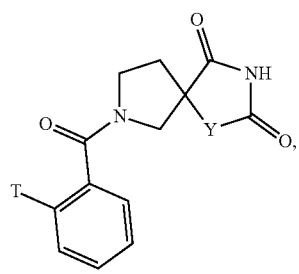
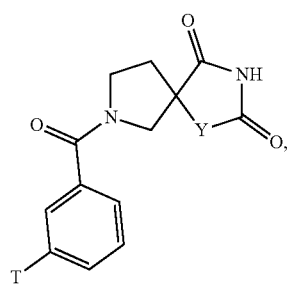
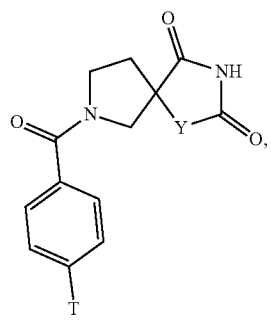
-continued
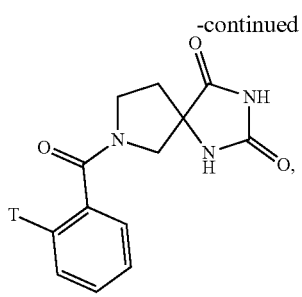
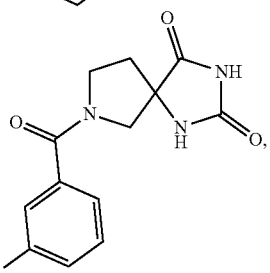
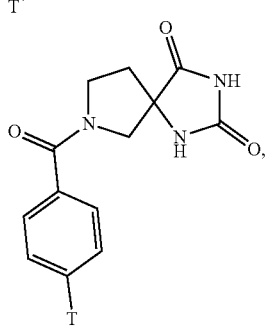
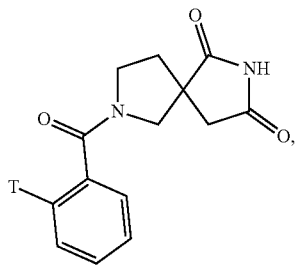
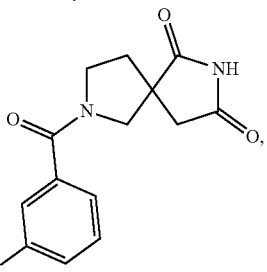
and 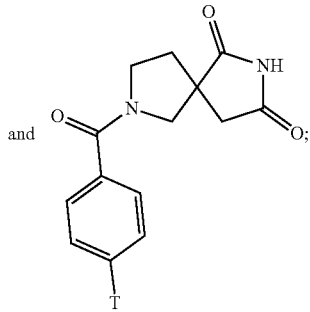

wherein T is
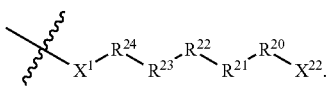
In some embodiments of Formula XVI, a compound is provided selected from:
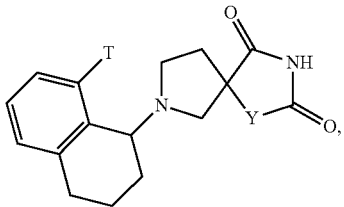
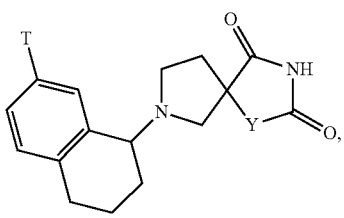
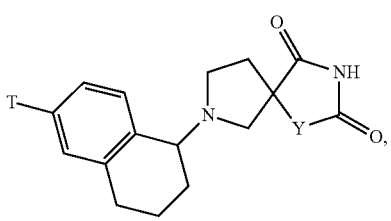
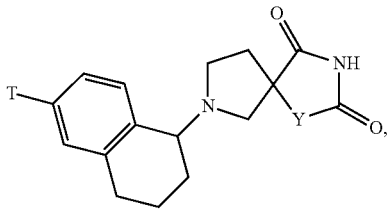
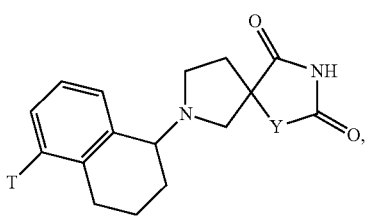
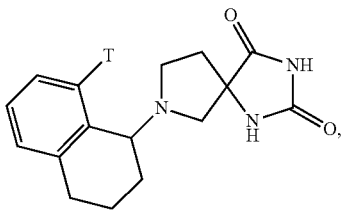
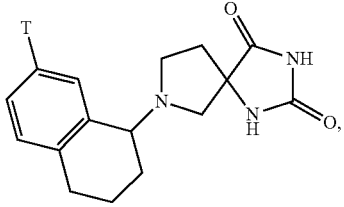
-continued
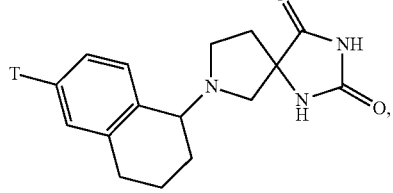
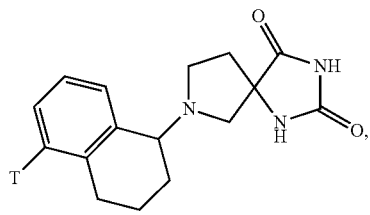
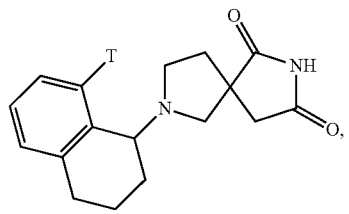
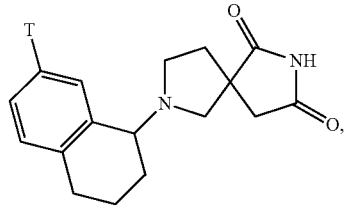
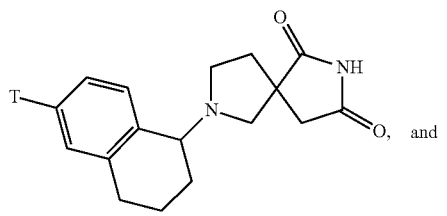, and
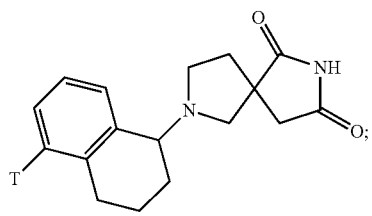;
wherein T is
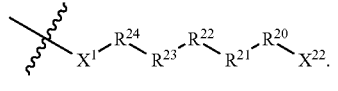

In some embodiments of Formula XVI, a compound is provided selected from:
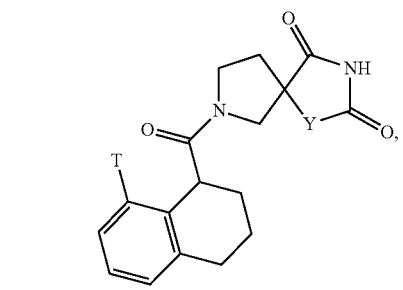
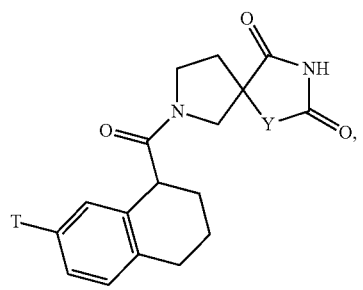
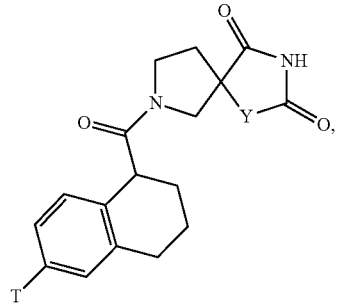
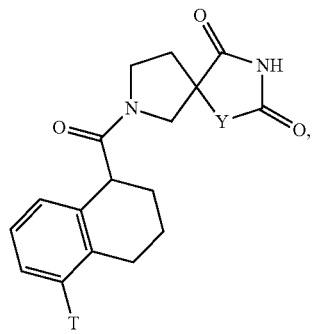
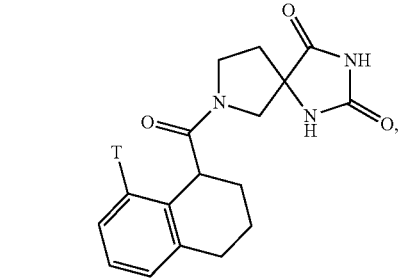
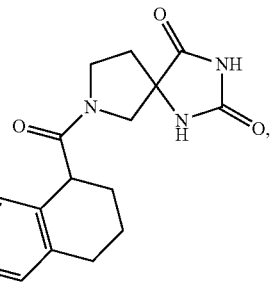
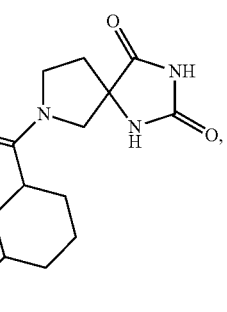
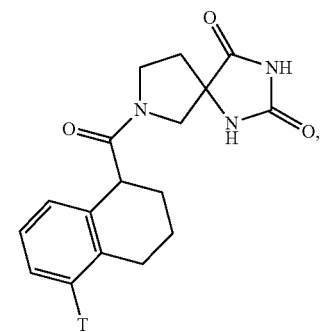
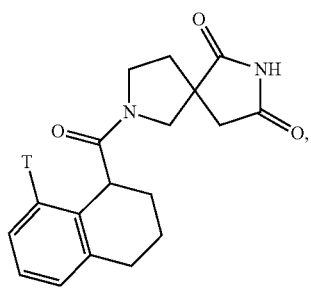
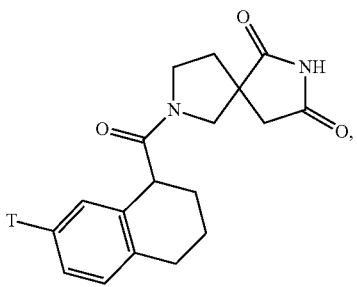

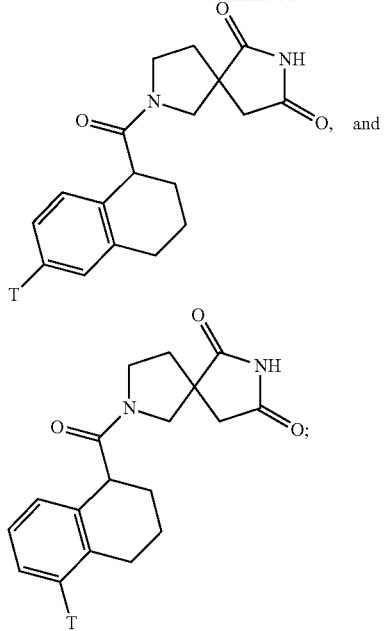
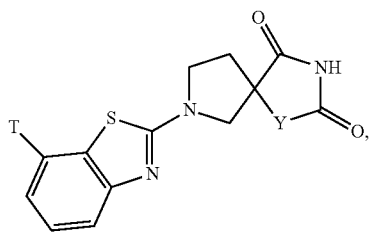
wherein T is
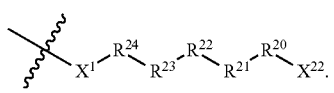
In some embodiments of Formula XVI, a compound is provided selected from:
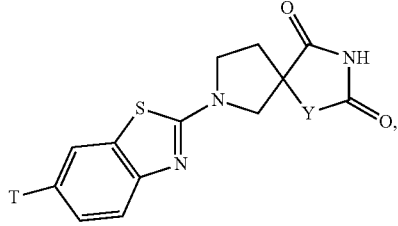
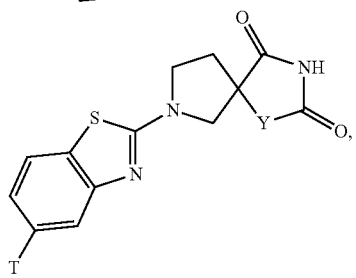
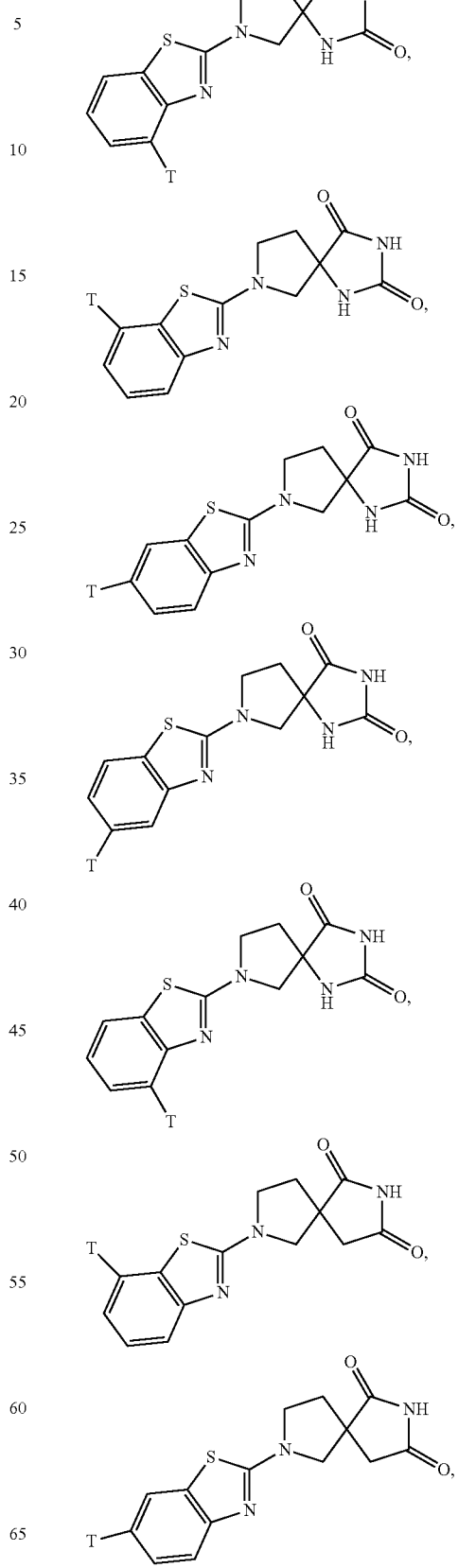

-continued
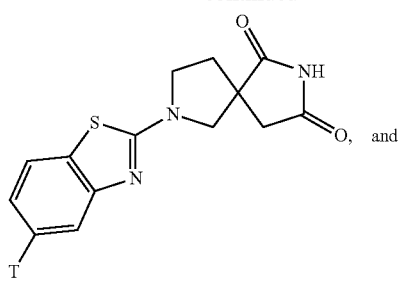
and
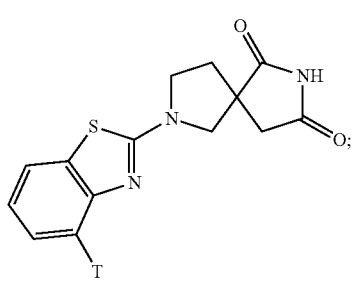
wherein T is
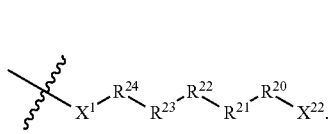
In some embodiments of Formula XVI, a compound is provided selected from:
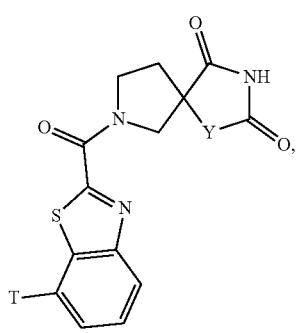
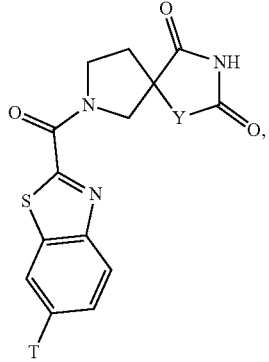
-continued
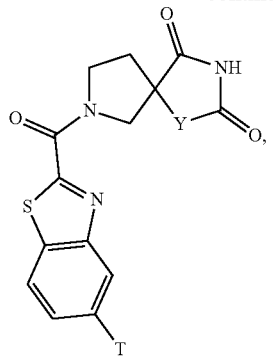
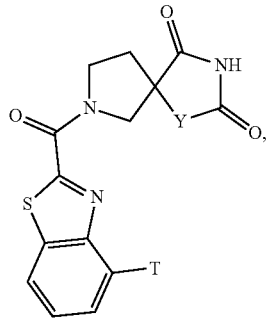
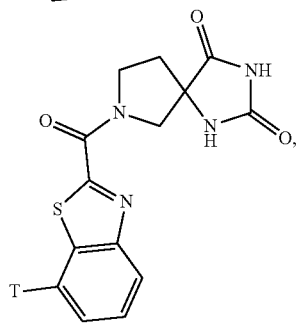
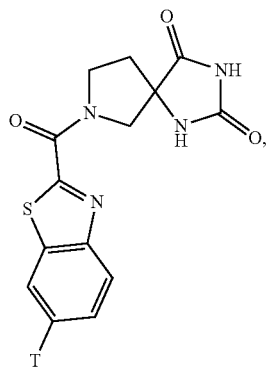
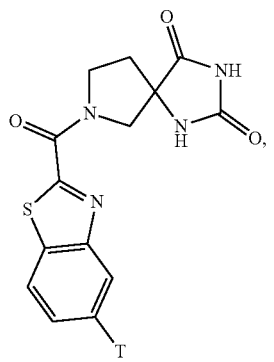

143
-continued
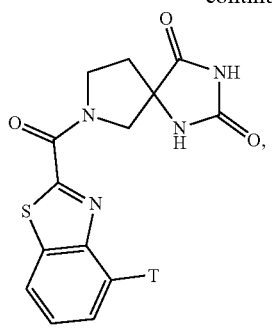
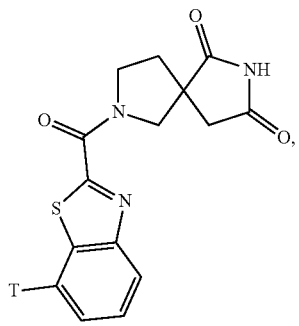
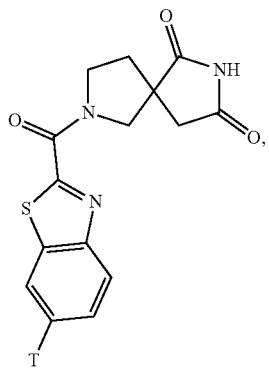
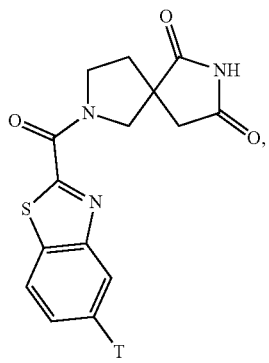
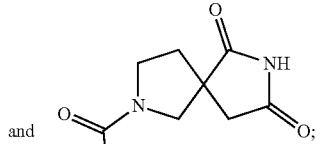
and
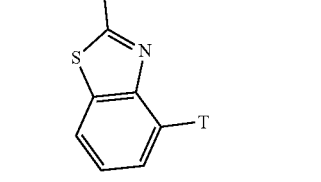
144
wherein T is
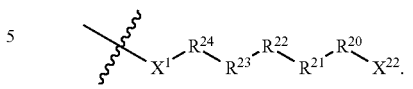
In some embodiments of Formula XVI, a compound is provided selected from:
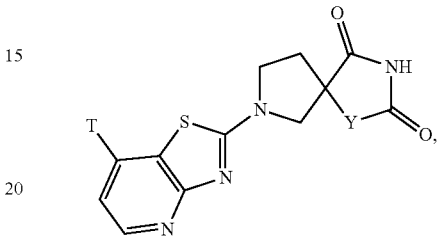
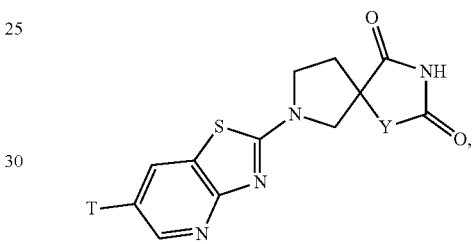
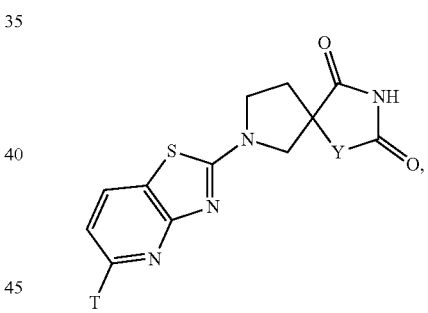
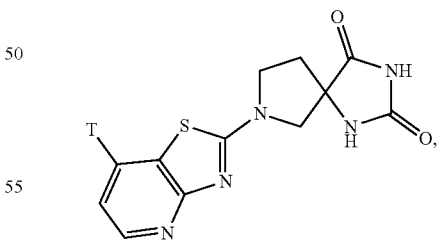
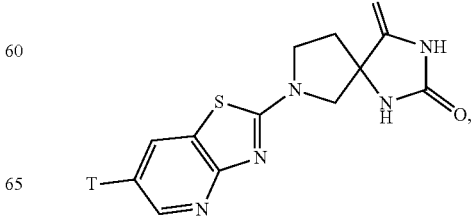

-continued
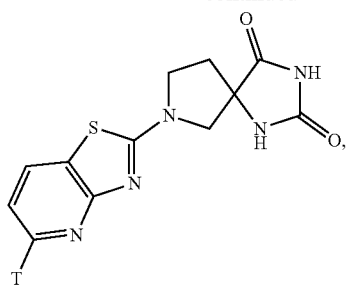
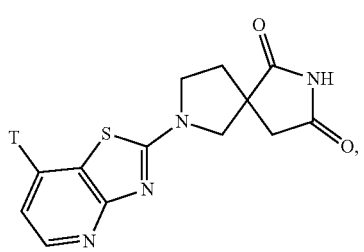
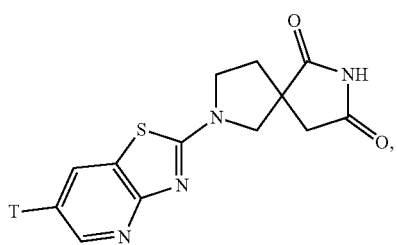
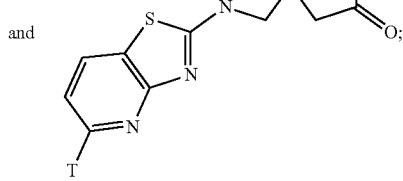
and
wherein T is
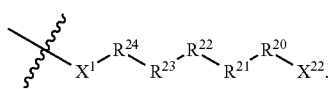
In some embodiments of Formula XVI, a compound is provided selected from:
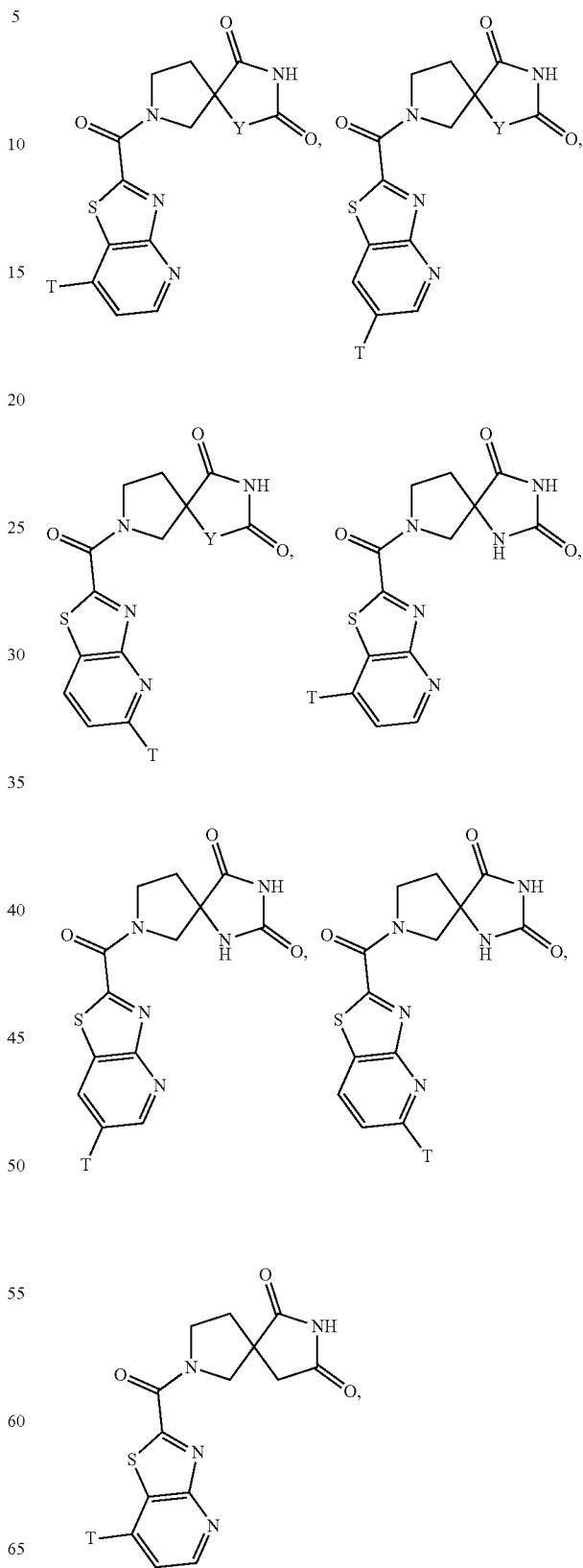

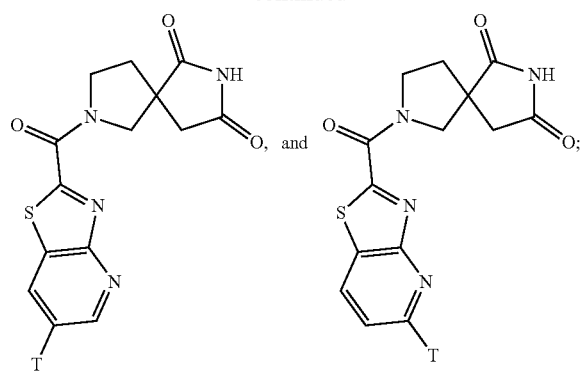
wherein T is
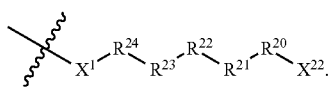
In some embodiments of Formula XVI, a compound is provided selected from
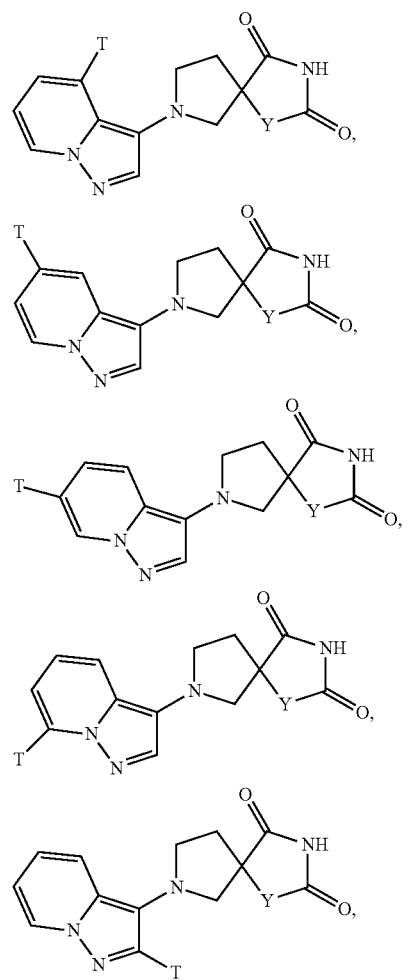
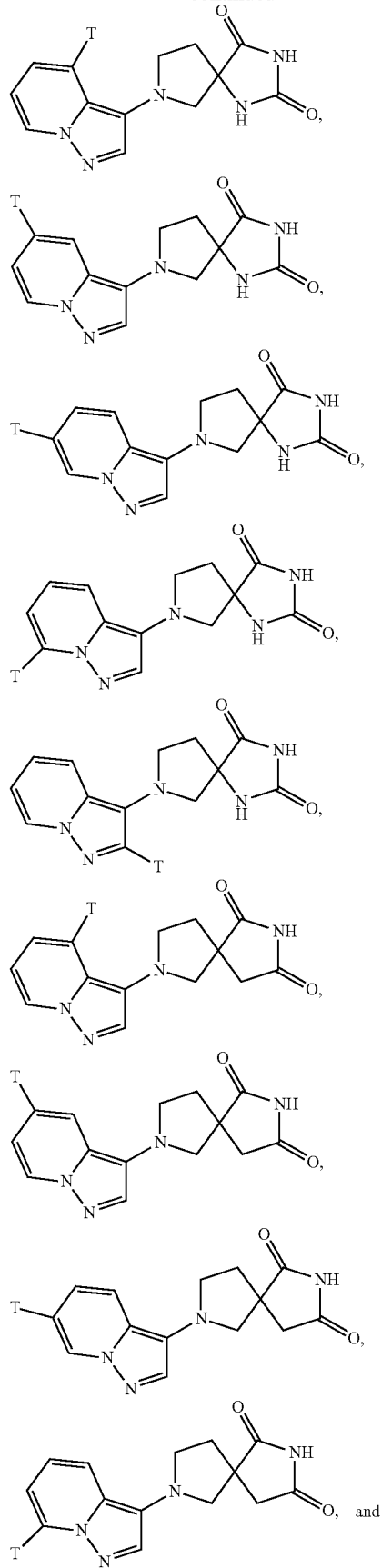

149
-continued
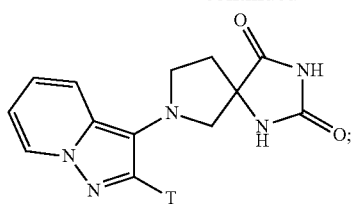
wherein T is
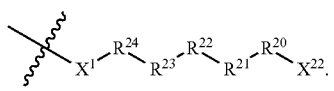
In some embodiments of Formula XVI, a compound is provided selected from:
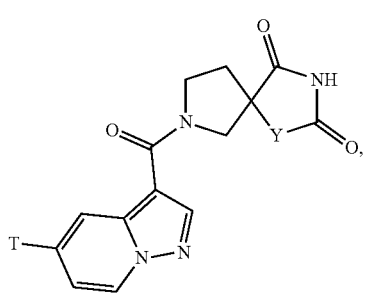
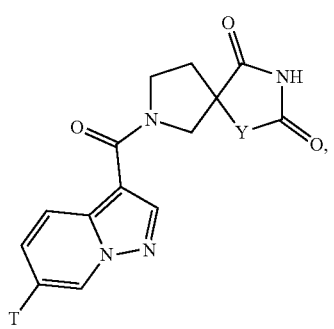
150
-continued
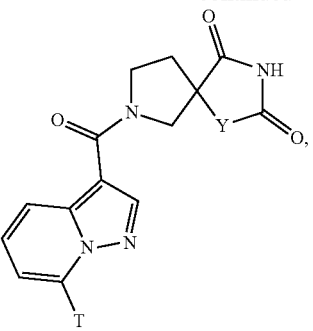
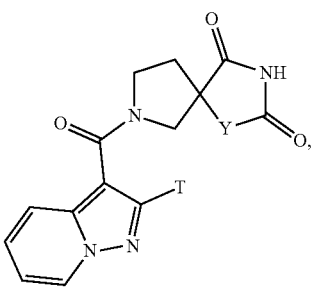
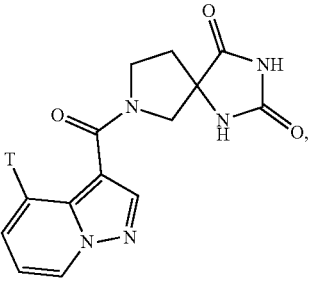
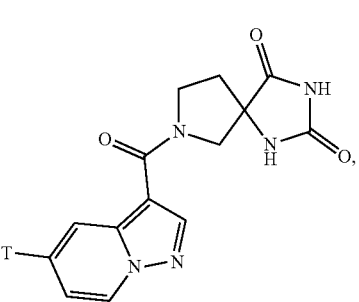
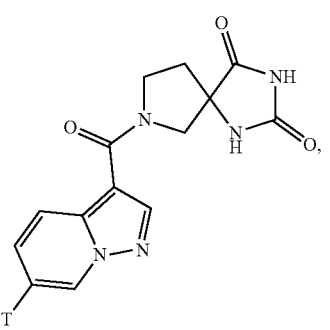

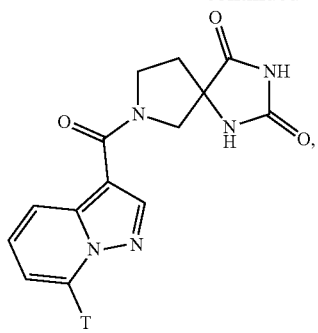
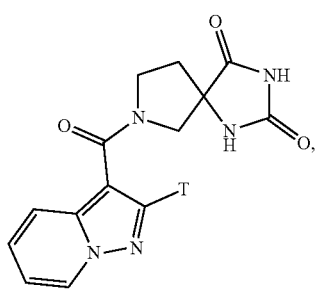
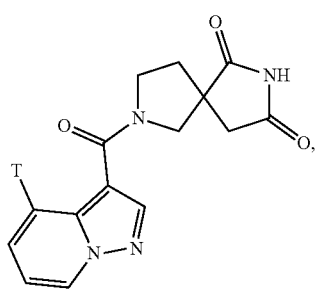
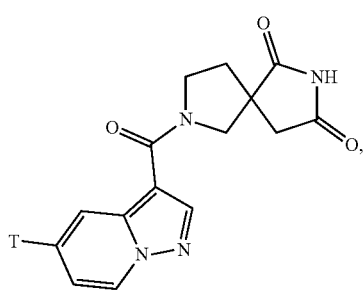
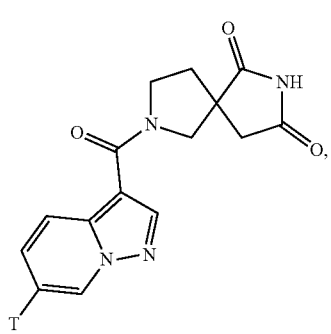
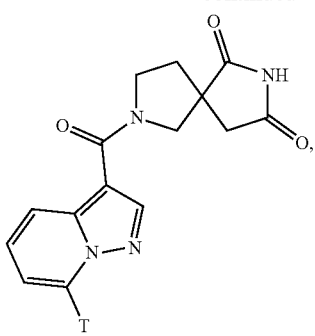
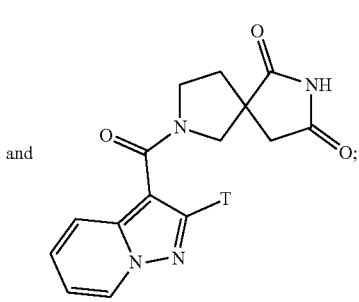
and
wherein T is
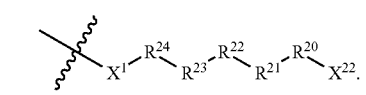
In some embodiments of Formula XVI, a compound is provided selected from:
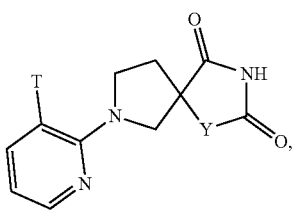
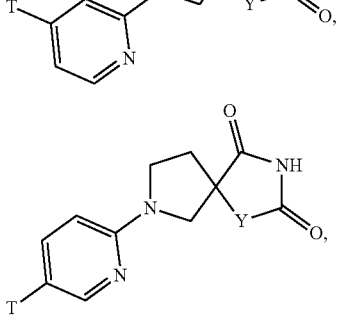

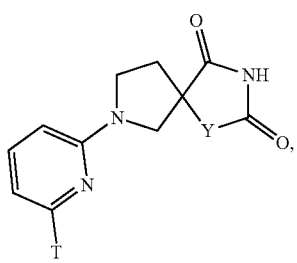
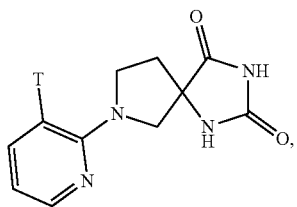
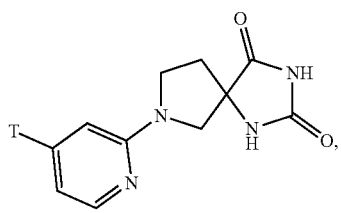
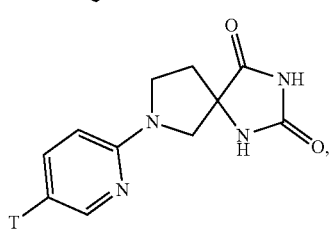
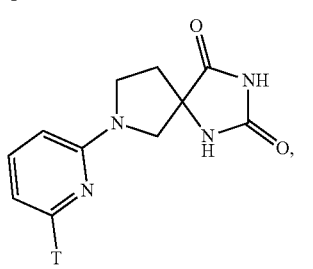
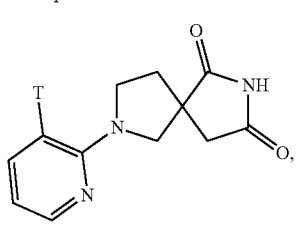
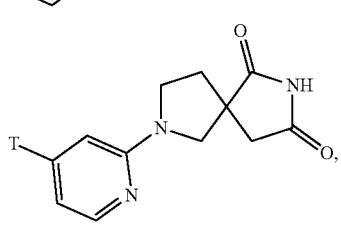
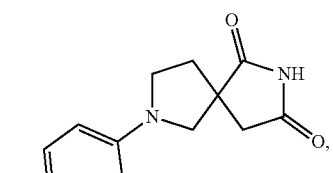
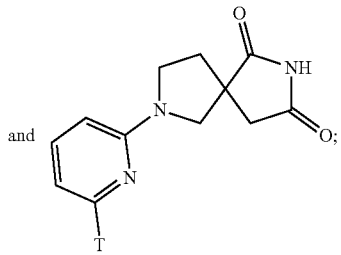
and
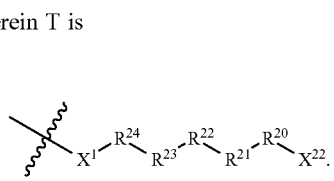
wherein T is
In some embodiments of Formula XVI, a compound is provided selected from:
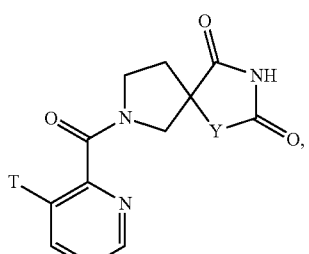
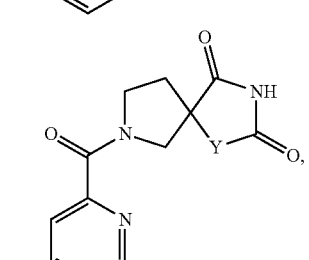
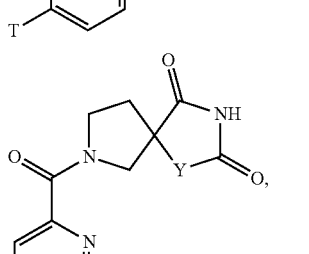

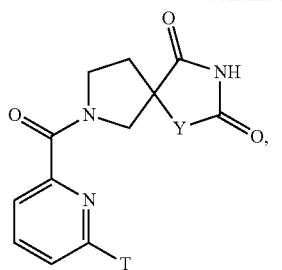
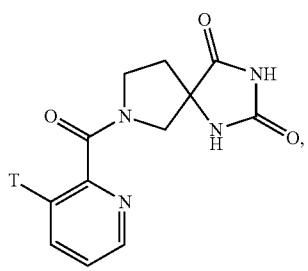
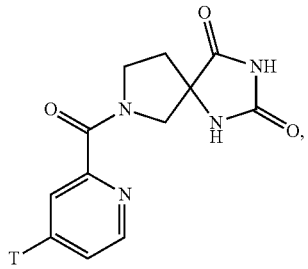
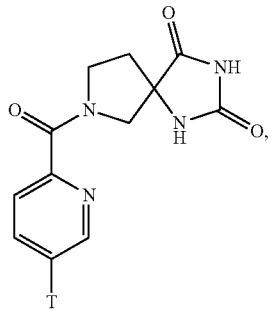
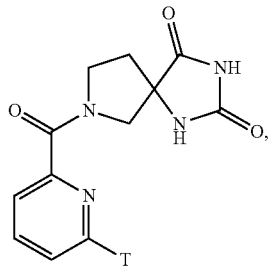
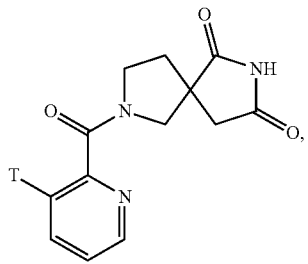
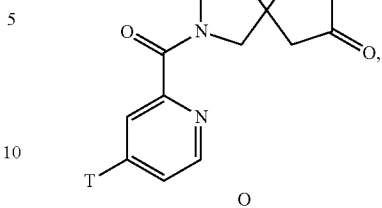
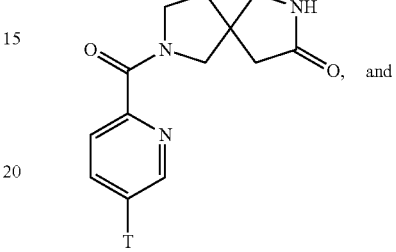
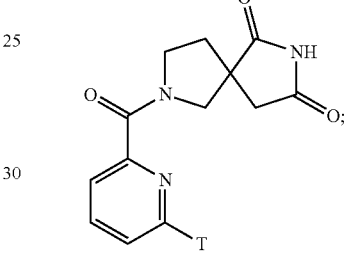
wherein T is
$$\text{-}X^1\text{-}R^{24}\text{-}R^{23}\text{-}R^{22}\text{-}R^{21}\text{-}R^{20}\text{-}X^{22}.$$
In some embodiments of Formula XVI, a compound is provided selected from:
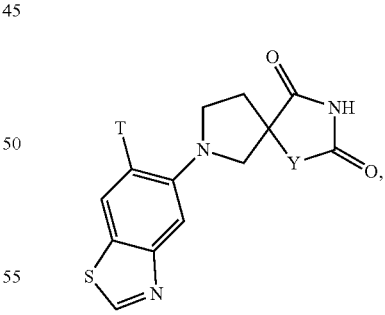
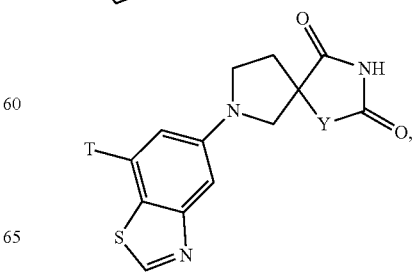

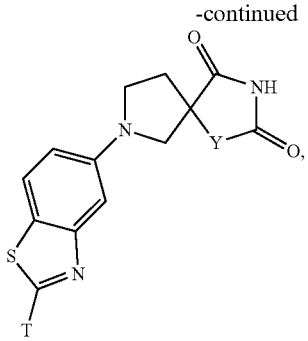
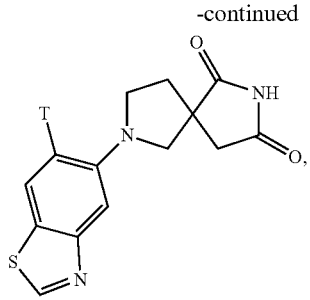
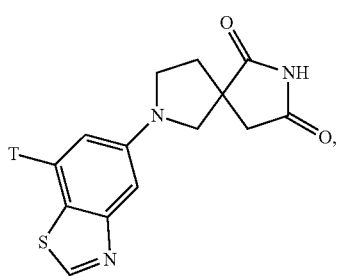
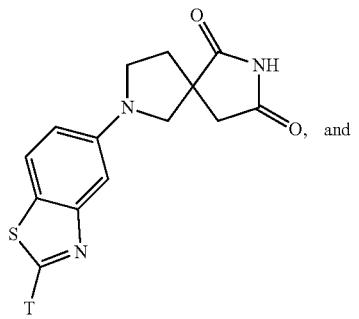
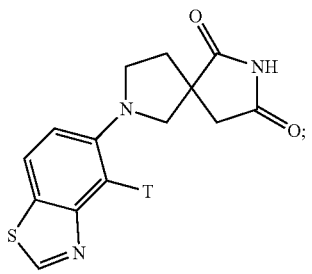
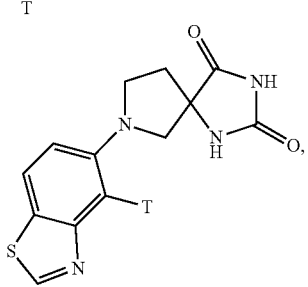
wherein T is
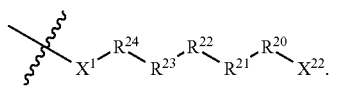

In some embodiments of Formula XVI, a compound is provided selected from:
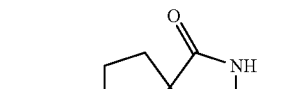
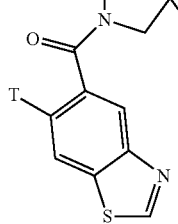
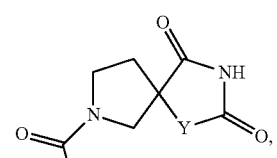
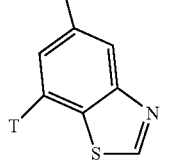
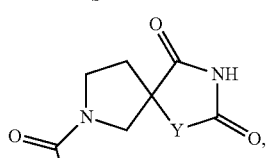
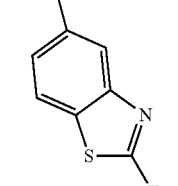
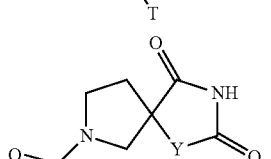
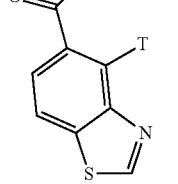
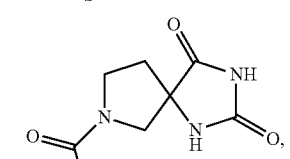
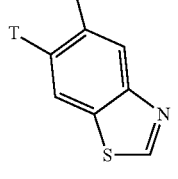
-continued
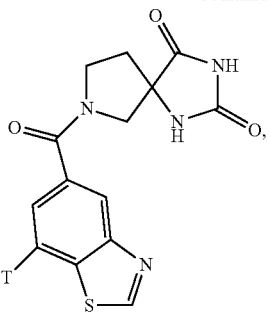
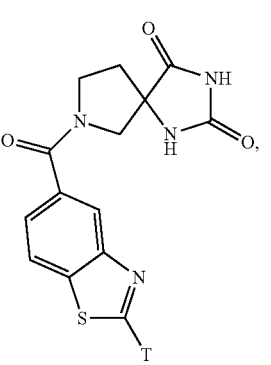
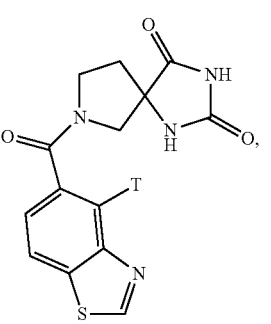
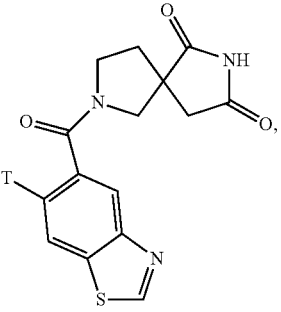
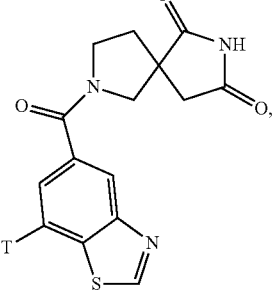

-continued

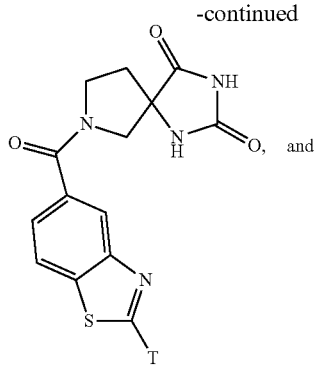

O, and

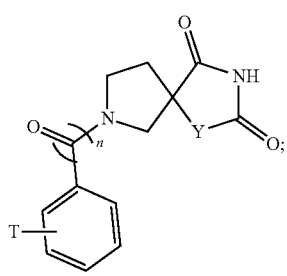

wherein T is

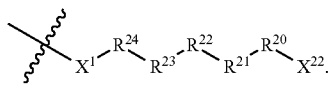

Compound of Formulas XVII-a to XVII-g

In one embodiment, a compound is provided of Formula XVII-a:

(XVII-a)

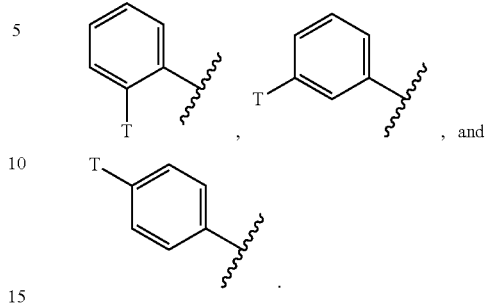

wherein all variables are as defined herein.

In some embodiments of Formula XVI or XVII-a,

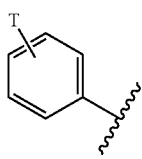

is selected from:

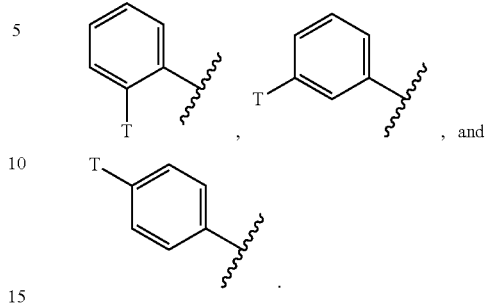

, and

In one embodiment, a compound is provide of Formula XVII-b:

(XVII-b)

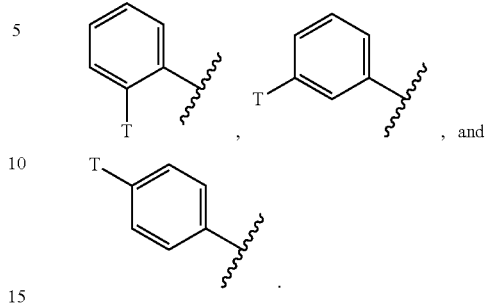

wherein all variables are as defined herein.

In some embodiments of Formula XVI or XVII-b,

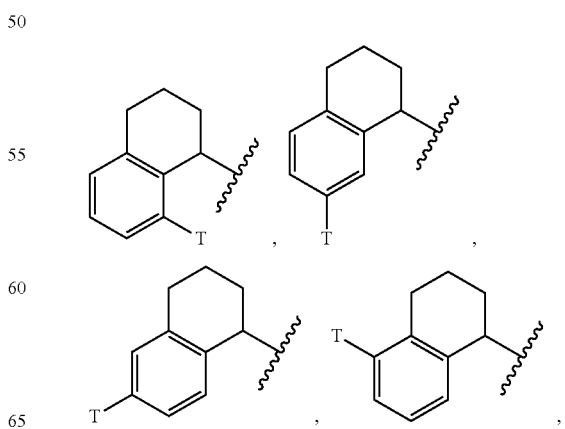

is selected from:

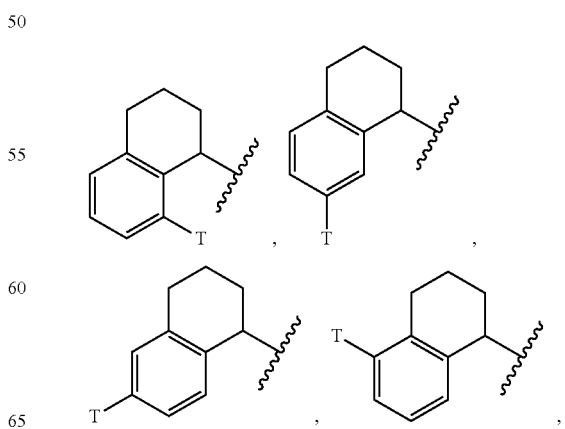

,

-continued
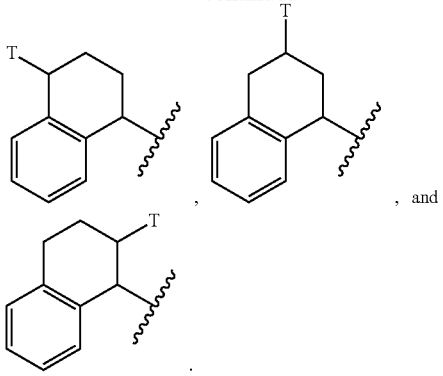
, and
.
In one embodiment, a compound is provided of Formula XVII-c:
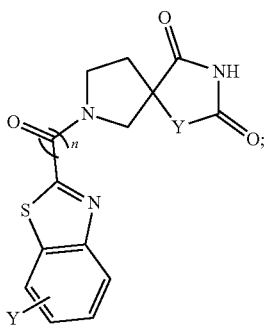
(XVII-c)
wherein all variables are as defined herein.
In some embodiments of Formula XVI or XVII-d,
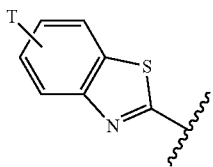
is selected from:
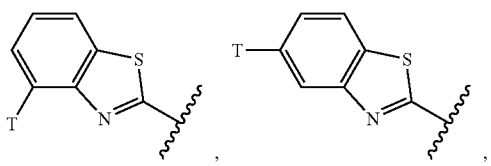
,
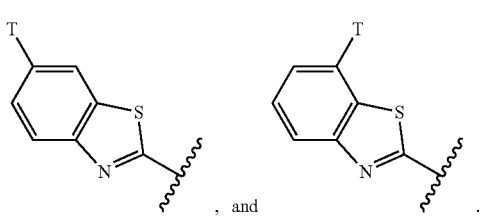
, and
.
In one embodiment, a compound is provided of Formula XVII-d:
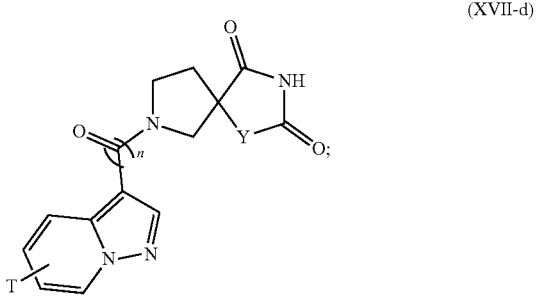
(XVII-d)
wherein all variables are as defined herein.
In some embodiments of Formula XVI or XVII-d,
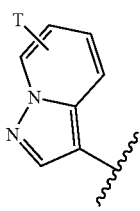
is selected from:
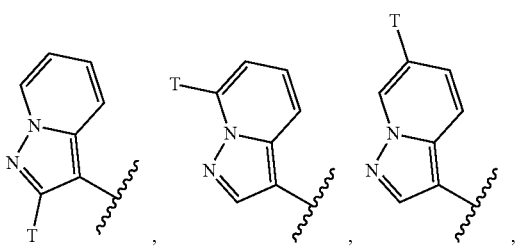
, , ,
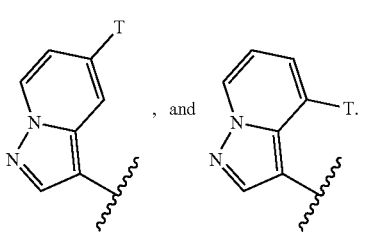
, and
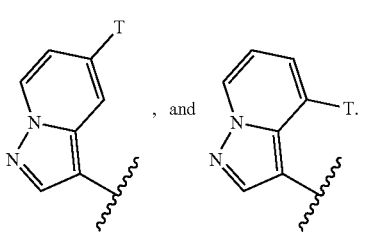
.

In one embodiment, a compound is provided of Formula XVII-e:

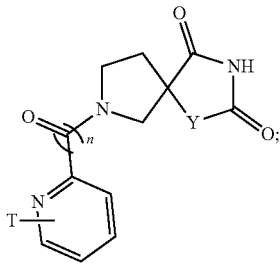

(XVII-e)

wherein all variables are as defined herein.

In some embodiments of XVI or XVII-e,

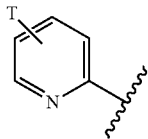

is selected from:

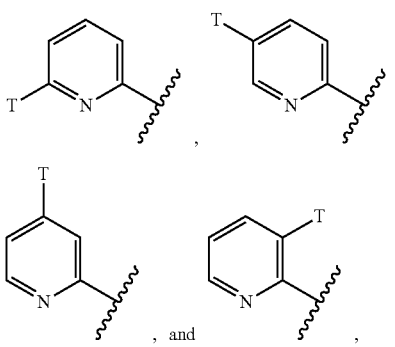

, and

In one embodiment, a compound of Formula XVII-f is provided:

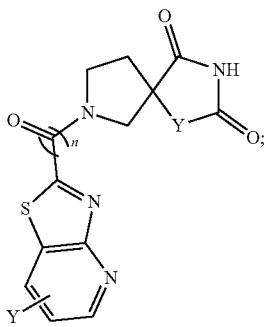

(XVII-f)

wherein all variables are as defined herein.

In some embodiments of Formula XVI or XVII-f,

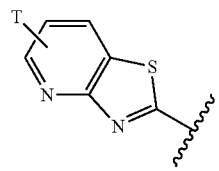

is selected from:

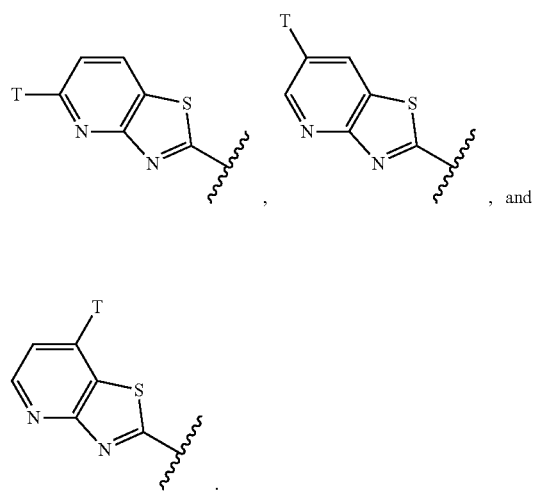

, and

In one embodiment, a compound of Formula XVII-g is provided:

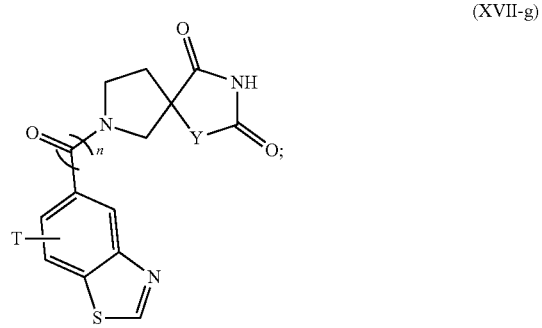

(XVII-g)

wherein all variables are as defined herein.

In some embodiments of Formula XVI or XVII-g,

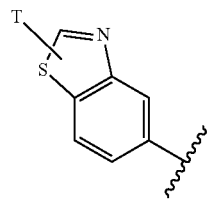

is selected from:

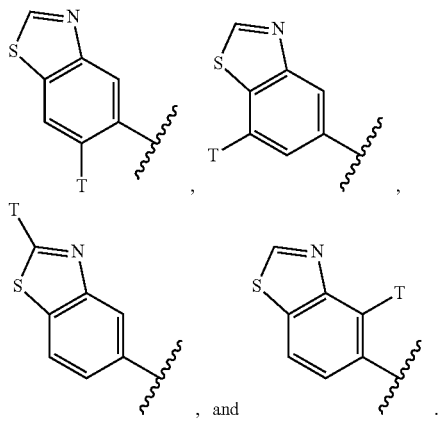

III. Tail Embodiments

In one embodiment, "Tail" is a moiety selected from Formula T-I, Formula T-II, Formula T-III, Formula T-IV, Formula T-V, Formula T-VI, and Formula T-VII:

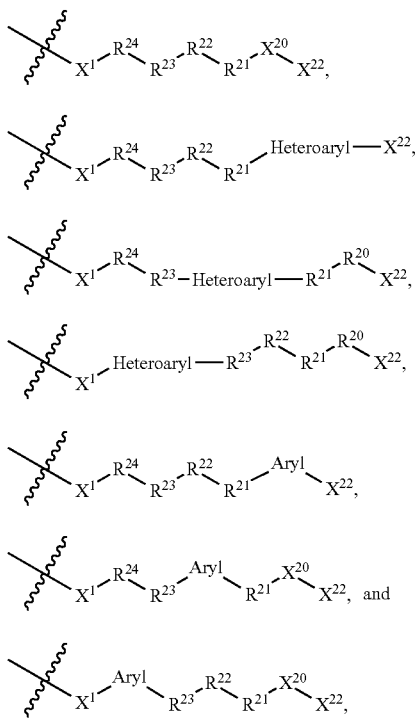

wherein all variables are defined as above.

In an additional embodiment, "Tail" is a moiety selected from Formula T-VIII, T-IX, and T-X:

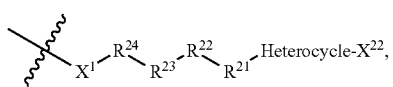

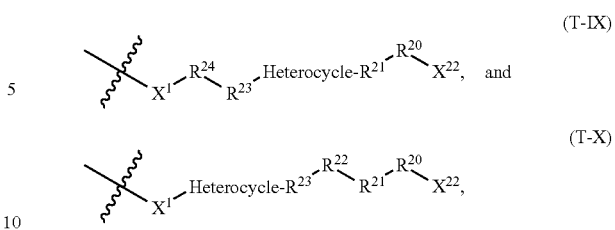

wherein all variables are defined as above. In other embodiments of T-VIII, T-IX and T-X, a carbocyclic ring is used in place of the heterocycle.

The following are non-limiting examples of "Tail" moieties that can be used in this invention. Based on this elaboration, those of skill in the art will understand how to use the full breadth of "Tail" moieties that will accomplish the goal of the invention.

As certain non-limiting examples, Formula T-I, Formula T-II, Formula T-III, Formula T-IV, Formula T-V, Formula T-VI, or Formula T-VII include:

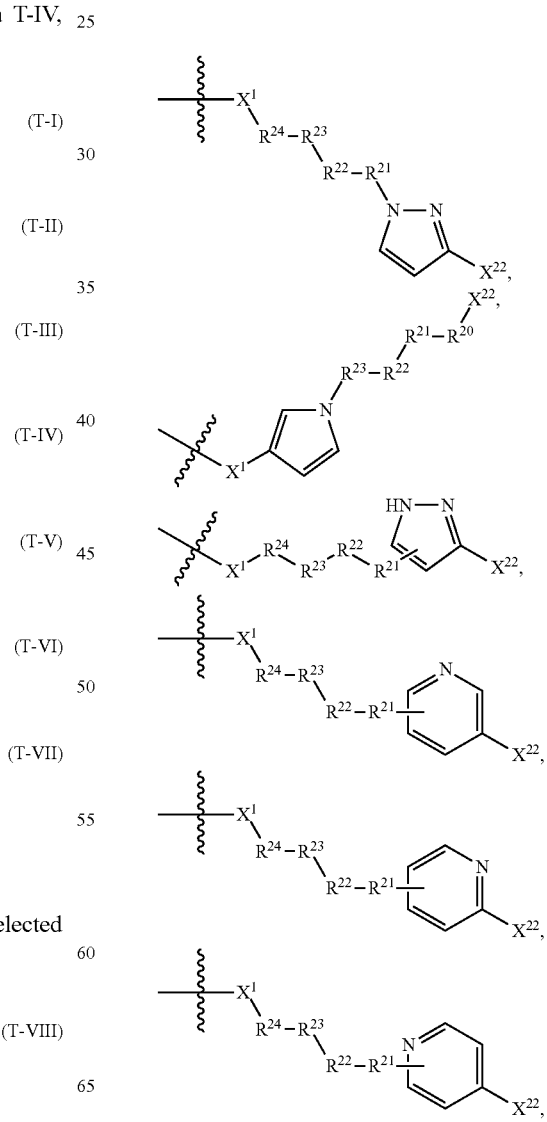

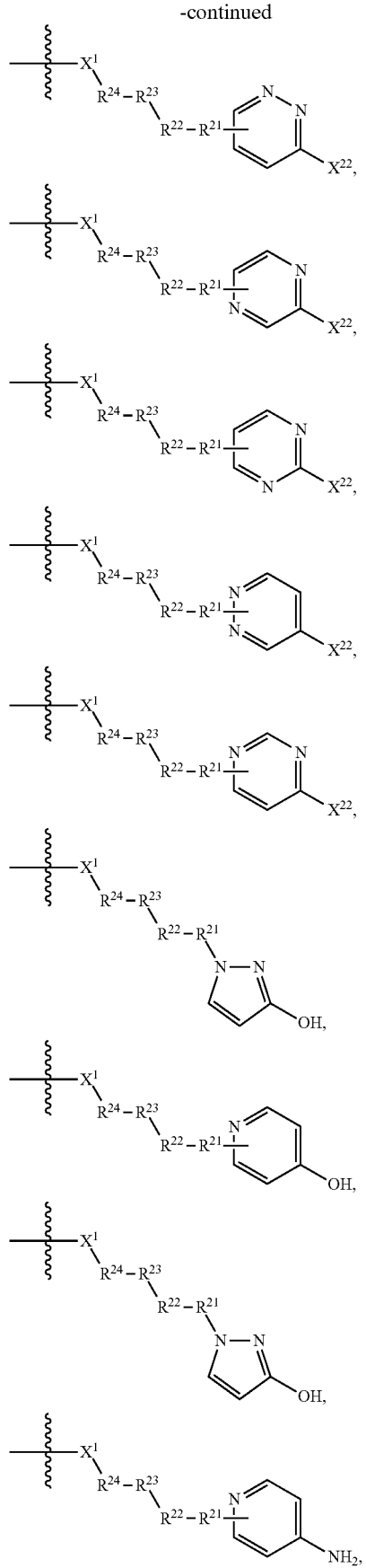
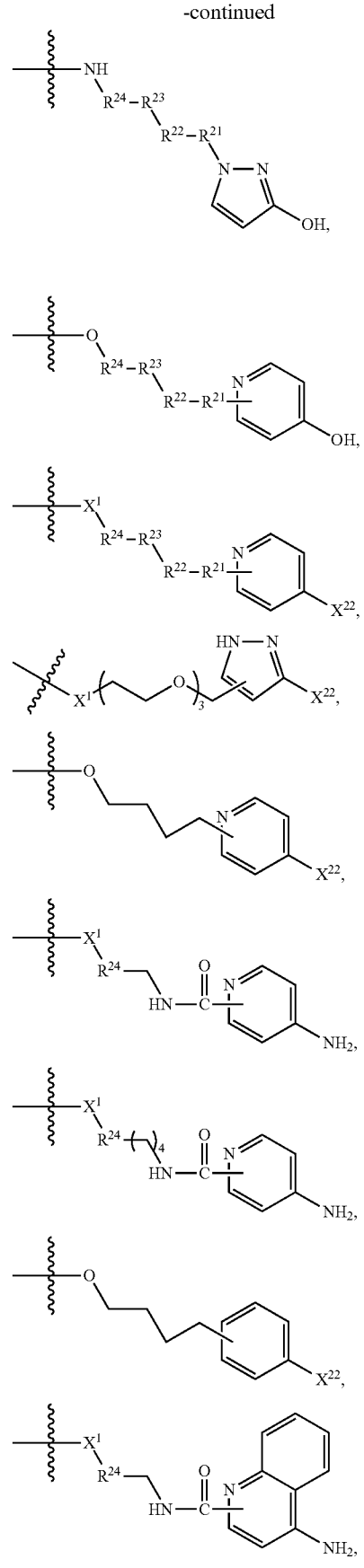

-continued
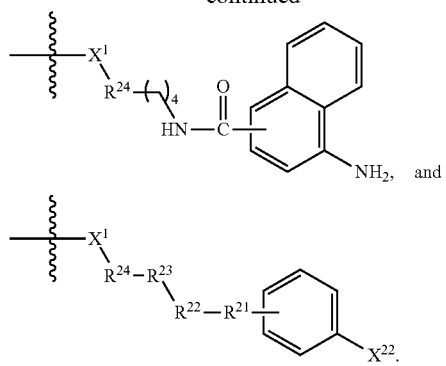
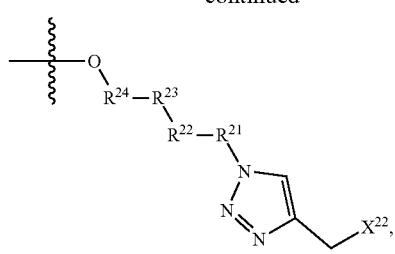
In an additional embodiment "Tail" is selected from:
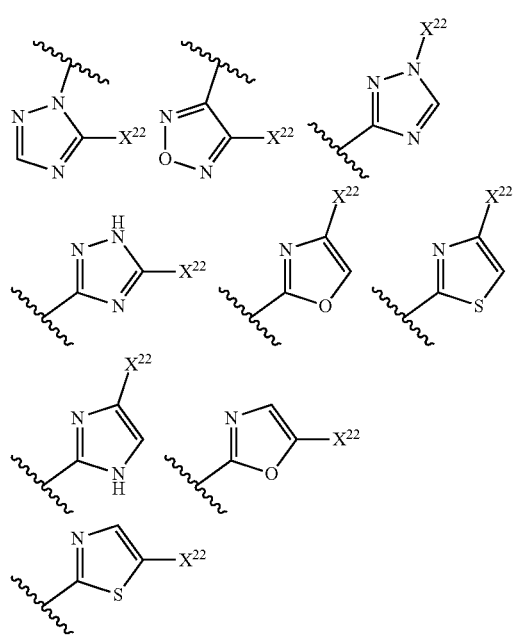
In an additional embodiment "Tail" is selected from:
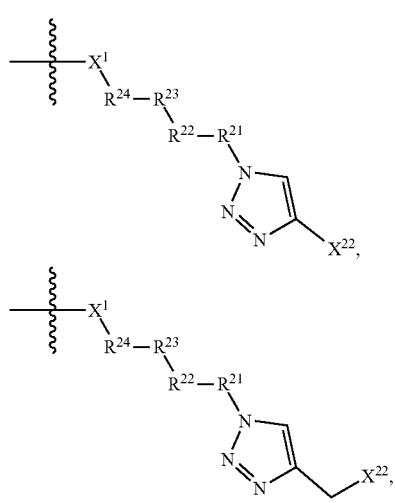
Non-limiting examples of moieties of $R^{20}$, $R^{21}$, $R^{22}$, $R^{23}$, and $R^{24}$ include:
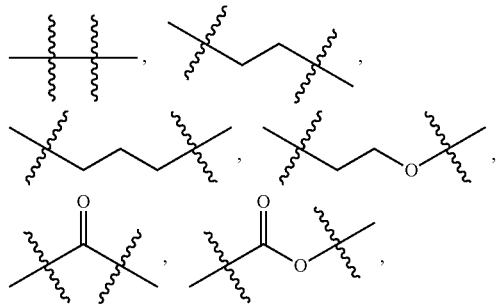

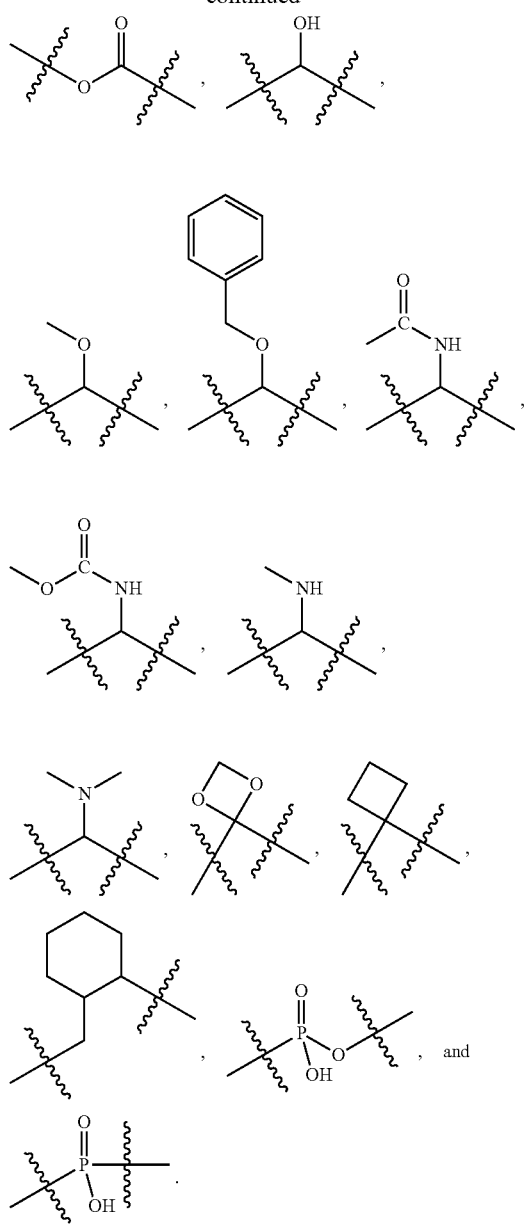
Additional non-limiting examples of moieties of $R^{20}$, $R^{21}$, $R^{22}$, $R^{23}$, and $R^{24}$ include:
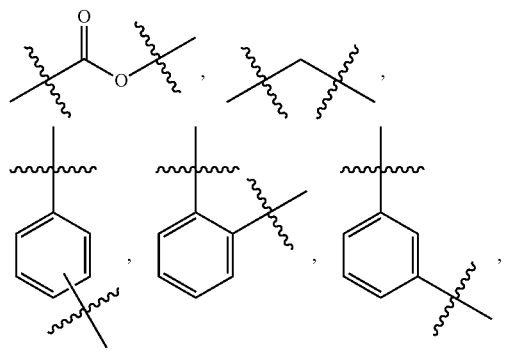
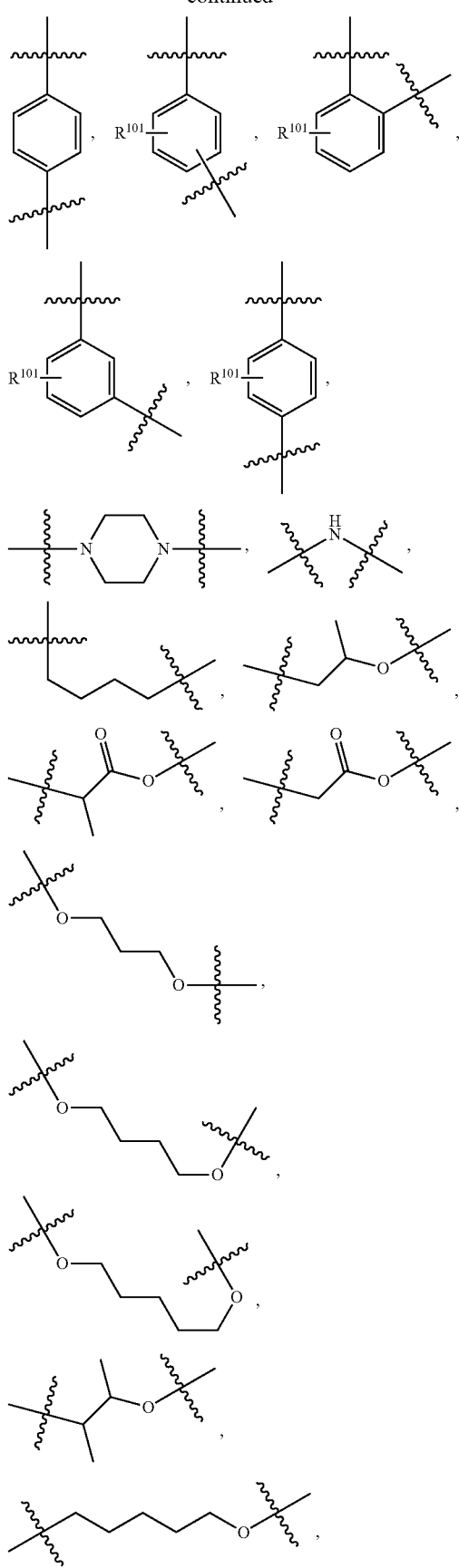

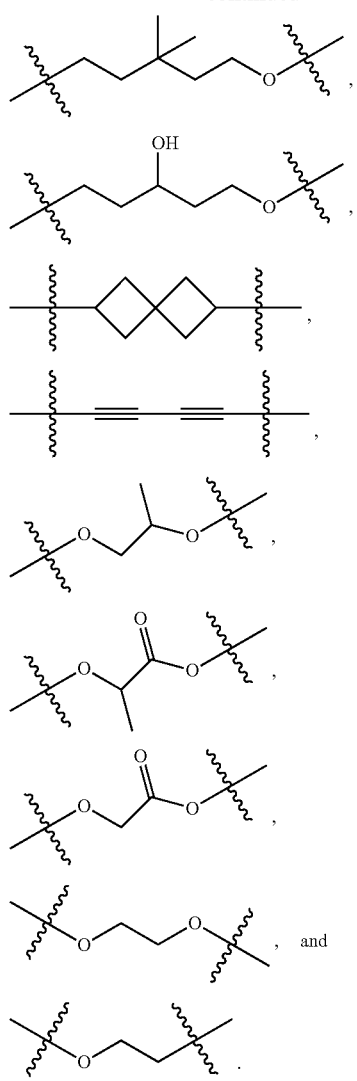
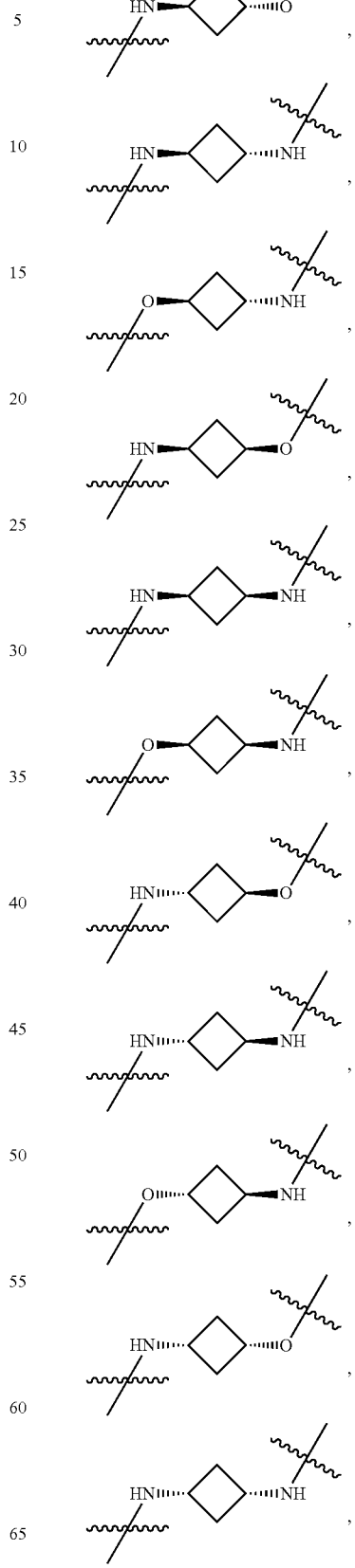
Additional non-limiting examples of moieties of $R^{20}$, $R^{21}$, $R^{22}$, $R^{23}$, and $R^{24}$ include
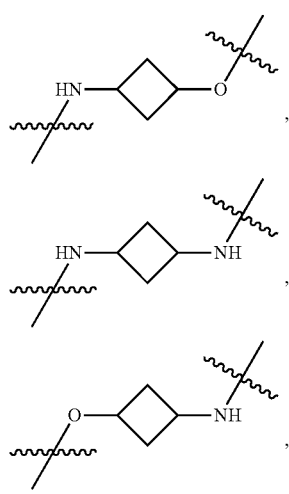

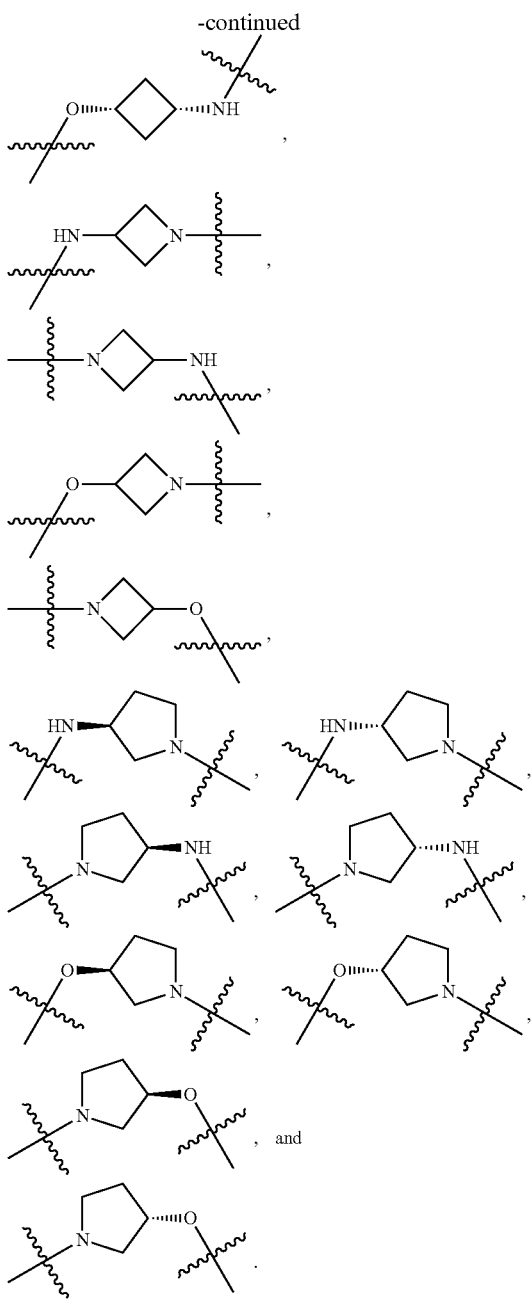

and

In additional embodiments, "Tail" is an optionally substituted ethylene glycol having at least 1, at least 2, at least 3, at least 4, at least 5, at least 6, at least 7, at least 8, at least 9, at least 10, ethylene glycol units, or optionally substituted alkyl groups interspersed with optionally substituted, O, N, S, P or Si atoms. In certain embodiments, "Tail" is flanked, substituted, or interspersed with an aryl, phenyl, benzyl, alkyl, alkylene, or heterocycle group. In certain embodiments, "Tail" may be asymmetric or symmetrical. In some embodiments, "Tail" is a substituted or unsubstituted polyethylene glycol group ranging in size from about 1 to about 12 ethylene glycol units, between 1 and about 10 ethylene glycol units, about 2 about 6 ethylene glycol units, between about 2 and 5 ethylene glycol units, between about 2 and 4 ethylene glycol units. In any of the embodiments of the compounds described herein, "Tail" group may be any suitable moiety as described herein.

In additional embodiments, the "Tail" is selected from:
—NR$^{61}$(CH$_2$)$_{n1}$-(lower alkyl)-X$^{22}$, —NR$^{61}$(CH$_2$)$_{n1}$-(lower alkoxyl)-X$^{22}$,
—NR$^{61}$(CH$_2$)$_{n1}$-(lower alkoxyl)-OCH$_2$—X$^{22}$, —NR$^{61}$(CH$_2$)$_{n1}$-(lower alkoxyl)-(lower alkyl)-OCH$_2$—X$^{22}$,
—NR$^{61}$(CH$_2$)$_{n1}$-(cycloalkyl)-(lower alkyl)-OCH$_2$—X$^{22}$,
—NR$^{61}$(CH$_2$)$_{n1}$-(heterocycloalkyl)-X$^{22}$,
—NR$^{61}$(CH$_2$CH$_2$O)$_{n1}$-(lower alkyl)-O—CH$_2$—X$^{22}$,
—NR$^{61}$(CH$_2$CH$_2$O)$_{n1}$-(heterocycloalkyl)-O—CH$_2$—X$^{22}$,
—NR$^{61}$(CH$_2$CH$_2$O)$_{n1}$-Aryl-O—CH$_2$—X$^{22}$, —NR$^{61}$(CH$_2$CH$_2$O)$_{n1}$-(heteroaryl)-O—CH$_2$—X$^{22}$,
—NR$^{61}$(CH$_2$CH$_2$O)$_{n1}$-(cycloalkyl)-O-(heteroaryl)-O—CH$_2$—X$^{22}$,
—NR$^{61}$(CH$_2$CH$_2$O)$_{n1}$-(cycloalkyl)-O-Aryl-O—CH$_2$—X$^{22}$,
—NR$^{61}$(CH$_2$CH$_2$O)$_{n1}$-(lower alkyl)-NH-Aryl-O— CH$_2$—X$^{22}$,
—NR$^{61}$(CH$_2$CH$_2$O)$_{n1}$-(lower alkyl)-O-Aryl-CH$_2$—X$^{22}$,
—NR$^{61}$(CH$_2$CH$_2$O)$_{n1}$-cycloalkyl-O-Aryl-X$^{22}$, —NR$^{61}$(CH$_2$CH$_2$O)$_{n1}$-cycloalkyl-O-heteroaryl-X$^{22}$,
—NR$^{61}$(CH$_2$CH$_2$)$_{n1}$-(cycloalkyl)-O-(heterocycle)-CH$_2$—X$^{22}$
—NR$^{61}$(CH$_2$CH$_2$)$_{n1}$-(heterocycle)-(heterocycle)-CH$_2$—X$^{22}$, and —NR$^{61}$-(heterocycle)-CH$_2$—X$^{22}$;
wherein n1 is 0, 1, 2, 3, 4, 5, 6, 7, 8, 9, or 10; and R$^{61}$ is H, methyl, or ethyl.

In additional embodiments, "Tail" is selected from:
—N(R$^{61}$)—(CH$_2$)$_{m1}$—O(CH$_2$)$_{n2}$—O(CH$_2$)$_{o1}$—O(CH$_2$)$_{p1}$—O(CH$_2$)$_{q1}$—O(CH$_2$)$_{r1}$—OCH$_2$—X$^{22}$
—O—(CH$_2$)$_{m1}$—O(CH$_2$)$_{n2}$—O(CH$_2$)$_{o1}$—O(CH$_2$)$_{p1}$—O(CH$_2$)$_{q1}$—O(CH$_2$)$_{r1}$—OCH$_2$—X$^{22}$
—O—(CH$_2$)$_{m1}$—O(CH$_2$)$_{n2}$—O(CH$_2$)$_{o1}$—O(CH$_2$)$_{p1}$—O(CH$_2$)$_{q1}$—O(CH$_2$)$_{r1}$—OH;
—N(R$^{61}$)—(CH$_2$)$_{m1}$—O(CH$_2$)$_{n2}$—O(CH$_2$)$_{o1}$—O(CH$_2$)$_{p1}$—O(CH$_2$)$_{q1}$—O(CH$_2$)$_{r1}$—OH;
—(CH$_2$)$_{m1}$—O(CH$_2$)$_{n2}$—O(CH$_2$)$_{o1}$—O(CH$_2$)$_{p1}$—O(CH$_2$)$_{q1}$—O(CH$_2$)$_{r1}$—OH;
—(CH$_2$)$_{m1}$—O(CH$_2$)$_{n2}$—O(CH$_2$)$_{o1}$—O(CH$_2$)$_{p1}$—O(CH$_2$)$_{q1}$—O(CH$_2$)$_{r1}$—OCH$_2$—X$^{22}$;
—O(CH$_2$)$_{m1}$O(CH$_2$)$_{n2}$O(CH$_2$)$_{p1}$O(CH$_2$)$_{q1}$OCH$_2$—X$^{22}$;
—O(CH$_2$)$_{m1}$O(CH$_2$)$_{n2}$O(CH$_2$)$_{p1}$O(CH$_2$)$_{q1}$OCH$_2$—X$^{22}$;
wherein
m1, n2, o1, p1, q1, and r1 are independently 1, 2, 3, 4, or 5; and
R$^{61}$ is H, methyl, or ethyl.

In additional embodiments, "Tail" is selected from:

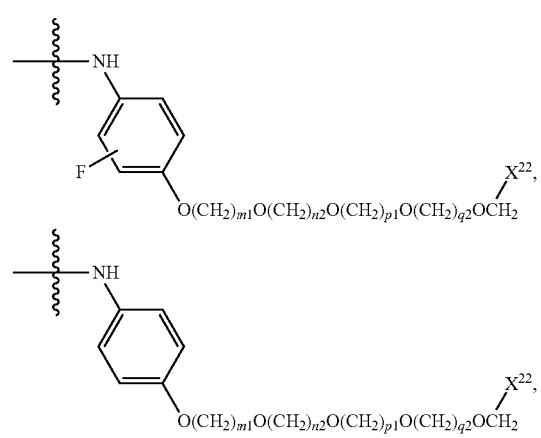

-continued
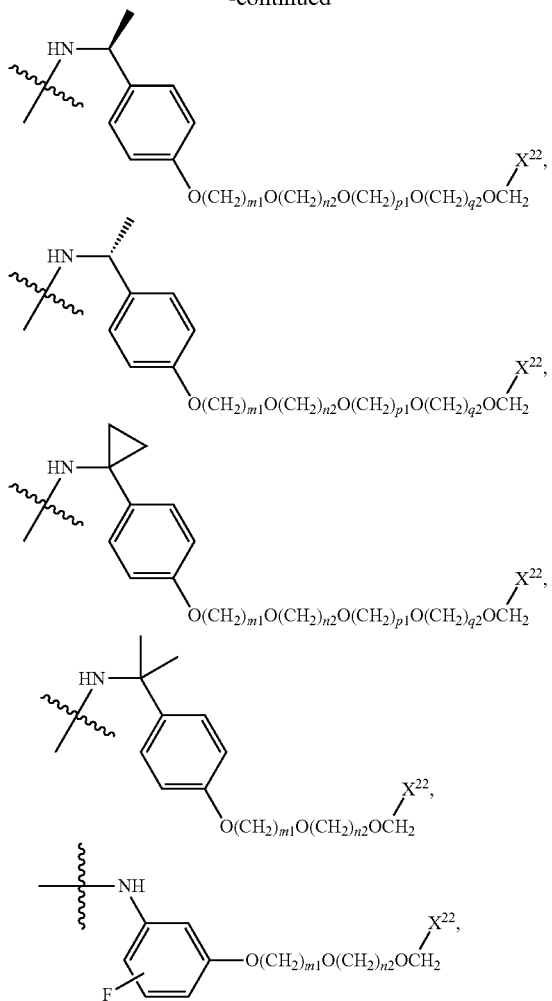
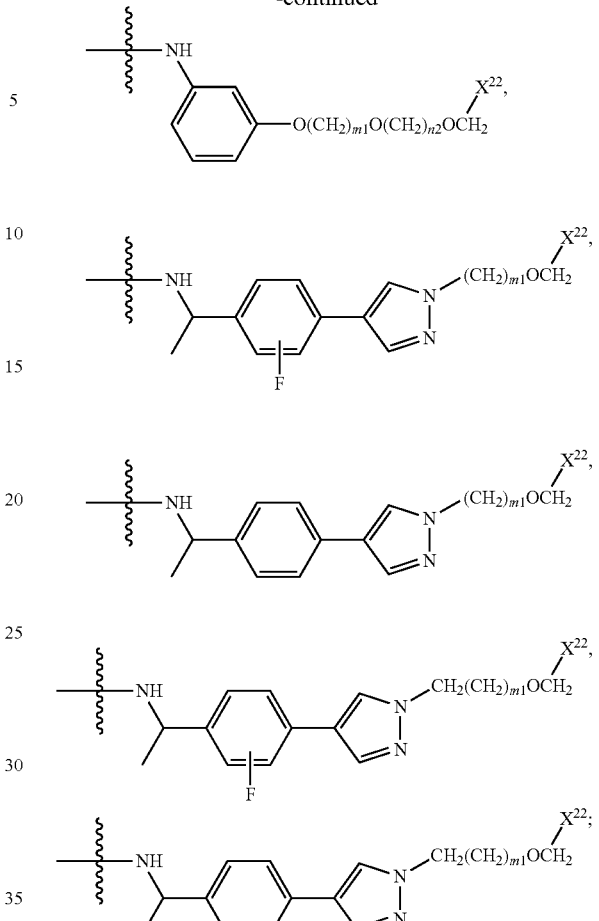
m1, n2, o1, p1, q2, and r1 are independently 1, 2, 3, 4, or 5.
In additional embodiments, "Tail" is selected from:
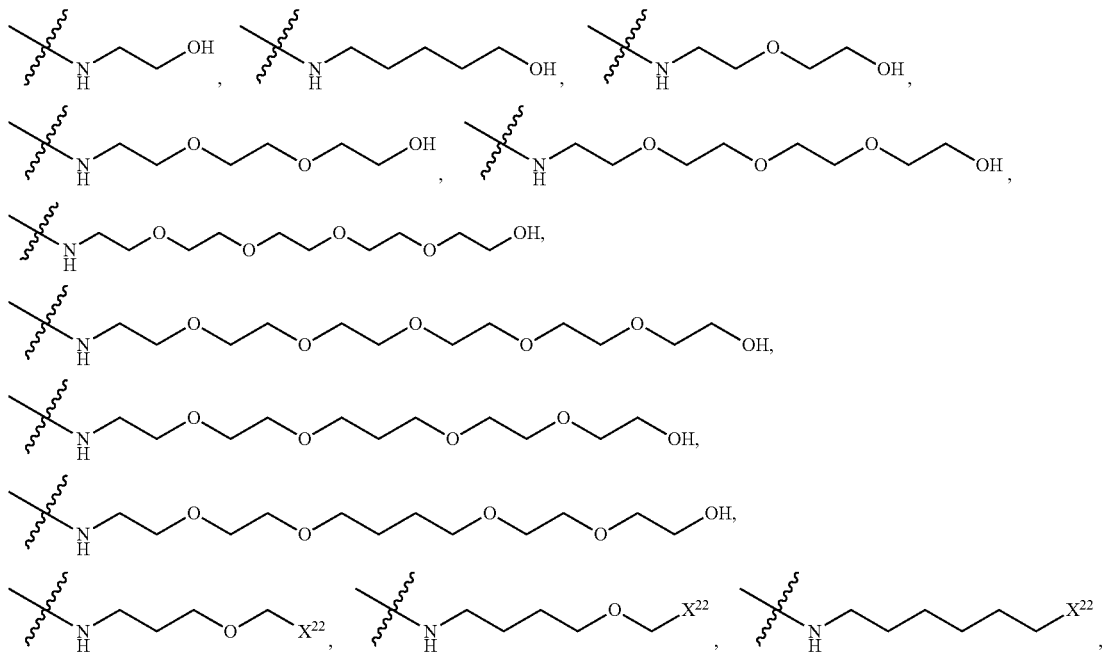

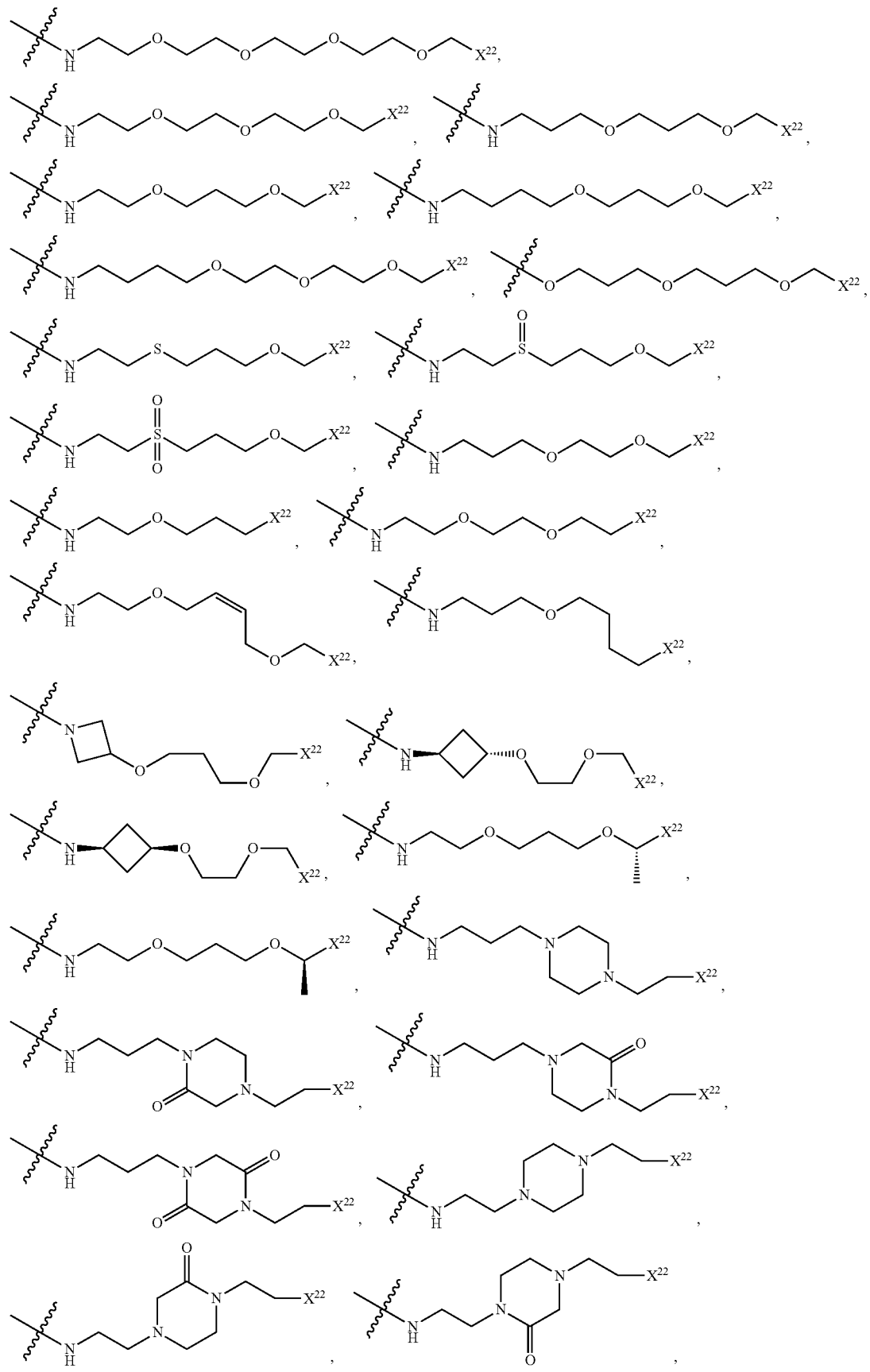

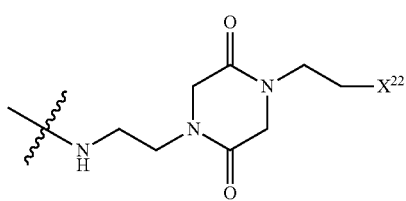
In additional embodiments, "Tail" is selected from:
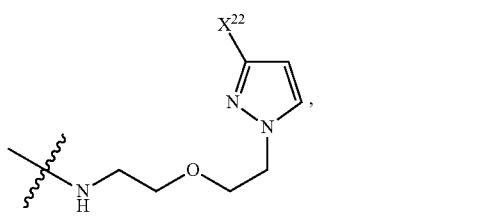
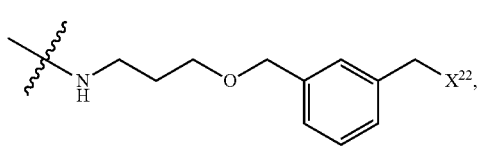
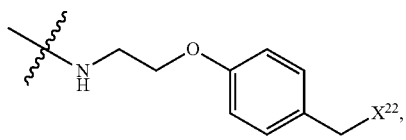
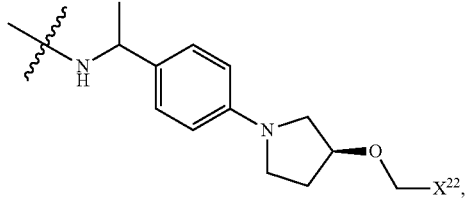
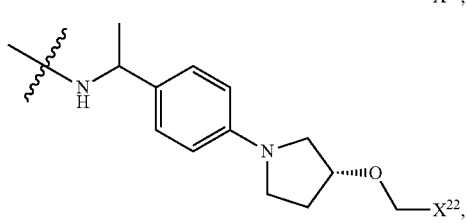
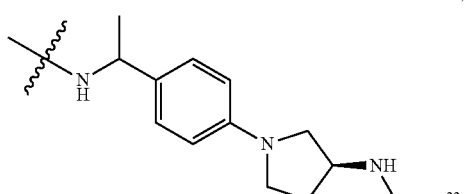
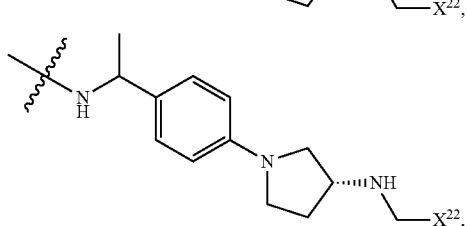
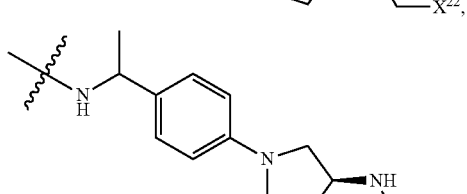
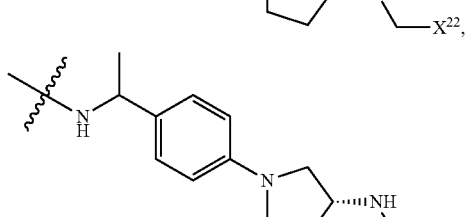
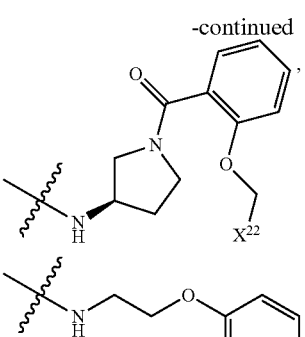
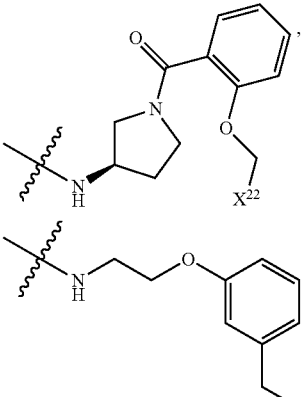
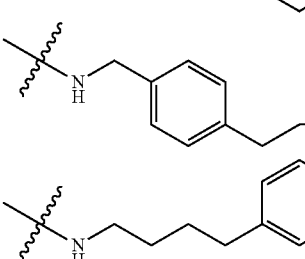
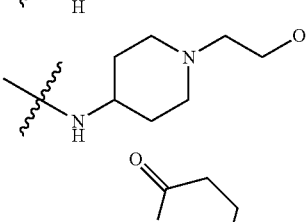
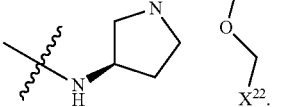
In additional embodiments, "Tail" is selected from:
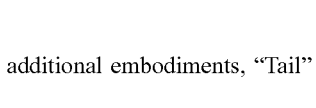
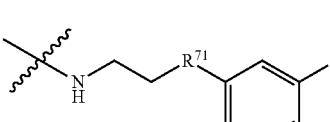
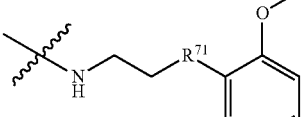

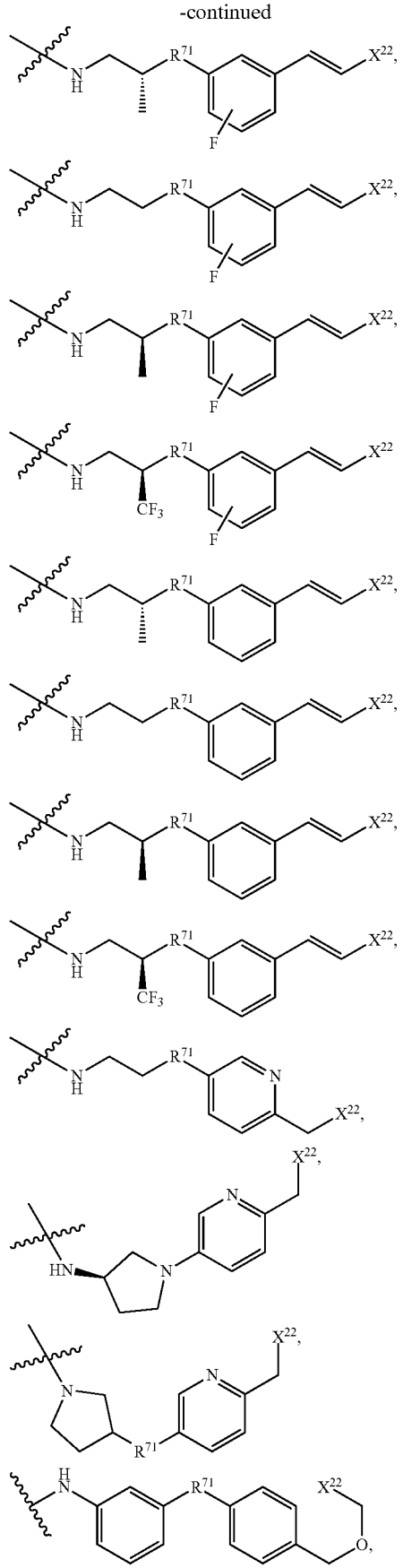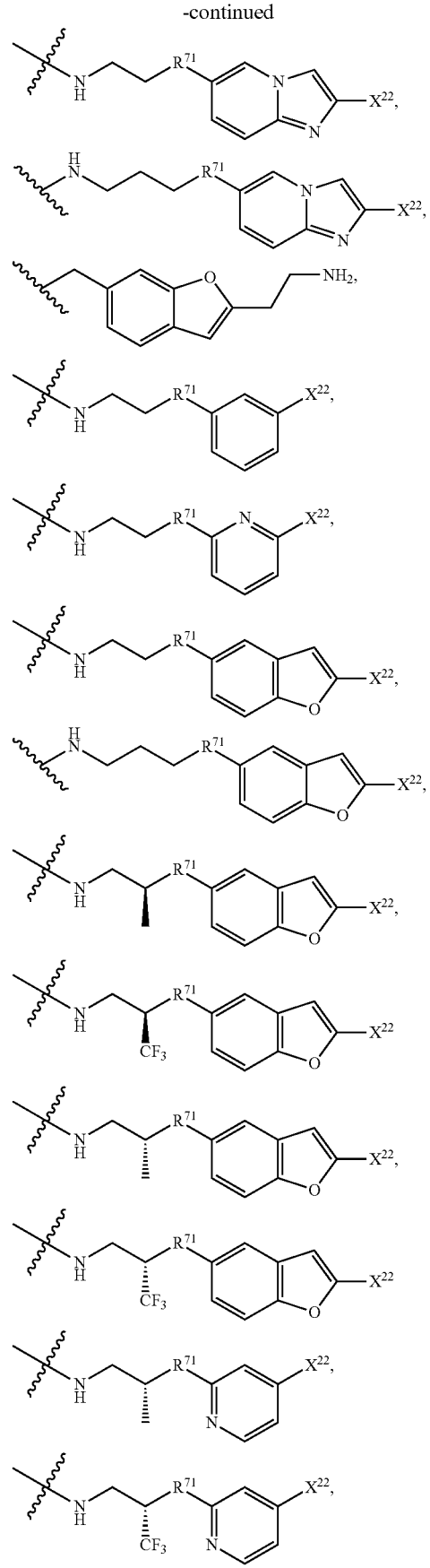

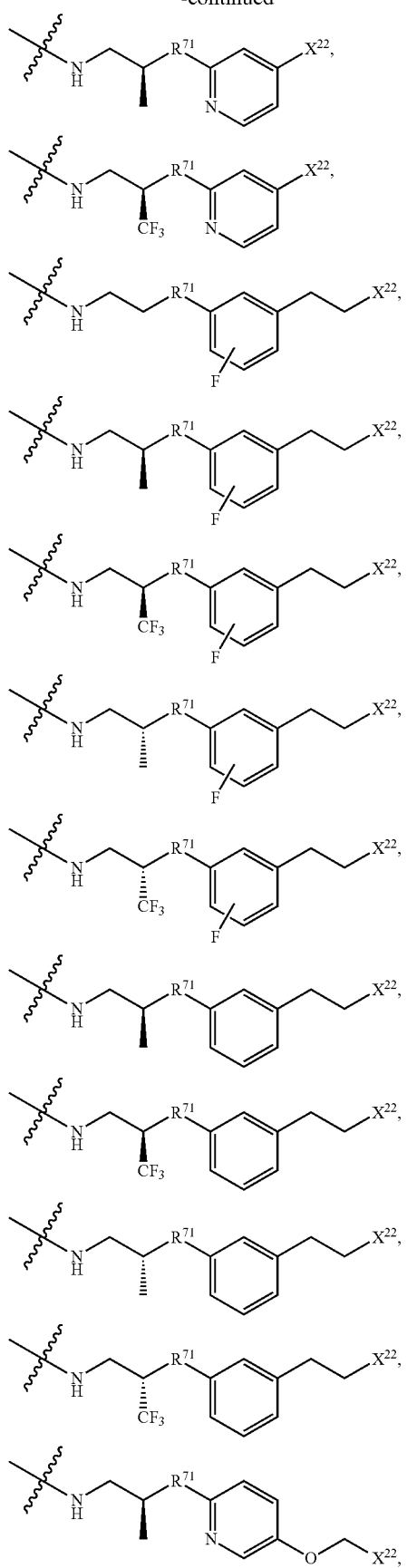
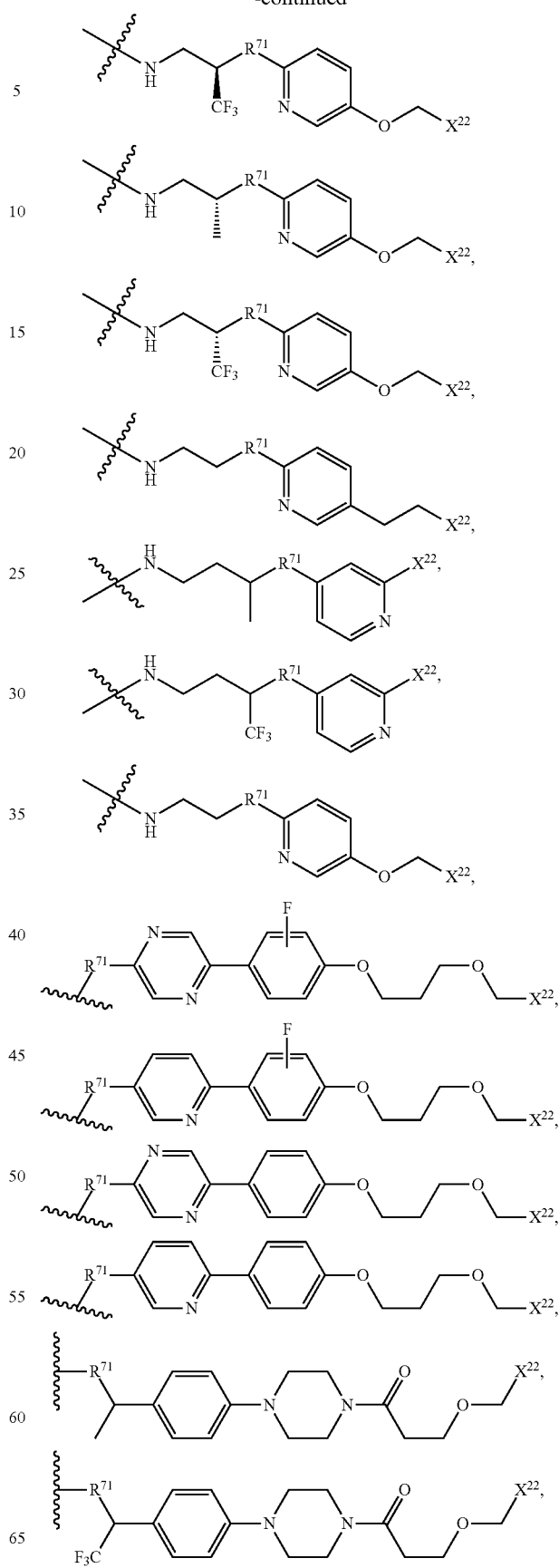

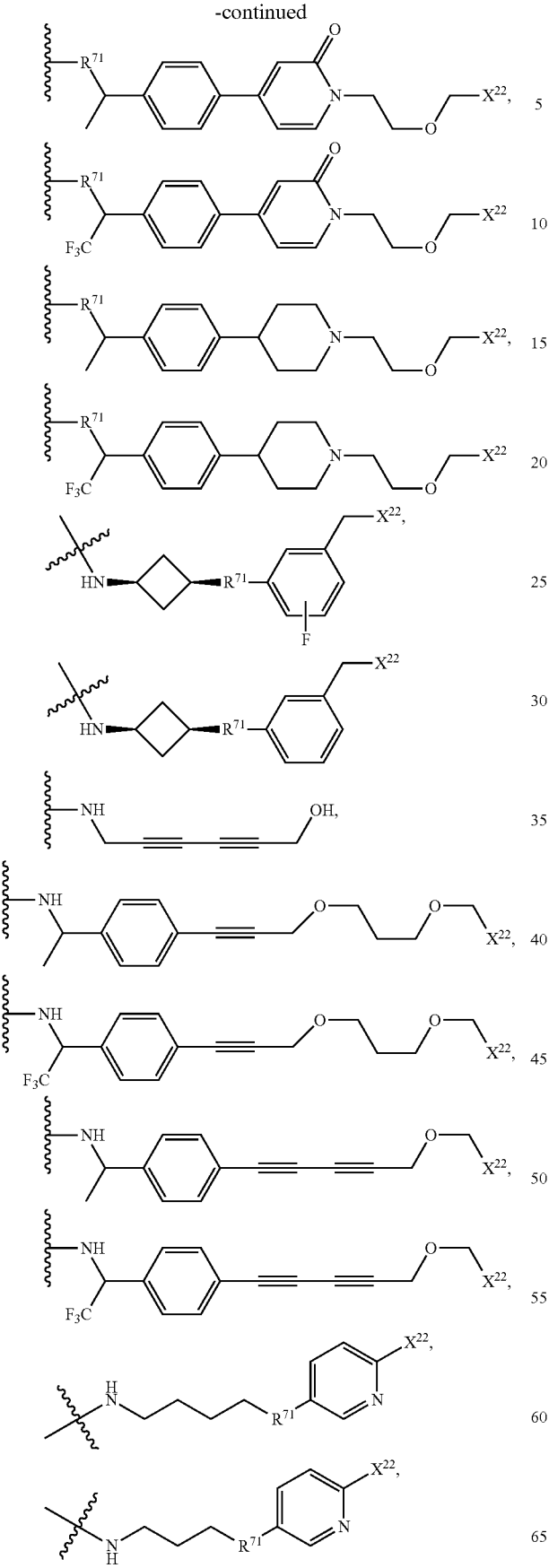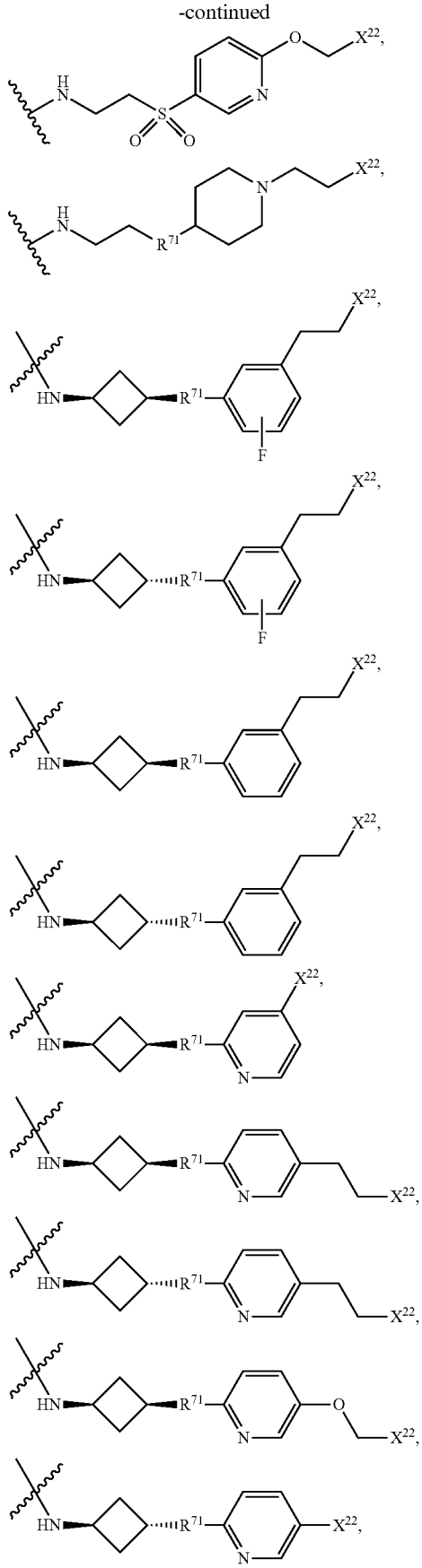

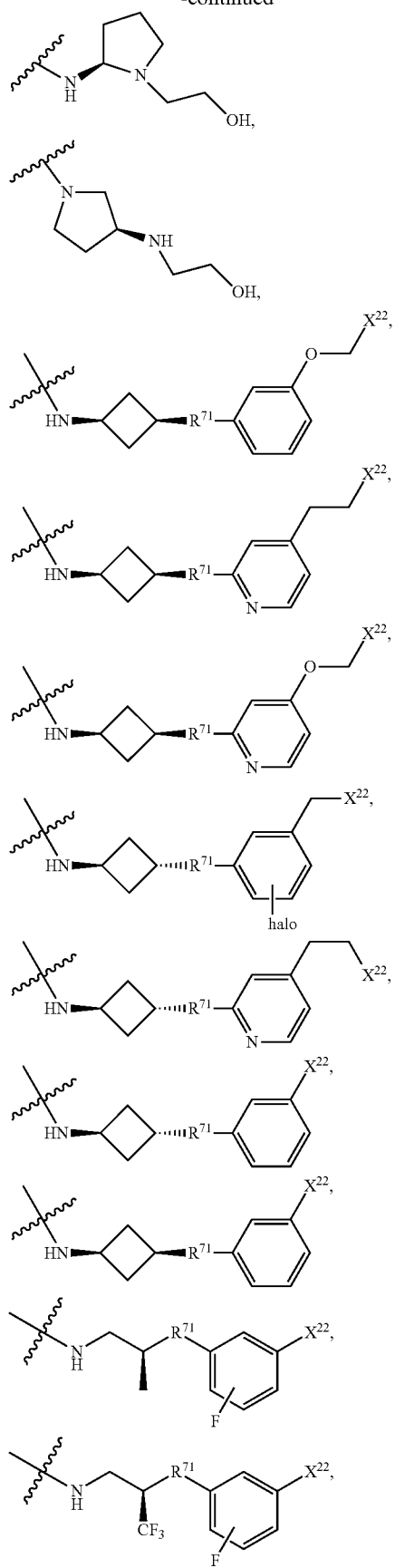
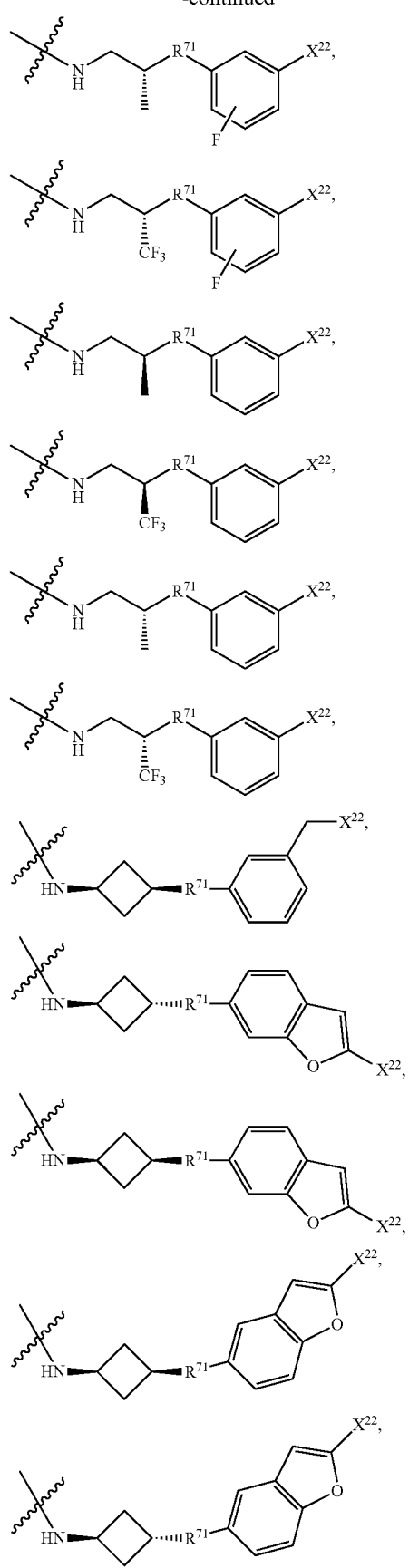

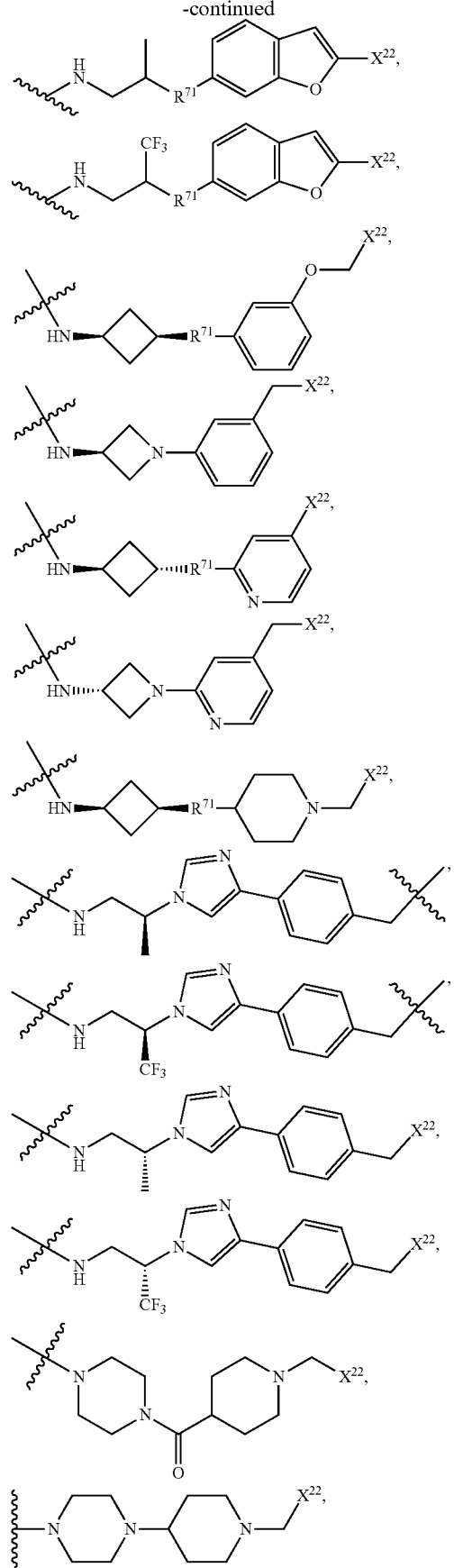
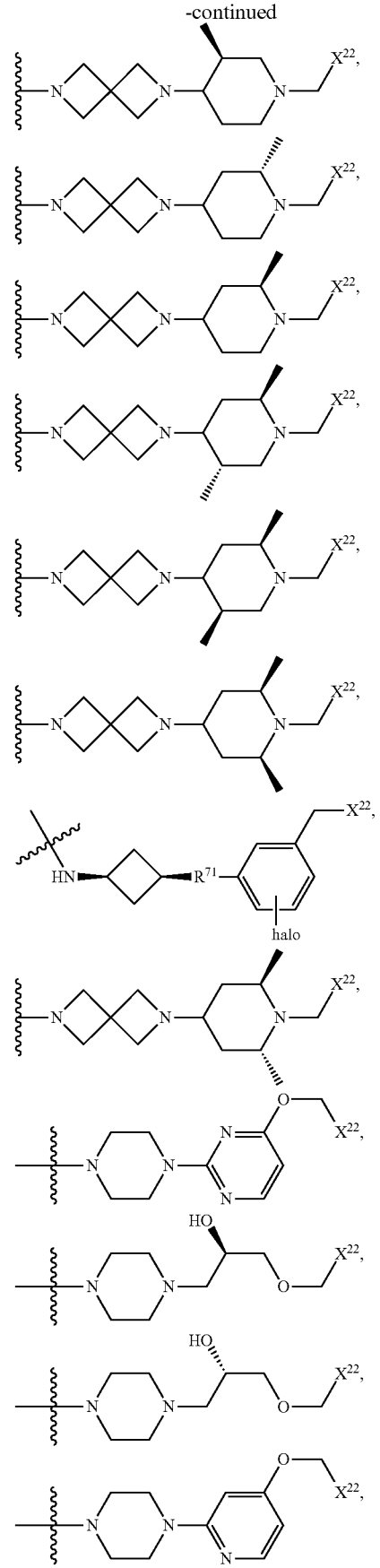

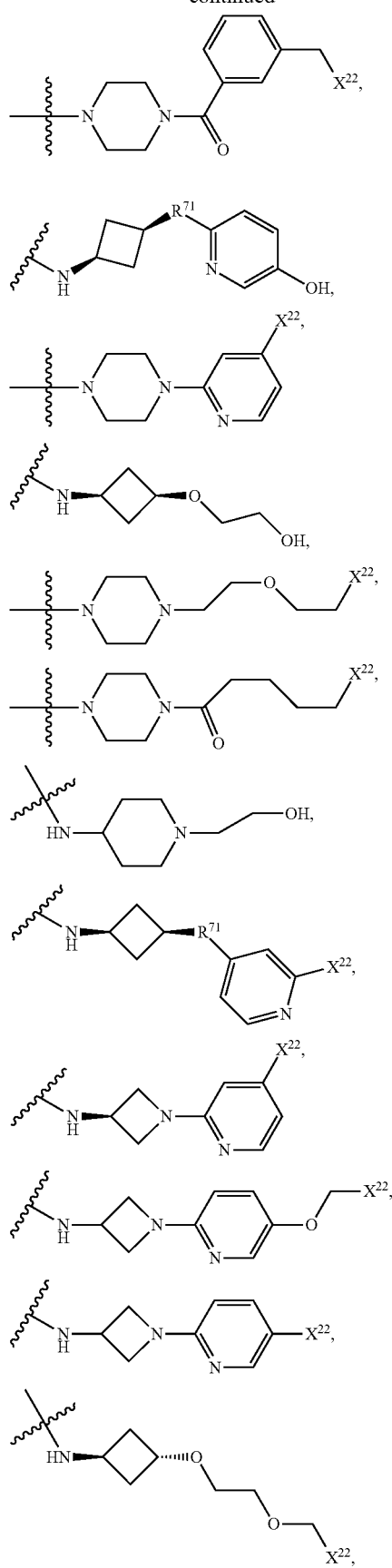
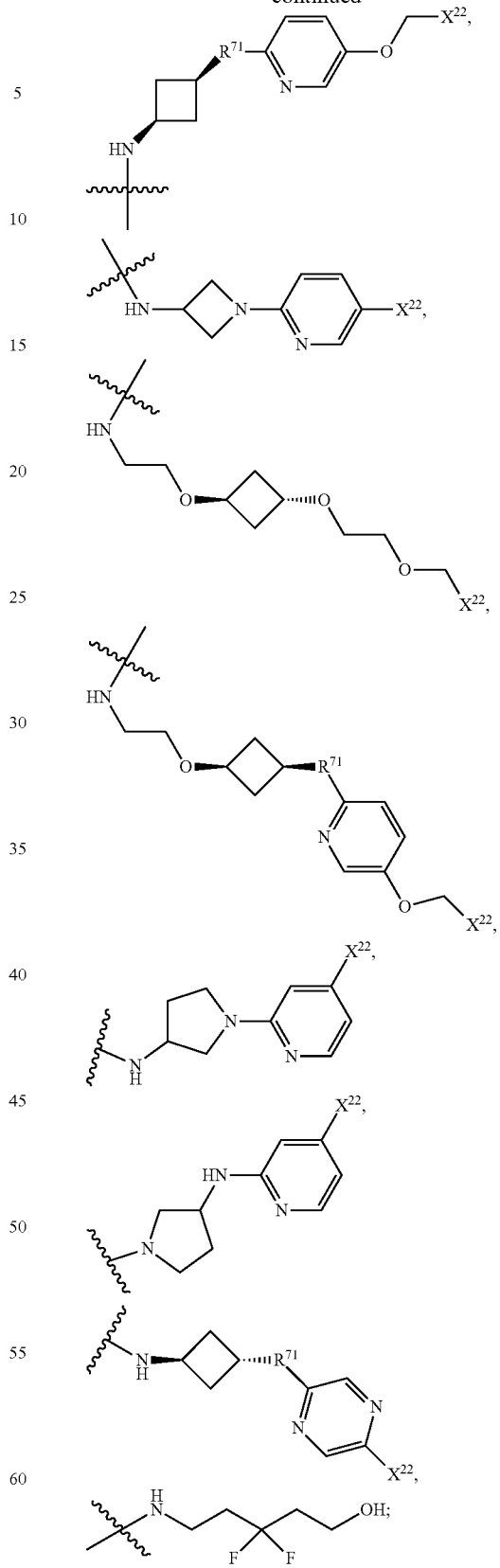
wherein R[71] is —O—, —NH, Nalkyl, heteroaliphatic, aliphatic, or —NMe.

In additional embodiments "Tail" is selected from:
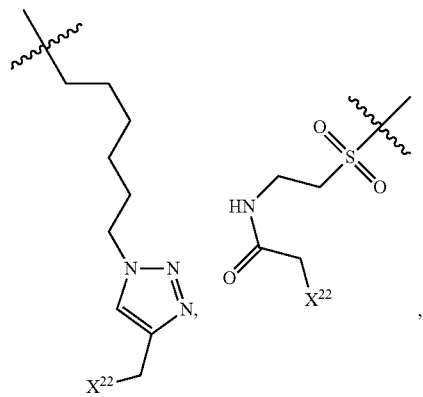
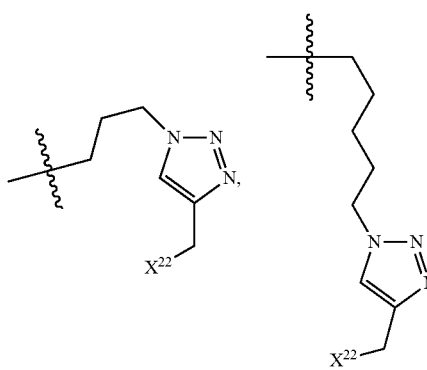
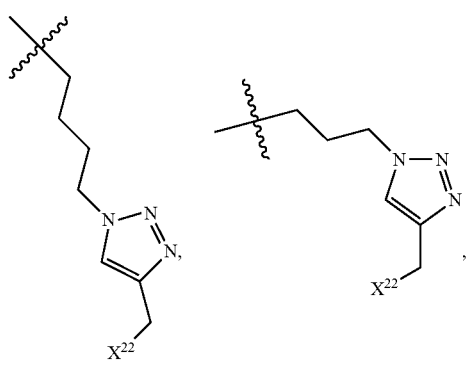
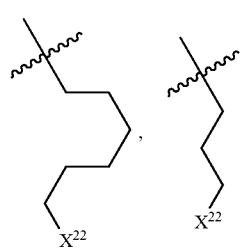
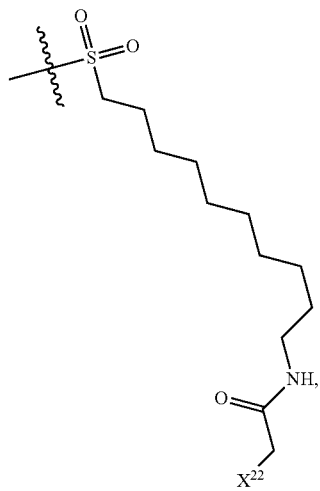
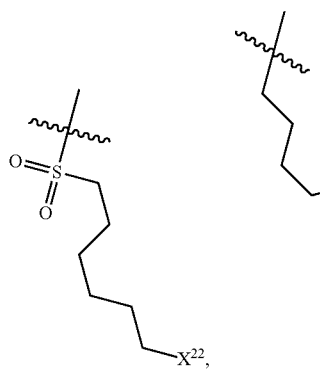
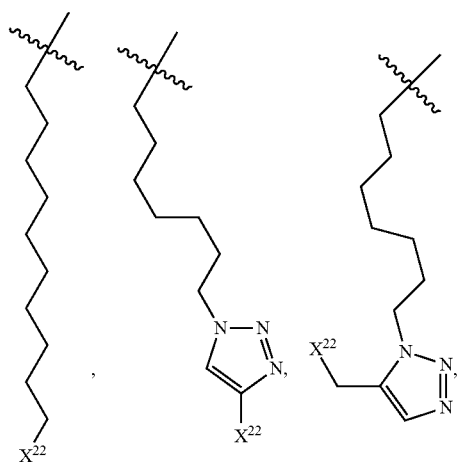

199
-continued
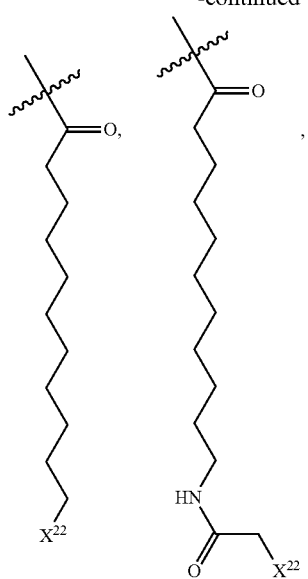
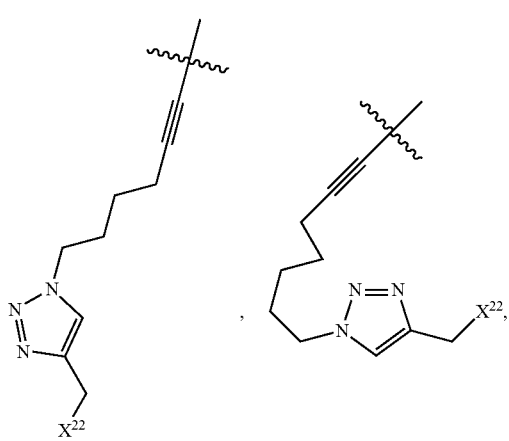
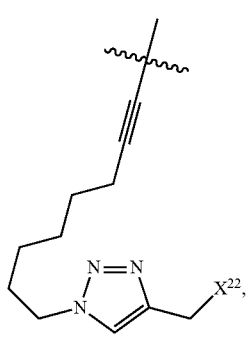
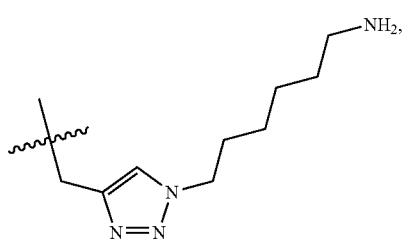
200
-continued
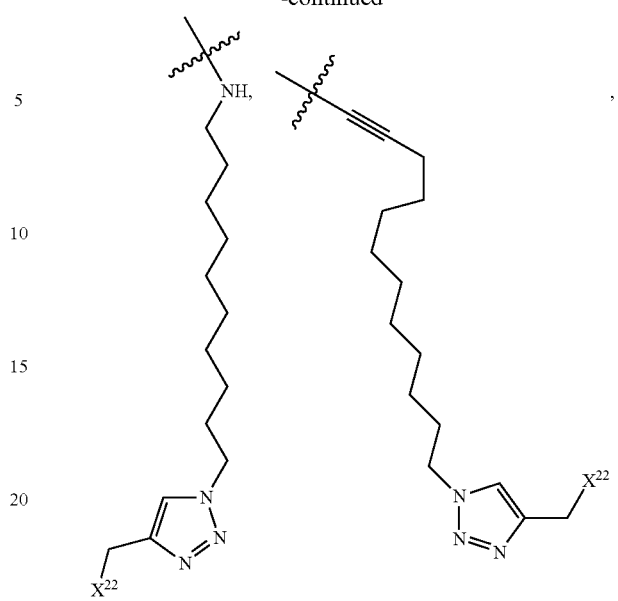
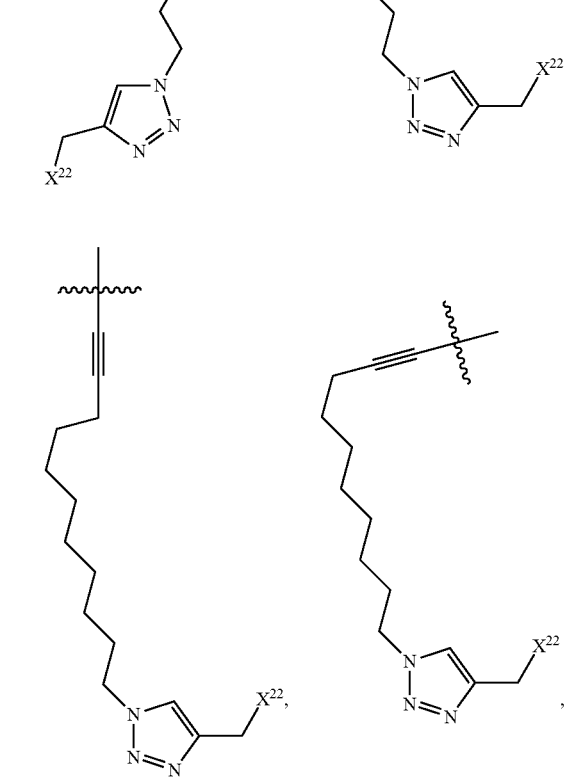
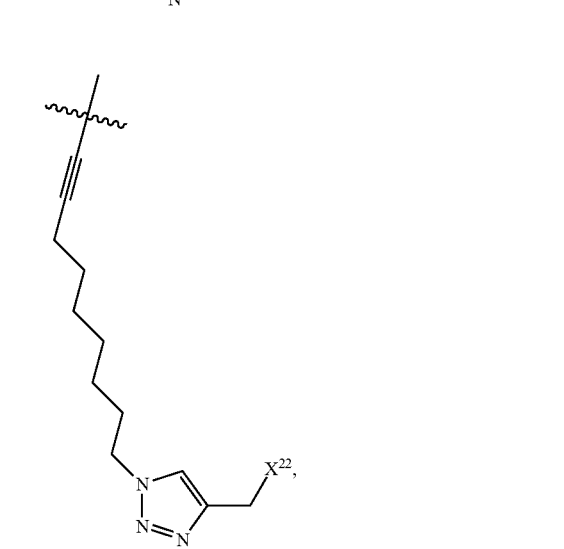

201
-continued
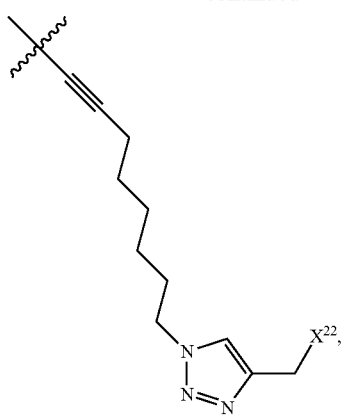
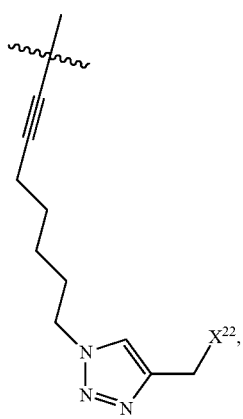
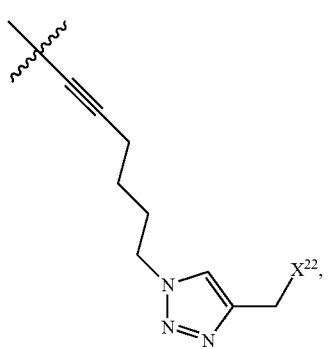
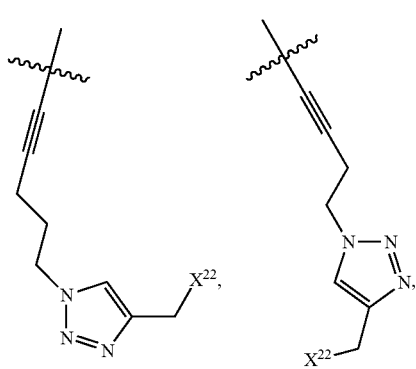
202
-continued
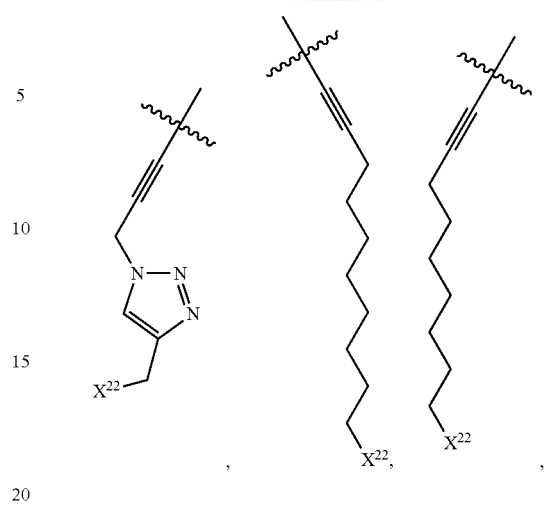
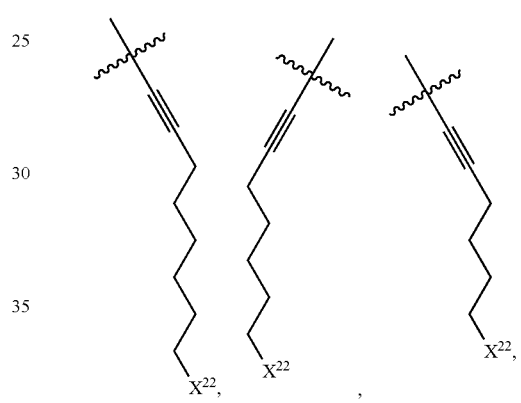
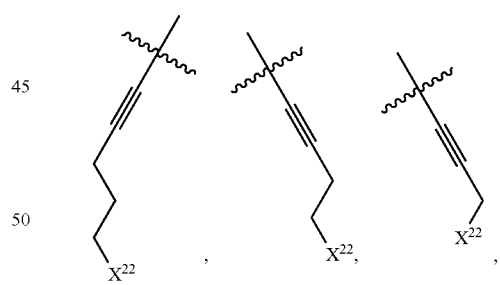
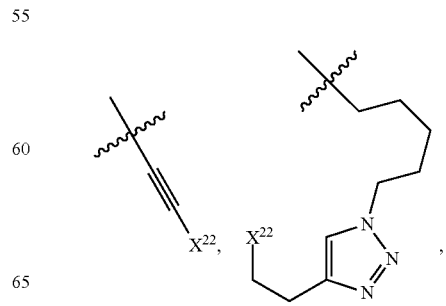

203
-continued
204
-continued
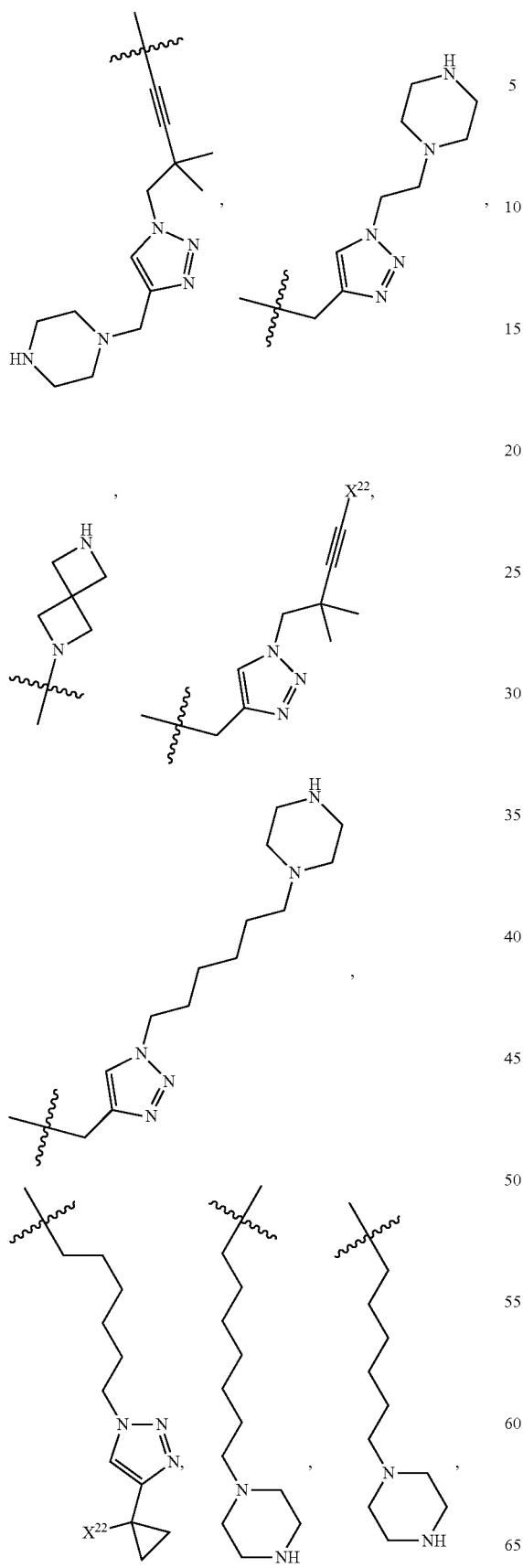
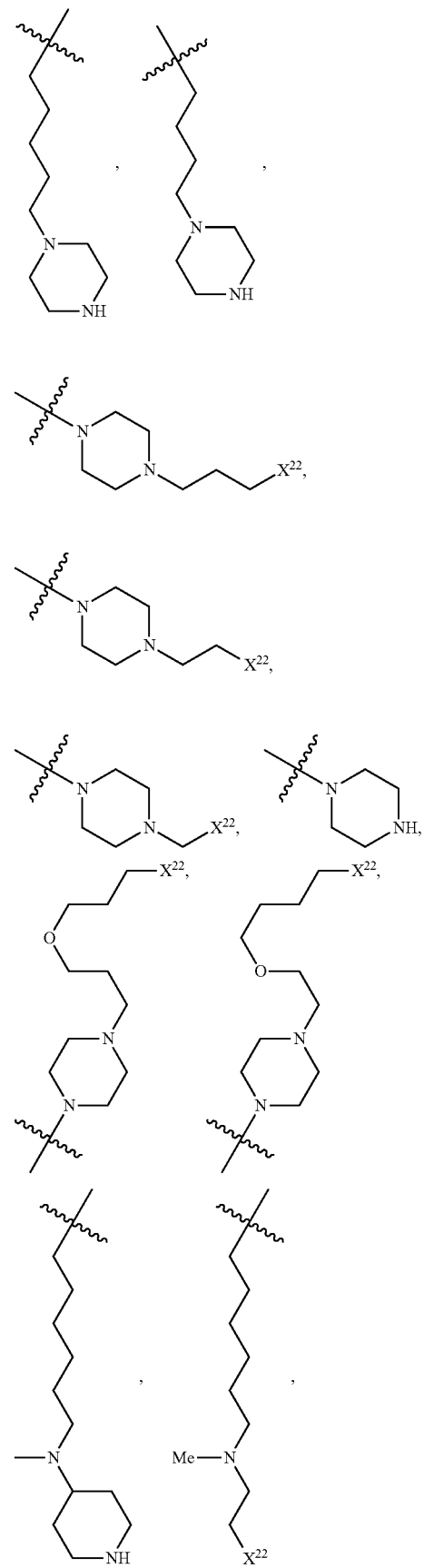

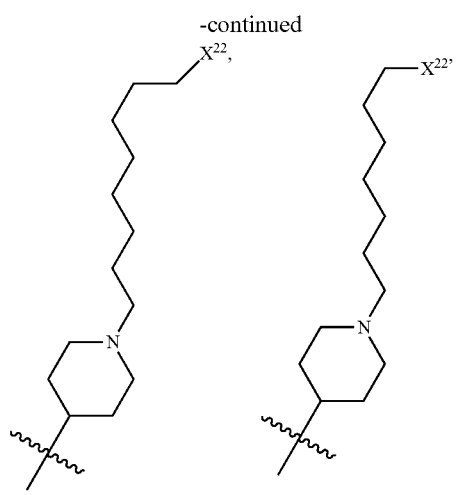
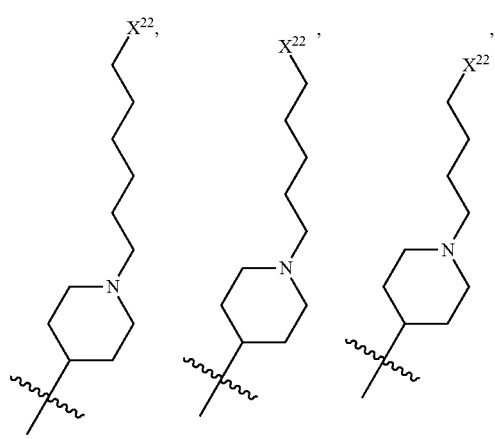
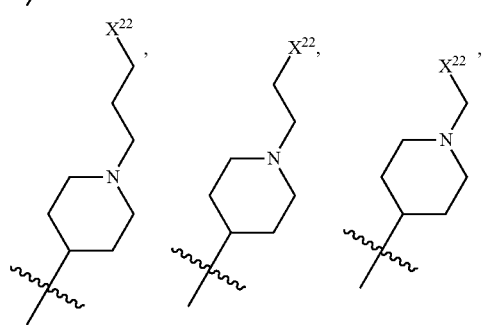
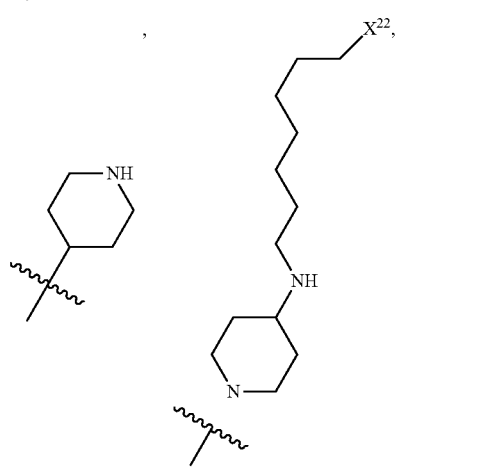
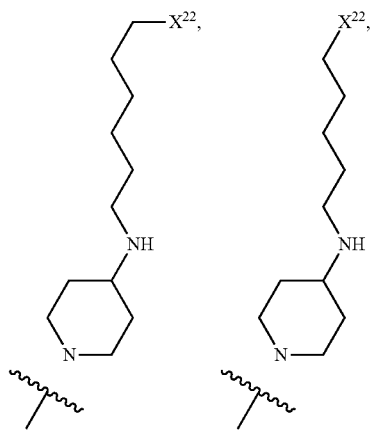
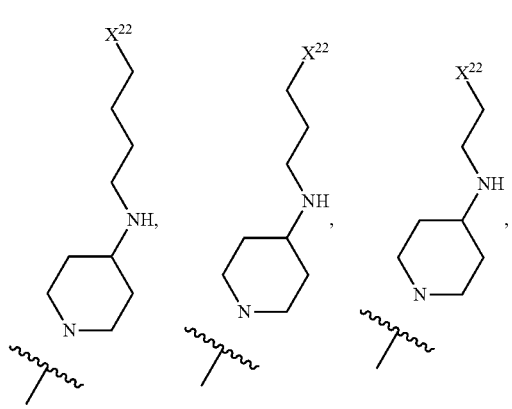
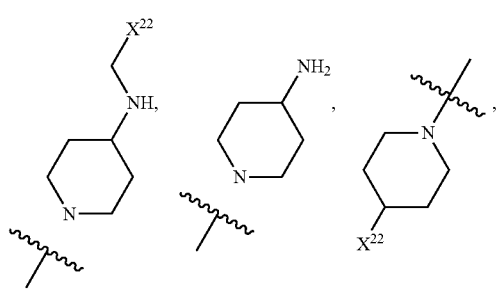
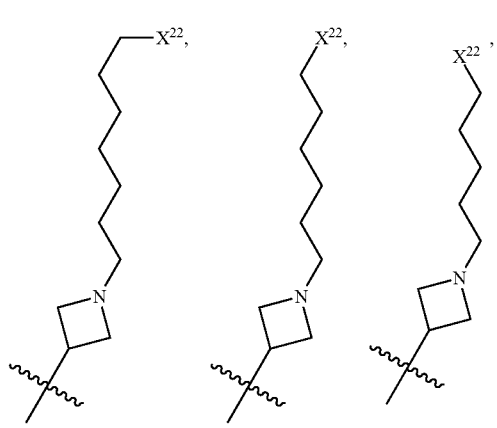

207
-continued
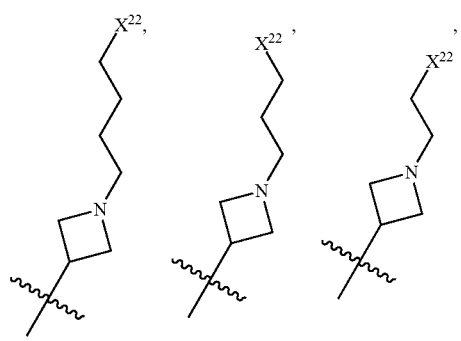
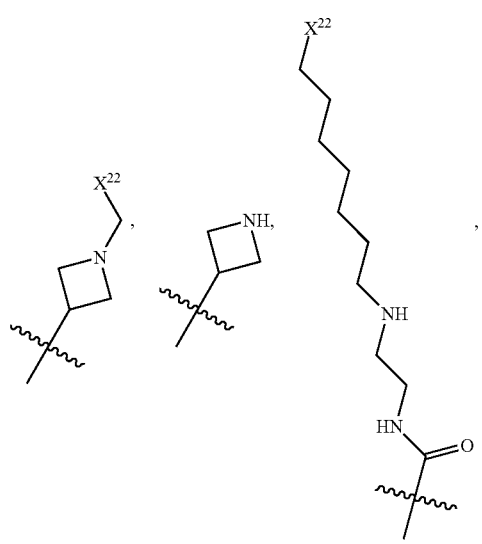
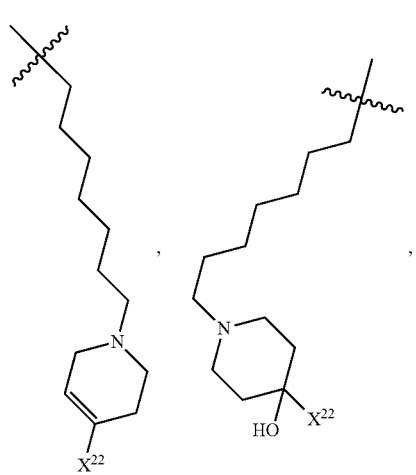
208
-continued
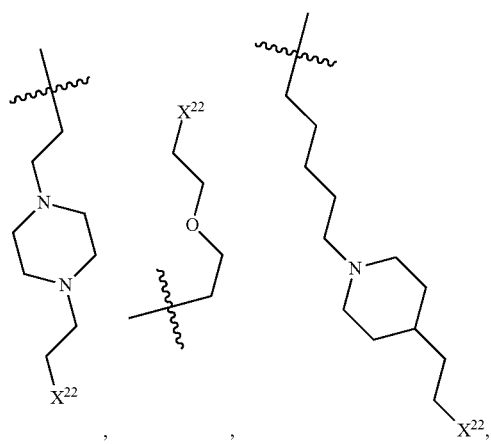
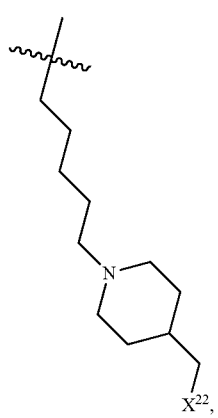
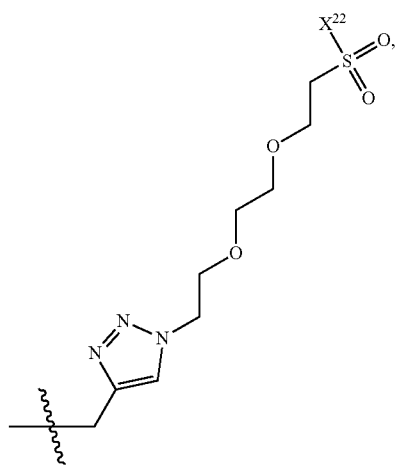

209
-continued
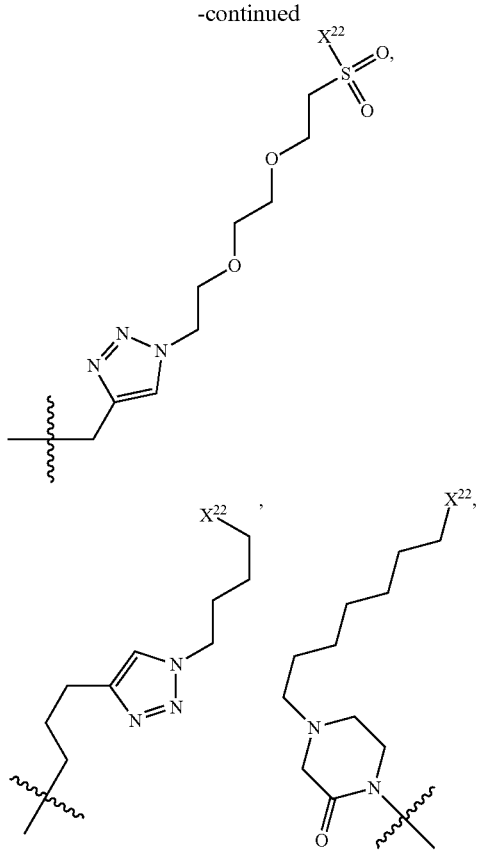
210
-continued
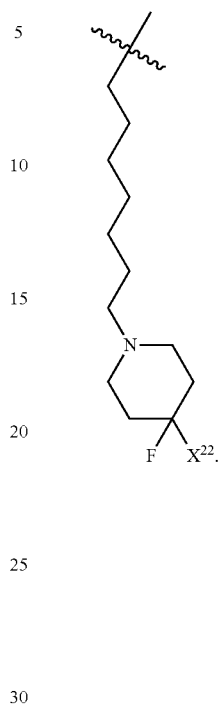
In additional embodiments, "Tail" is selected from:
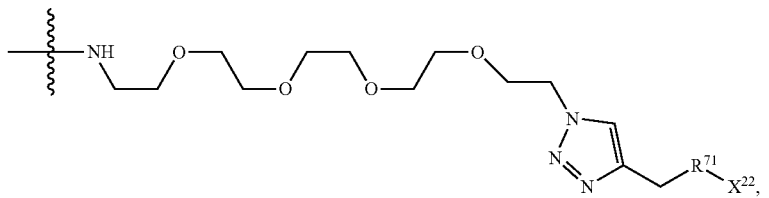
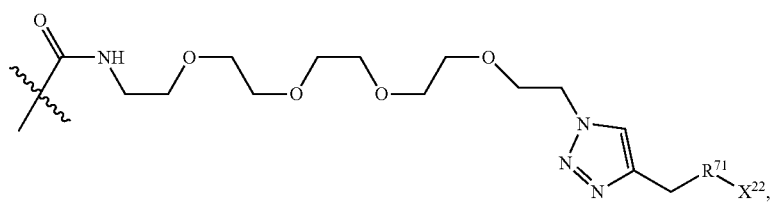
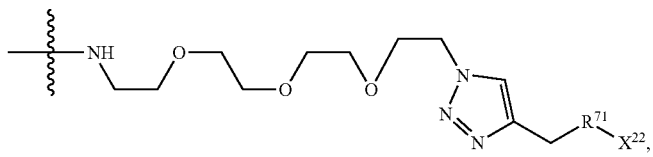
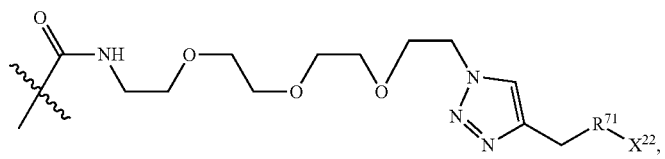

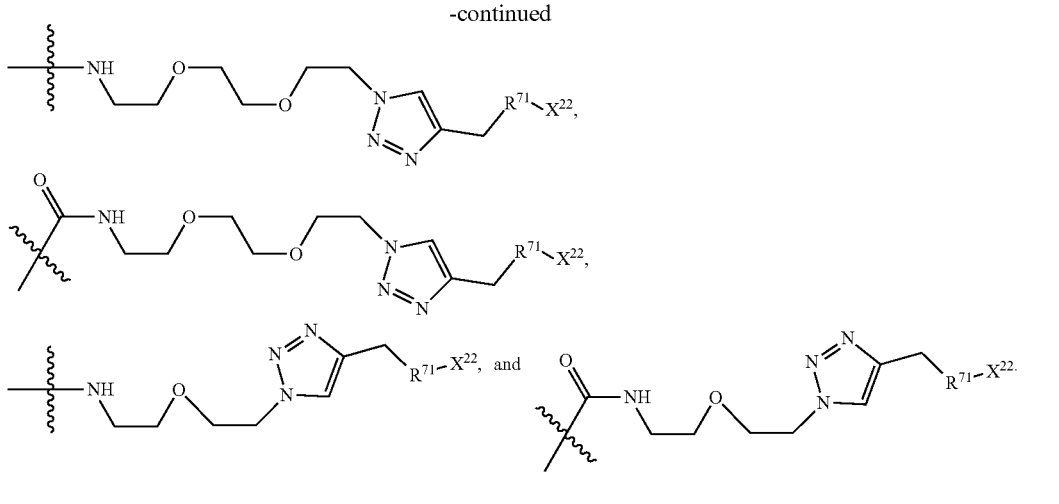
In additional embodiments, "Tail" is selected from:
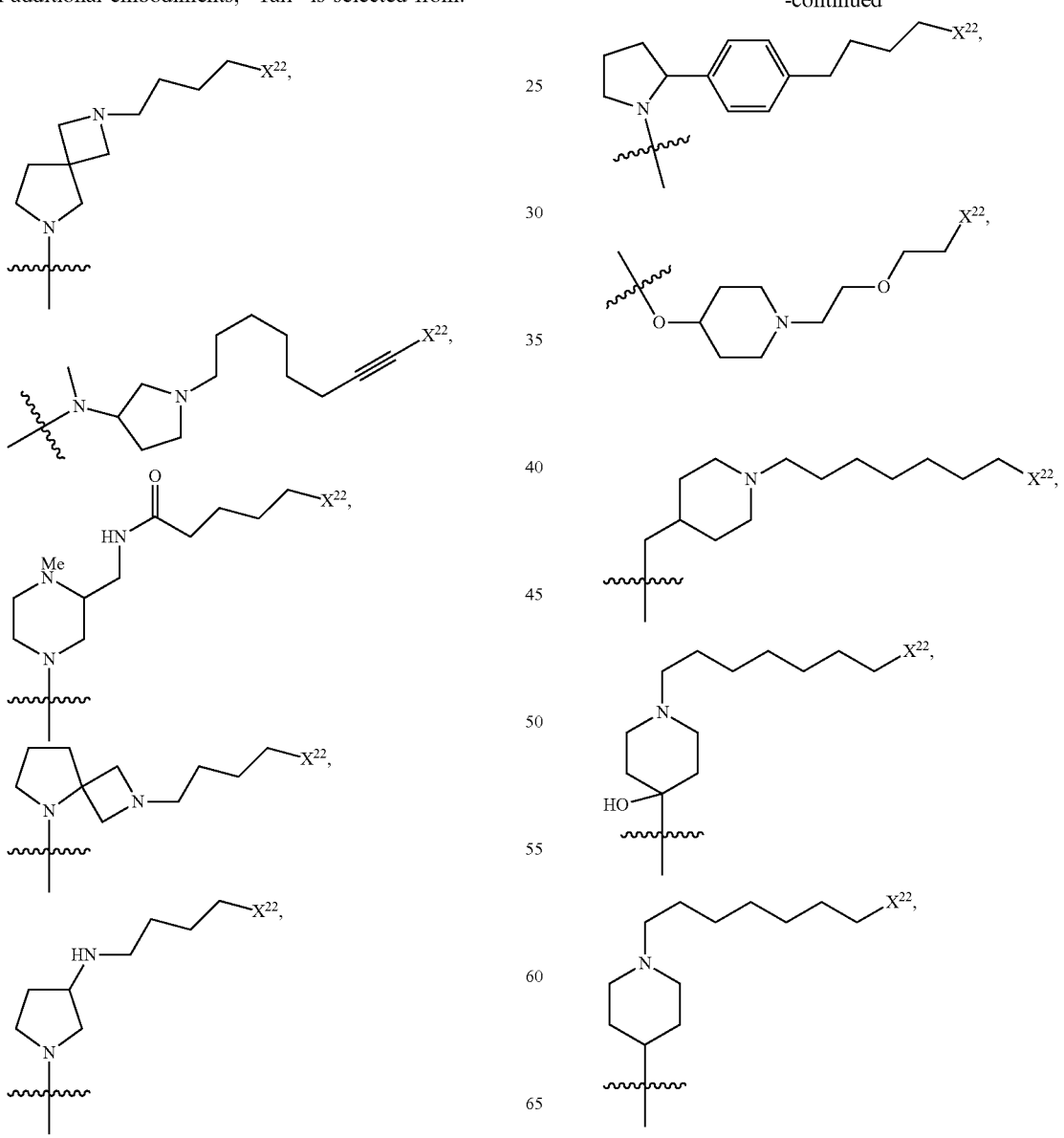

213
-continued
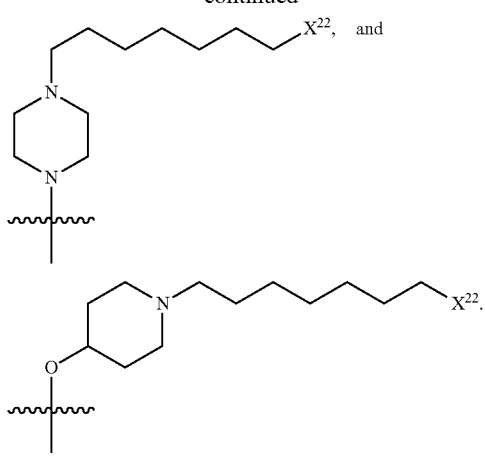
In additional embodiments, "Tail" is selected from:
214
-continued
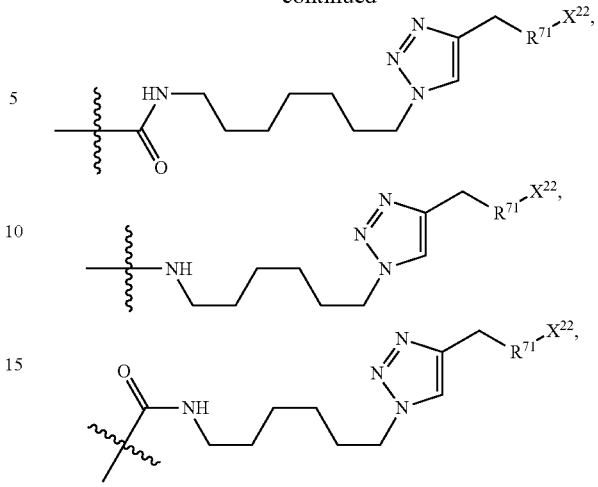
In additional embodiments, "Tail" is selected from:

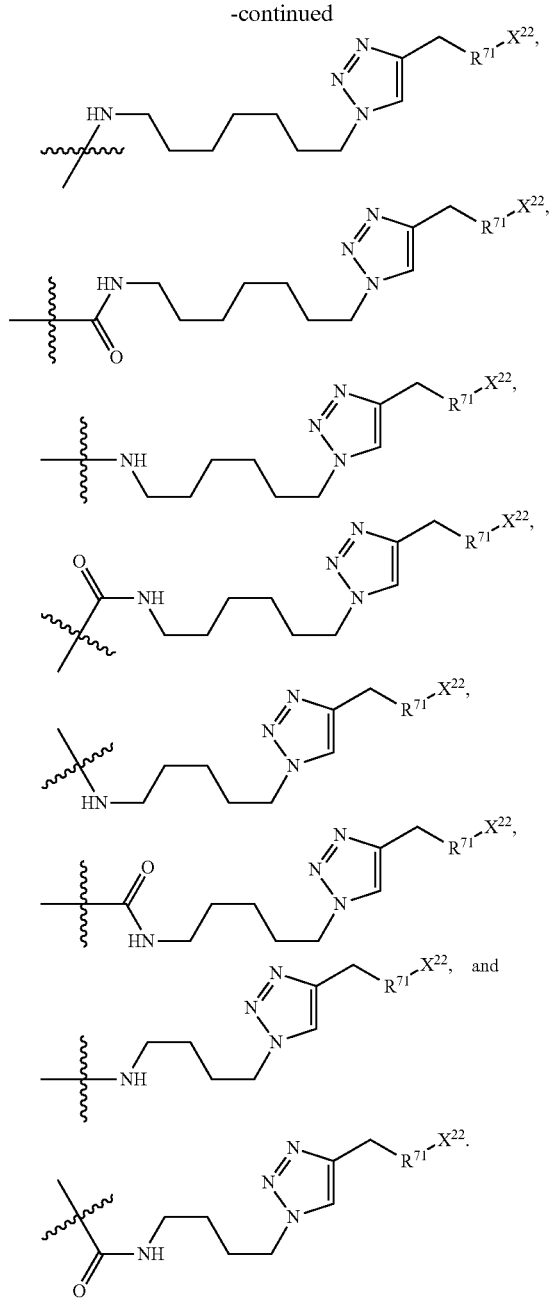
In the above embodiments $X^{22}$ is selected such that a compound sufficiently stable or the intended use results.
In additional embodiments "Tail" is selected from:
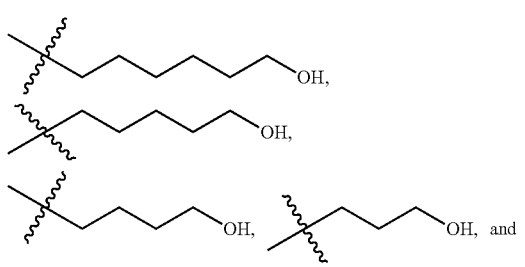
In certain embodiments, "Tail" is selected from:
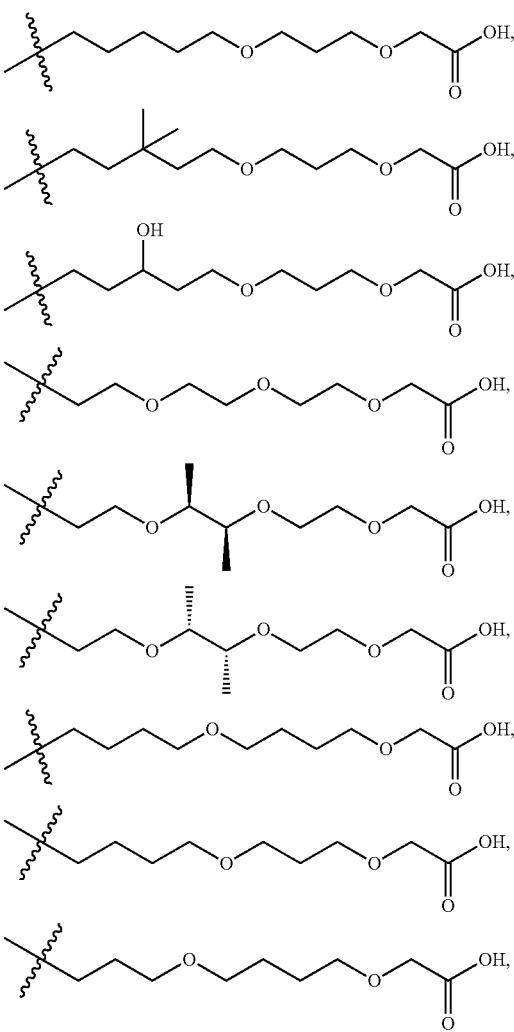
In certain embodiments "Tail" is selected from:
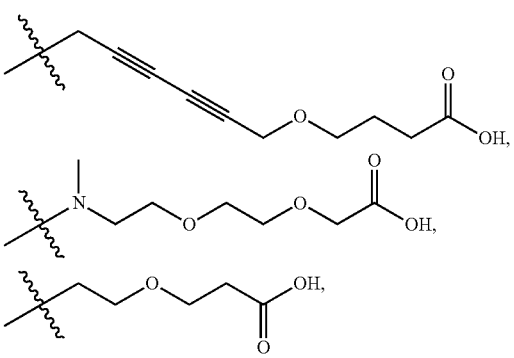

217
-continued
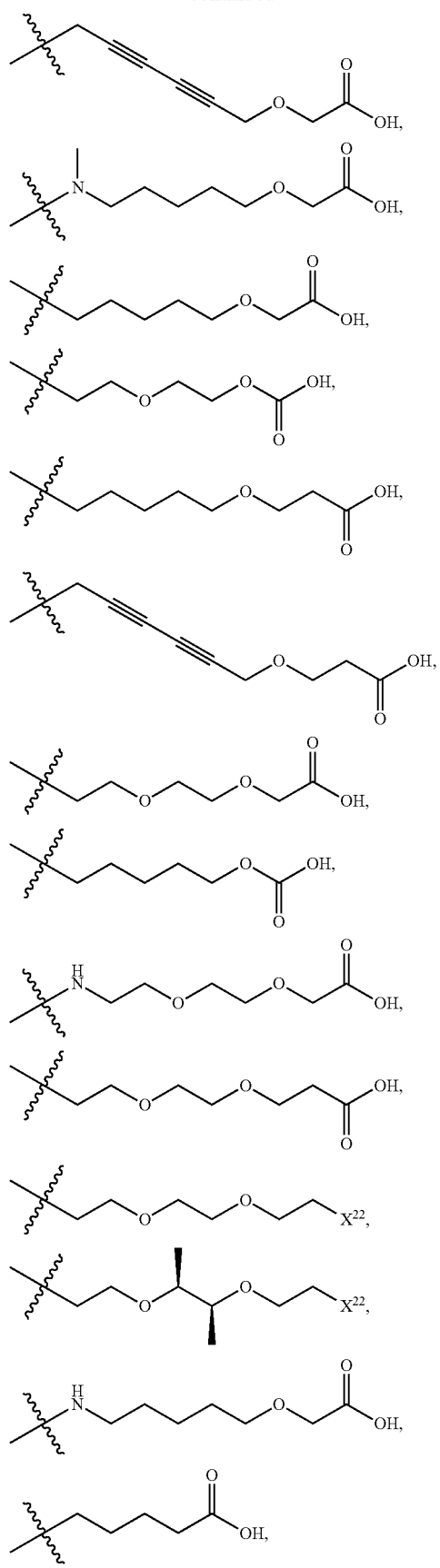
218
-continued
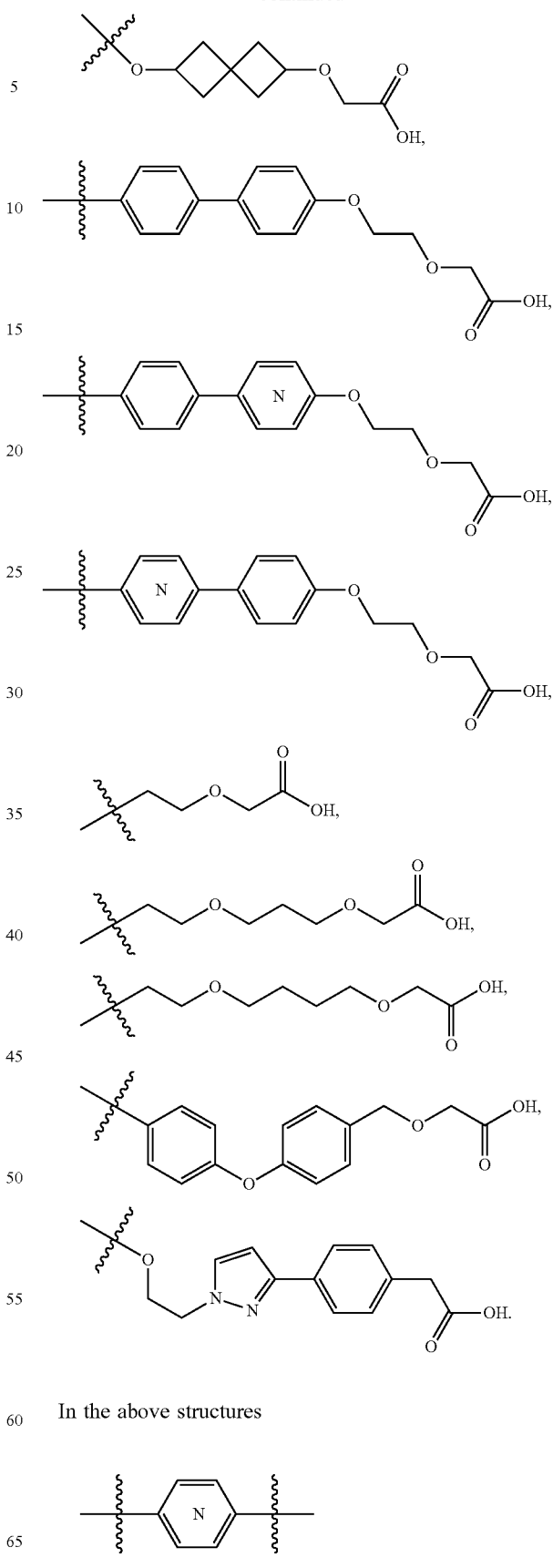
In the above structures

represents
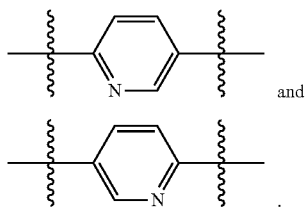 and
In certain embodiments, "Tail" can be a 4-24 carbon atom linear chains, wherein one or more the carbon atoms in the linear chain can be replaced or substituted with oxygen, nitrogen, amide, fluorinated carbon, etc., such as the following:
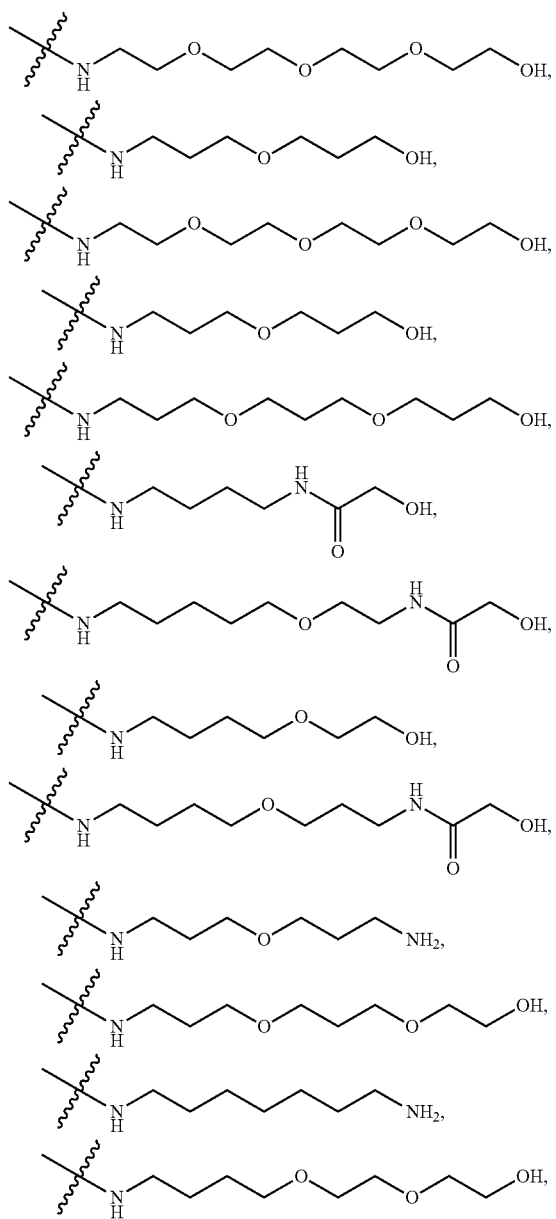
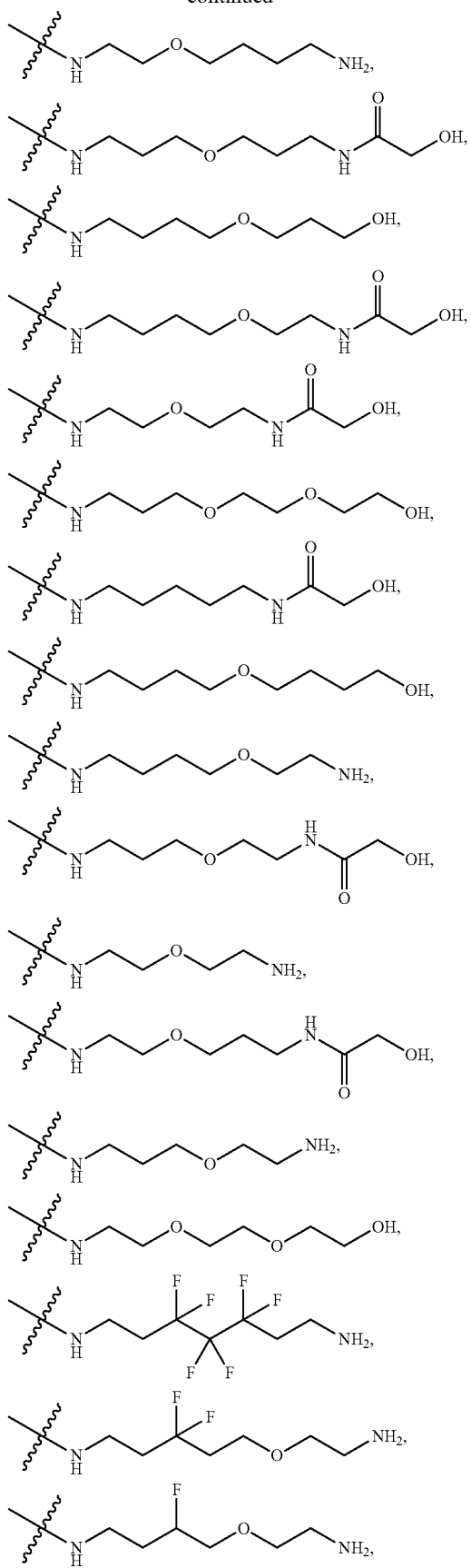

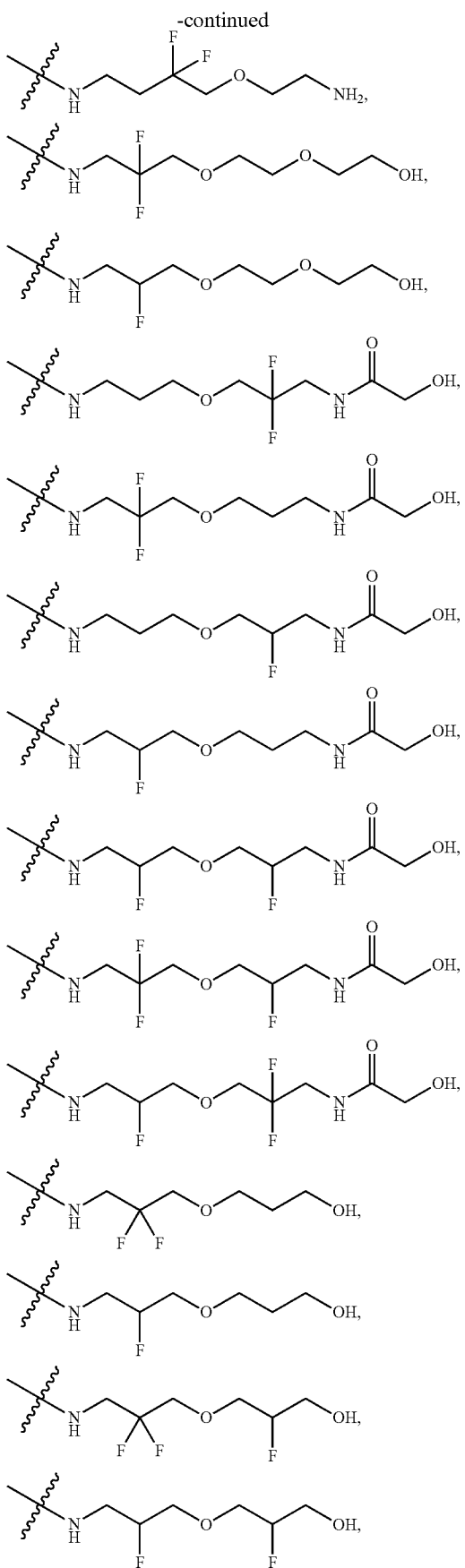
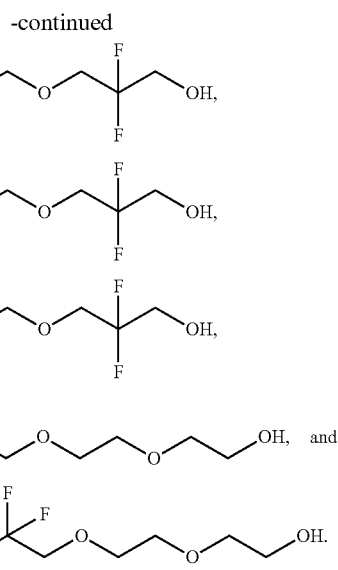

In certain embodiments, "Tail" can be a nonlinear chain, and can be, or include, aliphatic or aromatic or heteroaromatic cyclic moieties.

In certain embodiments, "Tail" may include contiguous, partially contiguous or non-contiguous ethylene glycol unit groups ranging in size from about 1 to about 12 ethylene glycol units, between 1 and about 10 ethylene glycol units, about 2 about 6 ethylene glycol units, between about 2 and 5 ethylene glycol units, between about 2 and 4 ethylene glycol units, for example, 1, 2, 3, 4, 6, 6, 7, 8, 9, 10, 11 or 12 ethylene glycol units.

In certain embodiments, "Tail" may have 1, 2, 3, 4, 5, 6, 7, 8, 9, 10, 11, 12, 13, 14, or 15 fluorine substituents. In another embodiment "Tail" is perfluorinated. In yet another embodiment "Tail" is a partially or fully fluorinated poly ether. Nonlimiting examples of fluorinated "Tail" moieties include:

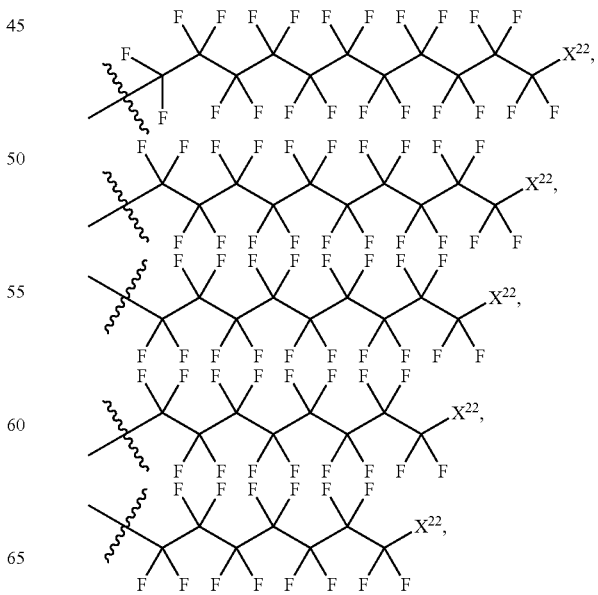

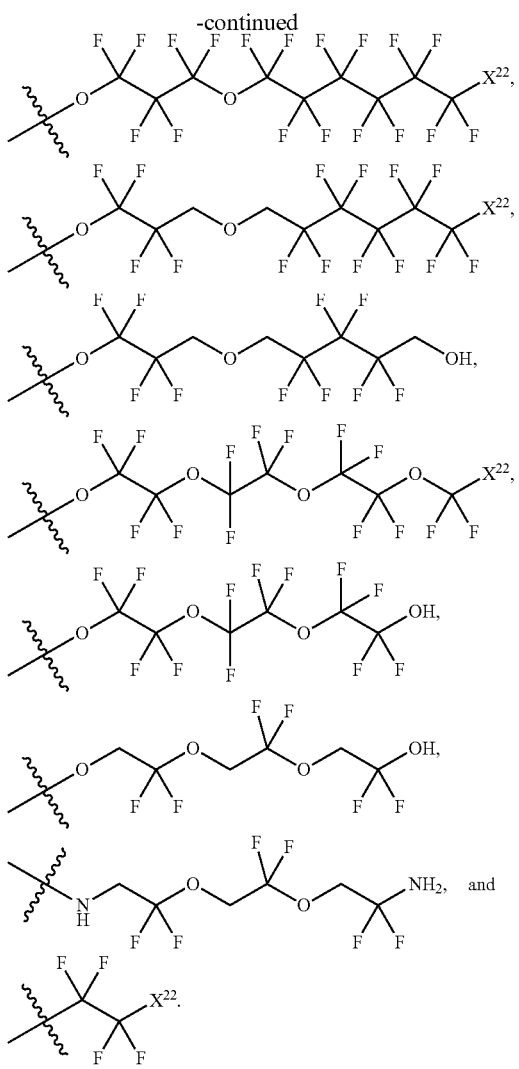

Representative examples of $X^{22}$ include:

In certain embodiments, the length can be adjusted as desired or as found necessary for the desired application.

IV. Methods of Treatment

The compounds of Formula Ia, Formula Ib, Formula II, Formula III a, Formula IIIb, Formula IV, Formula V, Formula VI, Formula VII, Formula VIII, Formula IX, Formula X, Formula XI, Formula XII, Formula XIII, Formula XIV, Formula XV, Formula XIV-a to XIV-x, or Formula XV-a to XV-t can be used in an effective amount to treat a host, including a human, in need thereof, optionally in a pharmaceutically acceptable carrier to treat any of the disorders described herein.

The terms "treat", "treating", and "treatment", etc., as used herein, refer to any action providing a benefit to a patient for which the present compounds may be administered, including the treatment of any disease state or condition which is modulated through the protein to which the present compounds bind. Illustrative non-limiting disease states or conditions, including cancer, which may be treated using compounds according to the present invention are set forth hereinabove.

The term "disease state or condition" when used in connection with a Formula Ia, Formula Ib, Formula II, Formula III a, Formula IIIb, Formula IV, Formula V, Formula VI, Formula VII, Formula VIII, Formula IX, Formula X, Formula XI, Formula XII, Formula XIII, Formula XIV, Formula XV, Formula XIV-a to XIV-x, or Formula XV-a to XV-t compound for example, refers to any therapeutic indication which can be treated by decreasing the activity of cereblon or a cereblon-containing E3 Ligase. Nonlimiting examples of uses for cereblon binders are multiple myeloma, a hematological disorder such as myelodysplastic syndrome, cancer, tumor, abnormal cellular proliferation, HIV/AIDS, HBV, HCV, hepatitis, Crohn's disease, sarcoidosis, graft-versus-host disease, rheumatoid arthritis, Behcet's disease, tuberculosis, and myelofibrosis. Other indications include a myelo- or lymphoproliferative disorder such as B- or T-cell lymphomas, Waldenstrom's macroglobulinemia, Wiskott-Aldrich syndrome, or a post-transplant lymphoproliferative disorder; an immune disorder, including autoimmune disorders such as Addison disease, Celiac disease, dermatomyositis, Graves disease, thyroiditis, multiple sclerosis, pernicious anemia, arthritis, and in particular rheumatoid arthritis, lupus, or type I diabetes; a disease of cardiologic malfunction, including hypercholesterolemia; an infectious disease, including viral and/or bacterial infection, as described generally herein; an inflammatory condition, including asthma, chronic peptic ulcers, tuberculosis, rheumatoid arthritis, periodontitis and ulcerative colitis.

In certain embodiments, the present invention provides for administering a compound of Formula Ia, Formula Ib, Formula II, Formula III a, Formula IIIb, Formula IV, Formula V, Formula VI, Formula VII, Formula VIII, Formula IX, Formula X, Formula XI, Formula XII, Formula XIII, Formula XIV, Formula XV, Formula XIV-a to XIV-x, or Formula XV-a to XV-t to a patient, for example, a human, having an infectious disease, wherein the therapy targets a protein of the infectious agent, optionally in combination with another bioactive agent. The disease state or condition may be a disease caused by a microbial agent or other exogenous agent such as a virus (as non-limiting examples, HIV, HBV, HCV, HSV, HPV, RSV, CMV, Ebola, Flavivirus, Pestivirus, Rotavirus, Influenza, Coronavirus, EBV, viral pneumonia, drug-resistant viruses, Bird flu, RNA virus, DNA virus, adenovirus, poxvirus, Picornavirus, Togavirus, Orthomyxovirus, Retrovirus or Hepadnovirus), bacteria (Gram-negative, Gram-positive, fungus, protozoa, helminth, worms, prion, parasite, or other microbe or may be a disease state, which is caused by overexpression of a protein, which leads to a disease state and/or condition.

In certain embodiments, the condition treated with a compound of the present invention is a disorder related to abnormal cellular proliferation. Abnormal cellular proliferation, notably hyperproliferation, can occur as a result of a wide variety of factors, including genetic mutation, infection, exposure to toxins, autoimmune disorders, and benign or malignant tumor induction.

There are a number of skin disorders associated with cellular hyperproliferation. Psoriasis, for example, is a benign disease of human skin generally characterized by plaques covered by thickened scales. The disease is caused by increased proliferation of epidermal cells of unknown cause. Chronic eczema is also associated with significant hyperproliferation of the epidermis. Other diseases caused by hyperproliferation of skin cells include atopic dermatitis, lichen planus, warts, pemphigus vulgaris, actinic keratosis, basal cell carcinoma and squamous cell carcinoma.

Other hyperproliferative cell disorders include blood vessel proliferation disorders, fibrotic disorders, autoimmune disorders, graft-versus-host rejection, tumors and cancers.

Blood vessel proliferative disorders include angiogenic and vasculogenic disorders. Proliferation of smooth muscle cells in the course of development of plaques in vascular tissue cause, for example, restenosis, retinopathies and atherosclerosis. Both cell migration and cell proliferation play a role in the formation of atherosclerotic lesions.

Fibrotic disorders are often due to the abnormal formation of an extracellular matrix. Examples of fibrotic disorders include hepatic cirrhosis and mesangial proliferative cell disorders. Hepatic cirrhosis is characterized by the increase in extracellular matrix constituents resulting in the formation of a hepatic scar. Hepatic cirrhosis can cause diseases such as cirrhosis of the liver. An increased extracellular matrix resulting in a hepatic scar can also be caused by viral infection such as hepatitis. Lipocytes appear to play a major role in hepatic cirrhosis.

Mesangial disorders are brought about by abnormal proliferation of mesangial cells. Mesangial hyperproliferative cell disorders include various human renal diseases, such as glomerulonephritis, diabetic nephropathy, malignant nephrosclerosis, thrombotic micro-angiopathy syndromes, transplant rejection, and glomerulopathies.

Another disease with a proliferative component is rheumatoid arthritis. Rheumatoid arthritis is generally considered an autoimmune disease that is thought to be associated with activity of autoreactive T cells, and to be caused by autoantibodies produced against collagen and IgE.

Other disorders that can include an abnormal cellular proliferative component include Bechet's syndrome, acute respiratory distress syndrome (ARDS), ischemic heart disease, post-dialysis syndrome, leukemia, acquired immune deficiency syndrome, vasculitis, lipid histiocytosis, septic shock and inflammation in general.

Cutaneous contact hypersensitivity and asthma are just two examples of immune responses that can be associated with significant morbidity. Others include atopic dermatitis, eczema, Sjogren's Syndrome, including keratoconjunctivitis sicca secondary to Sjogren's Syndrome, alopecia areata, allergic responses due to arthropod bite reactions, Crohn's disease, aphthous ulcer, iritis, conjunctivitis, keratoconjunctivitis, ulcerative colitis, cutaneous lupus erythematosus, scleroderma, vaginitis, proctitis, and drug eruptions. These conditions may result in any one or more of the following symptoms or signs: itching, swelling, redness, blisters, crusting, ulceration, pain, scaling, cracking, hair loss, scarring, or oozing of fluid involving the skin, eye, or mucosal membranes.

In atopic dermatitis, and eczema in general, immunologically mediated leukocyte infiltration (particularly infiltration of mononuclear cells, lymphocytes, neutrophils, and eosinophils) into the skin importantly contributes to the pathogenesis of these diseases. Chronic eczema also is associated with significant hyperproliferation of the epidermis. Immunologically mediated leukocyte infiltration also occurs at sites other than the skin, such as in the airways in asthma and in the tear producing gland of the eye in keratoconjunctivitis sicca.

In one non-limiting embodiment compounds of the present invention are used as topical agents in treating contact dermatitis, atopic dermatitis, eczematous dermatitis, psoriasis, Sjogren's Syndrome, including keratoconjunctivitis sicca secondary to Sjogren's Syndrome, alopecia areata, allergic responses due to arthropod bite reactions, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, and drug eruptions. The novel method may also be useful in reducing the infiltration of skin by malignant leukocytes in diseases such as mycosis fungoides. These compounds can also be used to treat an aqueous-deficient dry eye state (such as immune mediated keratoconjunctivitis) in a patient suffering therefrom, by administering the compound topically to the eye.

Disease states of conditions which may be treated using compounds according to the present invention include, for example, asthma, autoimmune diseases such as multiple sclerosis, various cancers, ciliopathies, cleft palate, diabetes, heart disease, hypertension, inflammatory bowel disease, mental retardation, mood disorder, obesity, refractive error, infertility, Angelman syndrome, Canavan disease, Coeliac disease, Charcot-Marie-Tooth disease, Cystic fibrosis, Duchenne muscular dystrophy, Haemochromatosis, Haemophilia, Klinefelter's syndrome, Neurofibromatosis, Phenylketonuria, Polycystic kidney disease 1 (PKD1) or 2 (PKD2) Prader-Willi syndrome, Sickle-cell disease, Tay-Sachs disease, Turner syndrome.

Further disease states or conditions which may be treated by compounds according to the present invention include Alzheimer's disease, Amyotrophic lateral sclerosis (Lou Gehrig's disease), Anorexia nervosa, Anxiety disorder, Atherosclerosis, Attention deficit hyperactivity disorder, Autism, Bipolar disorder, Chronic fatigue syndrome, Chronic obstructive pulmonary disease, Crohn's disease, Coronary heart disease, Dementia, Depression, Diabetes mellitus type 1, Diabetes mellitus type 2, Epilepsy, Guillain-Barre syndrome, Irritable bowel syndrome, Lupus, Metabolic syndrome, Multiple sclerosis, Myocardial infarction, Obesity, Obsessive-compulsive disorder, Panic disorder, Parkinson's disease, Psoriasis, Rheumatoid arthritis, Sarcoidosis, Schizophrenia, Stroke, Thromboangiitis obliterans, Tourette syndrome, Vasculitis.

Still additional disease states or conditions which can be treated by compounds according to the present invention include aceruloplasminemia, Achondrogenesis type II, achondroplasia, Acrocephaly, Gaucher disease type 2, acute intermittent porphyria, Canavan disease, Adenomatous Polyposis Coli, ALA dehydratase deficiency, adenylosuccinate lyase deficiency, Adrenogenital syndrome, Adrenoleukodystrophy, ALA-D porphyria, ALA dehydratase deficiency, Alkaptonuria, Alexander disease, Alkaptonuric ochronosis, alpha 1-antitrypsin deficiency, alpha-1 proteinase inhibitor, emphysema, amyotrophic lateral sclerosis Alström syndrome, Alexander disease, Amelogenesis imperfecta, ALA dehydratase deficiency, Anderson-Fabry disease, androgen insensitivity syndrome, Anemia Angiokeratoma Corporis Diffusum, Angiomatosis retinae (von Hippel-Lindau disease) Apert syndrome, Arachnodactyly (Marfan syndrome), Stickler syndrome, Arthrochalasis multiplex congenital (Ehlers-Danlos syndrome #arthrochalasia type) ataxia telangiectasia, Rett syndrome, primary pulmonary hypertension, Sandhoff disease, neurofibromatosis type II, Beare-Stevenson cutis gyrata syndrome, Mediterranean fever, familial, Benjamin syndrome, beta-thalassemia, Bilateral Acoustic Neurofibromatosis (neurofibromatosis type II), factor V Leiden thrombophilia, Bloch-Sulzberger syndrome (incontinentia pigmenti), Bloom syndrome, X-linked sideroblastic anemia, Bonnevie-Ullrich syndrome (Turner syndrome), Bourneville disease (tuberous sclerosis), prion disease, Birt-Hogg-Dubé syndrome, Brittle bone disease (osteogenesis imperfecta), Broad Thumb-Hallux syndrome (Rubinstein-Taybi syndrome), Bronze Diabetes/Bronzed Cirrhosis (hemochromatosis), Bulbospinal muscular atrophy (Kennedy's disease), Burger-Grutz syndrome (lipoprotein lipase deficiency), CGD Chronic granulomatous disorder, Campomelic dysplasia, biotinidase deficiency, Cardiomyopathy (Noonan syndrome), Cri du chat, CAVD (congenital absence of the vas deferens), Caylor cardiofacial syndrome (CBAVD), CEP (congenital erythropoietic porphyria), cystic fibrosis, congenital hypothyroidism, Chondrodystrophy syndrome (achondroplasia), otospondylomegaepiphyseal dysplasia, Lesch-Nyhan syndrome, galactosemia, Ehlers-Danlos syndrome, Thanatophoric dysplasia, Coffin-Lowry syndrome, Cockayne syndrome, (familial adenomatous polyposis), Congenital erythropoietic porphyria, Congenital heart disease, Methemoglobinemia/Congenital methaemoglobinaemia, achondroplasia, X-linked sideroblastic anemia, Connective tissue disease, Conotruncal anomaly face syndrome, Cooley's Anemia (beta-thalassemia), Copper storage disease (Wilson's disease), Copper transport disease (Menkes disease), hereditary coproporphyria, Cowden syndrome, Craniofacial dysarthrosis (Crouzon syndrome), Creutzfeldt-Jakob disease (prion disease), Cockayne syndrome, Cowden syndrome, Curschmann-Batten-Steinert syndrome (myotonic dystrophy), Beare-Stevenson cutis gyrata syndrome, primary hyperoxaluria, spondyloepimetaphyseal dysplasia (Strudwick type), muscular dystrophy, Duchenne and Becker types (DBMD), Usher syndrome, Degenerative nerve diseases including de Grouchy syndrome and Dejerine-Sottas syndrome, developmental disabilities, distal spinal muscular atrophy, type V, androgen insensitivity syndrome, Diffuse Globoid Body Sclerosis (Krabbe disease), Di George's syndrome, Dihydrotestosterone receptor deficiency, androgen insensitivity syndrome, Down syndrome, Dwarfism, erythropoietic protoporphyria Erythroid 5-aminolevulinate synthetase deficiency, Erythropoietic porphyria, erythropoietic protoporphyria, erythropoietic uroporphyria, Friedreichs ataxia-familial paroxysmal polyserositis, porphyria cutanea tarda, familial pressure sensitive neuropathy, primary pulmonary hypertension (PPH), Fibrocystic disease of the pancreas, fragile X syndrome, galactosemia, genetic brain disorders, Giant cell hepatitis (Neonatal hemochromatosis), Gronblad-Strandberg syndrome (pseudoxanthoma elasticum), Gunther disease (congenital erythropoietic porphyria), haemochromatosis, Hallgren syndrome, sickle cell anemia, hemophilia, hepatoerythropoietic porphyria (HEP), Hippel-Lindau disease (von Hippel-Lindau disease), Huntington's disease, Hutchinson-Gilford progeria syndrome (progeria), Hyperandrogenism, Hypochondroplasia, Hypochromic anemia, Immune system disorders, including X-linked severe combined immunodeficiency, Insley-Astley syndrome, Jackson-Weiss syndrome, Joubert syndrome, Lesch-Nyhan syndrome, Jackson-Weiss syndrome, Kidney diseases, including hyperoxaluria, Klinefelter's syndrome, Kniest dysplasia, Lacunar dementia, Langer-Saldino achondrogenesis, ataxia telangiectasia, Lynch syndrome, Lysylhydroxylase deficiency, Machado-Joseph disease, Metabolic disorders, including Kniest dysplasia, Marfan syndrome, Movement disorders, Mowat-Wilson syndrome, cystic fibrosis, Muenke syndrome, Multiple neurofibromatosis, Nance-Insley syndrome, Nance-Sweeney chondrodysplasia, Niemann-Pick disease, Noack syndrome (Pfeiffer syndrome), Osler-Weber-Rendu disease, Peutz-Jeghers syndrome, Polycystic kidney disease, polyostotic fibrous dysplasia (McCune-Albright syndrome), Peutz-Jeghers syndrome, Prader-Labhart-Willi syndrome, hemochromatosis, primary hyperuricemia syndrome (Lesch-Nyhan syndrome), primary pulmonary hypertension, primary senile degenerative dementia, prion disease, progeria (Hutchinson Gilford Progeria Syndrome), progressive chorea, chronic hereditary (Huntington) (Huntington's disease), progressive muscular atrophy, spinal muscular atrophy, propionic acidemia, protoporphyria, proximal myotonic dystrophy, pulmonary arterial hypertension, PXE (pseudoxanthoma elasticum), Rb (retinoblastoma), Recklinghausen disease (neurofibromatosis type I), Recurrent polyserositis, Retinal disorders, Retinoblastoma, Rett syndrome, RFALS type 3, Ricker syndrome, Riley-Day syndrome, Roussy-Levy syndrome, severe achondroplasia with developmental delay and acanthosis nigricans (SADDAN), Li-Fraumeni syndrome, sarcoma, breast, leukemia, and adrenal gland (SBLA) syndrome, sclerosis tuberose (tuberous sclerosis), SDAT, SED congenital (spondyloepiphyseal dysplasia congenita), SED Strudwick (spondyloepimetaphyseal dysplasia, Strudwick type), SEDc (spondyloepiphyseal dysplasia congenita) SEMD, Strudwick type (spondyloepimetaphyseal dysplasia, Strudwick type), Shprintzen syndrome, Skin pigmentation disorders, Smith-Lemli-Opitz syndrome, South-African genetic porphyria (variegate porphyria), infantile-onset ascending hereditary spastic paralysis, Speech and communication disorders, sphingolipidosis, Tay-Sachs disease, spinocerebellar ataxia, Stickler syndrome, stroke, androgen insensitivity syndrome, tetrahydrobiopterin deficiency, beta-thalassemia, Thyroid disease, Tomaculous neuropathy (hereditary neuropathy with liability to pressure palsies), Treacher Collins syndrome, Triplo X syndrome (triple X syndrome), Trisomy 21 (Down syndrome), Trisomy X, VHL syndrome (von Hippel-Lindau disease), Vision impairment and blindness (Alström syndrome), Vrolik disease, Waardenburg syndrome, Warburg Sjo Fledelius Syndrome, Weissenbacher-Zweymüller syndrome, Wolf-Hirschhorn syndrome, Wolff Periodic disease, Weissenbacher-Zweymüller syndrome and Xeroderma pigmentosum, among others.

The term "neoplasia" or "cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated. As used herein, the term neoplasia is used to describe all cancerous disease states and embraces or encompasses the pathological process associated with malignant hematogenous, ascitic and solid tumors. Exemplary cancers which may be treated by the present compounds either alone or in combination with at least one additional anti-cancer agent include squamous-cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas. Additional cancers which may be treated using compounds according to the present invention include, for example, T-lineage Acute lymphoblastic Leukemia (T-ALL), T-lineage lymphoblastic Lymphoma (T-LL), Peripheral T-cell lymphoma, Adult T-cell Leukemia, Pre-B ALL, Pre-B Lymphomas, Large B-cell Lymphoma, Burkitts Lymphoma, B-cell ALL, Philadelphia chromosome positive ALL and Philadelphia chromosome positive CML.

Additional cancers which may be treated using the disclosed compounds according to the present invention include, for example, acute granulocytic leukemia, acute lymphocytic leukemia (ALL), acute myelogenous leukemia (AML), adenocarcinoma, adenosarcoma, adrenal cancer, adrenocortical carcinoma, anal cancer, anaplastic astrocytoma, angiosarcoma, appendix cancer, astrocytoma, Basal cell carcinoma, B-Cell lymphoma, bile duct cancer, bladder cancer, bone cancer, bone marrow cancer, bowel cancer, brain cancer, brain stem glioma, breast cancer, triple (estrogen, progesterone and HER-2) negative breast cancer, double negative breast cancer (two of estrogen, progesterone and HER-2 are negative), single negative (one of estrogen, progesterone and HER-2 is negative), estrogen-receptor positive, HER2-negative breast cancer, estrogen receptor-negative breast cancer, estrogen receptor positive breast cancer, metastatic breast cancer, luminal A breast cancer, luminal B breast cancer, Her2-negative breast cancer, HER2-positive or negative breast cancer, progesterone receptor-negative breast cancer, progesterone receptor-positive breast cancer, recurrent breast cancer, carcinoid tumors, cervical cancer, cholangiocarcinoma, chondrosarcoma, chronic lymphocytic leukemia (CLL), chronic myelogenous leukemia (CML), colon cancer, colorectal cancer, craniopharyngioma, cutaneous lymphoma, cutaneous melanoma, diffuse astrocytoma, ductal carcinoma in situ (DCIS), endometrial cancer, ependymoma, epithelioid sarcoma, esophageal cancer, ewing sarcoma, extrahepatic bile duct cancer, eye cancer, fallopian tube cancer, fibrosarcoma, gallbladder cancer, gastric cancer, gastrointestinal cancer, gastrointestinal carcinoid cancer, gastrointestinal stromal tumors (GIST), germ cell tumor glioblastoma multiforme (GBM), glioma, hairy cell leukemia, head and neck cancer, hemangioendothelioma, Hodgkin lymphoma, hypopharyngeal cancer, infiltrating ductal carcinoma (IDC), infiltrating lobular carcinoma (ILC), inflammatory breast cancer (IBC), intestinal Cancer, intrahepatic bile duct cancer, invasive/infiltrating breast cancer, Islet cell cancer, jaw cancer, Kaposi sarcoma, kidney cancer, laryngeal cancer, leiomyosarcoma, leptomeningeal metastases, leukemia, lip cancer, liposarcoma, liver cancer, lobular carcinoma in situ, low-grade astrocytoma, lung cancer, lymph node cancer, lymphoma, male breast cancer, medullary carcinoma, medulloblastoma, melanoma, meningioma, Merkel cell carcinoma, mesenchymal chondrosarcoma, mesenchymous, mesothelioma metastatic breast cancer, metastatic melanoma metastatic squamous neck cancer, mixed gliomas, monodermal teratoma, mouth cancer mucinous carcinoma, mucosal melanoma, multiple myeloma, Mycosis Fungoides, myelodysplastic syndrome, nasal cavity cancer, nasopharyngeal cancer, neck cancer, neuroblastoma, neuroendocrine tumors (NETs), non-Hodgkin's lymphoma, non-small cell lung cancer (NSCLC), oat cell cancer, ocular cancer, ocular melanoma, oligodendroglioma, oral cancer, oral cavity cancer, oropharyngeal cancer, osteogenic sarcoma, osteosarcoma, ovarian cancer, ovarian epithelial cancer ovarian germ cell tumor, ovarian primary peritoneal carcinoma, ovarian sex cord stromal tumor, Paget's disease, pancreatic cancer, papillary carcinoma, paranasal sinus cancer, parathyroid cancer, pelvic cancer, penile cancer, peripheral nerve cancer, peritoneal cancer, pharyngeal cancer, pheochromocytoma, pilocytic astrocytoma, pineal region tumor, pineoblastoma, pituitary gland cancer, primary central nervous system (CNS) lymphoma, prostate cancer, rectal cancer, renal cell carcinoma, renal pelvis cancer, rhabdomyosarcoma, salivary gland cancer, soft tissue sarcoma, bone sarcoma, sarcoma, sinus cancer, skin cancer, small cell lung cancer (SCLC), small intestine cancer, spinal cancer, spinal column cancer, spinal cord cancer, squamous cell carcinoma, stomach cancer, synovial sarcoma, T-cell lymphoma, testicular cancer, throat cancer, thymoma/thymic carcinoma, thyroid cancer, tongue cancer, tonsil cancer, transitional cell cancer, tubal cancer, tubular carcinoma, undiagnosed cancer, ureteral cancer, urethral cancer, uterine adenocarcinoma, uterine cancer, uterine sarcoma, vaginal cancer, vulvar cancer, T-cell lineage acute lymphoblastic leukemia (T-ALL), T-cell lineage lymphoblastic lymphoma (T-LL), peripheral T-cell lymphoma, Adult T-cell leukemia, Pre-B ALL, Pre-B lymphomas, large B-cell lymphoma, Burkitts lymphoma, B-cell ALL, Philadelphia chromosome positive ALL, Philadelphia chromosome positive CML, juvenile myelomonocytic leukemia (JMML), acute promyelocytic leukemia (a subtype of AML), large granular lymphocytic leukemia, Adult T-cell chronic leukemia, diffuse large B cell lymphoma, follicular lymphoma; Mucosa-Associated Lymphatic Tissue lymphoma (MALT), small cell lymphocytic lymphoma, mediastinal large B cell lymphoma, nodal marginal zone B cell lymphoma (NMZL); splenic marginal zone lymphoma (SMZL); intravascular large B-cell lymphoma; primary effusion lymphoma; or lymphomatoid granulomatosis; B-cell prolymphocytic leukemia; splenic lymphoma/leukemia, unclassifiable, splenic diffuse red pulp small B-cell lymphoma; lymphoplasmacytic lymphoma; heavy chain diseases, for example, Alpha heavy chain disease, Gamma heavy chain disease, Mu heavy chain disease, plasma cell myeloma, solitary plasmacytoma of bone; extraosseous plasmacytoma; primary cutaneous follicle center lymphoma, T cell/histocyte rich large B-cell lymphoma, DLBCL associated with chronic inflammation; Epstein-Barr virus (EBV)+DLBCL of the elderly; primary mediastinal (thymic) large B-cell lymphoma, primary cutaneous DLBCL, leg type, ALK+ large B-cell lymphoma, plasmablastic lymphoma; large B-cell lymphoma arising in HHV8-associated multicentric, Castleman disease; B-cell lymphoma, unclassifiable, with features intermediate between diffuse large B-cell lymphoma, or B-cell lymphoma, unclassifiable, with features intermediate between diffuse large B-cell lymphoma and classical Hodgkin lymphoma.

In one embodiment the cancer is NUT midline cardinioma.

In one embodiment the cancer is adenoid cystic carcinoma.

The term "bioactive agent" is used to describe an agent, other than a compound according to the present invention, which is used in combination with the present compounds as an agent with biological activity to assist in effecting an intended therapy, inhibition and/or prevention/prophylaxis for which the present compounds are used. Preferred bioactive agents for use herein include those agents which have pharmacological activity similar to that for which the present compounds are used or administered and include for example, anti-cancer agents, antiviral agents, especially including anti-HIV agents and anti-HCV agents, antimicrobial agents, antifungal agents, etc.

In one embodiment, a method is provided for treating multiple myeloma comprising administering to a patient an effective amount of a compound described herein, or a pharmaceutically acceptable salt, isotopic analog, or prodrug thereof, optionally in a pharmaceutically acceptable carrier to form a composition. In another embodiment, a compound described herein or a pharmaceutically acceptable salt, isotopic analog, or prodrug thereof, optionally in a pharmaceutically acceptable carrier to form a composition, for use in a method of treating multiple myeloma, wherein the method comprises administering the compound to a patient.

In one embodiment, a method is provided for managing the progression of multiple myeloma comprising administering to a patient an effective amount of a compound described herein, or a pharmaceutically acceptable salt, isotopic analog, or prodrug thereof, optionally in a pharmaceutically acceptable carrier to form a composition. In another embodiment, a compound described herein, or a pharmaceutically acceptable salt, isotopic analog, or prodrug thereof, optionally in a pharmaceutically acceptable carrier to form a composition, for use in a method of managing the progression of multiple myeloma, wherein the method comprises administering the compound to a patient.

In one embodiment, a method is provided for inducing a therapeutic response as assessed by the International Uniform Response Criteria (IURC) for Multiple Myeloma (described in Durie B. G. M; et al. "International uniform response criteria for multiple myeloma. *Leukemia* 2006, 10(10):1-7) in a patient having multiple myeloma comprising administering to the patient an effective amount of a compound described herein, or a pharmaceutically acceptable salt, isotopic analog, or prodrug thereof, optionally in a pharmaceutically acceptable carrier to form a composition.

In another embodiment, a method is provided to achieve a stringent complete response, complete response, or very good partial response, as assessed by the IURC for Multiple Myeloma in a patient having multiple myeloma comprising administering to the patient an effective amount of a compound described herein, or a pharmaceutically acceptable salt, isotopic analog, or prodrug thereof, optionally in a pharmaceutically acceptable carrier to form a composition.

In another embodiment, a method is provided to achieve an increase in overall survival, progression-free survival, event-free survival, time to process, or disease-free survival in a patient having multiple myeloma comprising administering to the patient an effective amount of a compound described herein, or a pharmaceutically acceptable salt, isotopic analog, or prodrug thereof, optionally in a pharmaceutically acceptable carrier to form a composition.

In another embodiment, a method is provided to achieve an increase in overall survival in a patient having multiple myeloma comprising administering to the patient an effective amount of a compound described herein, or a pharmaceutically acceptable salt, isotopic analog, or prodrug thereof, optionally in a pharmaceutically acceptable carrier to form a composition.

In another embodiment, a method is provided to achieve an increase in progression-free survival in a patient having multiple myeloma comprising administering to the patient an effective amount of a compound described herein, or a pharmaceutically acceptable salt, isotopic analog, or prodrug thereof, optionally in a pharmaceutically acceptable carrier to form a composition.

In another embodiment, a method is provided to achieve an increase in event-free survival in a patient having multiple myeloma comprising administering to the patient an effective amount of a compound described herein, or a pharmaceutically acceptable salt, isotopic analog, or prodrug thereof, optionally in a pharmaceutically acceptable carrier to form a composition.

In another embodiment, a method is provided to achieve an increase in time to progression in a patient having multiple myeloma comprising administering to the patient an effective amount of a compound described herein, or a pharmaceutically acceptable salt, isotopic analog, or prodrug thereof, optionally in a pharmaceutically acceptable carrier to form a composition.

In another embodiment, a method is provided to achieve an increase in disease-free survival in a patient having multiple myeloma comprising administering to the patient an effective amount of a compound described herein, or a pharmaceutically acceptable salt, isotopic analog, or prodrug thereof, optionally in a pharmaceutically acceptable carrier to form a composition.

Methods are also provided to treat patients who have been previously treated for multiple myeloma but are non-responsive to standard therapies in addition to those who have not been previously treated. Additional methods are provided to treat patients who have undergone surgery in an attempt to treat multiple myeloma in addition to those who have not undergone surgery. Methods are also provided to treat patients who have previously undergone transplant therapy in addition to those who have not.

The compounds described herein may be used in the treatment or management of multiple myeloma that is relapsed, refractory, or resistant. In some embodiments, the multiple myeloma is primary, secondary, tertiary, quadruply or quintuply relapsed. In one embodiment, the compounds described herein may be used to reduce, maintain, or eliminate minimal residual disease (MRD).

The types of multiple myeloma that may be treated with the compounds described herein include, but are not limited to: monoclonal gammopathy of undetermined significance (MGUS); low risk, intermediate risk, or high risk multiple myeloma; newly diagnosed multiple myeloma, including low risk, intermediate risk, or high risk newly diagnosed multiple myeloma); transplant eligible and transplant ineligible multiple myeloma; smoldering (indolent) multiple myeloma (including low risk, intermediate risk, or high risk smoldering multiple myeloma); active multiple myeloma; solitary plasmocytoma; plasma cell leukemia; central nervous system multiple myeloma; light chain myeloma; non-secretory myeloma; Immunoglobulin D myeloma; and Immunoglobulin E myeloma.

In some embodiments, the compounds described herein may be used in the treatment or management of multiple myeloma characterized by genetic abnormalities, for example but not limited to: Cyclin D translocations (for example, t(11;14)(q13;q32); t(6;14)(p21;32); t(12;14)(p13; q32); or t(6;20);); MMSET translocations (for example t(4;14)(p16;q32); MAF translocations (for example t(14;16) (q32;a32); t(20;22); t(16;22)(q11;q13); or t(14;20)(q32; q11); or other chromosome factors (for example deletion of 17p13 or chromosome 13; del(17/17p), nonhyperdiploidy, and gain (1q)).

In one embodiment, a method is provided for treating or managing multiple myeloma comprising administering to a patient an effective amount of a compound described herein, or a pharmaceutically acceptable salt, isotopic analog, or prodrug thereof, optionally in a pharmaceutically acceptable carrier to form a composition, as induction therapy.

In one embodiment, a method is provided for treating or managing multiple myeloma comprising administering to a patient an effective amount of a compound described herein, or a pharmaceutically acceptable salt, isotopic analog, or prodrug thereof, optionally in a pharmaceutically acceptable carrier to form a composition, as consolidation therapy.

In one embodiment, a method is provided for treating or managing multiple myeloma comprising administering to a patient an effective amount of a compound described herein, or a pharmaceutically acceptable salt, isotopic analog, or prodrug thereof, optionally in a pharmaceutically acceptable carrier to form a composition, as maintenance therapy.

In one embodiment, the multiple myeloma is plasma cell leukemia.

In one embodiment, the multiple myeloma is high risk multiple myeloma. In some embodiments, the high risk multiple myeloma is relapsed or refractory. In one embodiment, the high risk multiple myeloma has relapsed within 12 months of the first treatment. In another embodiment, the high risk multiple myeloma is characterized by genetic abnormalities, for example, one or more of del(17/17p) and t(14;16)(q32;q32). In some embodiments, the high risk multiple myeloma is relapsed or refractory to one, two or three previous treatments.

In one embodiment, the multiple myeloma has a p53 mutation. In one embodiment, the p53 mutation is a Q331 mutation. In one embodiment, the p53 mutation is a R273H mutation. In one embodiment, the p53 mutation is a K132 mutation. In one embodiment, the p53 mutation is a K132N mutation. In one embodiment, the p53 mutation is a R337 mutation. In one embodiment, the p53 mutation is a R337L mutation. In one embodiment, the p53 mutation is a W146 mutation. In one embodiment, the p53 mutation is a S261 mutation. In one embodiment, the p53 mutation is a S261T mutation. In one embodiment, the p53 mutation is a E286 mutation. In one embodiment, the p53 mutation is a E286K mutation. In one embodiment, the p53 mutation is a R175 mutation. In one embodiment, the p53 mutation is a R175H mutation. In one embodiment, the p53 mutation is a E258 mutation. In one embodiment, the p53 mutation is a E258K mutation. In one embodiment, the p53 mutation is a A161 mutation. In one embodiment, the p53 mutation is a A161T mutation.

In one embodiment, the multiple myeloma has a homozygous deletion of p53. In one embodiment, the multiple myeloma has a homozygous deletion of wild-type p53. In one embodiment, the multiple myeloma has wild-type p53.

In one embodiment, the multiple myeloma shows activation of one or more oncogenic drivers. In one embodiment, the one or more oncogenic drivers are selected from the group consisting of C-MAF, MAFB, FGFR3, MMset, Cyclin D1, and Cyclin D. In one embodiment, the multiple myeloma shows activation of C-MAF. In one embodiment, the multiple myeloma shows activation of MAFB. In one embodiment, the multiple myeloma shows activation of FGFR3 and MMset. In one embodiment, the multiple myeloma shows activation of C-MAF, FGFR3, and MMset. In one embodiment, the multiple myeloma shows activation of Cyclin D1. In one embodiment, the multiple myeloma shows activation of MAFB and Cyclin D1. In one embodiment, the multiple myeloma shows activation of Cyclin D.

In one embodiment, the multiple myeloma has one or more chromosomal translocations. In one embodiment, the chromosomal translocation is t(14;16). In one embodiment, the chromosomal translocation is t(14;20). In one embodiment, the chromosomal translocation is t(4; 14). In one embodiment, the chromosomal translocations are t(4;14) and t(14;16). In one embodiment, the chromosomal translocation is t(11;14). In one embodiment, the chromosomal translocation is t(6;20). In one embodiment, the chromosomal translocation is t(20;22). In one embodiment, the chromosomal translocations are t(6;20) and t(20;22). In one embodiment, the chromosomal translocation is t(16;22). In one embodiment, the chromosomal translocations are t(14; 16) and t(16;22). In one embodiment, the chromosomal translocations are t(14;20) and t(11;14).

In one embodiment, the multiple myeloma has a Q331 p53 mutation, activation of C-MAF, and a chromosomal translocation at t(14; 16). In one embodiment, the multiple myeloma has homozygous deletion of p53, activation of C-MAF, and a chromosomal translocation at t(14; 16). In one embodiment, the multiple myeloma has a K132N p53 mutation, activation of MAFB, and a chromosomal translocation at t(14;20). In one embodiment, the multiple myeloma has wild type p53, activation of FGFR3 and MMset, and a chromosomal translocation at t(4; 14). In one embodiment, the multiple myeloma has wild type p53, activation of C-MAF, and a chromosomal translocation at t(14;16). In one embodiment, the multiple myeloma has homozygous deletion of p53, activation of FGFR3, MMset, and C-MAF, and chromosomal translocations at t(4;14) and t(14;16). In one embodiment, the multiple myeloma has homozygous deletion of p53, activation of Cyclin D1, and a chromosomal translocation at t(11;14). In one embodiment, the multiple myeloma has a R337L p53 mutation, activation of Cyclin D1, and a chromosomal translocation at t(11;14).

In one embodiment, the multiple myeloma has a W146 p53 mutation, activation of FGFR3 and MMset, and a chromosomal translocation at t(4; 14). In one embodiment, the multiple myeloma has a S261T p53 mutation, activation of MAFB, and chromosomal translocations at t(6;20) and t(20;22). In one embodiment, the multiple myeloma has a E286K p53 mutation, by activation of FGFR3 and MMset, and a chromosomal translocation at t(4; 14). In one embodiment, the multiple myeloma has a R175H p53 mutation, activation of FGFR3 and MMset, and a chromosomal translocation at t(4; 14). In one embodiment, the multiple myeloma has a E258K p53 mutation, activation of C-MAF, and chromosomal translocations at t(14;16) and t(16;22). In one embodiment, the multiple myeloma has wild type p53, activation of MAFB and Cyclin D1, and chromosomal translocations at t(14;20) and t(11;14). In one embodiment, the multiple myeloma has a A161T p53 mutation, activation of Cyclin D, and a chromosomal translocation at t(11;14).

In some embodiments, the multiple myeloma is transplant eligible newly diagnosed multiple myeloma. In other embodiments, the multiple myeloma is transplant ineligible newly diagnosed multiple myeloma.

In some embodiments, the multiple myeloma shows early progression (for example less than 12 months) following initial treatment. In other embodiments, the multiple myeloma shows early progression (for example less than 12 months) following autologous stem cell transplant. In another embodiment, the multiple myeloma is refractory to lenalidomide. In another embodiment, the multiple myeloma is refractory to pomalidomide. In some such embodiments, the multiple myeloma is predicted to be refractory to pomalidomide (for example, by molecular characterization). In another embodiment, the multiple myeloma is relapsed or refractory to 3 or more treatments and was exposed to a proteasome inhibitor (for example, bortezomib, carfilzomib, ixazomib, oprozomib, or marizomib) and an immunomodulatory compound (for example thalidomide, lenalidomide, pomalidomide, iberdomide, or avadomide), or double refractory to a proteasome inhibitor and an immunomodulatory compound. In still other embodiments, the multiple myeloma is relapsed or refractory to 3 or more prior therapies, including for example, a CD38 monoclonal antibody (CD38 mAb, for example, daratumumab or isatuximab), a proteasome inhibitor (for example, bortezomib, carfilzomib, ixazomib, or marizomib), and an immunomodulatory compound (for example thalidomide, lenalidomide, pomalidomide, iberdomide, or avadomide) or double refractory to a proteasome inhibitor or immunomodulatory compound and a CD38 mAb. In still other embodiments, the multiple myeloma is triple refractory, for example, the multiple myeloma is refractory to a proteasome inhibitor (for example, bortezomib, carfilzomib, ixazomib, oprozomib or marizomib), an immunomodulatory compound (for example thalidomide, lenalidomide, pomalidomide, iberdomide, or avadomide), and one other active agent, as described herein.

In one embodiment, a method is provided for treating or managing relapsed or refractory multiple myeloma in patients with impaired renal function or a symptom thereof comprising administering to a patient an effective amount of a compound described herein, or a pharmaceutically acceptable salt, isotopic analog, or prodrug thereof, optionally in a pharmaceutically acceptable carrier to form a composition.

In another embodiment, a method is provided for treating or managing relapsed or refractory multiple myeloma in frail patients comprising administering to a patient an effective amount of a compound described herein, or a pharmaceutically acceptable salt, isotopic analog, or prodrug thereof, optionally in a pharmaceutically acceptable carrier to form a composition, wherein the frail patient is characterized by ineligibility for induction therapy or intolerance to dexamethasone treatment. In other embodiments, the frail patient is elderly, for example, older than 65 years old.

In another embodiment, a method is provided for treating or managing fourth line relapsed or refractory multiple myeloma comprising administering to a patient an effective amount of a compound described herein, or a pharmaceutically acceptable salt, isotopic analog, or prodrug thereof, optionally in a pharmaceutically acceptable carrier to form a composition.

In another embodiment, a method is provided for treating or managing newly diagnosed, transplant-ineligible multiple myeloma comprising administering to a patient an effective amount of a compound described herein, or a pharmaceutically acceptable salt, isotopic analog, or prodrug thereof, optionally in a pharmaceutically acceptable carrier to form a composition.

In another embodiment, a method is provided for treating or managing newly diagnosed, transplant-ineligible multiple myeloma comprising administering to a patient an effective amount of a compound described herein, or a pharmaceutically acceptable salt, isotopic analog, or prodrug thereof, optionally in a pharmaceutically acceptable carrier to form a composition, as maintenance therapy after another therapy or transplant.

In another embodiment, a method is provided for treating or managing high risk multiple myeloma that is relapsed or refractory to one, two, or three previous treatments comprising administering to a patient an effective amount of a compound described herein, or a pharmaceutically acceptable salt, isotopic analog, or prodrug thereof, optionally in a pharmaceutically acceptable carrier to form a composition.

In some embodiments, the patient to be treated by one of the compounds described herein has not be treated with multiple myeloma therapy prior to administration. In some embodiments, the patient to be treated by one of the compounds described herein has been treated by multiple myeloma therapy prior to administration. In some embodiments, the patient to be treated by one of the compounds described herein has developed drug resistant to the multiple myeloma therapy. In some embodiments, the patient to be treated by one of the compounds described herein has developed resistance to one, two, or three multiple myeloma therapies, wherein the therapies are selected from a CD38 antibody (CD38 mAB, for example, daratumumab or isatuximab), a proteasome inhibitor (for example, bortezomib, carfilzomib, ixazomib, or marizomib), and an immunomodulatory compound (for example thalidomide, lenalidomide, pomalidomide, iberdomide, or avodomide).

The compounds described herein can be used to treat a patient regardless of patient's age. In some embodiments, the subject is 18 years or older. In other embodiments, the subject is more than 18, 25, 35, 40, 45, 50, 55, 60, 65, or 70 years old. In other embodiments, the patient is less than 65 years old. In other embodiments, the patient is more than 65 years old. In one embodiment, the patient is an elderly multiple myeloma patient, such as a patient older than 65 years old. In one embodiment, the patient is an elderly multiple myeloma patient, such as a patient older than 75 years old.

V. Combination Therapy

The compounds of Formula Ia, Formula Ib, Formula II, Formula III a, Formula IIIb, Formula IV, Formula V, Formula VI, Formula VII, Formula VIII, Formula IX, Formula X, Formula XI, Formula XII, Formula XIII, Formula XIV, Formula XV, Formula XIV-a to XIV-x, or Formula XV-a to XV-t can be used in an effective amount alone or in combination to treat a host such as a human with a disorder as described herein.

The disclosed compounds described herein can be used in an effective amount alone or in combination with another compound of the present invention or another bioactive agent to treat a host such as a human with a disorder as described herein.

The term "bioactive agent" is used to describe an agent, other than the selected compound according to the present invention, which can be used in combination or alternation with a compound of the present invention to achieve a desired result of therapy. In one embodiment, the compound of the present invention and the bioactive agent are administered in a manner that they are active in vivo during overlapping time periods, for example, have time-period overlapping Cmax, Tmax, AUC or other pharmacokinetic parameter. In another embodiment, the compound of the present invention and the bioactive agent are administered to a host in need thereof that do not have overlapping pharmacokinetic parameter, however, one has a therapeutic impact on the therapeutic efficacy of the other.
In one aspect of this embodiment, the bioactive agent is an immune modulator, including but not limited to a checkpoint inhibitor, including as non-limiting examples, a PD-1 inhibitor, PD-L1 inhibitor, PD-L2 inhibitor, CTLA-4 inhibitor, LAG-3 inhibitor, TIM-3 inhibitor, V-domain Ig suppressor of T-cell activation (VISTA) inhibitors, small molecule, peptide, nucleotide, or other inhibitor. In certain aspects, the immune modulator is an antibody, such as a monoclonal antibody.

VI. Pharmaceutical Compositions

The compounds of Formula Ia, Formula Ib, Formula II, Formula III a, Formula IIIb, Formula IV, Formula V, Formula VI, Formula VII, Formula VIII, Formula IX, Formula X, Formula XI, Formula XII, Formula XIII, Formula XIV, Formula XV, Formula XIV-a to XIV-x, or Formula XV-a to XV-t as disclosed herein can be administered as the neat chemical, but are more typically administered as a pharmaceutical composition, that includes an effective amount for a host, typically a human, in need of such treatment for any of the disorders described herein. Accordingly, the disclosure provides pharmaceutical compositions comprising an effective amount of compound or pharmaceutically acceptable salt together with at least one pharmaceutically acceptable carrier for any of the uses described herein. The pharmaceutical composition may contain a compound or salt as the only active agent, or, in an alternative embodiment, the compound and at least one additional active agent.

In certain embodiments the pharmaceutical composition is in a dosage form that contains from about 0.1 mg to about 2000 mg, from about 10 mg to about 1000 mg, from about 100 mg to about 800 mg, or from about 200 mg to about 600 mg of the active compound and optionally from about 0.1 mg to about 2000 mg, from about 10 mg to about 1000 mg, from about 100 mg to about 800 mg, or from about 200 mg to about 600 mg of an additional active agent in a unit dosage form. Examples are dosage forms with at least 0.1, 1, 5, 10, 25, 50, 100, 200, 250, 300, 400, 500, 600, 700, or 750 mg of active compound, or its salt. The pharmaceutical composition may also include a molar ratio of the active compound and an additional active agent. For example the pharmaceutical composition may contain a molar ratio of about 0.5:1, about 1:1, about 2:1, about 3:1 or from about 1.5:1 to about 4:1 of an anti-inflammatory or immunosuppressing agent. Compounds disclosed herein may be administered orally, topically, parenterally, by inhalation or spray, sublingually, via implant, including ocular implant, transdermally, via buccal administration, rectally, as an ophthalmic solution, injection, including ocular injection, intraveneous, intra-aortal, intracranial, subdermal, intraperitoneal, subcutaneous, transnasal, sublingual, or rectal or by other means, in dosage unit formulations containing conventional pharmaceutically acceptable carriers. For ocular delivery, the compound can be administered, as desired, for example, via intravitreal, intrastromal, intracameral, sub-tenon, sub-retinal, retro-bulbar, peribulbar, suprachorodial, conjunctival, subconjunctival, episcleral, periocular, transscleral, retrobulbar, posterior juxtascleral, circumcorneal, or tear duct injections, or through a mucus, mucin, or a mucosal barrier, in an immediate or controlled release fashion or via an ocular device.

The pharmaceutical composition may be formulated as any pharmaceutically useful form, e.g., as an aerosol, a cream, a gel, a pill, an injection or infusion solution, a capsule, a tablet, a syrup, a transdermal patch, a subcutaneous patch, a dry powder, an inhalation formulation, in a medical device, suppository, buccal, or sublingual formulation, parenteral formulation, or an ophthalmic solution. Some dosage forms, such as tablets and capsules, are subdivided into suitably sized unit doses containing appropriate quantities of the active components, e.g., an effective amount to achieve the desired purpose.

Carriers include excipients and diluents and must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound.

Classes of carriers include, but are not limited to binders, buffering agents, coloring agents, diluents, disintegrants, emulsifiers, flavorants, glidents, lubricants, preservatives, stabilizers, surfactants, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin; talc, and vegetable oils. Optional active agents may be included in a pharmaceutical composition, which do not substantially interfere with the activity of the compound of the present invention.

The pharmaceutical compositions/combinations can be formulated for oral administration. These compositions can contain any amount of active compound that achieves the desired result, for example between 0.1 and 99 weight % (wt. %) of the compound and usually at least about 5 wt. % of the compound. Some embodiments contain from about 25 wt. % to about 50 wt. % or from about 5 wt. % to about 75 wt. % of the compound.

Formulations suitable for rectal administration are typically presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound. In one embodiment, microneedle patches or devices are provided for delivery of drugs across or into biological tissue, particularly the skin. The microneedle patches or devices permit drug delivery at clinically relevant rates across or into skin or other tissue barriers, with minimal or no damage, pain, or irritation to the tissue.

Formulations suitable for administration to the lungs can be delivered by a wide range of passive breath driven and active power driven single/-multiple dose dry powder inhalers (DPI). The devices most commonly used for respiratory delivery include nebulizers, metered-dose inhalers, and dry powder inhalers. Several types of nebulizers are available, including jet nebulizers, ultrasonic nebulizers, and vibrating mesh nebulizers. Selection of a suitable lung delivery device depends on parameters, such as nature of the drug and its formulation, the site of action, and pathophysiology of the lung.

The compounds described herein and the pharmaceutically acceptable salts can be used as therapeutically active substances, e.g. in the form of pharmaceutical preparations. The pharmaceutical preparations can be administered orally, e.g. in the form of tablets, coated tablets, dragées, hard and soft gelatin capsules, solutions, emulsions or suspensions. The administration can, however, also be effected rectally, e.g. in the form of suppositories, or parenterally, e.g. in the form of injection solutions.

The compounds described herein and the pharmaceutically acceptable salts thereof can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain pharmaceutically acceptable auxiliary substances such as preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of the present invention or a pharmaceutically acceptable salt thereof and a therapeutically inert carrier are also provided by the present invention, as is a process for their production, which comprises bringing one or more compounds of Formula I and/or pharmaceutically acceptable salts thereof and, if desired, one or more other therapeutically valuable substances into a galenical administration form together with one or more therapeutically inert carriers.

The dosage can vary within wide limits and will, of course, have to be adjusted to the individual requirements in each particular case. In the case of oral administration the dosage for adults can vary from about 0.01 mg to about 1000 mg per day of a compound of general Formula VII, Formula XIII, or of the corresponding amount of a pharmaceutically acceptable salt thereof. The daily dosage may be administered as single dose or in divided doses and, in addition, the upper limit can also be exceeded when this is found to be indicated.

The following examples illustrate the present invention without limiting it, but serve merely as representative thereof. The pharmaceutical preparations conveniently contain about 1-500 mg, particularly 1-100 mg, of a compound of Formula XIV. Examples of compositions according to the invention are:

Example A

Tablets of the following composition are manufactured in the usual manner:

TABLE 1 possible tablet composition

| ingredient | mg/tablet | | | |
|---|---|---|---|---|
| | 5 | 25 | 100 | 500 |
| Compound of Formula VII or XIII | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure

1. Mix ingredients 1, 2, 3 and 4 and granulate with purified water.

2. Dry the granules at 50° C.

3. Pass the granules through suitable milling equipment.

4. Add ingredient 5 and mix for three minutes; compress on a suitable press.

Example B-1

Capsules of the following composition are manufactured:

TABLE 2 possible capsule ingredient composition

| ingredient | mg/capsule | | | |
|---|---|---|---|---|
| | 5 | 25 | 100 | 500 |
| Compound of Formula VII or XIII | 5 | 25 | 100 | 500 |
| Hydrous Lactose | 159 | 123 | 148 | — |
| Corn Starch | 25 | 35 | 40 | 70 |
| Talk | 10 | 15 | 10 | 25 |
| Magnesium Stearate | 1 | 2 | 2 | 5 |
| Total | 200 | 200 | 300 | 600 |

Manufacturing Procedure
1. Mix ingredients 1, 2 and 3 in a suitable mixer for 30 minutes.
2. Add ingredients 4 and 5 and mix for 3 minutes.
3. Fill into a suitable capsule.

The compound of Formula VII or XIII, lactose and corn starch are firstly mixed in a mixer and then in a comminuting machine. The mixture is returned to the mixer; the talc is added thereto and mixed thoroughly. The mixture is filled by machine into suitable capsules, e.g. hard gelatin capsules.

Example B-2

Soft Gelatin Capsules of the following composition are manufactured:

TABLE 3 possible soft gelatin capsule ingredient composition

| ingredient | mg/capsule |
|---|---|
| Compound of Formula VII or XIII | 5 |
| Yellow wax | 8 |
| Hydrogenated Soya bean oil | 8 |
| Partially hydrogenated plant oils | 34 |
| Soya bean oil | 110 |
| Total | 165 |

TABLE 4 possible soft gelatin capsule composition

| ingredient | mg/capsule |
|---|---|
| Gelatin | 75 |
| Glycerol 85% | 32 |
| Karion 83 | 8 (dry matter) |
| Titan dioxide | 0.4 |
| Iron oxide yellow | 1.1 |
| Total | 116.5 |

Manufacturing Procedure
The compound of Formula VII or XIII is dissolved in a warm melting of the other ingredients and the mixture is filled into soft gelatin capsules of appropriate size. The filled soft gelatin capsules are treated according to the usual procedures.

Example C

Suppositories of the following composition are manufactured:

TABLE 5 possible suppository composition

| ingredient | mg/supp. |
|---|---|
| Compound of Formula VII or XIII | 15 |
| Suppository mass | 1285 |
| Total | 1300 |

Manufacturing Procedure
The suppository mass is melted in a glass or steel vessel, mixed thoroughly and cooled to 45° C. Thereupon, the finely powdered compound of Formula VII or XIII is added thereto and stirred until it has dispersed completely. The mixture is poured into suppository molds of suitable size, left to cool; the suppositories are then removed from the molds and packed individually in wax paper or metal foil.

Example D

Injection solutions of the following composition are manufactured:

TABLE 6 possible injection solution composition

| ingredient | mg/injection solution. |
|---|---|
| Compound of Formula VII or XIII | 3 |
| Polyethylene Glycol 400 | 150 |
| acetic acid | q.s. ad pH 5.0 |
| water for injection solutions | ad 1.0 ml |

Manufacturing Procedure
The compound of Formula VII or XIII is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

Example E

Sachets of the following composition are manufactured:

TABLE 7 possible sachet composition

| ingredient | mg/sachet |
|---|---|
| Compound of Formula VII or XIII | 50 |
| Lactose, fine powder | 1015 |
| Microcrystalline cellulose (AVICEL PH 102) | 1400 |
| Sodium carboxymethyl cellulose | 14 |
| Polyvinylpyrrolidon K 30 | 10 |
| Magnesium stearate | 10 |
| Flavoring additives | 1 |
| Total | 2500 |

Manufacturing Procedure
The compound of Formula VII or XIII is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

VII. Use of Compounds

The compounds of Formula Ia, Formula Ib, Formula II, Formula III a, Formula IIIb, Formula IV, Formula V, Formula VI, Formula VII, Formula VIII, Formula IX, Formula X, Formula XI, Formula XII, Formula XIII, Formula XIV, Formula XV, Formula XIV-a to XIV-x, or Formula XV-a to XV-t of the present invention bind to the ubiquitously expressed E3 ligase protein cereblon (CRBN) and alter the substrate specificity of the CRBN E3 ubiquitin ligase complex, resulting in breakdown of intrinsic downstream proteins. The present compounds are thus useful for the treatment or prophylaxis of various cancers.

In one aspect, the present invention provides compounds Formula Ia, Formula Ib, Formula II, Formula III a, Formula IIIb, Formula IV, Formula V, Formula VI, Formula VII, Formula VIII, Formula IX, Formula X, Formula XI, Formula XII, Formula XIII, Formula XIV, Formula XV, Formula XIV-a to XIV-x, or Formula XV-a to XV-t as described herein for use as therapeutically active substance.

In a further aspect, the present invention provides compounds of Formula Ia, Formula Ib, Formula II, Formula III a, Formula IIIb, Formula IV, Formula V, Formula VI, Formula VII, Formula VIII, Formula IX, Formula X, Formula XI, Formula XII, Formula XIII, Formula XIV, Formula XV, Formula XIV-a to XIV-x, or Formula XV-a to XV-t as defined herein, for use in the treatment or prophylaxis of cancer.

In a further aspect, the present invention provides the use of a compound of Formula Ia, Formula Ib, Formula II, Formula III a, Formula IIIb, Formula IV, Formula V, Formula VI, Formula VII, Formula VIII, Formula IX, Formula X, Formula XI, Formula XII, Formula XIII, Formula XIV, Formula XV, Formula XIV-a to XIV-x, or Formula XV-a to XV-t as defined herein for the treatment or prophylaxis of cancer.

In a further aspect, the present invention provides a method of treating or preventing cancer, comprising administering a therapeutically effective amount of a compound of Formula Ia, Formula Ib, Formula II, Formula III a, Formula IIIb, Formula IV, Formula V, Formula VI, Formula VII, Formula VIII, Formula IX, Formula X, Formula XI, Formula XII, Formula XIII, Formula XIV, Formula XV, Formula XIV-a to XIV-x, or Formula XV-a to XV-t as defined herein to a subject.

In a further aspect, the present invention provides the use of a compound of Formula Ia, Formula Ib, Formula II, Formula III a, Formula IIIb, Formula IV, Formula V, Formula VI, Formula VII, Formula VIII, Formula IX, Formula X, Formula XI, Formula XII, Formula XIII, Formula XIV, Formula XV Formula XIV-a to XIV-x, or Formula XV-a to XV-t as defined herein for the manufacture of a medicament for the treatment or prophylaxis of cancer.

The compounds of Formula Ia, Formula Ib, Formula II, Formula III a, Formula IIIb, Formula IV, Formula V, Formula VI, Formula VII, Formula VIII, Formula IX, Formula X, Formula XI, Formula XII, Formula XIII, Formula XIV, Formula XV, Formula XIV-a to XIV-x, or Formula XV-a to XV-t may also be used to prepare bifunctional degrader compounds by linking them to a protein-targeting moiety that binds to a target protein or to a target polypeptide, in analogy to the bifunctional compounds which have been described e.g. in W2013020557, WO2013063560, WO 2013106643, WO2015160845, WO2016011906, WO2016105518, WO2017007612, WO2017024318, and WO2017117473.

General Synthetic Examples

The preparation of compounds of the present invention may be carried out in sequential or convergent synthetic routes. Syntheses of the compounds of the invention are shown in the following schemes 1-2 and in the description of the specific examples. The skills required for carrying out the reaction and purification of the resulting products are known to those skilled in the art. The substituents and indices used in the following description of the processes have the significance given herein before unless indicated to the contrary.

In more detail, the compounds of the present invention can be manufactured by the methods given below, by the methods given in the examples or by analogous methods. Appropriate reaction conditions for the individual reaction steps are known to a person skilled in the art. The reaction sequence is not limited to the one displayed in schemes below, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

In more detail, the compounds of the present invention can be manufactured by the methods given below, by the methods given in the examples or by analogous methods. Appropriate reaction conditions for the individual reaction steps are known to a person skilled in the art. The reaction sequence is not limited to the one displayed in schemes 1-2, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

Scheme 1

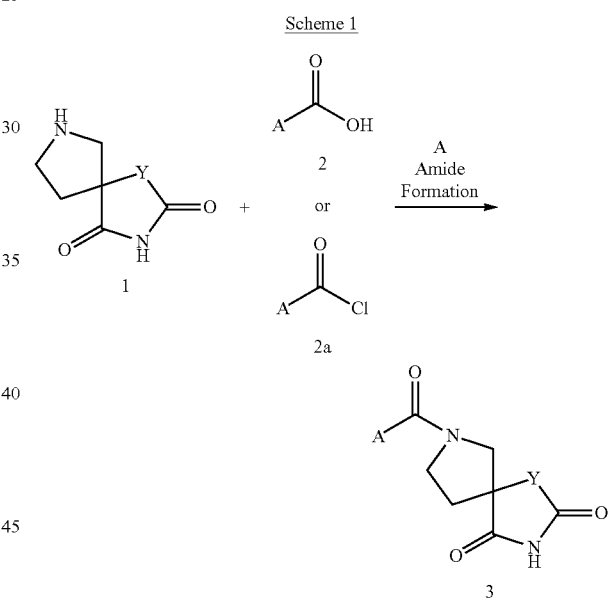

The substituents are as described in the claims and Y is NH or $CH_2$

Step A: Amide bond formation can be accomplished by a coupling reaction between a spiro-piperidine 1 and a carboxylic acid 2 in the presence of a coupling reagent such as DCC, EDC, TBTU or HATU in the presence of an organic base such as triethylamine, N,N-diisopropylethylamine or N-methylmorpholine in halogenated solvents such as dichloromethane or 1,2-dichloroethane or ethereal solvents such as diethyl ether, dioxane, THF, DME or TBME or polar non-protic organic solvent such as N,N-dimethylformamide at room temperature or at elevated temperatures for 2-18 hours.

Preferred conditions are HATU with N,N-diisopropylethylamine in N,N-dimethylformamide at room temperature for 15 hours.

Alternatively, amide bond formation can be accomplished by a coupling reaction between a spiro-piperidine 1 and an acyl chloride compound 2a that has been preformed in situ from a carboxylic acid 2. The acyl chloride compound 2a can be prepared in situ from the corresponding carboxylic acid 2 by treatment with 1-chloro-N,N,2-trimethylpropenylamine (CAS 26189-59-3) in halogenated solvents such as dichloromethane or 1,2-dichloroethane, or in ethereal solvents such as diethyl ether, dioxane, THF, DME or TBME, at a temperature between 0° C. and room temperature, according to the method of Ghosez and co-workers (*J. Chem. Soc., Chem. Commun.* 1979, 1180; *Org. Synth.* 1980, 59, 26-34). Amide bond formation can then be accomplished by reaction of the acyl chloride compound 2a with spiropiperidine 1 in the presence of an organic base such as triethylamine, N,N-diisopropylethylamine or N-methylmorpholine in halogenated solvents such as dichloromethane or 1,2-dichloroethane, or in ethereal solvents such as diethyl ether, dioxane, THF, DME or TBME. Preferred conditions are N,N-diisopropylethylamine in THF at room temperature for 1 hour.

Scheme 2

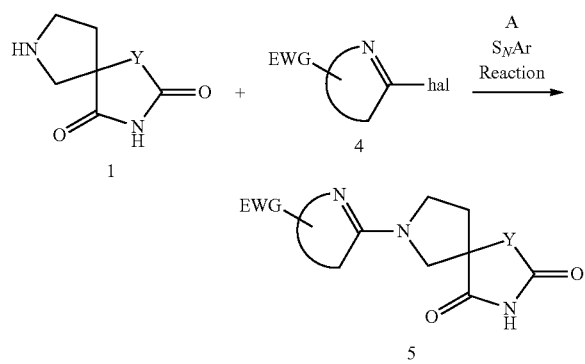

The substituents are as described in the claims and Y is NH or $CH_2$. EWG is an electron-withdrawing group such as —CN, —$CO_2R$, —$SO_2R$ or —$NO_2$ and hal is F or Cl Step A: Nucleophilic aromatic substitution ($S_NAr$) reaction can be accomplished by reaction of a spiro-piperidine 1 with an electron-deficient mono- or fused bicyclic heteroaromatic compound 4 bearing a suitable leaving group such as fluorine or chlorine in the presence of an organic base such as triethylamine, N,N-diisopropylethylamine or N-methylmorpholine in polar non-protic organic solvent such as N,N-dimethylformamide or N-methylpyrrolidone at elevated temperature.

Examples of suitable spiro-piperidine compounds 1 include, but are not limited to, 1,3,7-triazaspiro[4.4]nonane-2,4-dione (CAS 908099-69-4) or 2,7-diazaspiro[4.4]nonane-1,3-dione (CAS 1308384-60-2), or their corresponding salts 1,3,7-triazaspiro[4.4]nonane-2,4-dione hydrochloride (CAS 1334146-82-5) or 2,7-diazaspiro[4.4]nonane-1,3-dione hydrochloride (CAS 1609399-87-2).

Examples of suitable electron-deficient heteroaromatic compounds 4 bearing a suitable leaving group include, but are not limited to, 2-chlorobenzo[d]thiazole (CAS 615-20-3), methyl 6-chloronicotinate (CAS 73781-91-6), or 2-chlorothiazolo[4,5-b]pyridine (CAS 152170-30-4).

Preferred conditions are N,N-diisopropylethylamine in N,N-dimethylformamide at 100° C. for 1 hour.

Representative Examples of the Present Invention

The following examples are provided for illustration of the invention. They should not be considered as limiting the scope of the invention, but merely as being representative thereof.

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the preparations and examples herein below. However, other equivalent separation or isolation procedures could, of course, also be used. Racemic mixtures of chiral compounds of the present invention can be separated using chiral HPLC. Racemic mixtures of chiral synthetic intermediates may also be separated using chiral HPLC.

Example 1: Synthesis of 7-Benzoyl-1,3,7-triazaspiro[4.4]nonane-2,4-dione: To a solution of 1,3,7-triazaspiro[4.4]nonane-2,4-dione (100 mg, 645 μmol, eq: 1; CAS 908099-69-4) and benzoic acid (82.6 mg, 677 μmol, eq: 1.05; CAS 65-85-0), in N,N-dimethylformamide (1 ml) were added DIPEA (110 mg, 149 μl, 851 μmol, eq: 4; CAS 7087-68-5) and HATU (121 mg, 319 μmol, eq: 1.5; CAS 148893-10-1). The reaction mixture was stirred at room temperature for 15 hours. The reaction mixture was partitioned between ethyl acetate (50 ml) and water (30 ml) and the layers were separated. The aqueous layer was washed with two 20 ml portions of ethyl acetate. The combined organic layers were washed with one 30 ml portion of water/brine (1:1), dried over anhydrous sodium sulfate and concentrated in vacuo. The crude material was purified by preparative HPLC. (YMC-Triart C18, 12 nm, 5 μm, 100×30 mm, $CH_3CN/H_2O$+ 0.1% HCOOH) to afford 7-benzoyl-1,3,7-triazaspiro[4.4] nonane-2,4-dione (14.1 mg, 54.4 μmol, 8.4% yield) as a white solid, MS (ISP): 260.0 ([M+H]$^+$).

Example 2: Synthesis of 7-((S)-1,2,3,4-Tetrahydronaphthalene-1-carbonyl)-1,3,7-triazaspiro[4.4]nonane-2,4-dione (EPIMERS 1:1): The title compound was obtained (as a 1:1 mixture of epimers) in analogy to Example 1 using (S)-1,2,3,4-tetrahydronaphthalene-1-carboxylic acid (CAS 85977-52-2) in place of benzoic acid to afford a white solid. MS (ISP): 314.1 ([M+H]$^+$).

Example 3: Synthesis of 7-(Benzo[d]thiazol-2-yl)-1,3,7-triazaspiro[4.4]nonane-2,4-dione: To a suspension of 2-chlorobenzo[d]thiazole (21.9 mg, 129 μmol, eq: 1; CAS 615-20-3) and DIPEA (50 mg, 67.5 μl, 387 μmol, eq: 3) in N,N-dimethylformamide (435 μl) was added 1,3,7-triazaspiro[4.4]nonane-2,4-dione (20 mg, 129 μmol, eq: 1; CAS 908099-69-4). The reaction mixture was stirred at 100° C. for 1 hour. The reaction mixture was poured into ethyl acetate/tetrahydrofuran (1:1) and washed sequentially with water and with saturated brine. The organic layer was dried over sodium sulfate and concentrated in vacuo. The crude material was purified by flash chromatography (silica gel, 4 g, 0% to 5% methanol in dichloromethane) to afford 7-(benzo[d]thiazol-2-yl)-1,3,7-triazaspiro[4.4]nonane-2,4-dione (18 mg, 62.4 μmol, 48.4% yield) as a white solid. MS (ISP): 289.2 ([M+H]$^+$).

Example 4: Synthesis of 7-(Pyrazolo[1,5-a]pyridine-3-carbonyl)-1,3,7-triazaspiro[4.4]nonane-2,4-dione: The title compound was obtained in analogy to Example 1 using pyrazolo[1,5-a]pyridine-3-carboxylic acid (CAS 16205-46-2) in place of benzoic acid to afford a white solid. MS (ISP): 300.1 ([M+H]+).

Example 5: Synthesis of Methyl 6-(2,4-dioxo-1,3,7-triazaspiro[4.4]nonan-7-yl)nicotinate: The title compound was obtained in analogy to Example 3 using methyl 6-chloronicotinate (CAS 73781-91-6) in place of 2-chlorobenzo[d]thiazole to afford a white solid. MS (ISP): 291.1 ([M+H]+).

Example 6: Synthesis of N-(3-(2,4-Dioxo-1,3,7-triazaspiro[4.4]nonane-7-carbonyl)phenyl)acetamide: The title compound was obtained in analogy to Example 1 using 3-acetamidobenzoic acid (CAS 587-48-4) in place of benzoic acid to afford a white solid. MS (ISP): 633.3 ([2 M+H]+).

Example 7: Synthesis of N-(4-(2,4-Dioxo-1,3,7-triazaspiro[4.4]nonane-7-carbonyl)phenyl)acetamide: The title compound was obtained in analogy to Example 1 using 4-acetamidobenzoic acid (CAS 556-08-1) in place of benzoic acid to afford a white solid. MS (ISP): 317.1 ([M+H]+).

Example 8: Synthesis of 7-(Thiazolo[4,5-b]pyridin-2-yl)-1,3,7-triazaspiro[4.4]nonane-2,4-dione: The title compound was obtained in analogy to Example 3 using 2-chlorothiazolo[4,5-b]pyridine (CAS 152170-30-4) in place of 2-chlorobenzo[d]thiazole to afford a white solid. MS (ISP): 290.0 ([M+H]+).

Example 9: Synthesis of 7-(Benzo[d]thiazole-5-carbonyl)-1,3,7-triazaspiro[4.4]nonane-2,4-dione: The title compound was obtained in analogy to Example 1 using benzo[d]thiazole-5-carboxylic acid (CAS 68867-17-4) in place of benzoic acid to afford a white solid. MS (ISP): 317.0 ([M+H]+).

Example 10: Synthesis of Methyl 6-(6,8-dioxo-2,7-diazaspiro[4.4]nonan-2-yl)nicotinate Step a) Synthesis of 7-Benzyl-2,7-diazaspiro[4.4]nonane-1,3-dione: 1-Benzyl-3-(carboxymethyl)pyrrolidine-3-carboxylic acid (310 mg, 1.18 mmol, eq: 1; CAS 885958-89-4) and urea (141 mg, 2.35 mmol, eq: 2; CAS 57-13-6) were combined. The neat reaction mixture was heated at 200° C. for 1 hour. The reaction mixture was poured into tetrahydrofuran and washed with brine. The organic layer was dried over sodium sulfate and concentrated in vacuo. The crude material was purified by flash chromatography (silica gel, 12 g, 0% to 10% methanol in dichloromethane) to afford 7-benzyl-2,7-diazaspiro[4.4]nonane-1,3-dione (133 mg, 544 µmol, 46.2% yield) as a colorless amorphous oil. MS (ISP): 245.2 ([M+H]+).

Step b) Synthesis of 2,7-Diazaspiro[4.4]nonane-1,3-dione hydrochloride: To a solution of 7-benzyl-2,7-diazaspiro[4.4]nonane-1,3-dione (130 mg, 532 µmol, eq: 1) in methanol (40 ml) was added 10% palladium on charcoal (28.3 mg, 26.6 µmol, eq: 0.05). The reaction mixture was stirred at room temperature for 3 hours under an atmosphere of hydrogen. The catalyst was collected by filtration washing with methanol. To the filtrate was added a 2 M solution of HCl in Et$_2$O (5.32 ml, 10.6 mmol, eq: 20). The filtrate was then concentrated in vacuo. The product was dissolved in water and freeze-dried to afford 2,7-diazaspiro[4.4]nonane-1,3-dione hydrochloride (91 mg, 477 µmol, 89.7% yield) as a white solid. MS (ISP): 155.1 ([M+H]+).

Step c) Synthesis of Methyl 6-(6,8-dioxo-2,7-diazaspiro[4.4]nonan-2-yl)nicotinate: To a suspension of 2,7-diazaspiro[4.4]nonane-1,3-dione hydrochloride (25 mg, 131 µmol, eq: 1) and methyl 6-chloronicotinate (22.5 mg, 131 µmol, eq: 1; CAS 73781-91-6) in N,N-dimethylformamide (0.5 ml) was added DIPEA (50.9 mg, 68.7 µl, 393 µmol, eq: 3). The reaction mixture was stirred at 100° C. for 2 hours. The reaction mixture was poured into ethyl acetate/tetrahydrofuran (1:2) and washed with brine. The organic layer was dried over sodium sulfate and concentrated in vacuo. The crude material was purified by flash chromatography (silica gel, 4 g, 0% to 10% methanol in dichloromethane) to afford methyl 6-(6,8-dioxo-2,7-diazaspiro[4.4]nonan-2-yl)nicotinate (13 mg, 44.9 µmol, 34.3% yield) as a white solid. MS (ISP): 290.0 ([M+H]+).

Example 11: Synthesis of 7-(Benzo[d]thiazol-2-yl)-2,7-diazaspiro[4.4]nonane-1,3-dione: The title compound was obtained in analogy to Example 10, Step c using 2-chlorobenzo[d]thiazole (CAS 615-20-3) in place of methyl 6-chloronicotinate to afford a white solid. MS (ISP): 288.0 ([M+H]+).

Example 12: Synthesis of 7-(Pyrazolo[1,5-a]pyridine-3-carbonyl)-2,7-diazaspiro[4.4]nonane-1,3-dione: To a suspension of pyrazolo[1,5-a]pyridine-3-carboxylic acid (18 mg, 111 µmol, eq: 1; CAS 16205-46-2) in tetrahydrofuran (0.5 ml) was added 1-chloro-N,N,2-trimethylpropenylamine (17.8 mg, 17.6 µl, 133 µmol, eq: 1.2; CAS 26189-59-3) at 0-5° C. The reaction mixture was stirred at room temperature for 1 hour to give a yellow solution. The acid chloride solution was then added to a suspension of 2,7-diazaspiro[4.4]nonane-1,3-dione hydrochloride (21.2 mg, 111 µmol, eq: 1) and DIPEA (43 mg, 58.2 µl, 333 µmol, eq: 3) in tetrahydrofuran (0.5 ml). The reaction mixture was stirred at room temperature for 30 minutes. The reaction mixture was poured into ethyl acetate/tetrahydrofuran (1:3) and washed with brine. The organic layer was dried over sodium sulfate and concentrated in vacuo. The crude material was purified by flash chromatography (silica gel, 4 g, 0% to 10% methanol in dichloromethane) to afford 7-(pyrazolo[1,5-a]pyridine-3-carbonyl)-2,7-diazaspiro[4.4]nonane-1,3-dione (9 mg, 30.2 µmol, 27.2% yield) as a white solid MS (ISP): 299.1 ([M+H]+).

Example 13: Synthesis of 7-Benzoyl-2,7-diazaspiro[4.4]nonane-1,3-dione: To a suspension of 2,7-diazaspiro[4.4]nonane-1,3-dione hydrochloride (21 mg, 110 µmol, eq: 1) and DIPEA (42.7 mg, 57.7 µl, 330 µmol, eq: 3) in tetrahydrofuran (0.5 ml) was added benzoyl chloride (15.5 mg, 12.8 µl, 110 µmol, eq: 1; CAS 98-88-4) in tetrahydrofuran (0.5 ml). The reaction mixture was stirred at room temperature for 1 hour. The reaction mixture was poured into ethyl acetate/tetrahydrofuran (1:3) and washed with brine. The organic layer was dried over Na$_2$SO$_4$ and concentrated in vacuo. The crude material was purified by flash chromatography (silica gel, 4 g, 0% to 10% methanol in dichloromethane) to afford 7-benzoyl-2,7-diazaspiro[4.4]nonane-1,3-dione (7 mg, 27.1 µmol, 24.6% yield) as a white solid. MS (ISP): 259.0 ([M+H]+).

Example 14: Synthesis of 7-(Benzo[d]thiazole-5-carbonyl)-1,3,7-triazaspiro[4.4]nonane-2,4-dione (ENANTIOMER 1): The enantiomers of 7-(benzo[d]thiazole-5-carbonyl)-1,3,7-triazaspiro[4.4]nonane-2,4-dione (Example 9) were separated using chiral HPLC: Reprosil Chiral NR column with n-heptane/ethanol+NH$_4$OAc: (60:40) affording 7-(benzo[d]thiazole-5-carbonyl)-1,3,7-triazaspiro[4.4]nonane-2,4-dione (ENANTIOMER 1) (4.7 mg, white solid), retention time=11.7 min. MS (ISP): 317.0 ([M+H]+).

Example 15: Synthesis of 7-(Benzo[d]thiazole-5-carbonyl)-1,3,7-triazaspiro[4.4]nonane-2,4-dione (ENANTIOMER 2): The enantiomers of 7-(benzo[d]thiazole-5-carbonyl)-1,3,7-triazaspiro[4.4]nonane-2,4-dione (Example 9) were separated using chiral HPLC: Reprosil Chiral NR column with n-heptane/ethanol+NH$_4$OAc: (60:40) affording 7-(benzo[d]thiazole-5-carbonyl)-1,3,7-triazaspiro[4.4]nonane-2,4-dione (ENANTIOMER 2) (5.1 mg, white solid), retention time=12.3 min. MS (ISP): 317.0 ([M+H]+).

Pharmacological Tests

The compounds of the present invention and their pharmaceutically acceptable salts possess valuable pharmacological properties. The compounds were investigated in accordance with the test given hereinafter.

Dual Fluorescent Reporter Assay

In order to measure BRD4 protein abundance in a mammalian cell system at medium throughput, a dual fluorescent reporter system was developed based on a principle described in Collins et al., *Biochem J*, 2017, 474(7), 1127-1147. Transient expression vectors were designed that contain the BRD4 coding sequence (NM_058243.2) fused to a fluorescent tag. Vectors were synthesized at ATUM (Newark, Calif., USA) using the pD2610 CMV backbone and were built up as follows: c-terminal version BRD4_eGFP-RES-FresnoRFP_NLS, n-terminal version eGFP_BRD4-RES-FresnoRFP_NLS, empty vector control eGFP-RES-FresnoRFP_NLS. The c-terminal version was used for the reporter assays, as it presented with the best assay window. HEK293A cells (Invitrogen, Cat. No. R705-07) were cultured in Dulbecco's Modified Eagle Medium (DMEM), 10% fetal calf serum, 2 mM L-Glutamine, 1% Penicillin/Streptomycin. Transfections of the plasmids were performed with Lipofectamine 2000 according to the manufacturer's protocol (Invitrogen, Carlsbad, Calif., USA). 40 hours after transfection, cells were seeded at a density of 40,000/100 μl/96well flat-bottom and 8 hours later treated with compounds (stocks 10 mM in DMSO) at a 10-point dilution ranging from 0-25 μM. After 16 hours of treatment, cells were washed with PBS, resuspended in Accumax solution (Sigma-Aldrich Cat. No. A7089) and analyzed by flow-cytometry (CytoFlex S, BeckmanCoulter). Single cells were gated based on their forward and side-scatter profiles and pulse-width was used to exclude doublets. A minimum of 20'000 cells was acquired per sample. Analysis was performed with the program Flow Jo V10.1 on BRD4-eGFP low/medium cells (<$10^6$ FL1-A Mean Fluorescence Intensity (MFI)). A factor was derived to normalize BRD4-eGFP values to the RFP protein abundance control (20×FL1A-GFP/FL11A-RFP), then Median and Mode values were calculated and used for comparisons between treatment conditions.

Capillary-Based Immunoassays to Measure Endogenous BRD4 Levels

The biological activity of selected compounds (cut-off >20% reduction in BRD4-eGFP levels) was confirmed in an additional assay which allowed the quantification of endogenous BRD4 levels. To this end, HEK293A cells (origin and culture conditions see above) were seeded at 400,000/300 μl/48 well and were treated 6 hours later with compound concentrations as indicated for. 16 hours after the treatment, the cells were washed with PBS and lysed in 50 μl of UREA lysis buffer (10 mM Tris-HCl pH 8, 2% CHAPS, 7M UREA, 0.4% DTT), supplemented with 1× protease inhibitor cocktail (Complete Mini, Roche) and 1× phosphatase inhibitor cocktail (PhosSTOP, Sigma-Aldrich). Samples were then analyzed by Peggy Sue or WES capillary-based immunoassay systems according to the manufacturer's protocol (Protein Simple/Bio-Techne, San Jose, Calif., 95134 USA). Antibodies used were anti-BRD4 (Cell signaling, CST 13440 1:50) and anti-Vinculin (Sigma, V9131, 1:4000). To quantify BRD4 protein levels, the peak signal areas were normalized to the vinculin loading control and to the DMSO condition (Yen, H.-C. S., et al. Global Protein Stability Profiling in Mammalian Cells. *Science* 322, 918-923, doi: 10.1126/science.1160489 (2008)).

Fluorescence Direct Binding Protocol

Determination of the affinities of compounds to protein containing one or more tryptophan is measurable by monitoring the fluorescence emission in direct mode. The measurements depending on the protein available amounts are performed either manually in a cuvette on ISS-PC1 photon counting spectrofluorometer or automatically in well plates on a fluorescence plate reader device. Fluorescence titrations are performed at 20° C. in the chosen binding assay buffer by using a defined constant protein concentration against ligand concentration variations. Small aliquots of known ligand concentration solubilized in DMSO were added and the fluorescence, excited at 280 nm, was recorded at 340 nm. The fluorescence intensity was corrected for protein dilution and for the filter effect (Birdsall, B., et al. (1983). *Anal. Biochem.* 132, 353-361). The corrected fluorescence intensity was plotted against the ligand concentration and fitted using a four-parameter sigmoidal function, from which the equilibrium dissociation constant $K_d$ was computed using the law of mass action assuming a 1:1 protein-ligand complex (Eftink, *Methods Enzymol.* 1997; 278:221-57).

The Fluorescence Direct Binding Protocol Process includes:

1) Optimization of measurement parameters to minimize protein consumption and to minimize the dilution effect and the DMSO content
2) Titration measurements of the protein against ligand by at least 12 titration steps to obtain a good s-curve fit
3) Repeat the same titration measurements with the ligand alone to enable correction
4) Check the stability of the protein once by titration against DMSO alone
5) Determination of the molar extinction coefficients of the ligand at 280 and 340 nm with help of an UV-spectrophotometer
6) Use Excel template for the correction of the measured raw data
7) Use GraphPad Prism software for the quadratic binding fit and the $K_D$ evaluation.

TABLE 8

Description of Protein and buffers (Reference compound: Thalidomide)

| | |
|---|---|
| Protein Batch # | Cereblon_17_13 |
| Construct name | hCereblon(M1-L442)_hDDB1(M1-H1140) |
| Concentration | 2.54 mg/ml |
| MW | 180180 Da |
| Molar extinction coefficient | $\square_{280}$ = 165045 $M^{-1} \cdot cm^{-1}$ |
| Storage buffer | 20 mM MES pH 6.5 200 mM NaCl 1 mM TCEP |
| Assay buffer | 50 mM Hepes 7.4 200 mM NaCl |

TABLE 9

Settings of ISS-PCI

| Device | ISS-PC1 |
|---|---|
| Excitation wavelength [nm] | 280 |
| Emission wavelength [nm] | 340 |
| Cuvette | Hellma 115F-QS |
| Volume [μL] | 500 |

TABLE 10

Protein Preparation

| Volume Protein [μL] | Volume buffer [μL] | Protein concentration [M] |
|---|---|---|
| 1.8 @ 2.54 mg/ml | 498.2 | 5.0 E−8 |

TABLE 11

Titration Steps

| C Lig [M] | C Aliquot [M] | V Aliquot [μL] | C Prot[M] | Dilution factor |
|---|---|---|---|---|
| 1E−10 | 1.0E−07 | 0.5 | 4.995E−08 | 1.001 |
| 1.1E−09 | 1.0E−06 | 0.5 | 4.990E−08 | 1.002 |
| 3.1E−09 | 1.0E−06 | 1 | 4.980E−08 | 1.004 |
| 5.1E−09 | 1.0E−06 | 1 | 4.970E−08 | 1.006 |
| 1.51E−08 | 1.0E−05 | 0.5 | 4.965E−08 | 1.007 |
| 2.51E−08 | 1.0E−05 | 0.5 | 4.960E−08 | 1.008 |
| 4.51E−08 | 1.0E−05 | 1 | 4.950E−08 | 1.01 |
| 6.51E−08 | 1.0E−05 | 1 | 4.941E−08 | 1.012 |
| 1.651E−07 | 1.0E−04 | 0.5 | 4.936E−08 | 1.013 |
| 3.651E−07 | 1.0E−04 | 1 | 4.926E−08 | 1.015 |
| 5.651E−07 | 1.0E−04 | 1 | 4.916E−08 | 1.017 |
| 7.651E−07 | 1.0E−04 | 1 | 4.907E−08 | 1.019 |
| 9.651E−07 | 1.0E−04 | 1 | 4.897E−08 | 1.021 |
| 1.9651E−06 | 1.0E−03 | 0.5 | 4.892E−08 | 1.022 |
| 2.9651E−06 | 1.0E−03 | 0.5 | 4.888E−08 | 1.023 |
| 1.29651E−05 | 1.0E−02 | 0.5 | 4.883E−08 | 1.024 |
| 2.29651E−05 | 1.0E−02 | 0.5 | 4.878E−08 | 1.025 |
| 4.29651E−05 | 1.0E−02 | 1 | 4.869E−08 | 1.027 |
| 6.29651E−05 | 1.0E−02 | 1 | 4.859E−08 | 1.029 |
| 8.29651E−05 | 1.0E−02 | 1 | 4.850E−08 | 1.031 |

TABLE 12

Affinities of Select Compounds to Protein

| Ex. | Name | Structure | Fluorescence h-Cereblon_DDB1 Mean $K_d\_EQ$ (μM) |
|---|---|---|---|
| 1 | 7-benzoyl-1,3,7-triazaspiro[4.4]nonane-2,4-dione | 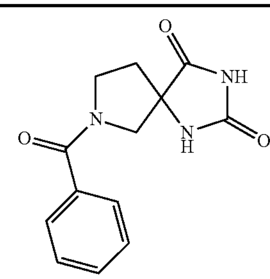 | 0.00400 |
| 2 | 7-((S)-1,2,3,4-tetrahydronaphthalene-1-carbonyl)-1,3,7-triazaspiro[4.4]nonane-2,4-dione | 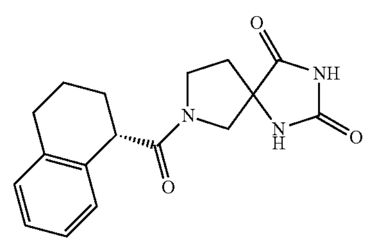 [SMILES: O=C1NC(=O)C2(CCN(C(=O)[C@H]3CCCc4ccccc43)C2)N1] | 0.00300 |
| 3 | 7-(benzo[d]thiazol-2-yl)-1,3,7-triazaspiro[4.4]nonane-2,4-dione | 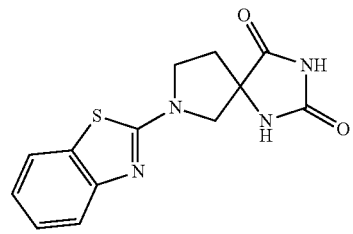 [SMILES: O=C1NC(=O)C2(CCN(c3nc4ccccc4s3)C2)N1] | 0.03100 |
| 4 | 7-(pyrazolo[1,5-a]pyridine-3-carbonyl)-1,3,7-triazaspiro[4.4]nonane-2,4-dione | 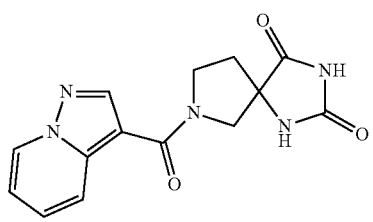 [SMILES: O=C1NC(=O)C2(CCN(C(=O)c3cnn4ccccc34)C2)N1] | 0.03700 |

TABLE 12-continued

Affinities of Select Compounds to Protein

| Ex. | Name | Structure | Fluorescence h-Cereblon_DDB1 Mean $K_d\_EQ$ (μM) |
|---|---|---|---|
| 5 | methyl 6-(2,4-dioxo-1,3,7-triazaspiro[4.4]nonan-7-yl)nicotinate | 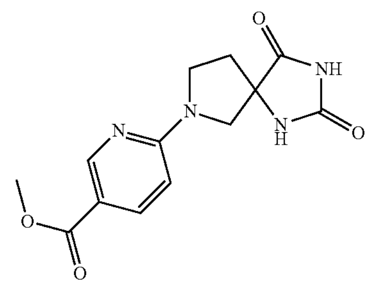 [SMILES: COC(=O)c1ccc(N2CCC3(C2)NC(=O)NC3=O)nc1] | 0.00200 |
| 6 | N-(3-(2,4-dioxo-1,3,7-triazaspiro[4.4]nonane-7-carbonyl)phenyl)acetamide | 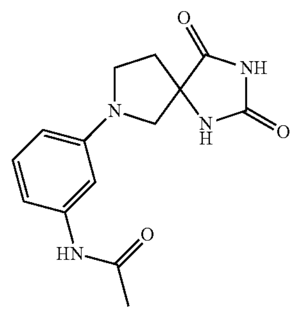 [SMILES: CC(=O)Nc1cccc(N2CCC3(C2)NC(=O)NC3=O)c1] | 0.01 |
| 7 | N-(4-(2,4-dioxo-1,3,7-triazaspiro[4.4]nonane-7-carbonyl)phenyl)acetamide | 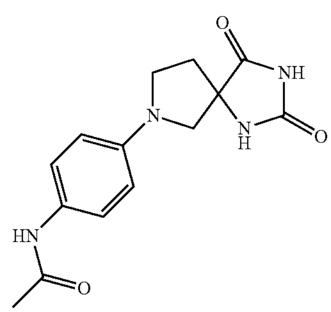 [SMILES: CC(=O)Nc1ccc(N2CCC3(C2)NC(=O)NC3=O)cc1] | 0.161 |
| 8 | 7-(thiazolo[4,5-b]pyridin-2-yl)-1,3,7-triazaspiro[4.4]nonane-2,4-dione | 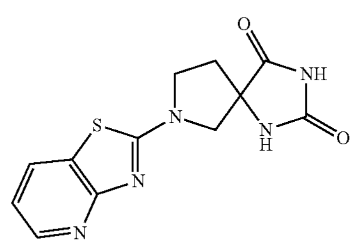 [SMILES: O=C1NC(=O)C2(CCN(c3nc4ncccc4s3)C2)N1] | 0.007 |
| 9 | 7-(benzo[d]thiazole-5-carbonyl)-1,3,7-triazaspiro[4.4]nonane-2,4-dione | 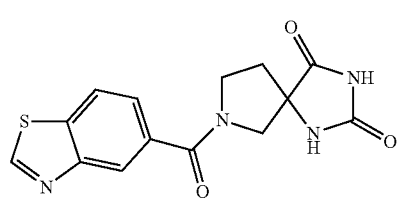 [SMILES: O=C1NC(=O)C2(CCN(C(=O)c3ccc4scnc4c3)C2)N1] | 0.03200 |

TABLE 12-continued

Affinities of Select Compounds to Protein

| Ex. | Name | Structure | Fluorescence h-Cereblon_DDB1 Mean $K_d$_EQ (μM) |
|---|---|---|---|
| 10 | methyl 6-(6,8-dioxo-2,7-diazaspiro[4.4]nonan-2-yl)nicotinate | 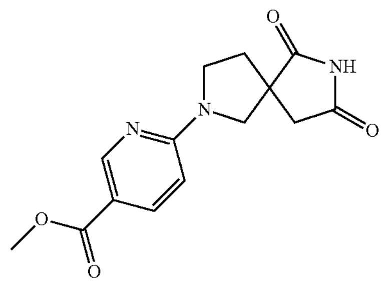 [SMILES: COC(=O)c1ccc(N2CCC3(CC(=O)NC3=O)C2)nc1] | 0.01000 |
| 11 | 7-(benzo[d]thiazol-2-yl)-2,7-diazaspiro[4.4]nonane-1,3-dione | 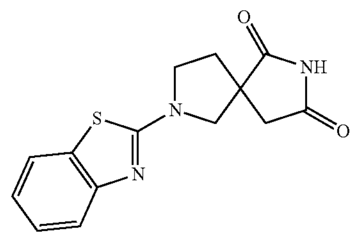 [SMILES: O=C1CC2(CCN(c3nc4ccccc4s3)C2)C(=O)N1] | 0.01800 |
| 12 | 7-(pyrazolo[1,5-a]pyridine-3-carbonyl)-2,7-diazaspiro[4.4]nonane-1,3-dione | 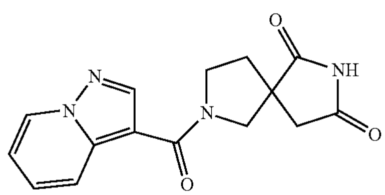 [SMILES: O=C1CC2(CCN(C(=O)c3cnn4ccccc34)C2)C(=O)N1] | 0.00600 |
| 13 | 7-benzoyl-2,7-diazaspiro[4.4]nonane-1,3-dione | 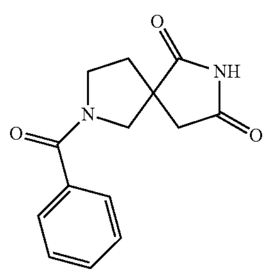 [SMILES: O=C1CC2(CCN(C(=O)c3ccccc3)C2)C(=O)N1] | 0.01500 |
| 14 | (R)-7-(benzo[d]thiazole-5-carbonyl)-1,3,7-triazaspiro[4.4]nonane-2,4-dione | 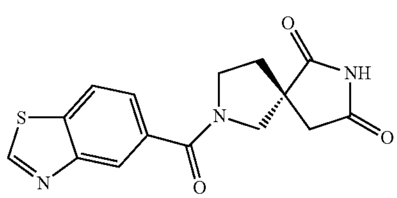 [SMILES: O=C1C[C@@]2(CCN(C(=O)c3ccc4scnc4c3)C2)C(=O)N1] | 0.02600 |
| 15 | (S)-7-(benzo[d]thiazole-5-carbonyl)-1,3,7-triazaspiro[4.4]nonane-2,4-dione | 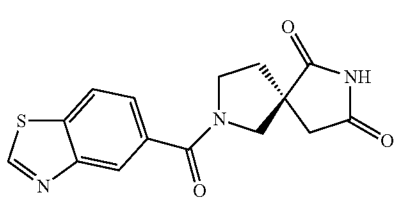 [SMILES: O=C1C[C@]2(CCN(C(=O)c3ccc4scnc4c3)C2)C(=O)N1] | 0.02300 |

All publications and patent applications cited in this specification are herein incorporated by reference as if each individual publication or patent application were specifically and individually indicated to be incorporated by reference.

Although the foregoing invention has been described in some detail by way of illustration and example for the purposes of clarity of understanding, it will be readily apparent to one of ordinary skill in the art in light of the teaching of this invention that certain changes and modification may be made thereto without departing from the spirit or scope of the invention as defined in the claims.

We claim:

1. A compound selected from:

(I)
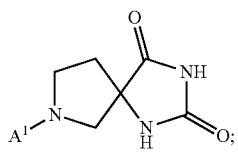

(II)
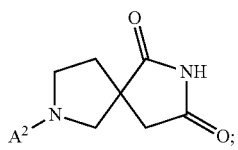

(III)
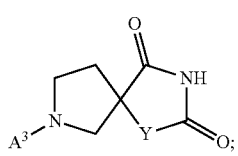

(IV)
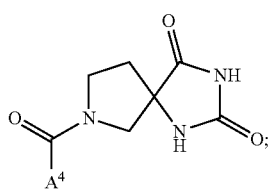

(V)
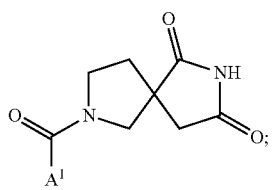

(VI)
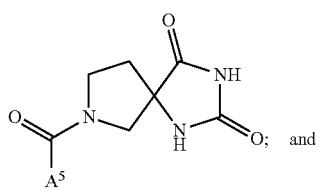 and (VII)
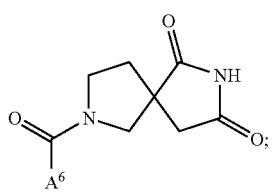

(VIII-a)
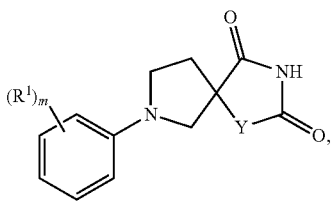

(VIII-b)
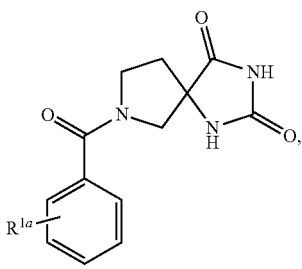

(VIII-c)
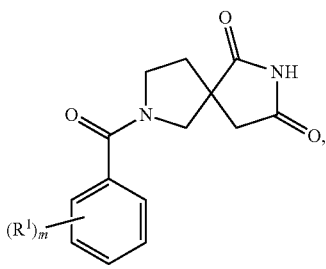

(IX)
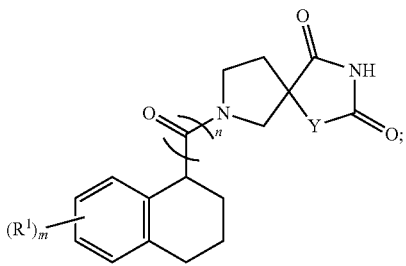

(X)
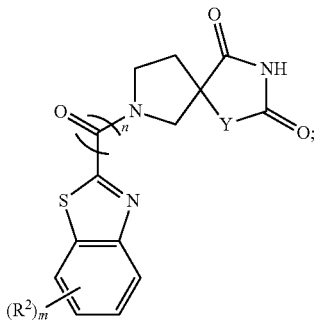

(XI)
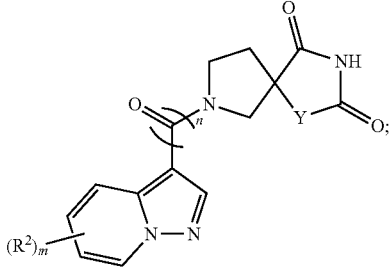

or a pharmaceutically acceptable salt thereof;
wherein:
Y is NH or CH$_2$;
A$^1$ is selected from the group consisting of aryl and aryl substituted with R$^1$;
A$^2$ is aryl substituted with R$^1$;
A$^3$ is selected from the group consisting of heteroaryl and heteroaryl substituted with R$^2$;
A$^4$ is aryl substituted with R$^{1a}$;
A$^5$ is heteroaryl substituted with R$^{2a}$;
A$^6$ is heteroaryl substituted with R$^2$;
R$^1$ is selected from the group consisting of: —C(=O)—O—C$_{1-6}$-alkyl; —COOH; —NH—(C=O)—C$_{1-6}$-alkyl; —NH$_2$; and —NO$_2$;
R$^{1a}$ is selected from the group consisting of: —C(=O)—O—C$_{1-6}$-alkyl; —COOH; and —NO$_2$;
R$^2$ is selected from the group consisting of: —COOH; —C(=O)—O—C$_{1-6}$-alkyl; —NH$_2$; and —NO$_2$;
R$^{2a}$ is —C(=O)—O—C$_{1-6}$-alkyl;
R$^{2b}$ is selected from the group consisting of: —COOH; —C(=O)—O—C$_{1-6}$-alkyl; and —NO$_2$;
m is 0 or 1;
n is 0 or 1;
Ax is selected from aryl and heteroaryl;
Tail is X$^1$ is selected from bond, NR$^{34}$, CH$_2$, CHR$^{34}$, C(R$^{34}$)$_2$, O, and S;
X$^{22}$ is selected from halo, —NH$_2$, —NHR$^{34}$, thiol, —B(OH)$_2$, —Sn(R$^{36}$)$_3$, —Si(R$^{36}$)$_3$, —OS(O)$_2$alkyl, —OS(O)$_2$haloalkyl, alkenyl, alkynyl, —C(O)H, —NR$^{34}$C(O)alkene, —NR$^{34}$C(O)alkyne, cyano, —SC(O)alkyl, OC(O)alkyl, heterocycle, —C(O)OH, hydrogen, alkyl, aryl, heteroaryl, and carbocyclic;
R$^{34}$ and R$^{34'}$ are independently selected at each occurrence from hydrogen, C$_1$-C$_6$alkyl, C$_1$-C$_6$haloalkyl, C$_2$-C$_6$alkenyl, C$_2$-C$_6$alkynyl, C$_3$-C$_6$cycloalkyl, C$_3$-C$_6$heterocycle, aryl, heteroaryl, —(CO)R$^{36}$, —(CS)R$^{36}$, —(C=NH)R$^{36}$, —(SO)R$^{36}$, and —(SO$_2$)R$^{36}$;
R$^{36}$ is independently selected at each occurrence from hydrogen, C$_1$-C$_6$alkyl, C$_1$-C$_6$haloalkyl, C$_2$-C$_6$alkenyl, C$_2$-C$_6$alkynyl, C$_3$-C$_6$cycloalkyl, C$_3$-C$_6$heterocycle, aryl, heteroaryl, hydroxyl, C$_1$-C$_6$alkoxy, thio, C$_1$-C$_6$thioalkyl, —NH$_2$, —NH(C$_1$-C$_6$alkyl, C$_3$-C$_7$cycloalkyl, C$_3$-C$_7$heterocycle, aryl, or heteroaryl), and —N(independently C$_1$-C$_6$alkyl, C$_3$-C$_7$cycloalkyl, C$_3$-C$_7$heterocycle, aryl, or heteroaryl)$_2$;
R$^{20}$, R$^{21}$, R$^{22}$, R$^{23}$, and R$^{24}$ are independently selected from covalent bond, alkyl, —C(O)—, —C(O)alkyl, —C(O)Oalkyl, —C(S)—, —SO$_2$—, —S(O)—, —C(S)—, —C(O)NH—, —NHC(O)—, —N(alkyl)C(O)—, —C(O)N(alkyl)-, —S—, —NH—, —CH(—O—R$^{26}$)—, —C(NR$^{34}$R$^{34'}$)alkyl-, —C(R$^{40}$R$^{40}$)—, -alkyl(R$^{27}$)-alkyl(R$^{28}$)—, —C(R$^{27}$R$^{28}$)—, —P(O)(OR$^{26}$)O—, —P(O)(OR$^{26}$)—, —NR$^{34}$C(O)NR$^{34'}$—, alkene, haloalkyl, alkoxy, alkyneheteroarylalkyl, aryl, arylalkyl, heterocycle, aliphatic, heteroaryl, lactic acid, glycolic acid, carbocycle, -(ethylene glycol)$_{1-6}$-, -(lactic-co-glycolic acid)$_{1-6}$-, -(propylene glycol)$_{1-6}$-, —O—(CH$_2$)$_{1-12}$—O—, —NH—(CH$_2$)$_{1-12}$—NH—, —NH—(CH$_2$)$_{1-12}$—O—, —O—(CH$_2$)$_{1-12}$—NH—, —S—

—(CH$_2$)$_{1-12}$—O—, —O—(CH$_2$)$_{1-12}$—S—, —S—(CH$_2$)$_{1-12}$—S—, —S—(CH$_2$)$_{1-12}$—NH—, and —NH—(CH$_2$)$_{1-12}$—S—;

each of which R$^{20}$, R$^{21}$, R$^{22}$, R$^{23}$, and R$^{24}$ is optionally substituted with one or more substituents selected from R$^{101}$;

wherein at least one of R$^{20}$, R$^{21}$, R$^{22}$, R$^{23}$, and R$^{24}$ is not a bond;

R$^{101}$ is independently selected at each occurrence from hydrogen, alkyl, alkene, alkyne, haloalkyl, alkoxy, aryl, heteroaryl, heterocycle, arylalkyl, heteroarylalkyl, heterocycloalkyl, aryloxy, heteroaryloxy, CN, —COOalkyl, COOH, NO$_2$, F, Cl, Br, I, CF$_3$, NH$_2$, NHalkyl, and aliphatic;

R$^{26}$ is selected from hydrogen, alkyl, silane, arylalkyl, heteroarylalkyl, alkene, alkyne, aryl, heteroaryl, heterocyclic, aliphatic and heteroaliphatic;

R$^{27}$ and R$^{28}$ are independently selected from hydrogen, alkyl, or together with the carbon atom to which they are attached, form C(O), C(S), C=CH$_2$, a C$_3$-C$_6$ spirocarbocycle, or a 4-, 5-, or 6-membered spiroheterocycle comprising 1 or 2 heteroatoms selected from N and O, or form a 1 or 2 carbon bridged ring; and R$^{40}$ is selected at each instance from: hydrogen, alkyl, alkene, alkyne, halogen, alkoxy, azide, amino, cyano, —NH(aliphatic), —NHSO$_2$(aliphatic), —N(aliphatic)SO$_2$alkyl, —NHSO$_2$(aryl, heteroaryl or heterocyclic), —N(alkyl)SO$_2$(aryl, heteroaryl or heterocyclic) —NHSO$_2$alkenyl, —N(alkyl)SO$_2$alkenyl, —NHSO$_2$alkynyl, —N(alkyl)SO$_2$alkynyl, haloalkyl, aryl, heteroaryl, heterocyclic, and carbocyclic.

2. The compound of claim 1, wherein R$^1$ is —C(=O)—O—C$_{1-6}$-alkyl or —COOH.

3. The compound of claim 1, wherein R$^1$ is —NH—(C=O)—C$_{1-6}$-alkyl.

4. The compound of claim 1, wherein R$^1$ is —NH$_2$ or —NO$_2$.

5. The compound of claim 1, wherein R$^2$ is —C(=O)—O—C$_{1-6}$-alkyl or —COOH.

6. The compound of claim 1, wherein R$^2$ is —NH$_2$ or —NO$_2$.

7. The compound of claim 1, wherein n is 0.

8. The compound of claim 1, wherein n is 1.

9. The compound of claim 1, wherein m is 0.

10. The compound of claim 1, wherein m is 1.

11. The compound of claim 1, wherein Y is NH.

12. The compound of claim 1, wherein Y is CH$_2$.

13. The compound of claim 1 of formula:

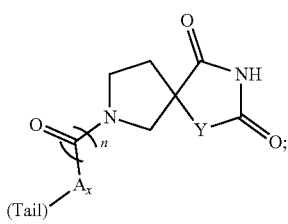

(XVI)

or a pharmaceutically acceptable salt thereof.

14. The compound of claim 13, wherein Ax is aryl.

15. The compound of claim 13, wherein Ax is heteroaryl.

16. The compound of claim 13 selected from:

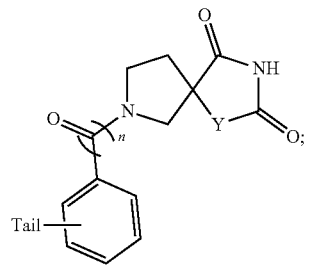

(XVII-a)

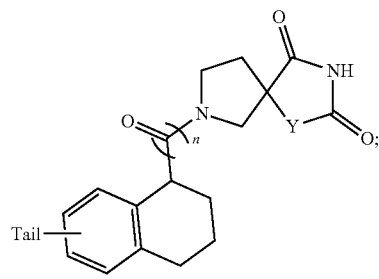

(XVII-b)

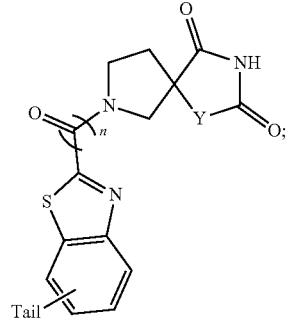

(XVII-c)

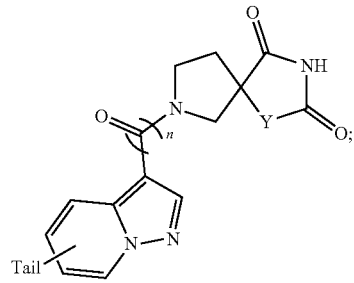

(XVII-d)

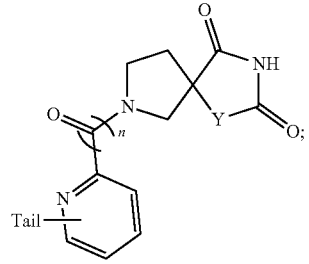

(XVII-e)

263
-continued
(XVII-f)
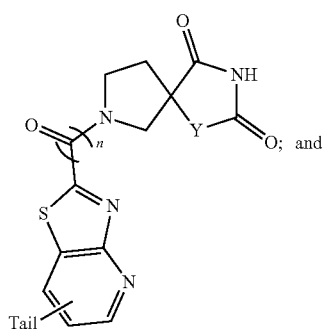
(XVII-g)
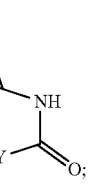
or a pharmaceutically acceptable salt thereof.
17. The compound of claim 1 selected from:
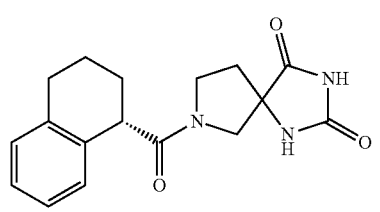
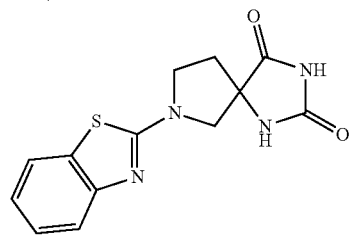
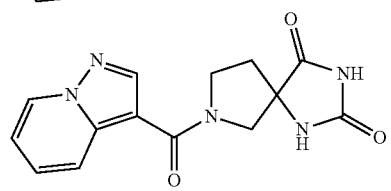
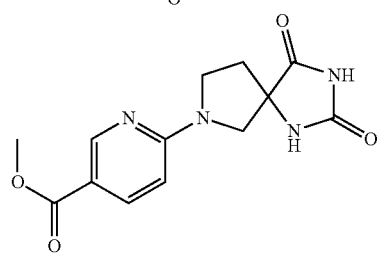
264
-continued
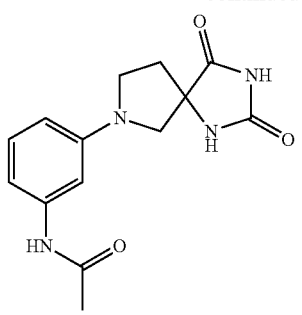
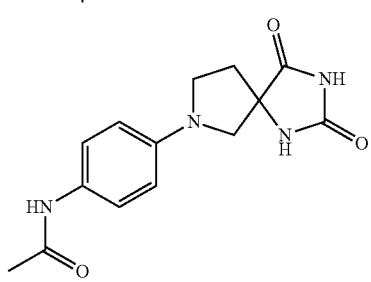
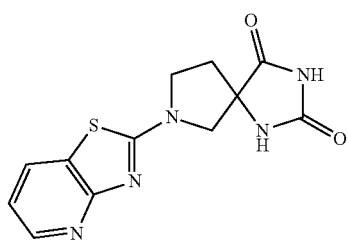
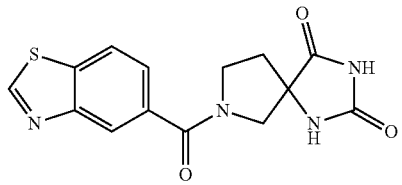
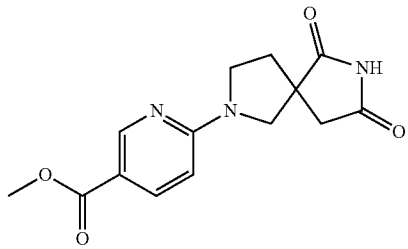
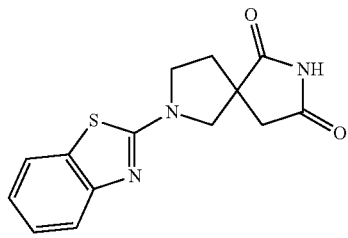
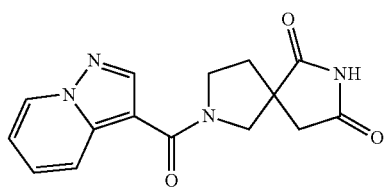

-continued

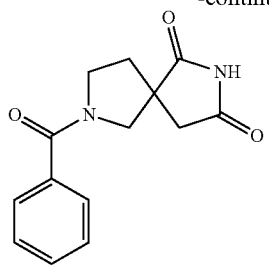

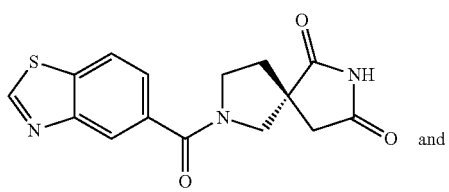 and

-continued

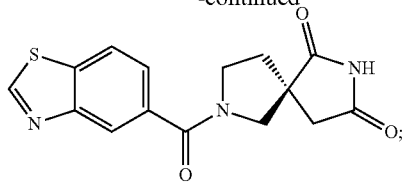

or a pharmaceutically acceptable salt thereof.

18. A pharmaceutical composition comprising a compound of claim 1 and a pharmaceutically acceptable excipient.

19. A method of treating abnormal cellular proliferation in a subject in need thereof comprising administering an effective amount of a compound of claim 1, or a pharmaceutically acceptable salt thereof, optionally in a pharmaceutical composition.

20. The method of claim 19, wherein the subject is a human.

* * * * *